US008163917B2

(12) United States Patent
Farmer et al.

(10) Patent No.: US 8,163,917 B2
(45) Date of Patent: *Apr. 24, 2012

(54) AZAINDOLES USEFUL AS INHIBITORS OF JANUS KINASES

(75) Inventors: Luc Farmer, Foxborough, MA (US); Gabriel Martinez-Botella, West Roxbury, MA (US); Albert Pierce, Cambridge, MA (US); Francesco Salituro, Marlboro, MA (US); Jian Wang, Newton, MA (US); Marion Wannamaker, Stow, MA (US); Tiansheng Wang, Concord, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/775,885

(22) Filed: May 7, 2010

(65) Prior Publication Data

US 2010/0311743 A1     Dec. 9, 2010

Related U.S. Application Data

(63) Continuation of application No. 11/654,375, filed on Jan. 17, 2007, now Pat. No. 7,767,816.

(60) Provisional application No. 60/759,367, filed on Jan. 17, 2006, provisional application No. 60/842,471, filed on Sep. 6, 2006.

(51) Int. Cl.
*C07D 471/02* (2006.01)
(52) U.S. Cl. ...................................... 546/113
(58) Field of Classification Search .................... 546/113
See application file for complete search history.

(56) References Cited

U.S. PATENT DOCUMENTS

| | | | |
|---|---|---|---|
| 5,338,849 A | 8/1994 | Festal et al. | |
| 6,265,403 B1 | 7/2001 | Fraley et al. | |
| 7,135,550 B2 | 11/2006 | Come | |
| 7,507,826 B2 * | 3/2009 | Salituro et al. | 546/113 |
| 2004/0043388 A1 | 3/2004 | Come | |
| 2005/0137201 A1 | 6/2005 | Aronov et al. | |
| 2006/0003968 A1 | 1/2006 | Green et al. | |
| 2006/0122213 A1 | 6/2006 | Pierard et al. | |
| 2006/0183761 A1 | 8/2006 | Ledeboer et al. | |
| 2007/0043063 A1 | 2/2007 | Salituro et al. | |
| 2007/0207995 A1 | 9/2007 | Salituro et al. | |

FOREIGN PATENT DOCUMENTS

| | | |
|---|---|---|
| EP | 0557171 | 8/1993 |
| WO | WO 88/01997 | 3/1988 |
| WO | WO 95/33748 | 12/1995 |
| WO | WO 99/21859 | 5/1999 |
| WO | WO 00/43393 | 7/2000 |
| WO | WO 01/01986 | 1/2001 |
| WO | WO 03/000688 | 1/2003 |
| WO | WO 03/091246 | 11/2003 |
| WO | WO 03/101990 | 12/2003 |
| WO | WO 2004/016609 | 2/2004 |
| WO | WO 2004/016610 | 2/2004 |
| WO | WO 2004/078756 | 9/2004 |
| WO | WO 2004/082638 | 9/2004 |
| WO | WO 2004/089913 | 10/2004 |
| WO | WO 2005/028475 | 3/2005 |
| WO | WO 2005/044181 | 5/2005 |
| WO | WO 2005/062795 | 7/2005 |
| WO | WO 2005/095400 | 10/2005 |
| WO | WO 2006/009755 | 1/2006 |
| WO | WO 2006/015123 | 2/2006 |
| WO | WO 2006/030031 | 3/2006 |
| WO | WO 2006/038001 | 4/2006 |
| WO | WO 2006/050076 | 5/2006 |
| WO | WO 2006/124863 | 11/2006 |
| WO | WO 2006/127587 | 11/2006 |
| WO | WO 2007/002433 | 1/2007 |
| WO | WO 2007/117494 | 10/2007 |

OTHER PUBLICATIONS

Alvarez, Mercedes, et al., "Synthesis of 3-Aryl- and 3-Heteroaryl-7-azaindoles", Synthesis, Thieme Stuttgart, New York, No. 4, 1999, pp. 615-620.

Fernandez, David, et al., "Synthesis of Polyheterocyclic Nitrogen-Containing Marine Natural Products#", Monatshefte Fur Chemie, Chemical Monthly, AU, vol. 135, 2004, pp. 615-627.

Fresneda, Pilar M., et al., "Synthesis of the indole alkaloids meridianins from the tunicate *Aplidium meridianum*", Tetrahedron, Pergamon, vol. 57, No. 12, 2001, pp. 2355-2363.

Herbert, R., et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.

International Search Report issued for PCT Application No. PCT/US2007/001225 Dated Jul. 20, 2007.

Kelly, Terence A., et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", Journal of Medicinal Chemistry, vol. 40, No. 15, 1997, pp. 2430-2433.

Pungpo, Pornpan, et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.

* cited by examiner

*Primary Examiner* — Nizal Chandrakumar
(74) *Attorney, Agent, or Firm* — Honigman Miller Schwartz and Cohn LLP; Jonathan P. O'Brien; Andrew N. Weber

(57) ABSTRACT

The present invention relates to compounds useful as inhibitors of protein kinases, particularly of JAK family kinases. The invention also provides pharmaceutically acceptable compositions comprising said compounds and methods of using the compositions in the treatment of various disease, conditions, or disorders.

58 Claims, No Drawings

AZAINDOLES USEFUL AS INHIBITORS OF JANUS KINASES

CROSS REFERENCE TO RELATED APPLICATIONS

This continuation application claims the benefit of U.S. application No. 11/654,375, filed Jan. 17, 2007, which claims the benefit of U.S. Provisional Application No. 60/759,367, filed Jan. 17, 2006 and U.S. Provisional Application No. 60/842,471, filed Sept. 6, 2006, each of which is herein incorporated by reference.

TECHNICAL FIELD OF THE INVENTION

The present invention relates to compounds useful as inhibitors of Janus kinases (JAK). The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Accordingly, there is a great need to develop compounds useful as inhibitors of protein kinases. In particular, it would be desirable to develop compounds that are useful as inhibitors of JAK family kinases.

SUMMARY OF THE INVENTION

It has now been found that compounds of this invention, and pharmaceutically acceptable compositions thereof, are effective as inhibitors of protein kinases, particularly the JAK family kinases. These compounds have the general formula I:

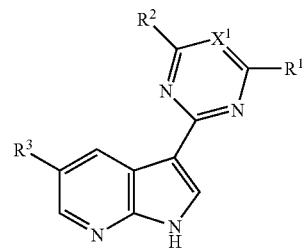

I or a pharmaceutically acceptable salt thereof, wherein $X^1$, $R^1$, $R^2$ and $R^3$ are as defined herein.

These compounds, and pharmaceutically acceptable compositions thereof, are useful for treating or lessening the severity of a variety of disorders, including proliferative disorders, cardiac disorders, neurodegenerative disorders, autoimmune disorders, conditions associated with organ transplantation, inflammatory disorders, or immunologically mediated disorders in a patient.

The compounds and compositions provided by this invention are also useful for the study of JAK kinases in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and In yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "cycloalkyl") refers to a hydrocarbon that is completely saturated or that contains one or more units of unsaturation, but which is not aromatic, that has a single point of attachment to the rest of the molecule, and wherein any individual ring in said bicyclic ring system has 3-7 members. Unless otherwise specified, the term "cycloaliphatic" refers to a monocyclic $C_3$-$C_8$ hydrocarbon or bicyclic $C_8$-$C_{12}$ hydrocarbon. Suitable cycloaliphatic groups include, but are not limited to, cycloalkyl, cycloalkenyl, and cycloalkynyl. Further examples of aliphatic groups include cyclopropyl, cyclobutyl, cyclopentyl, cyclopentenyl, cyclohexyl, cyclohexenyl, cycloheptyl, and cycloheptenyl.

The term "heterocycle", "heterocyclyl" or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl" or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definitions of $R^2$ and $R^4$ below. Other suitable substituents include: halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1-2}$(Ph), optionally substituted with $R^\circ$; —CH=CH(Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2 R^\circ$; —$NR^\circ NR^\circ C(O)R^\circ$; —$NR^\circ NR^\circ C(O)N(R^\circ)_2$; —$NR^\circ NR^\circ CO_2 R^\circ$; —C(O)C(O)$R^\circ$; —C(O)$CH_2$C(O)$R^\circ$; —$CO_2 R^\circ$; —C(O)$R^\circ$; —C(S)$R^\circ$; —C(O)$N(R^\circ)_2$; —C(S)N$(R^\circ)_2$; —OC(O)$N(R^\circ)_2$; —OC(O)$R^\circ$; —C(O)N(O$R^\circ$) $R^\circ$; —C(NO$R^\circ$)$R^\circ$; —$S(O)_2 R^\circ$; —$S(O)_3 R^\circ$; —$SO_2 N(R^\circ)_2$; —S(O)$R^\circ$; —$NR^\circ SO_2 N(R^\circ)_2$; —$NR^\circ SO_2 R^\circ$; —N(O$R^\circ$)$R^\circ$; —C(=NH)—N$(R^\circ)_2$; or —$(CH_2)_{0-2}$NHC(O)$R^\circ$; wherein each independent occurrence of $R^\circ$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, two independent occurrences of $R^\circ$, on the same substituent or different substituents, taken together with the atom(s) to which each $R^\circ$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of $R^\circ$ are selected from $NH_2$, NH($C_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$ aliphatic, wherein each of the foregoing C$_{1-4}$aliphatic groups of R$^o$ is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$aliphatic), or halo (C$_{1-4}$ aliphatic), wherein each of the foregoing C$_{1-4}$aliphatic groups of R$^+$ is unsubstituted.

As detailed above, in some embodiments, two independent occurrences of R$^o$ (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R$^o$ (or R$^+$, or any other variable similarly defined herein) are taken together with the atom(s) to which each variable is bound include, but are not limited to the following: a) two independent occurrences of R$^o$ (or R$^+$, or any other variable similarly defined herein) that are bound to the same atom and are taken together with that atom to form a ring, for example, N(R)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, or any other variable similarly defined herein) that are bound to different atoms and are taken together with both of those atoms to form a ring, for example where a phenyl group is substituted with two occurrences of OR$^o$

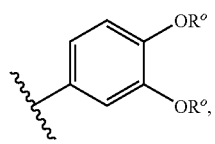

these two occurrences of R$^o$ are taken together with the oxygen atoms to which they are bound to form a fused 6-membered oxygen containing ring:

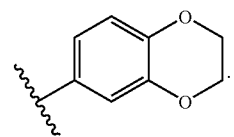

It will be appreciated that a variety of other rings can be formed when two independent occurrences of R$^o$ (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

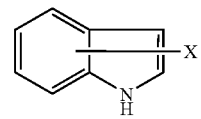

Figure a

-continued

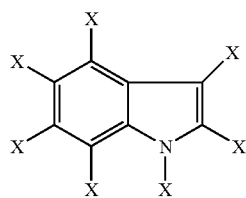

Figure b

This also applies to multiple ring systems fused to optional ring systems (which would be represented by dotted lines). For example, in Figure c, X is an optional substituent both for ring A and ring B.

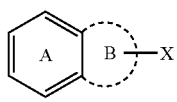

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

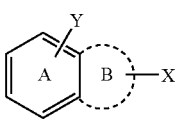

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Description of Compounds of the Invention

The present invention relates to a compound of formula I:

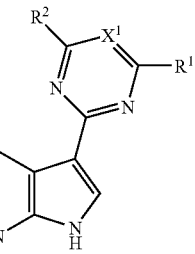

I or a pharmaceutically acceptable salt thereof, wherein
$R^3$ is H, Cl or F;
$X^1$ is N or $CR^4$;
$R^2$ is H, F, R', OH, OR', COR', COOH, COOR', $CONH_2$, CONHR', $CON(R')_2$, or CN;
$R^4$ is H, F, R', OH, OR', COR', COOH, COOR', $CONH_2$, CONHR', $CON(R')_2$, or CN;
or $R^2$ and $R^4$, taken together, form a 5-7 membered aryl or heteroaryl ring optionally substituted with 1-4 occurrences of $R^{10}$;
R' is a $C_{1-3}$ aliphatic optionally substituted with 1-4 occurrences of $R^5$;
each $R^5$ is independently selected from halogen, $CF_3$, $OCH_3$, OH, SH, $NO_2$, $NH_2$, $SCH_3$, $NCH_3$, CN or unsubstituted $C_{1-2}$ aliphatic, or two $R^5$ groups, together with the carbon to which they are attached, form a cyclopropyl ring or C=O;
each $R^{10}$ is independently selected from halogen, $OCH_3$, OH, $NO_2$, $NH_2$, SH, $SCH_3$, $NCH_3$, CN or unsubstituted $C_{1-2}$ aliphatic;
$R^1$ is R" is H or is a —$C_{1-2}$ aliphatic optionally substituted with 1-3 occurrences of $R^{11}$;
each $R^{11}$ is independently selected from halogen, $OCH_3$, OH, SH, $NO_2$, $NH_2$, $SCH_3$, $NCH_3$, CN, $CON(R^{15})_2$ or unsubstituted $C_{1-2}$ aliphatic, or two $R^{11}$ groups, together with the carbon to which they are attached, form a cyclopropyl ring or C=O;
$R^6$ is a $C_{1-4}$ aliphatic optionally substituted with 1-5 occurrences of $R^{12}$;
each $R^{12}$ is independently selected from halogen, $OCH_3$, OH, $NO_2$, $NH_2$, SH, $SCH_3$, $NCH_3$, CN or unsubstituted $C_{1-2}$ aliphatic, or two $R^{12}$ groups, together with the carbon to which they are attached, form a cyclopropyl ring;
Ring A is a 4-8 membered saturated nitrogen-containing ring comprising up to two additional heteroatoms selected from N, O or S and optionally substituted with 1-4 occurrences of $R^{13}$;

each $R^{13}$ is independently selected from halogen, R', $NH_2$, NHR', $N(R')_2$, SH, SR', OH, OR', $NO_2$, CN, $CF_3$, COOR', COOH, COR', OC(O)H, OC(O)R', $CONH_2$, CONHR', $CON(R')_2$, NHC(O)R' or NR'C(O)R'; or any two $R^{13}$ groups, on the same substituent or different substituents, together with the atom(s) to which each $R^{13}$ group is bound, form a 3-7 membered saturated, unsaturated, or partially saturated carbocyclic or heterocyclic ring optionally substituted with 1-3 occurrences of $R^5$;

$R^8$ is $C_{1-4}$ aliphatic optionally substituted with 1-5 occurrences of $R^{12}$;

$R^9$ is $C_{1-2}$ alkyl; or $R^8$ and $R^9$ are taken together to form a 3-7 membered carbocyclic or heterocyclic saturated ring optionally substituted with 1-5 occurrences of $R^{12}$;

$R^{14}$ is H or unsubstituted $C_{1-2}$ alkyl;

$R^{15}$ is H or unsubstituted $C_{1-2}$ alkyl; and $R^7$ is a $C_{2-3}$ aliphatic or cycloaliphatic optionally substituted with up to 6 occurrences of F.

In one embodiment, a compound of the invention has one of formulae I-A or I-B:

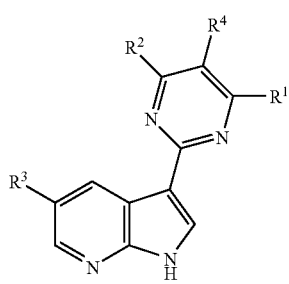

I-A

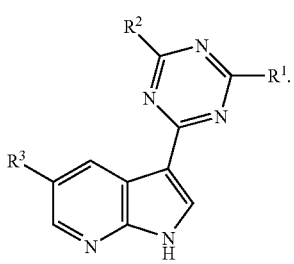

I-B

In one embodiment, $R^3$ is H or Cl. In a further embodiment, $R^3$ is Cl. In a further embodiment, $R^3$ is H.

In one embodiment, $R^2$ is H, F, R', OH or OR'. In a further embodiment, $R^2$ is H or F.

In one embodiment, the compound is of formula I-A and $R^4$ is H, F, R', OH or OR'. In another embodiment, $R^4$ is H or F. In a further embodiment, $R^4$ is F and $R^2$ is H. In another embodiment, $R^2$ is F and $R^4$ is H. In another embodiment, $R^2$ and $R^4$ are both H. In a further embodiment, $R^3$ is Cl. In an alternative embodiment, $R^3$ is H.

In another embodiment, the compound is of formula I-A and $R^2$ and $R^4$ are taken together to form a 6-membered aryl ring. In a further embodiment, $R^3$ is Cl. In an alternative embodiment, $R^3$ is H.

In another embodiment, $R^7$ is $CH_2CH_3$, $CH_2CF_3$, $CH_2CHF_2$, $CH_2CH_2F$, $CH_2CH_2CH_3$, $CH_2CH_2CF_3$, $CH_2CH_2CH_2F$ or $CH_2CH_2CHF_2$. In a further embodiment, $R^7$ is $CH_2CH_3$, $CH_2CF_3$, $CH_2CH_2CH_3$ or $CH_2CH_2CF_3$. In yet a further embodiment, $R^7$ is $CH_2CF_3$.

In another embodiment, R" is H or $CH_3$. In a further embodiment, R" is H.

In another embodiment, $R^{14}$ is H. In yet another embodiment, $R^{15}$, if present, is H. In another embodiment, $R^{15}$ is absent.

In another embodiment, the invention provides a compound of formula II:

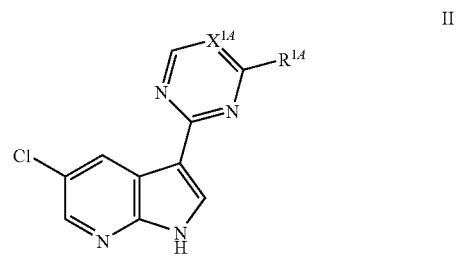

II wherein $X^{14}$ is N, CH or CF and $R^{14}$ is

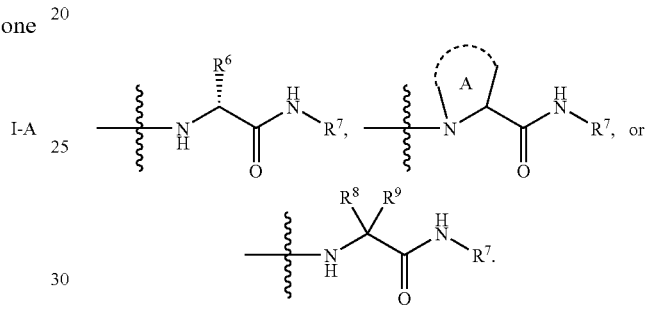

In a further embodiment, $R^7$ is $CH_2CH_3$, $CH_2CF_3$, $CH_2CH_2CH_3$ or $CH_2CH_2CF_3$. In yet a further embodiment, $R^7$ is $CH_2CF_3$.

In another embodiment, the invention provides a compound of formula III:

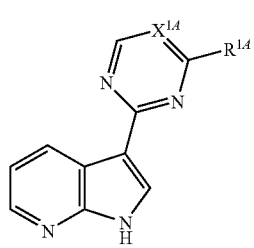

III wherein $X^{14}$ is N, CH or CF and $R^{14}$ is

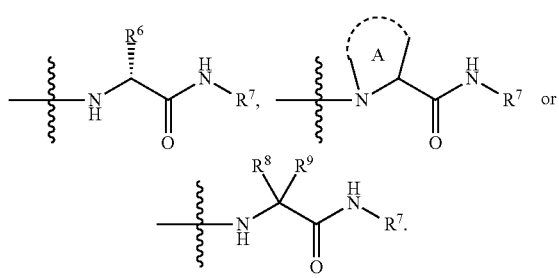

In a further embodiment, $R^7$ is $CH_2CH_3$, $CH_2CF_3$, $CH_2CH_2CH_3$ or $CH_2CH_2CF_3$. In yet a further embodiment, $R^7$ is $CH_2CF_3$.

In another embodiment of any of formulae I, II or III, $R^6$ is selected from

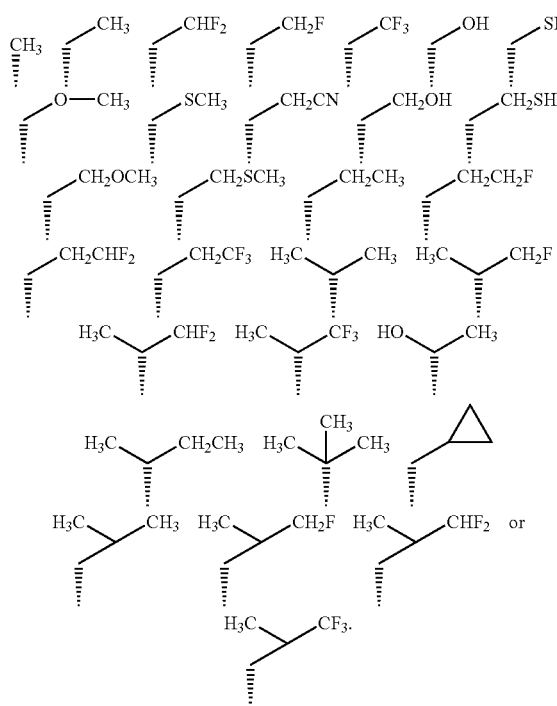

In a further embodiment, $R^6$ is selected from

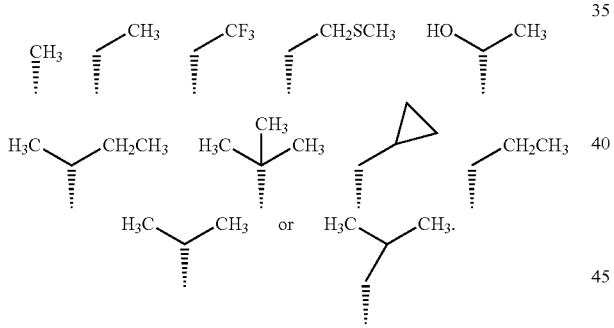

In yet a further embodiment, $R^6$ is selected from

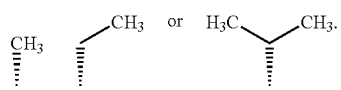

In another embodiment of any of formulae I, II or III, Ring A is

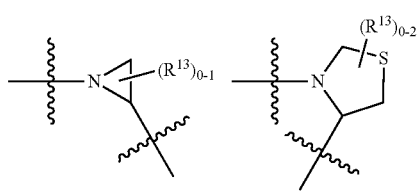

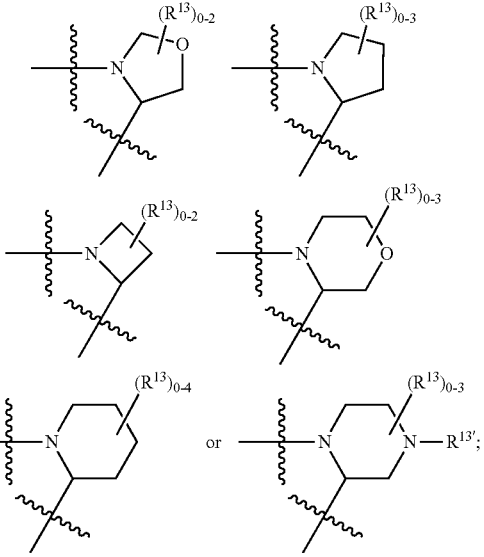

and
$R^{13'}$ is H or $R^{13}$.

In a further embodiment, Ring A is

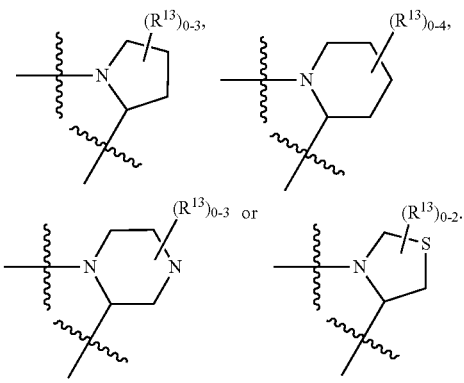

In a further embodiment, Ring A is

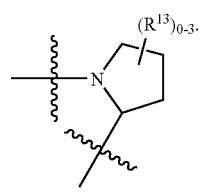

In one embodiment, each $R^{13}$ is independently selected from halogen, R', $NH_2$, NHR', $N(R')_2$, SH, SR', OH, OR', $NO_2$, CN, $CF_3$, COOR', COOH, COR', OC(O)R' or NHC(O)R'; or any two $R^{13}$ groups, on the same substituent or different substituents, together with the atom(s) to which each $R^{13}$ group is bound, form a 3-7 membered saturated, unsaturated, or partially saturated carbocyclic or heterocyclic ring optionally substituted with 1-3 occurrences of $R^5$.

In one embodiment of this invention, $R^{13}$ is absent. In another embodiment, Ring A is substituted with one occurrence of $R^{13}$. In a further embodiment, the one occurrence of $R^{13}$ is OH, $CH_3$, F, OR' or NHR'. In yet a further embodiment, R' is $C_{1-2}$ alkyl or $C_{2-3}$ alkenyl. In another embodiment, $R^{13}$ is OH.

In another embodiment of any of formulae I, II or III, $R^8$ and $R^9$ are taken together to form a ring selected from

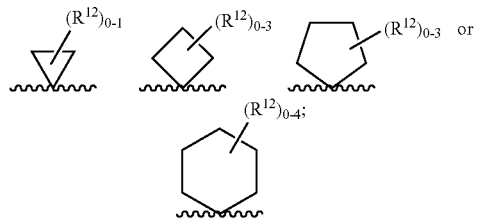

wherein one or more carbon atoms in of said ring are optionally and independently replaced by N, O or S.

In another embodiment of any of formulae I, II or III, $R^8$ and $R^9$ are

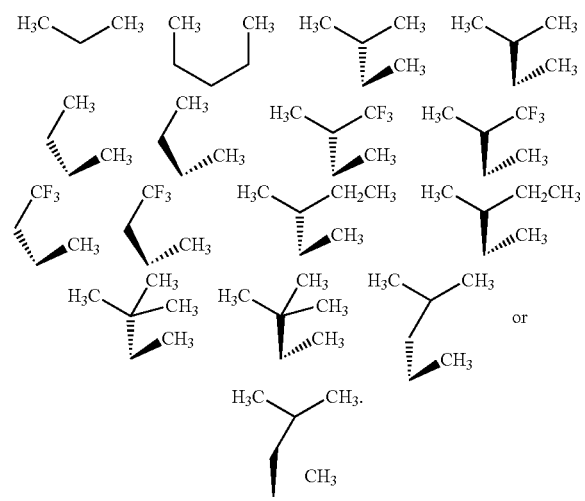

In a further embodiment, $R^8$ and $R^9$ are

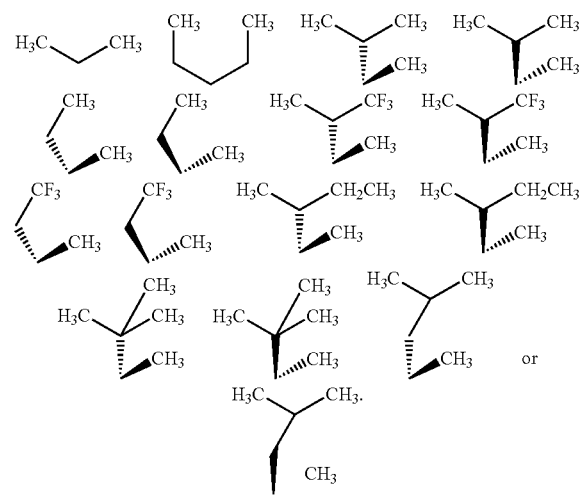

In yet a further embodiment, $R^8$ and $R^9$ are

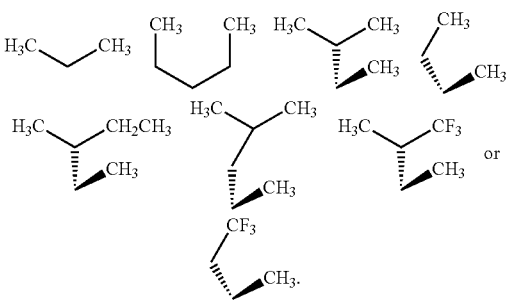

In still a further embodiment, $R^8$ and $R^9$ are

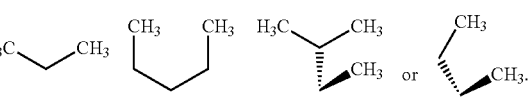

In another embodiment, the invention provides a compound of formulae I, IA, IB, II or III, wherein said compound inhibits a JAK kinase with a lower $K_i$ (i.e., is more potent) than said compounds inhibits one or more kinases selected from Aurora-1 (AUR-B), Aurora-2 (AUR-A), Src, CDK2, Flt-3 or c-Kit. In another embodiment, the invention provides a compound of formulae I, IA, IB, II or III, wherein said compound inhibits JAK3 with a lower $K_i$ than said compound inhibits one or more kinases selected from JAK2, Aurora-1, Aurora-2, Src, CDK2, Flt-3 or c-Kit.

In another embodiment, the invention provides a compound of any of formulae I, IA, IB, II or III, wherein said compound inhibits JAK3 with a $K_i$ of less than 0.1 µM. In a further embodiment, the invention provides a compound of any of formulae I, IA, IB, II or III, wherein said compound inhibits JAK3 with a $K_i$ of less than 0.01 µM. In another embodiment, the invention provides a compound of any of formulae I, IA, IB, II or III, wherein said compound inhibits JAK3 with a $K_i$ of less than 0.01 µM and inhibits Aurora-2 with a $K_i$ that is at least 5-fold higher than the $K_i$ of JAK3. In a further embodiment, the invention provides a compound of any of formulae I, IA, IB, II or III, wherein said compound inhibits JAK3 with a $K_i$ of less than 0.01 µM and inhibits Aurora-2 with a $K_i$ that is at least 10-fold higher than the $K_i$ of JAK3.

In another embodiment, the invention provides a compound of formulae I, IA, IB, II or III, wherein said compound inhibits JAK3 in a cellular assay with an $IC_{50}$ of less than 5 µM. In a further embodiment, said compound inhibits JAK3 in a cellular assay with an $IC_{50}$ of less than 1 µM.

In another embodiment, said compound inhibits JAK3 in a cellular assay with an $IC_{50}$ that is at least 5-fold less than said compound inhibits one or more kinases selected from JAK2, Aurora-1, Aurora-2, Src, CDK2, Flt-3 or c-Kit in a cellular assay. In another embodiment, the invention provides a compound of formulae I, IA, IB, II or III, wherein said compound inhibits JAK3 in a cellular assay with an $IC_{50}$ of less than 5 µM, wherein the $IC_{50}$ of JAK2 is at least 5-fold higher than the $IC_{50}$ of JAK3. In a further embodiment, said compound inhibits JAK3 in a cellular assay with an $IC_{50}$ of less than 1 µM, wherein the $IC_{50}$ of JAK2 is at least 5-fold higher than the $IC_{50}$ of JAK3. In a further embodiment, said compound inhibits JAK3 in a cellular assay with an $IC_{50}$ of less than 5 µM, wherein the $IC_{50}$ of JAK2 is at least 10-fold higher than the $IC_{50}$ of JAK3. In a further embodiment, said compound inhibits JAK3 in a cellular assay with an $IC_{50}$ of less than 1 µM, wherein the $IC_{50}$ of JAK2 is at least 10-fold higher than the $IC_{50}$ of JAK3. In yet a further embodiment, the invention provides a compound of formulae I, IA, IB, II or III, wherein said compound inhibits JAK3 in a cellular assay with an $IC_{50}$ of less than 1 µM, wherein the $IC_{50}$ of JAK2 is at least 5-fold higher than the $IC_{50}$ of JAK3, and wherein said compound inhibits JAK3 with a $K_i$ of less than 0.01 µM and inhibits Aurora-2 with a $K_i$ that is at least 5-fold higher than the $K_i$ of JAK3. In yet a further embodiment, said compound inhibits JAK3 in a cellular assay with an $IC_{50}$ of less than 1 µM, wherein the $IC_{50}$ of JAK2 is at least 10-fold higher than the $IC_{50}$ of JAK3, and wherein said compound inhibits JAK3 with a $K_i$ of less than 0.01 µM and inhibits Aurora-2 with a $K_i$ that is at least 10-fold higher than the $K_i$ of JAK3.

In another embodiment, the invention provides a compound of Table 1, Table 2 or Table 3:

TABLE 1

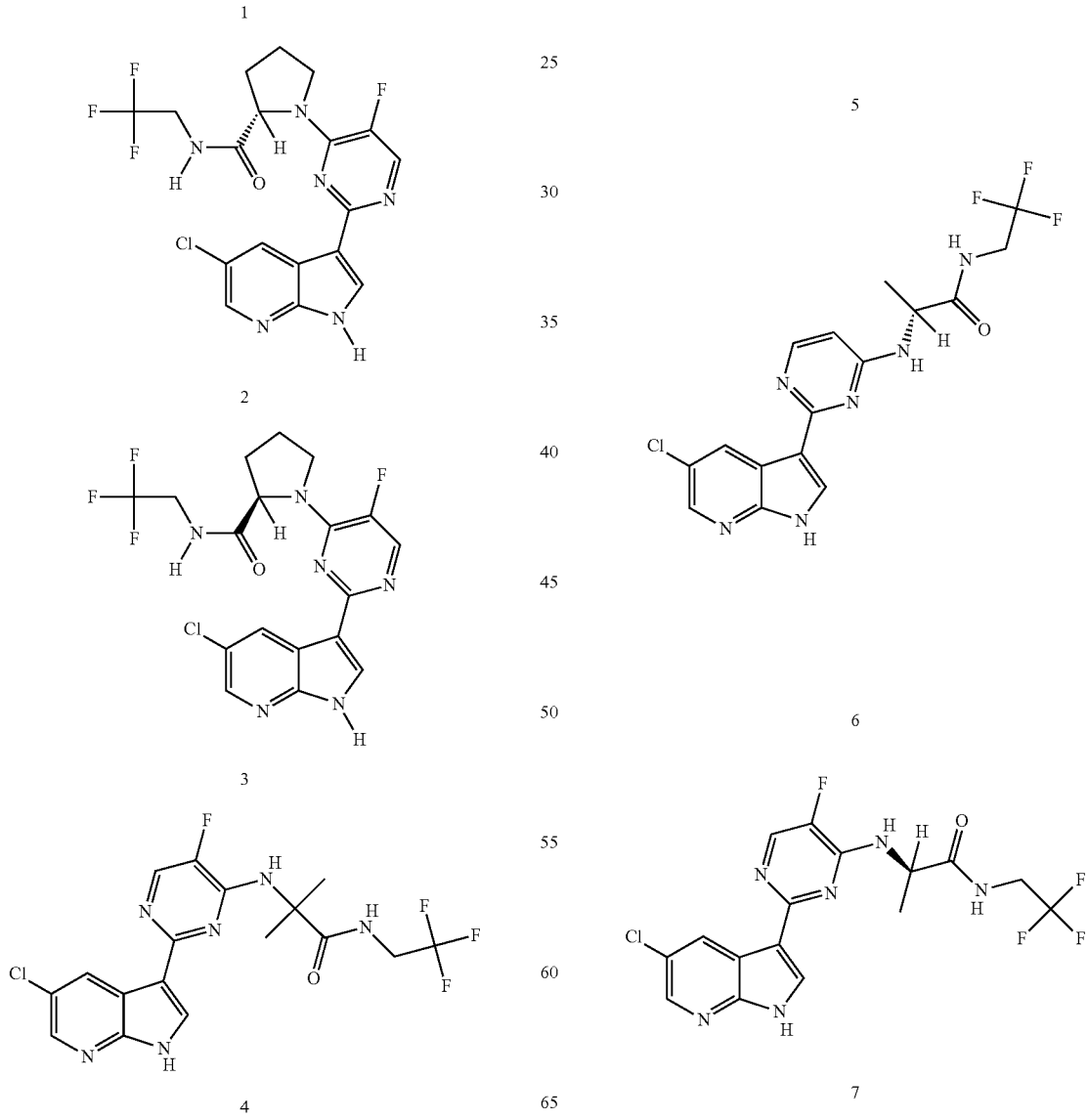
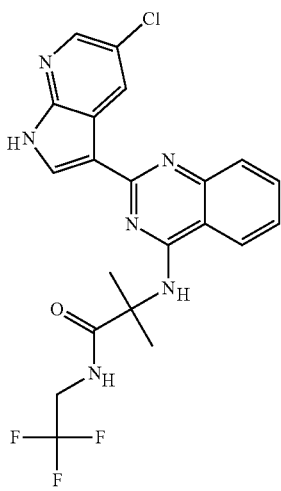

TABLE 1-continued
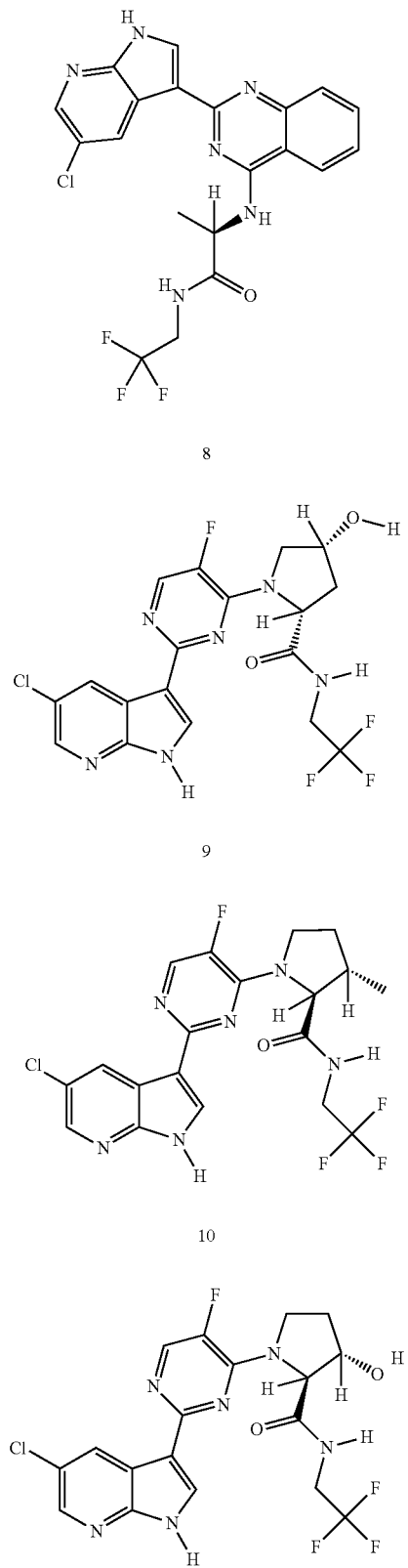
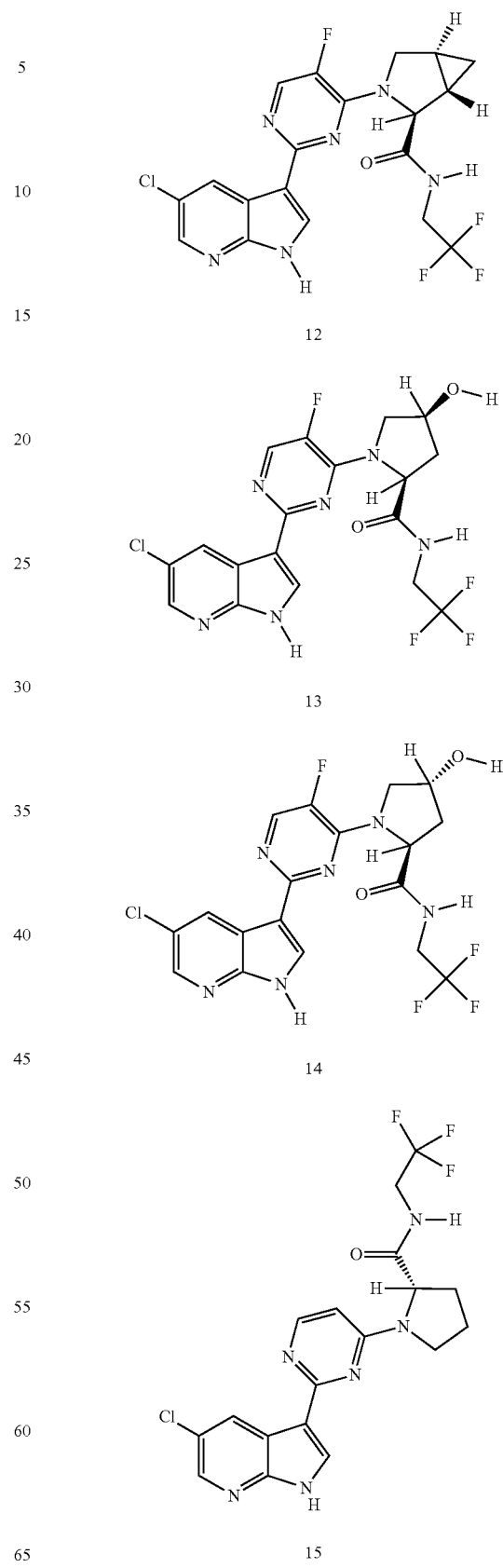

TABLE 1-continued
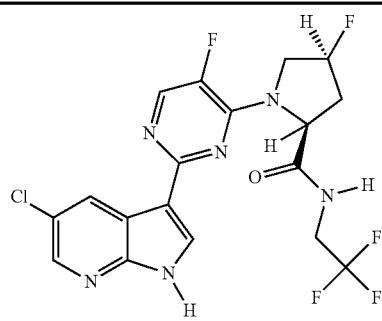
16
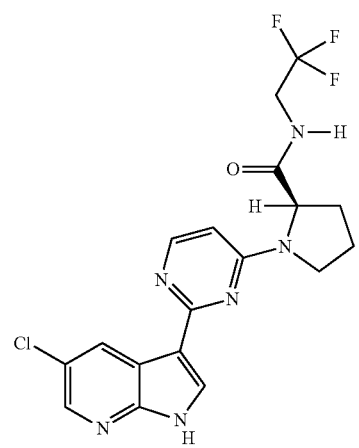
17
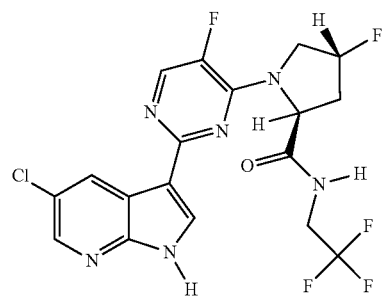
18
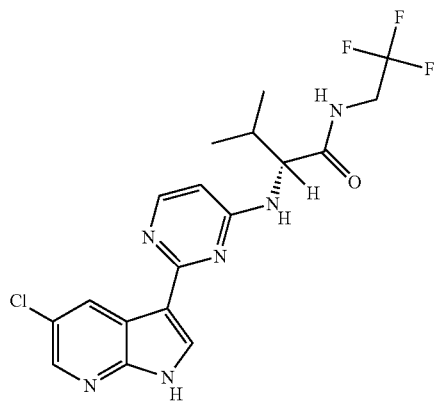
19
TABLE 1-continued
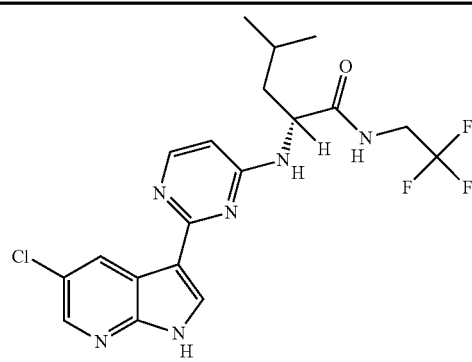
20
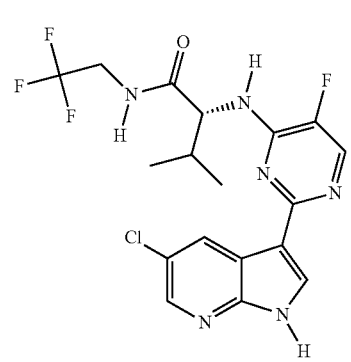
21
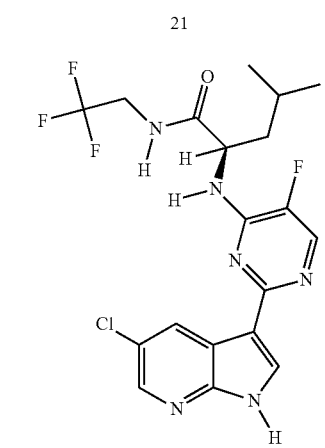
22
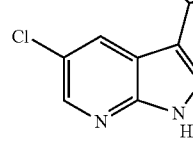
23

TABLE 1-continued
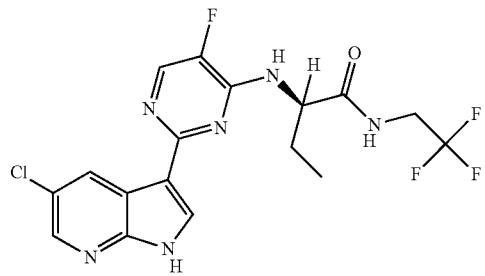
24
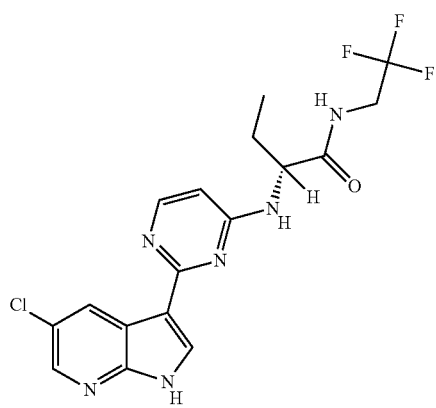
25
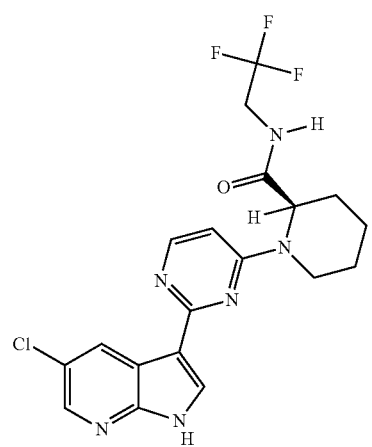
26
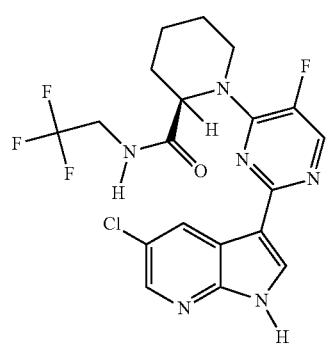
27
TABLE 1-continued
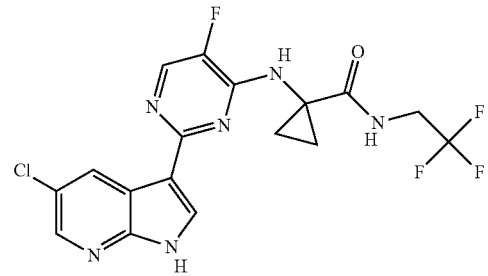
28
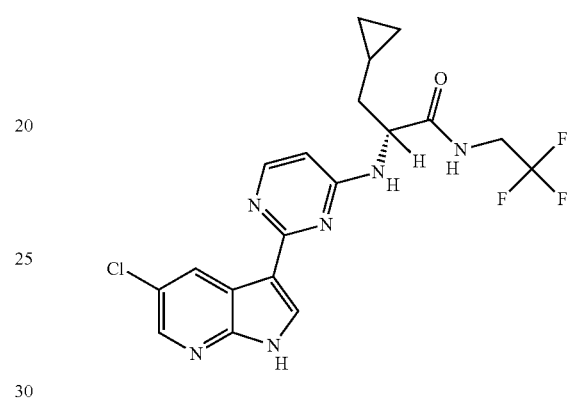
29
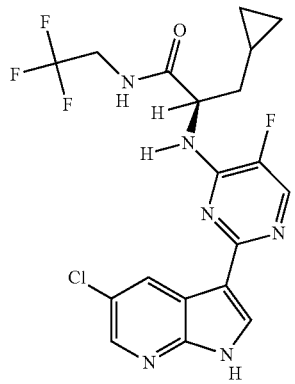
30
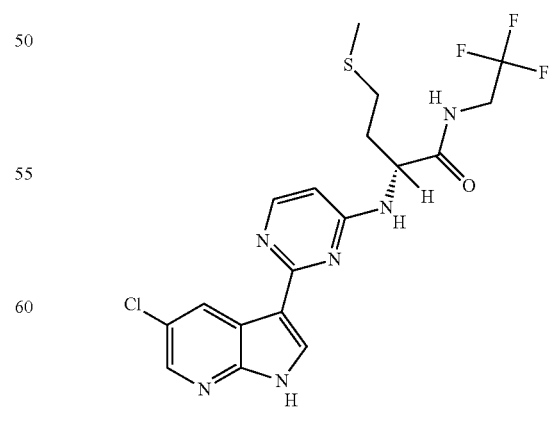
31

TABLE 1-continued
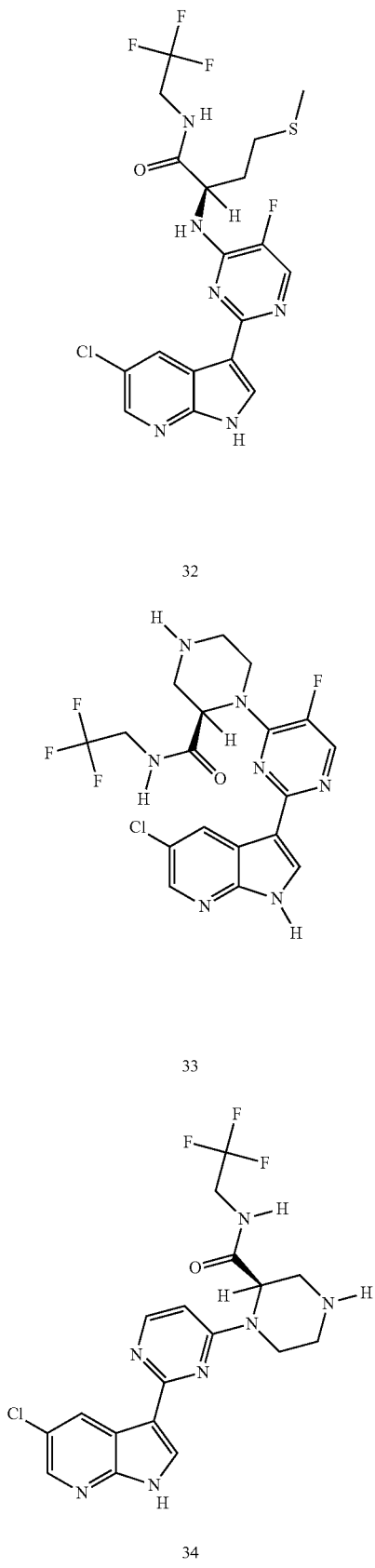
32
33
34
TABLE 1-continued
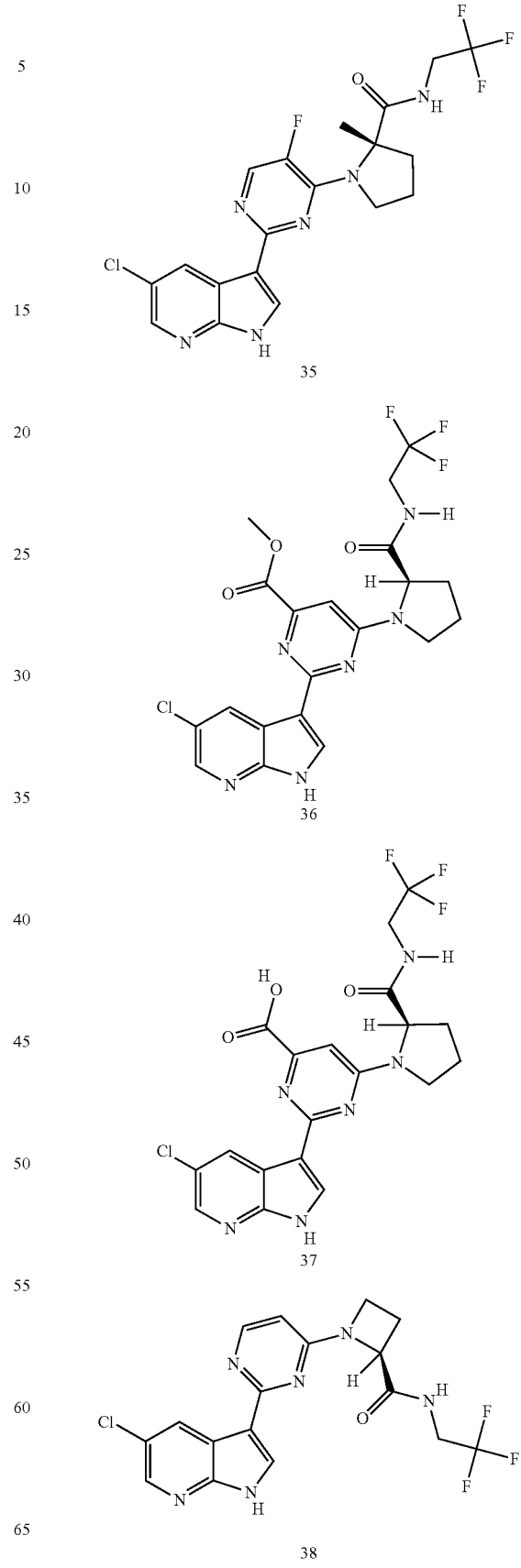
35
36
37
38

TABLE 1-continued
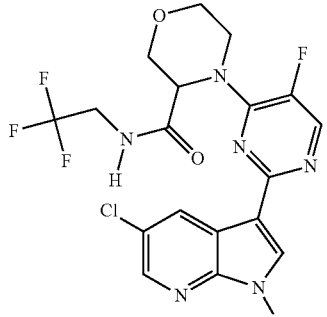
39
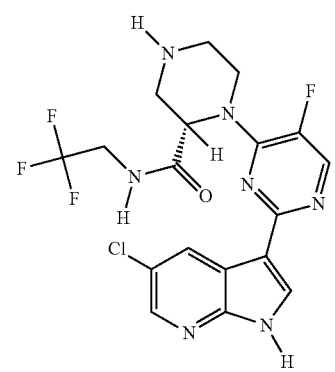
40
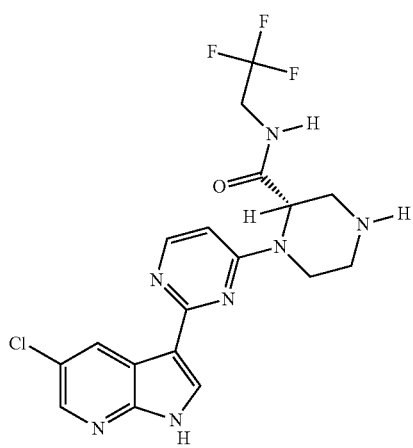
41
TABLE 1-continued
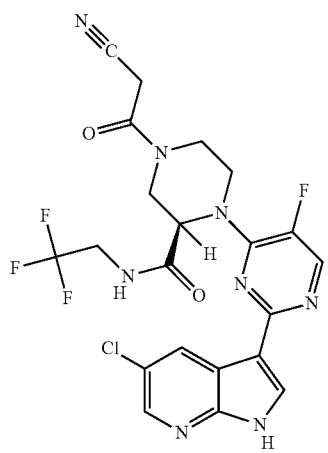
42
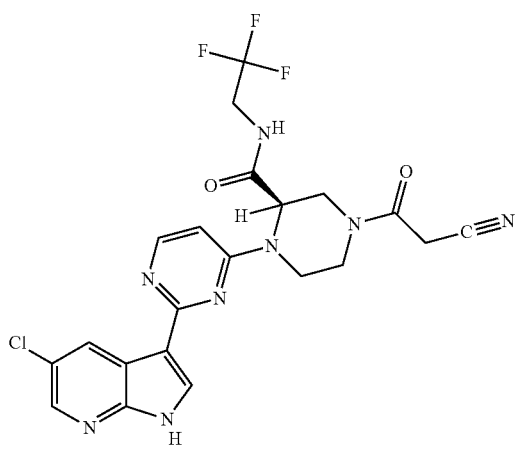
43
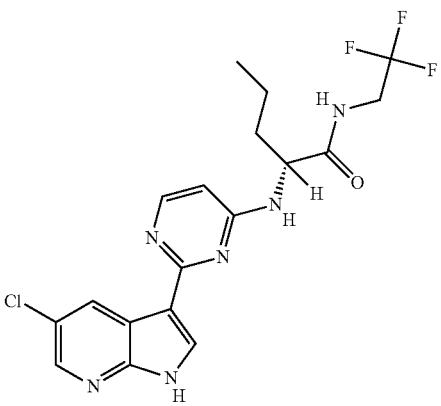
44

TABLE 1-continued
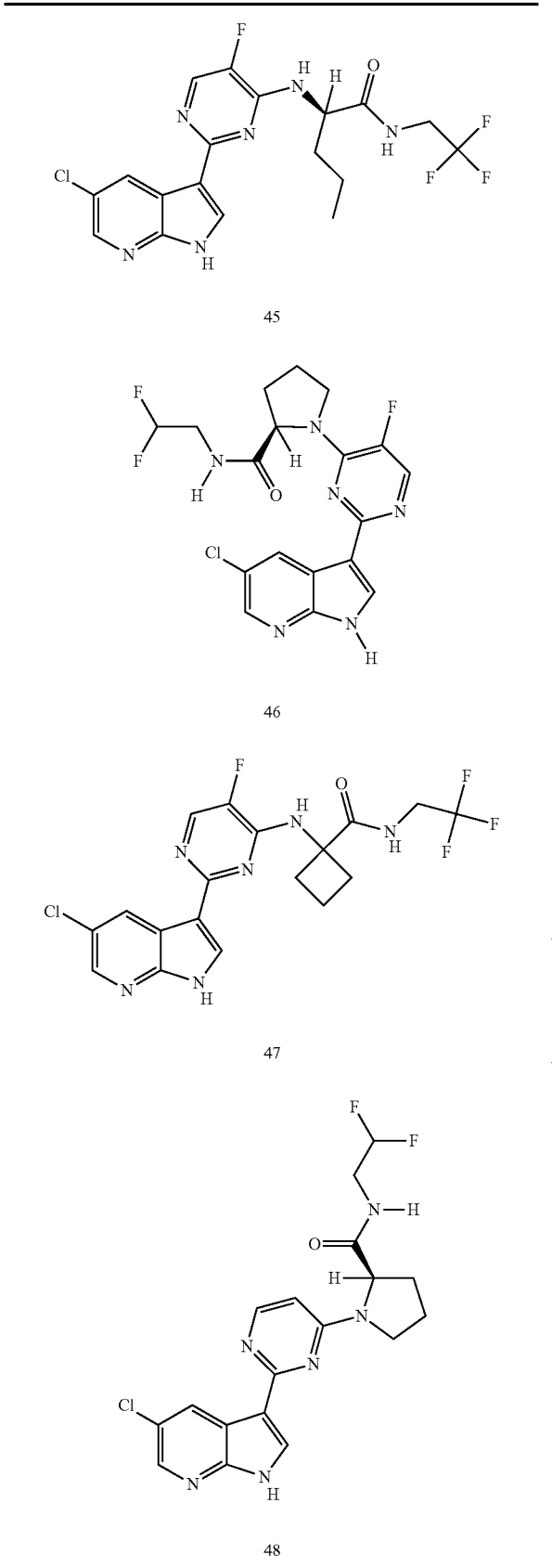
45
46
47
48
TABLE 1-continued
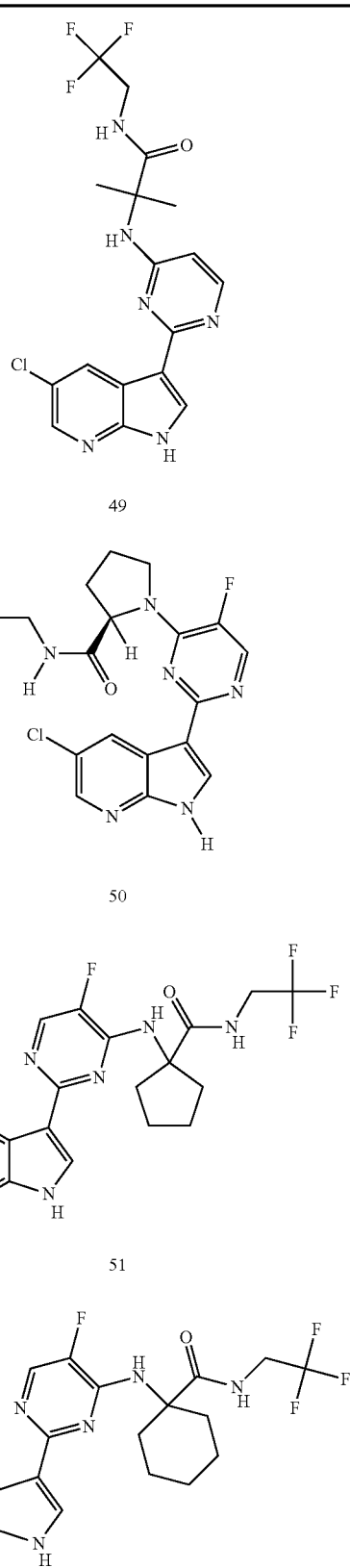
49
50
51
52

TABLE 1-continued
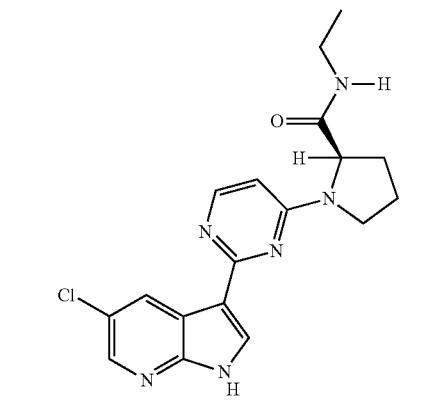
53
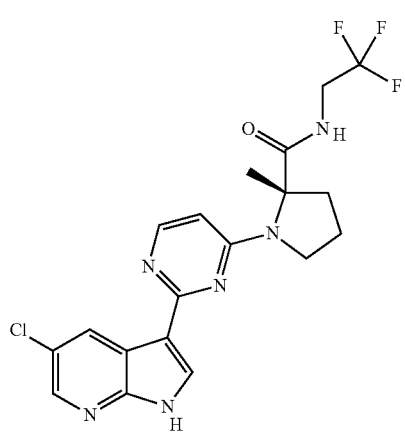
54
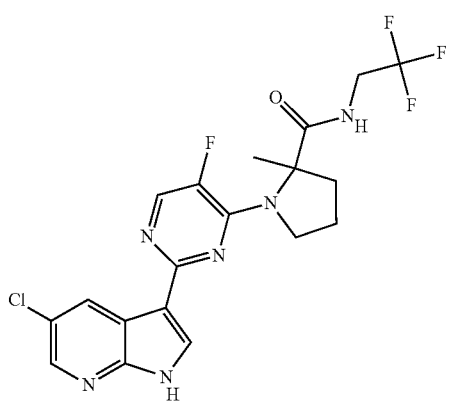
55
TABLE 1-continued
56
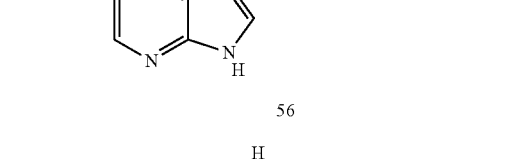
57
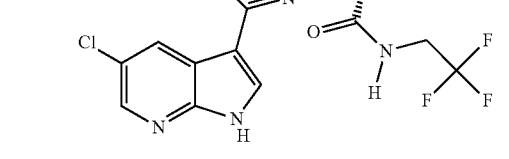
58
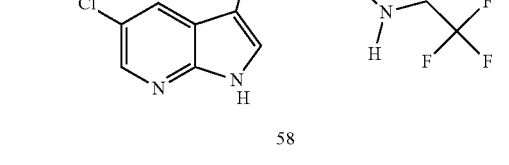
59

TABLE 1-continued
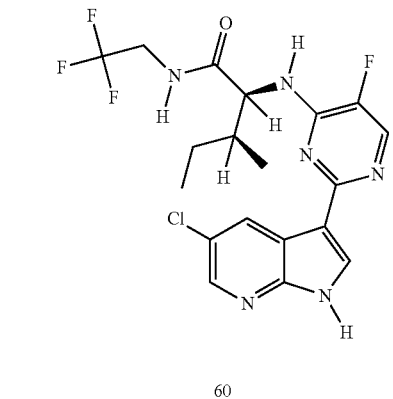
60
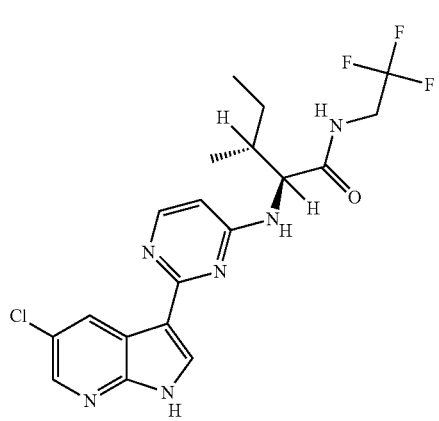
61
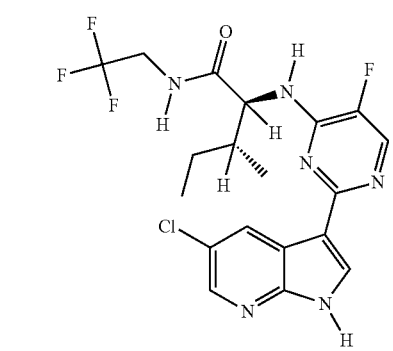
62
TABLE 1-continued
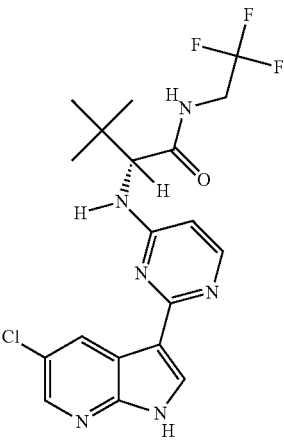
63
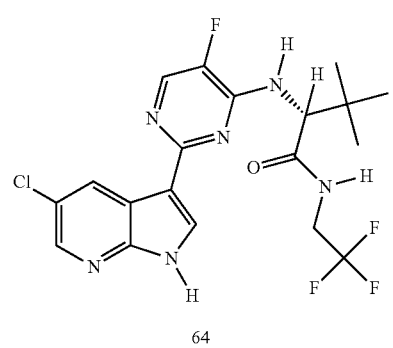
64
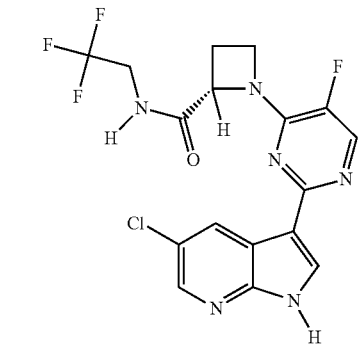
65
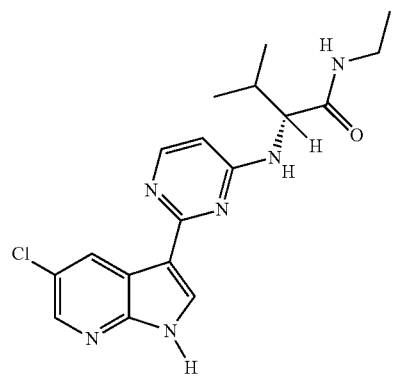
66

TABLE 1-continued
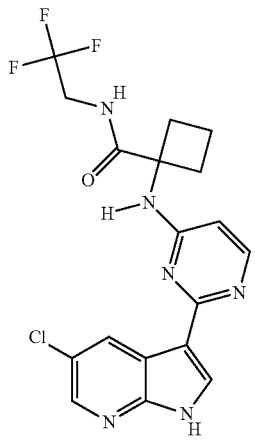
67
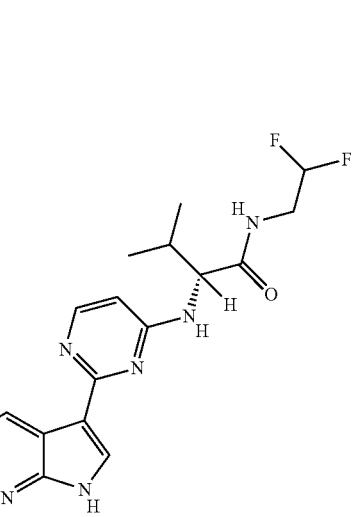
68
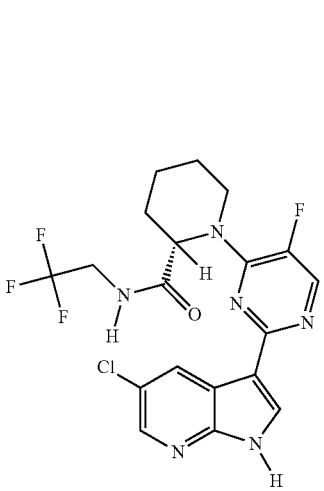
69
TABLE 1-continued
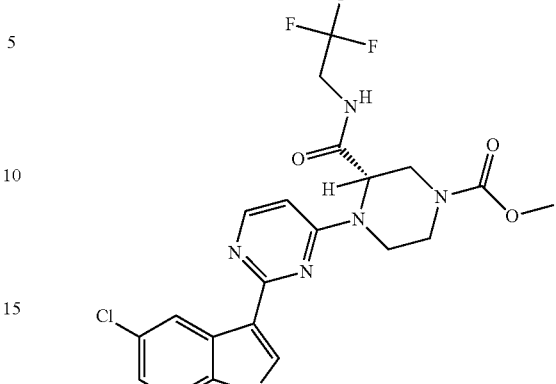
70
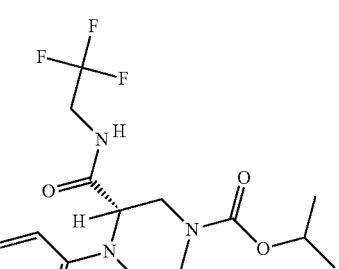
71
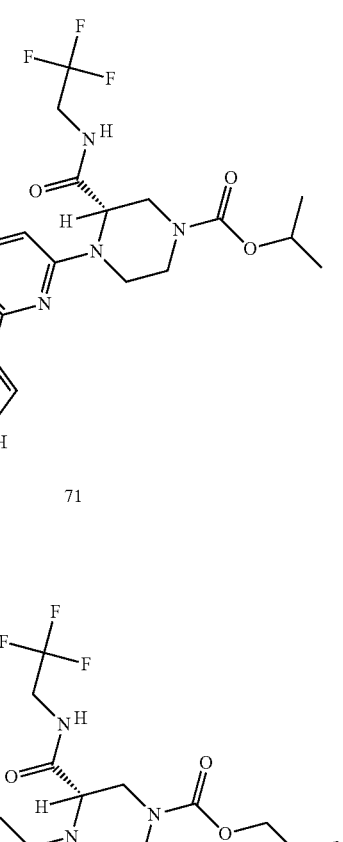
72

TABLE 1-continued
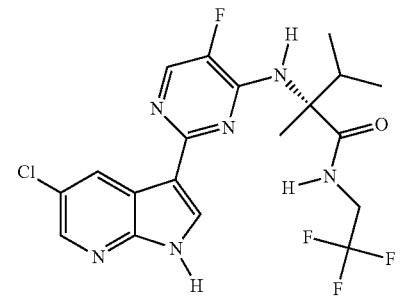
73
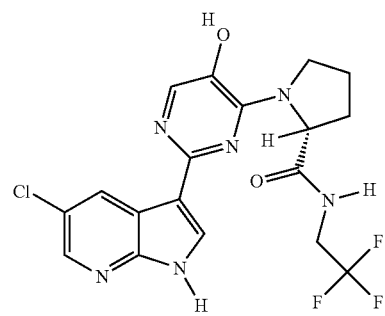
74
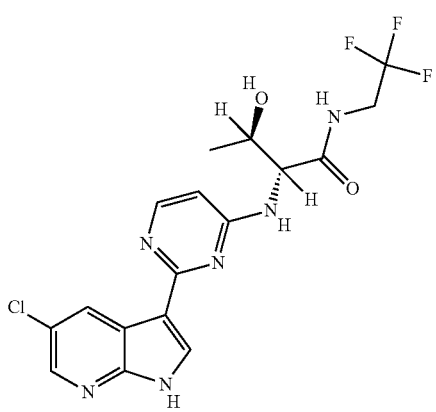
75
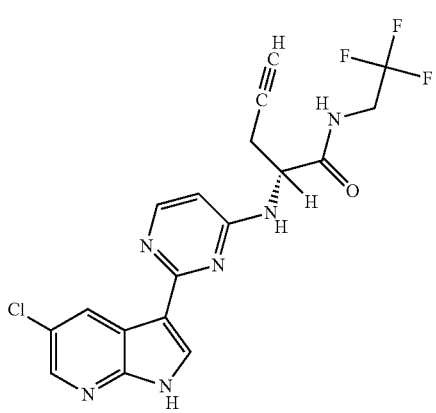
76
TABLE 1-continued
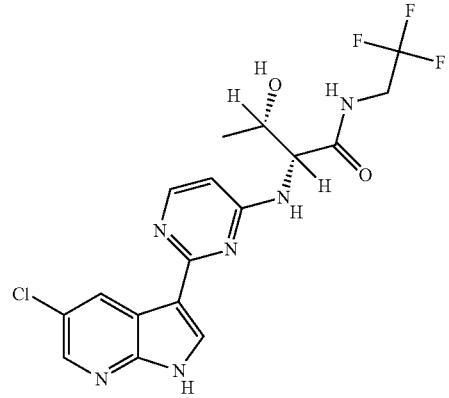
77
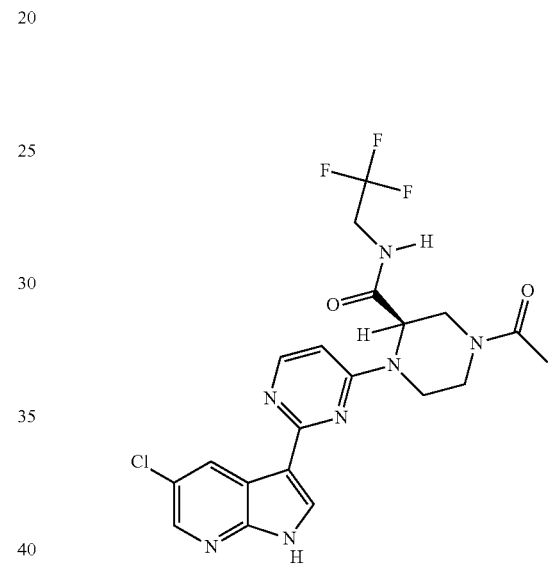
78
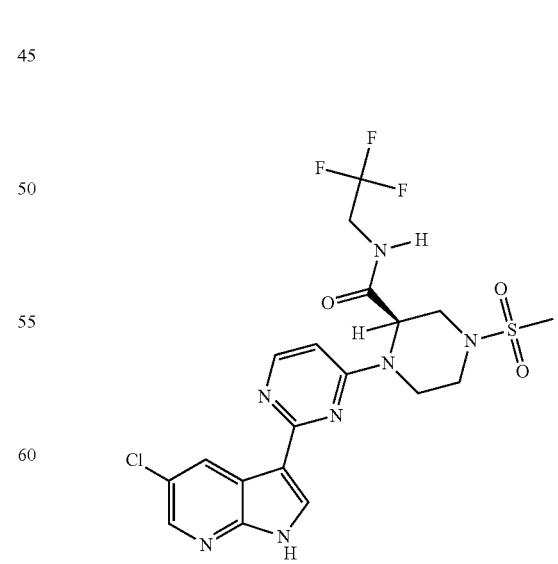
79

TABLE 1-continued
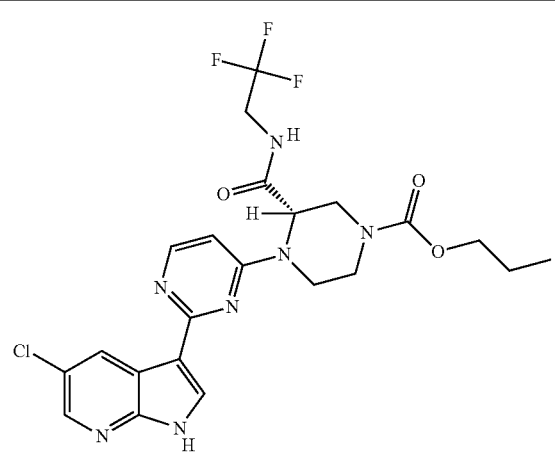
80
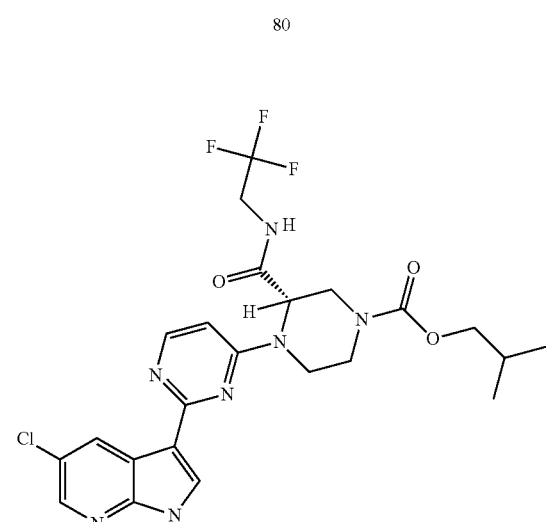
81
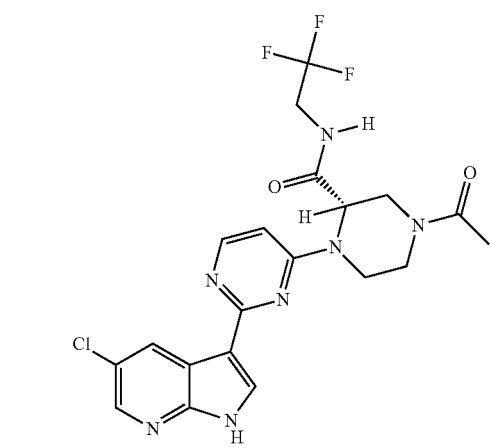
82
TABLE 1-continued
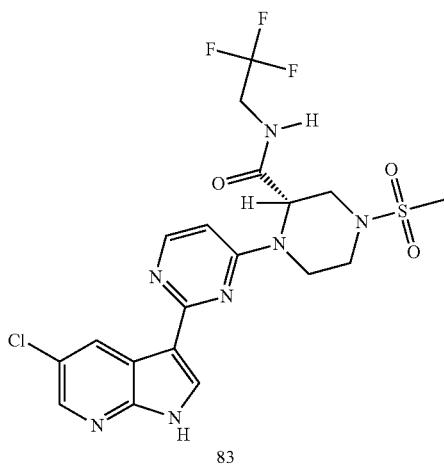
83
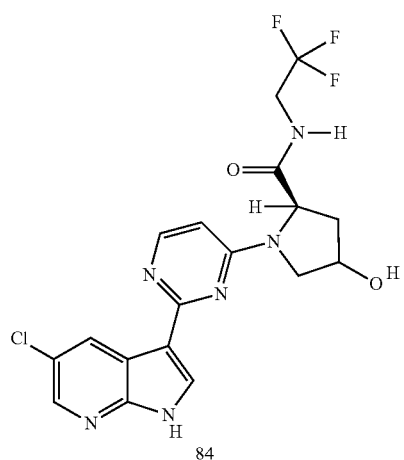
84
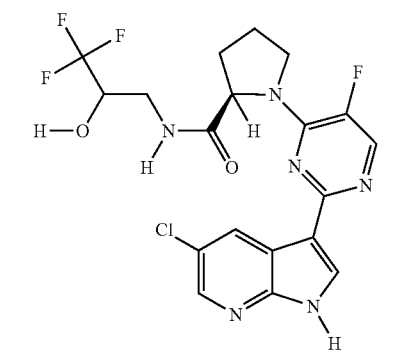
85
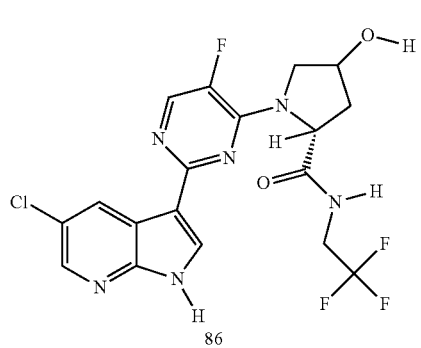
86

TABLE 1-continued
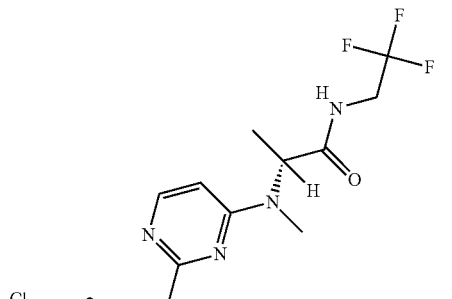
87
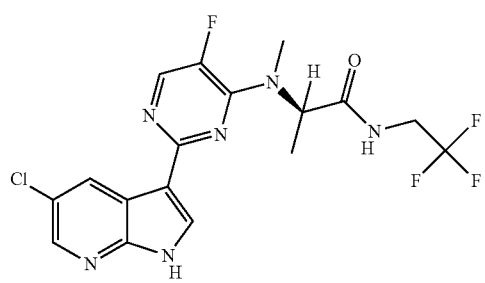
88
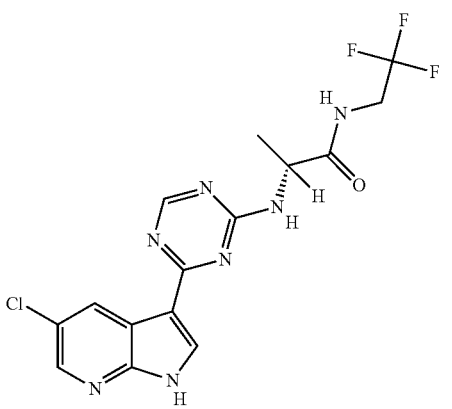
89
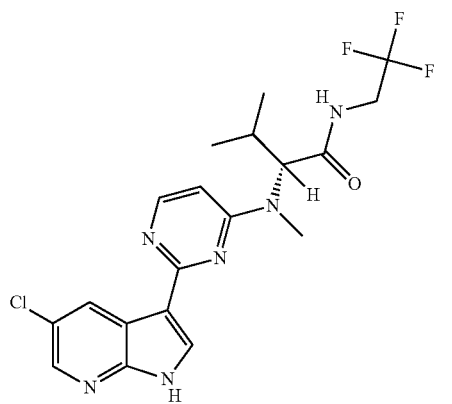
90
TABLE 1-continued
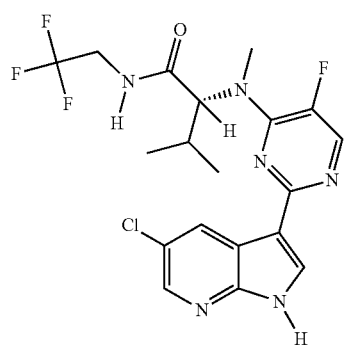
91
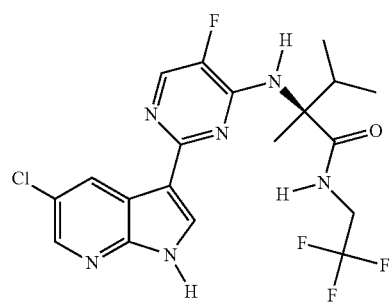
92
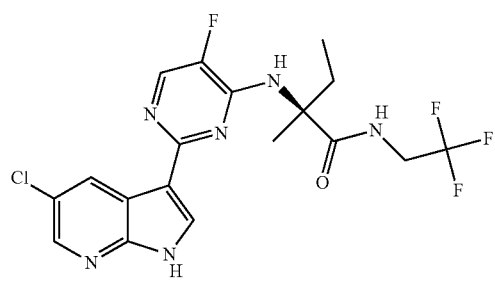
93
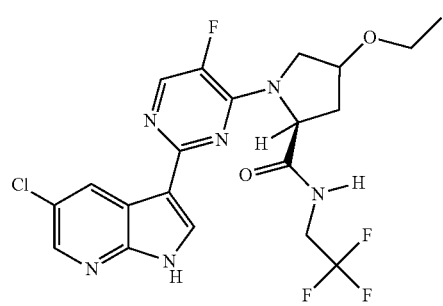
94

TABLE 1-continued
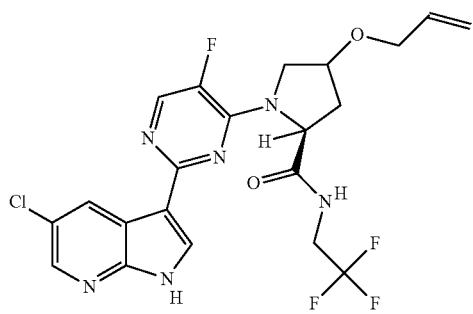
95
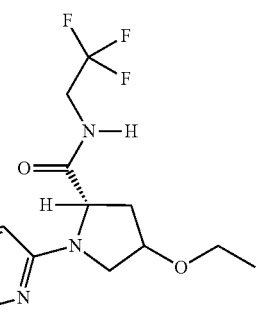
96
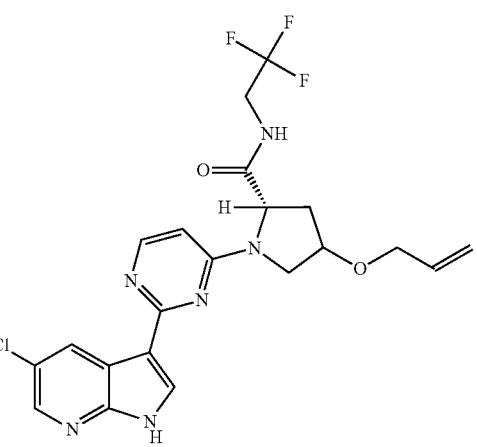
97
TABLE 1-continued
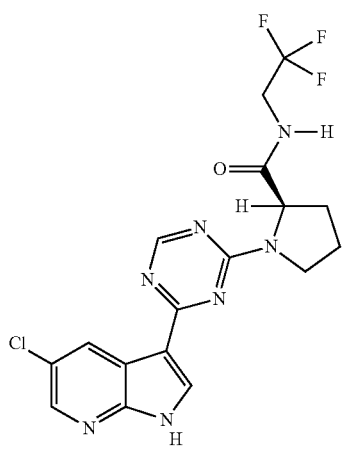
98
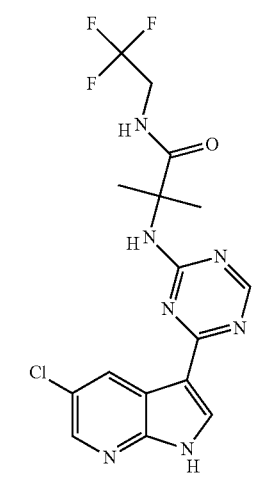
99
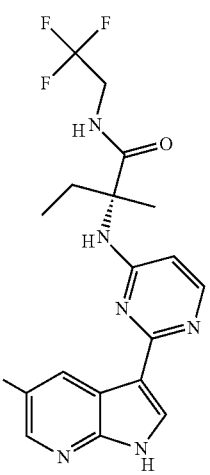
100

TABLE 1-continued
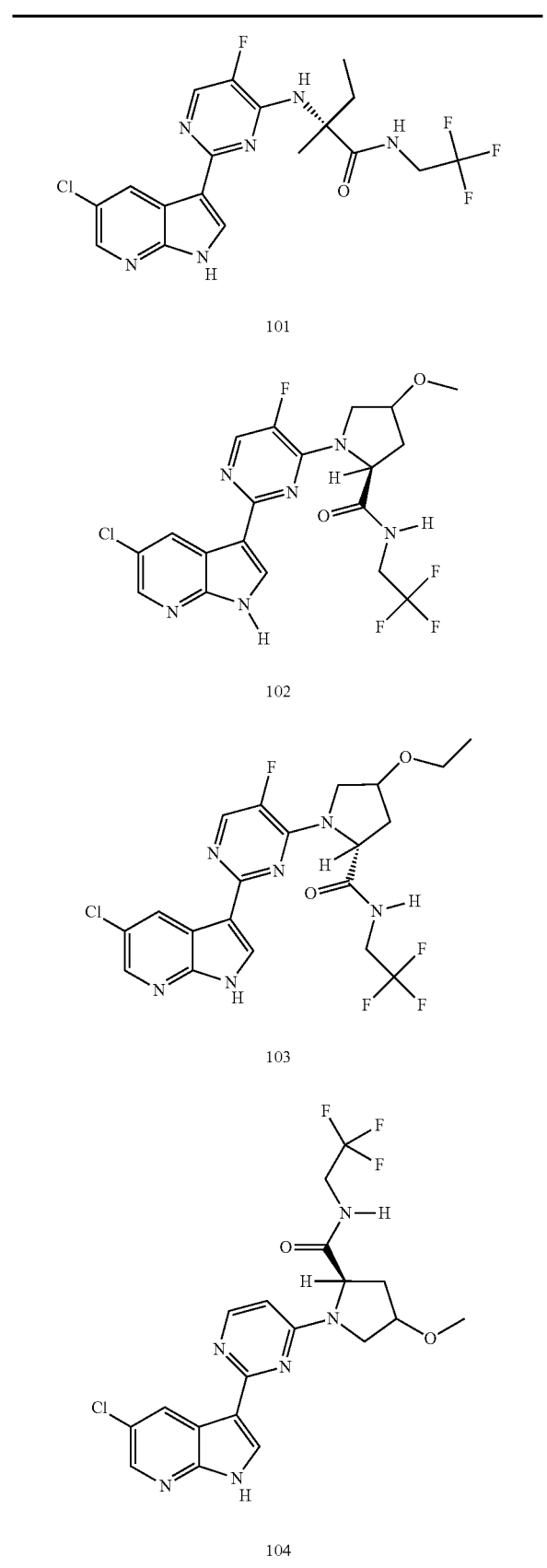
101
102
103
104
TABLE 1-continued
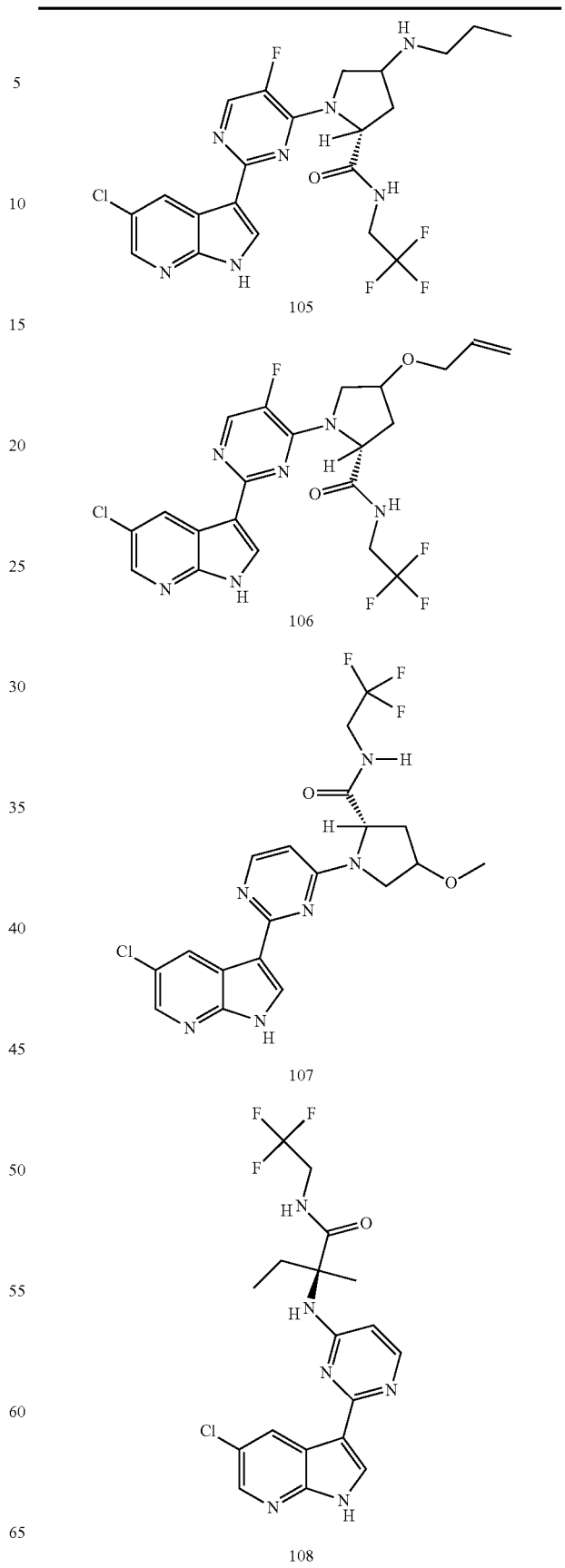
105
106
107
108

TABLE 1-continued
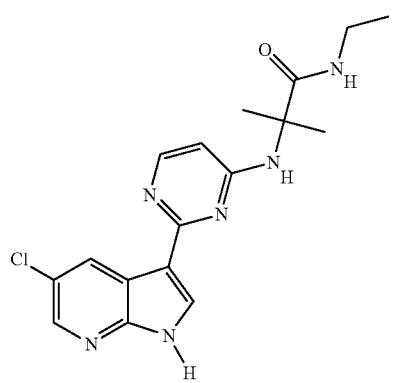
109
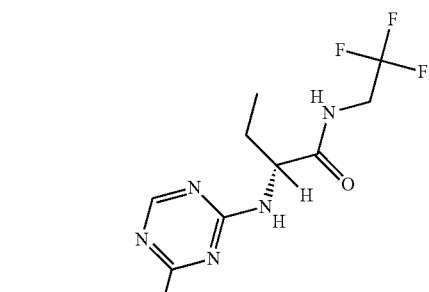
112
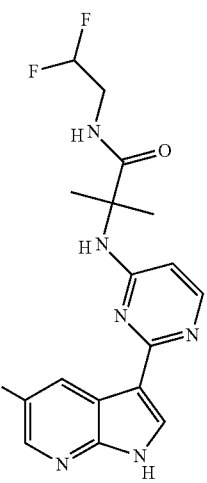
110
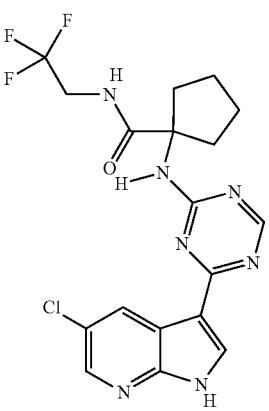
113
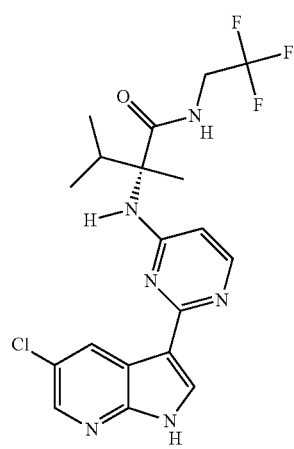
111
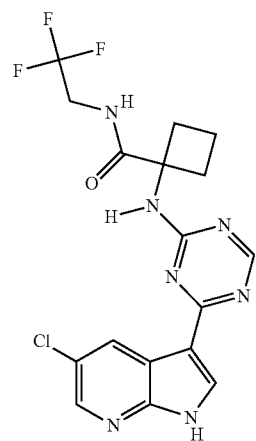
114

TABLE 1-continued
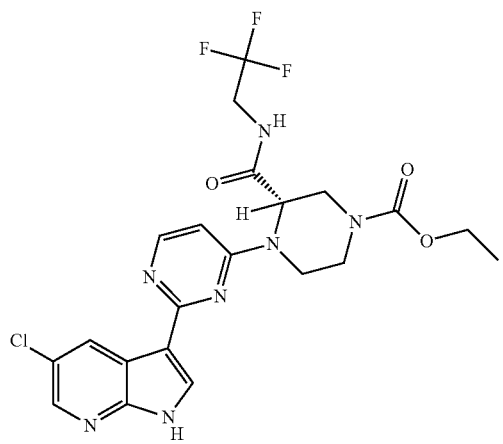
115
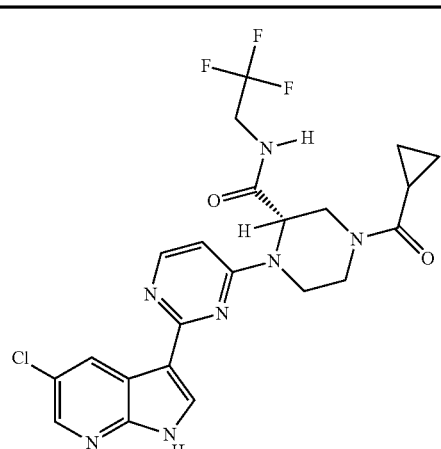
118
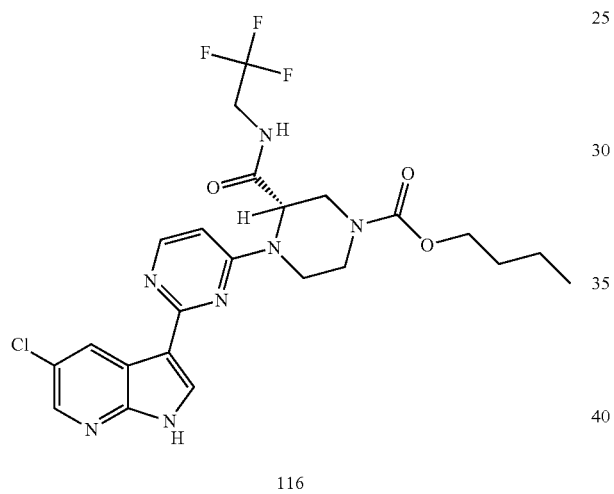
116
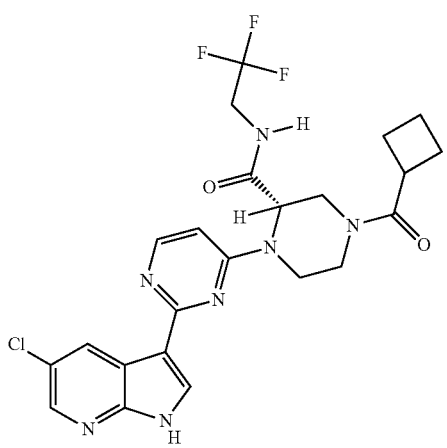
119
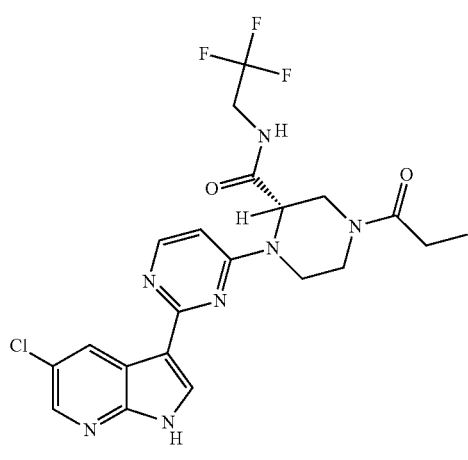
117
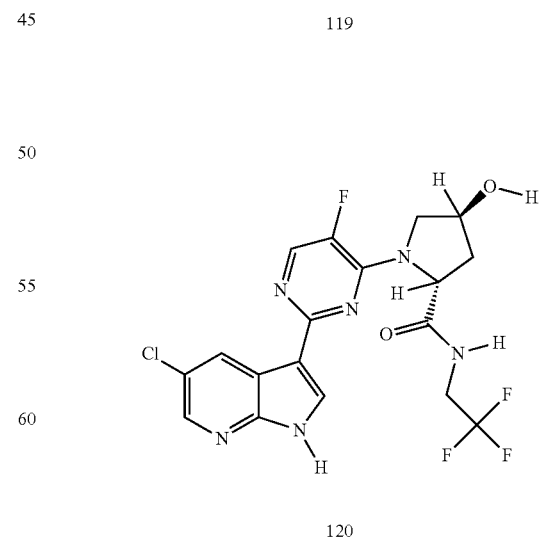
120

TABLE 1-continued
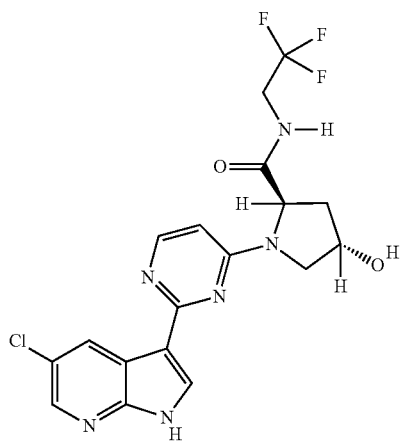
121
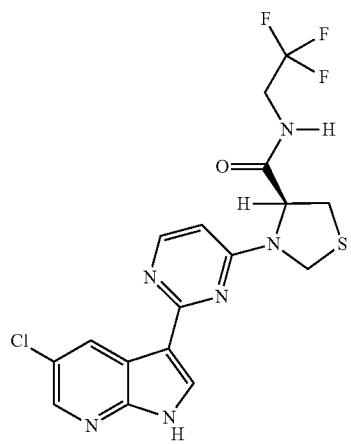
124
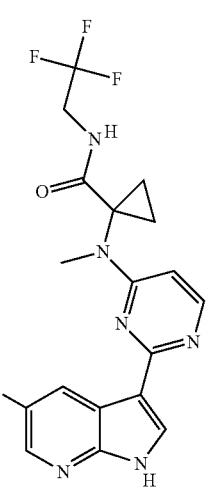
122
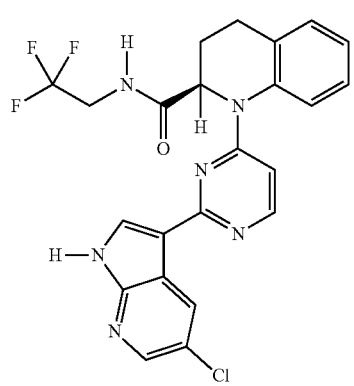
125
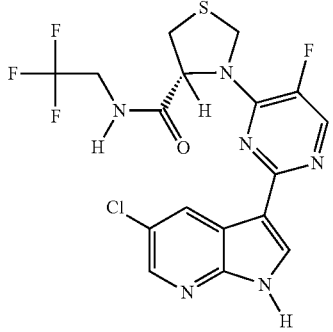
123
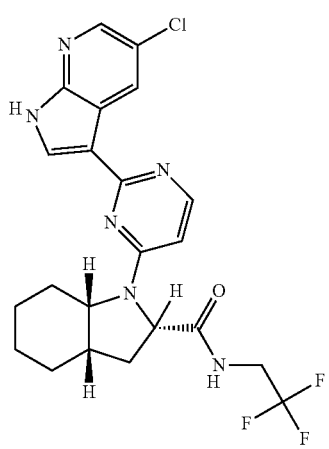
126

TABLE 1-continued
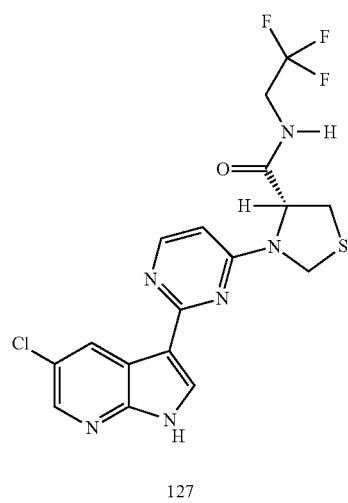
127
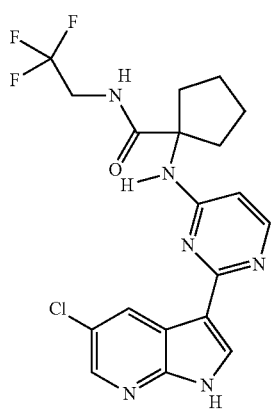
128
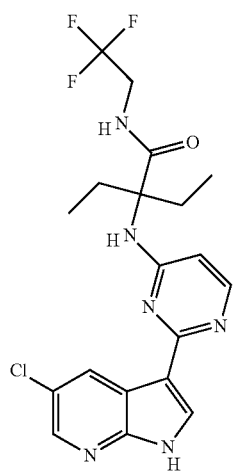
129
TABLE 1-continued
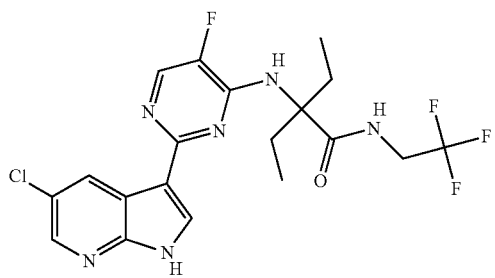
130
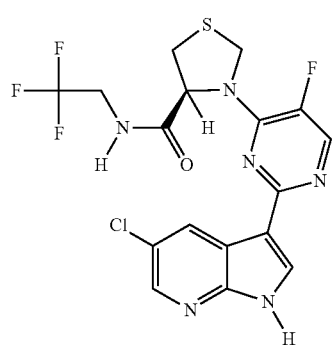
131
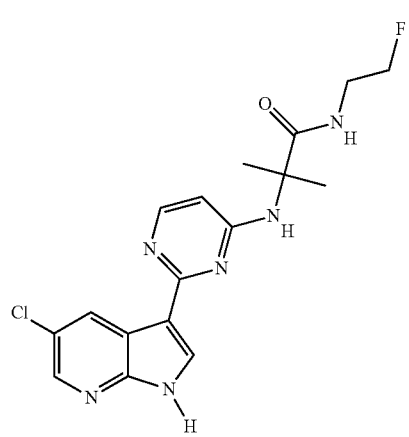
132
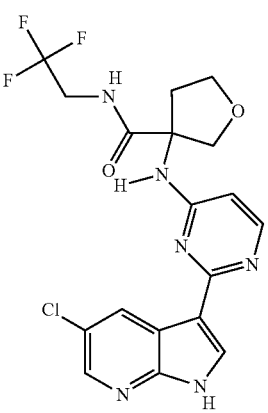
133

TABLE 1-continued
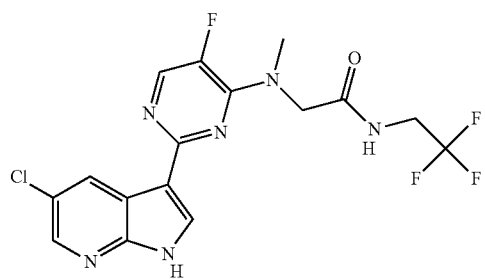
134
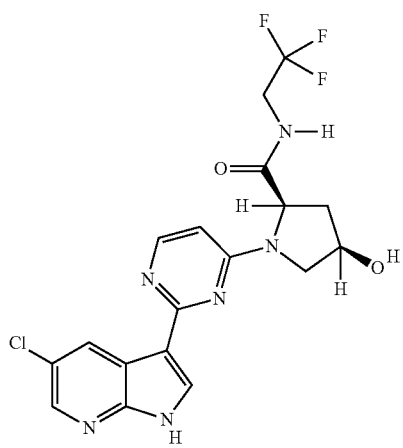
135
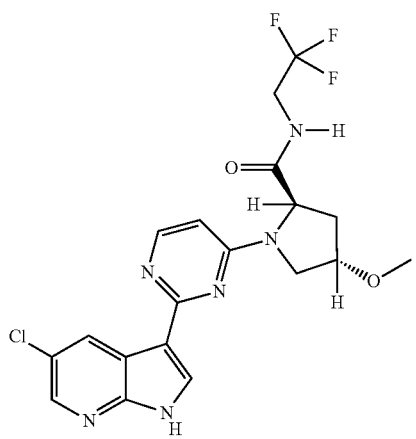
136
TABLE 1-continued
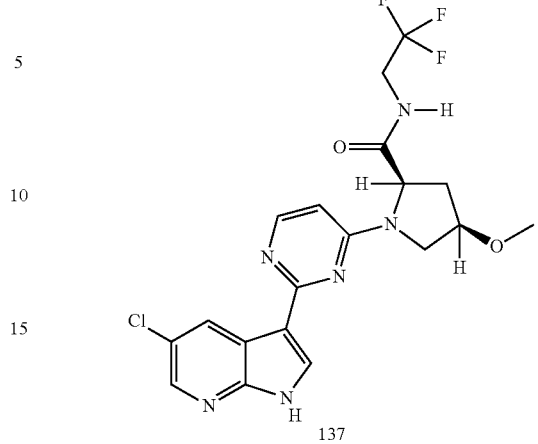
137
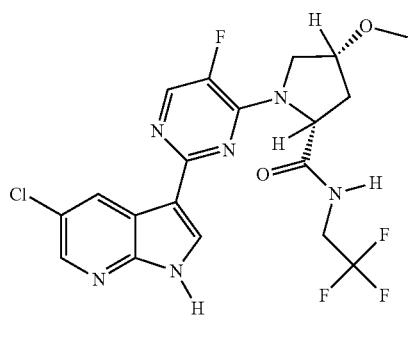
138
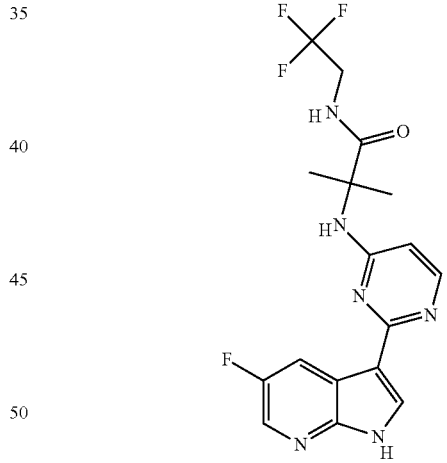
139
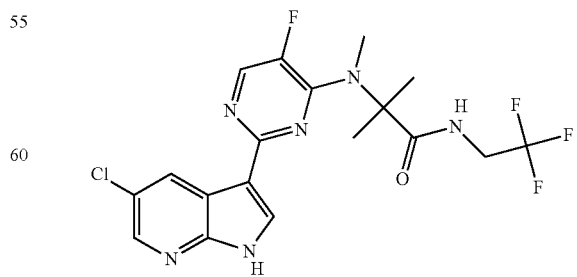
140

TABLE 1-continued
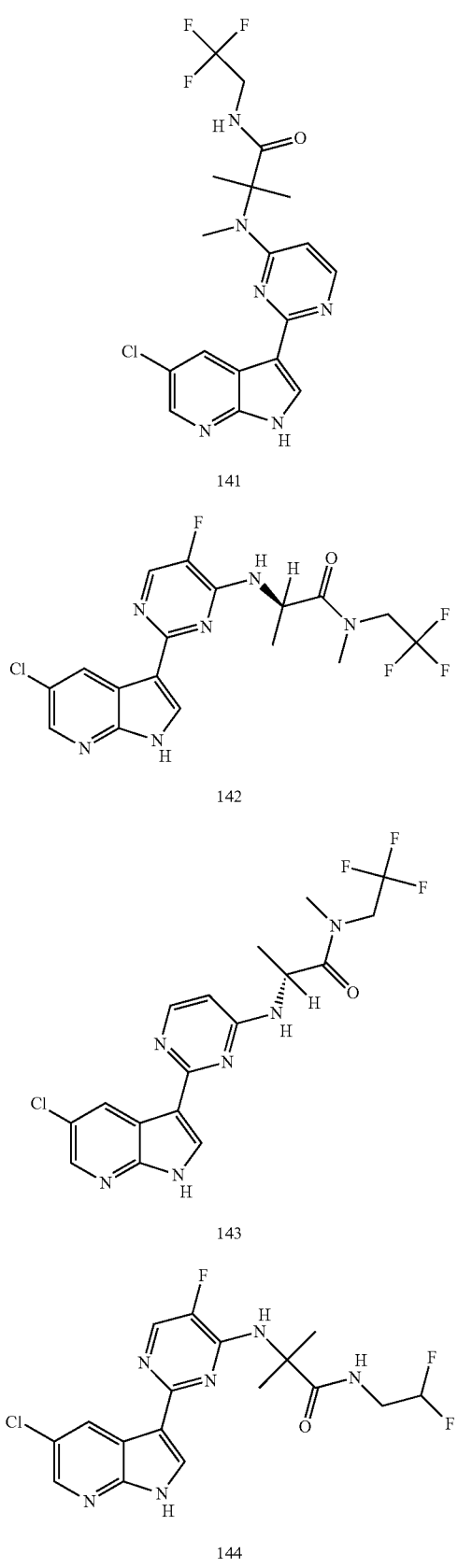
141
142
143
144
TABLE 1-continued
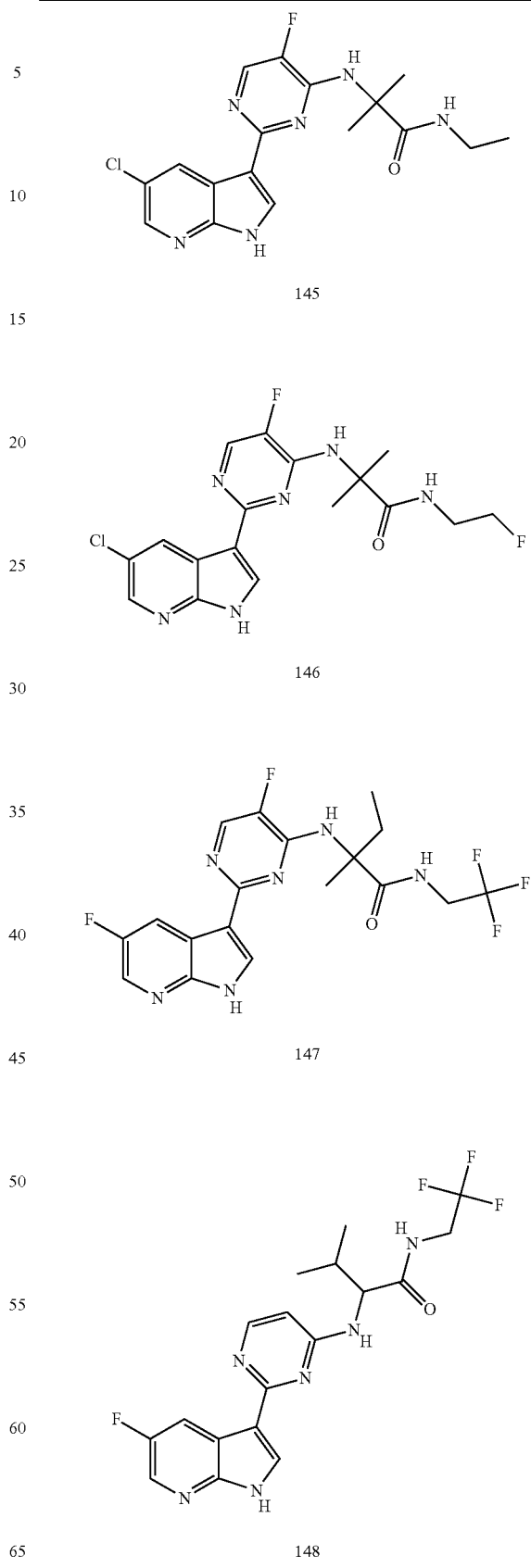
145
146
147
148

TABLE 1-continued
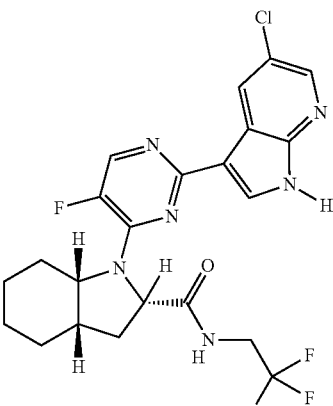
149
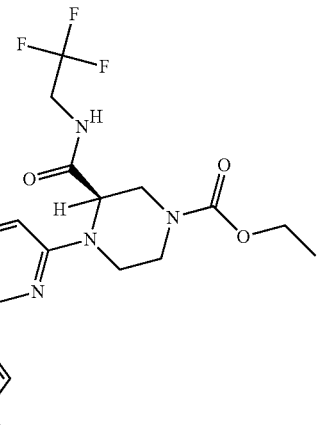
152
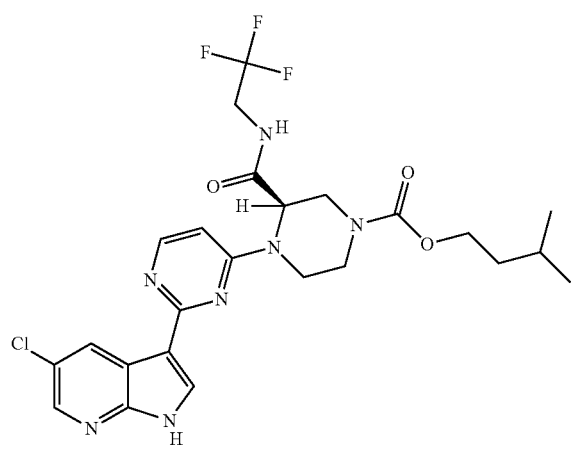
150
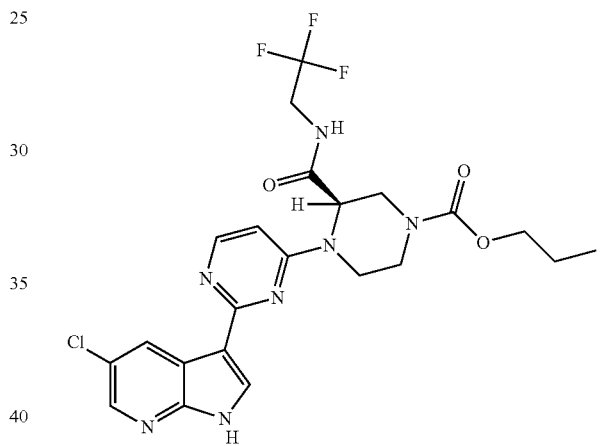
153
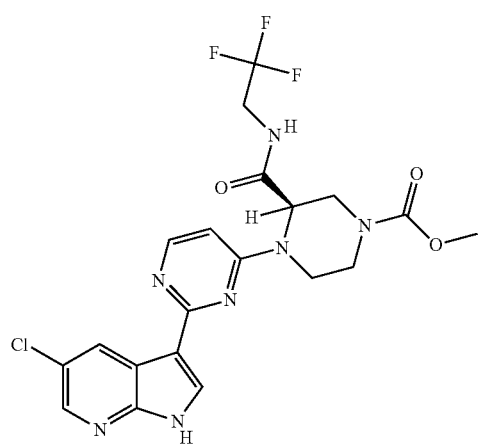
151
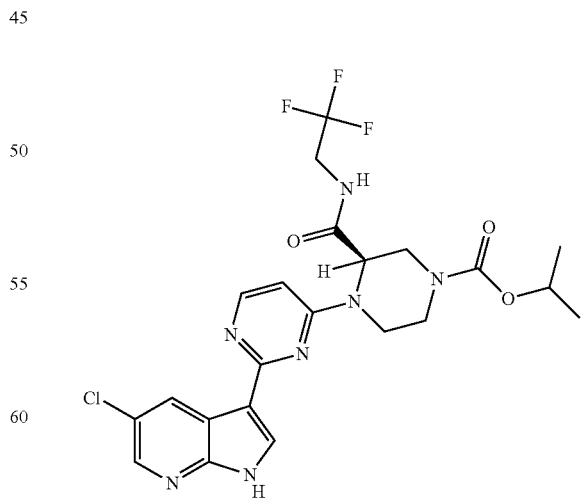
154

TABLE 1-continued
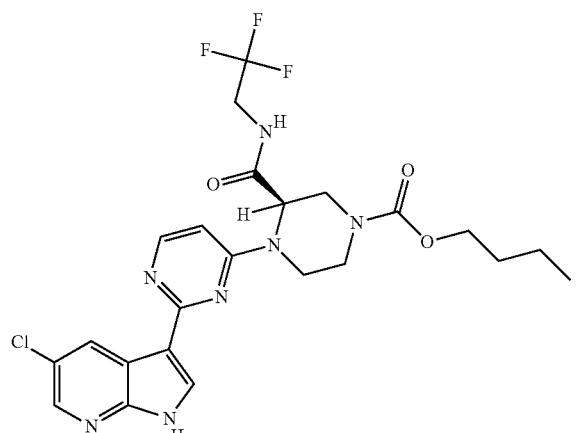
155
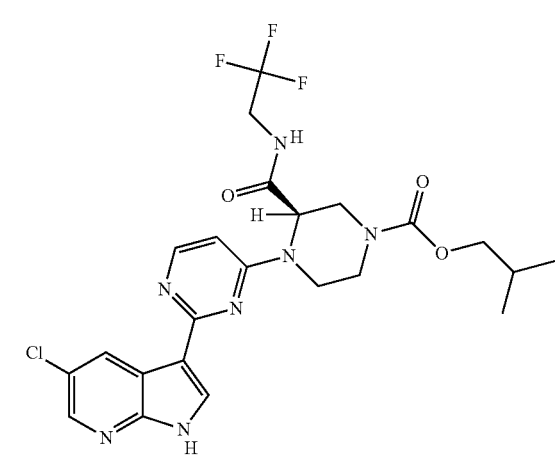
156
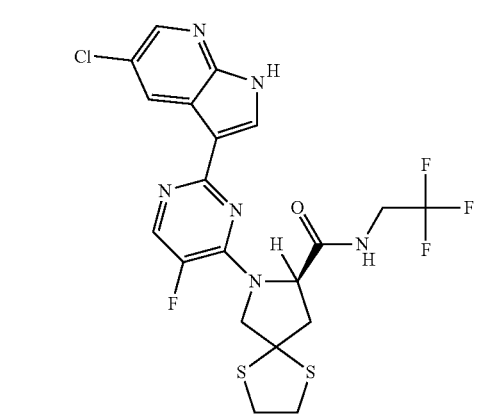
157
TABLE 1-continued
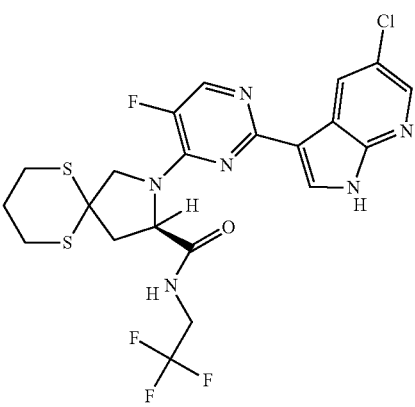
158
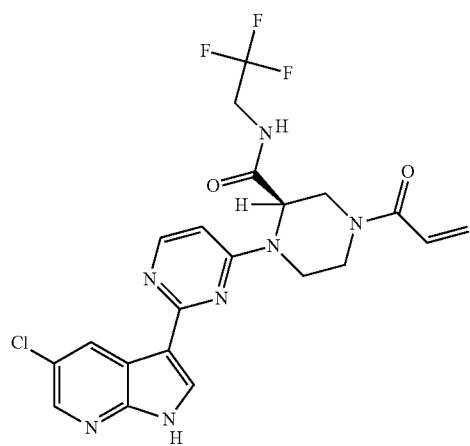
159
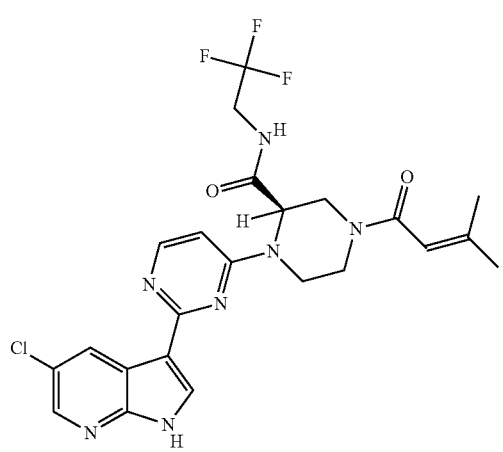
160

TABLE 1-continued
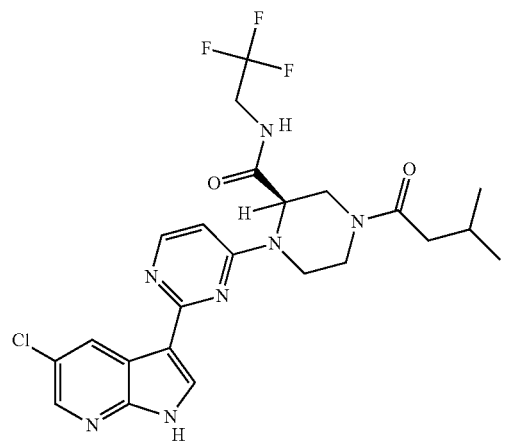
161
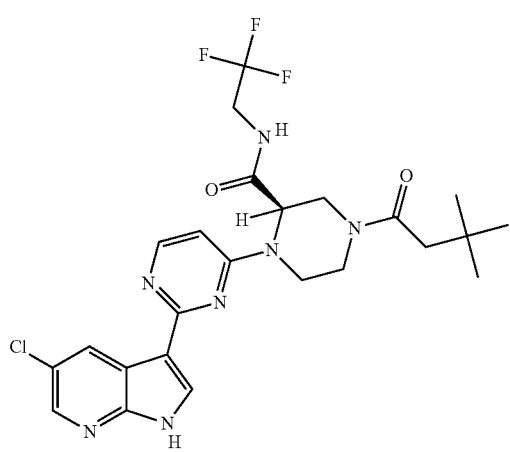
162
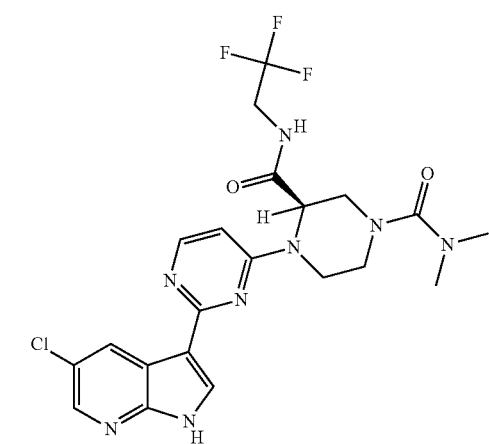
163
TABLE 1-continued
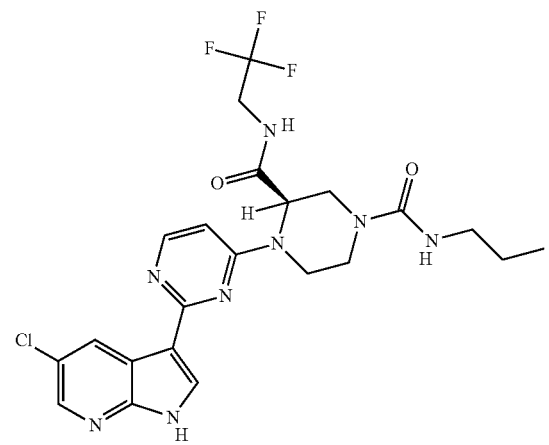
164
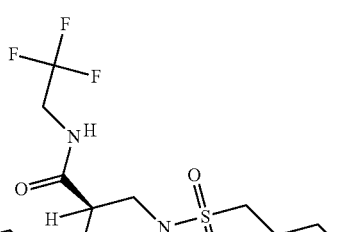
165
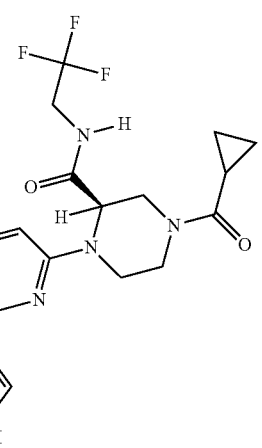
166

TABLE 1-continued
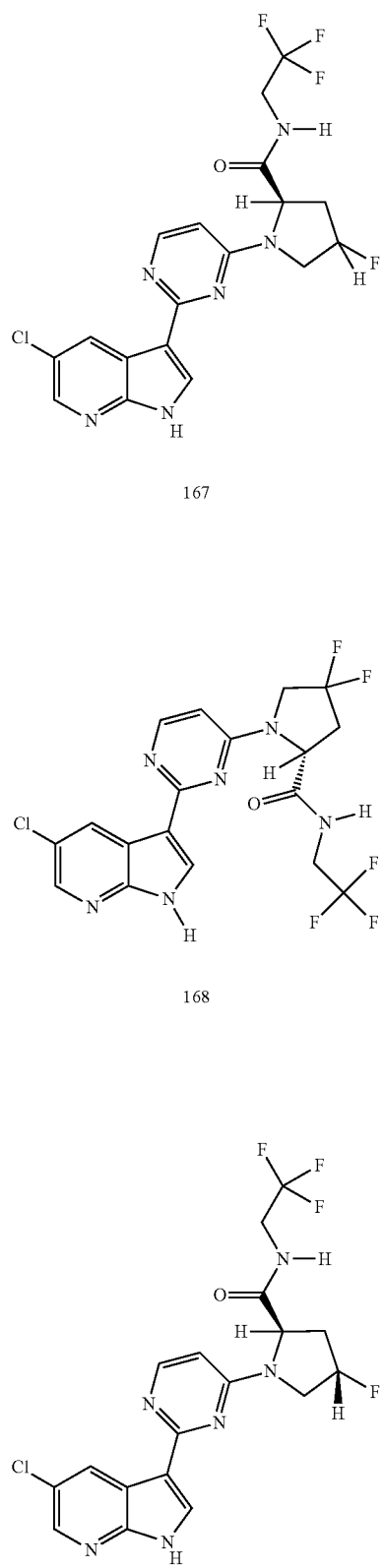
167
168
169
TABLE 1-continued
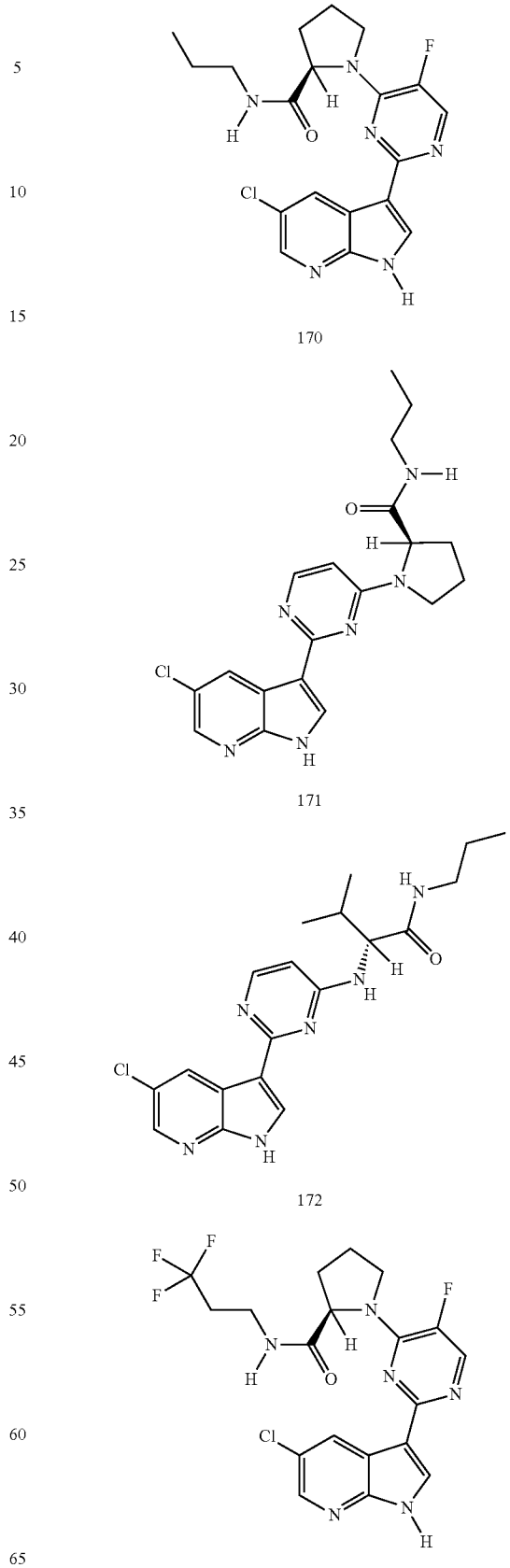
170
171
172
173

TABLE 1-continued
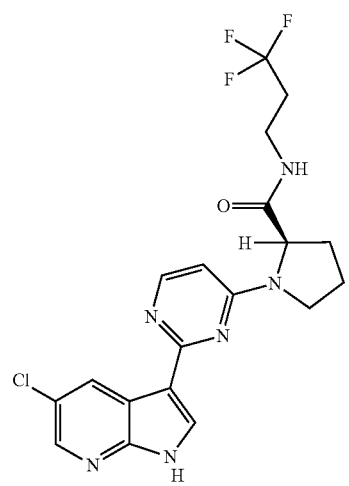
174
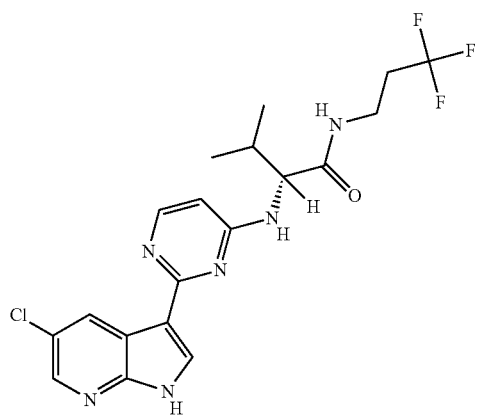
175
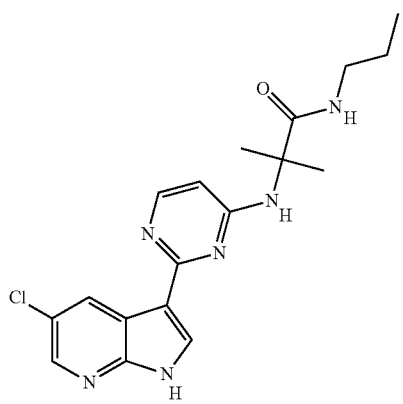
176
TABLE 1-continued
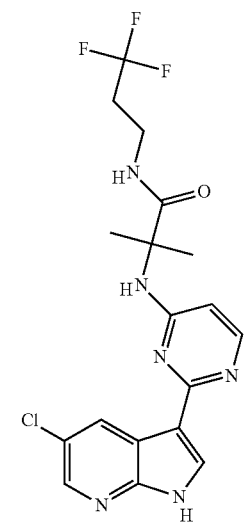
177
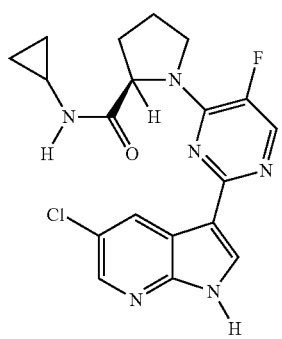
178
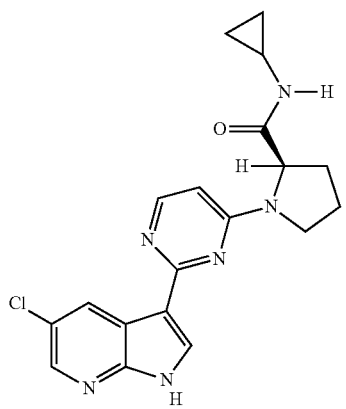
179

TABLE 1-continued
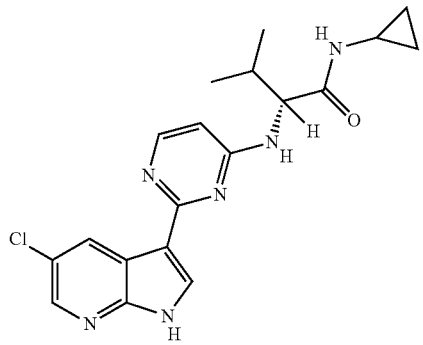
180
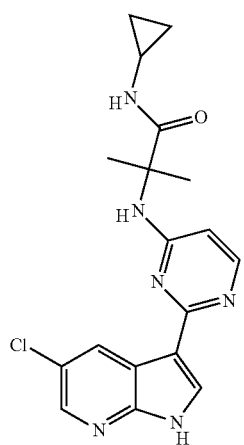
TABLE 2
181
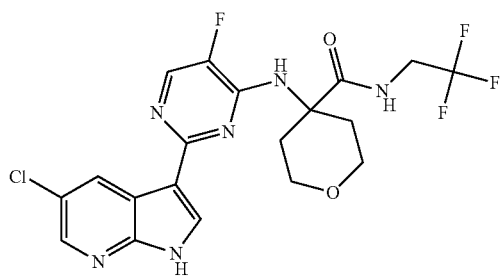
182
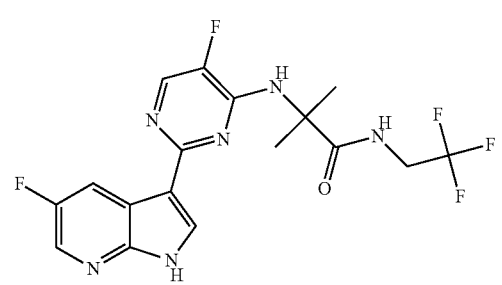
183
TABLE 2-continued
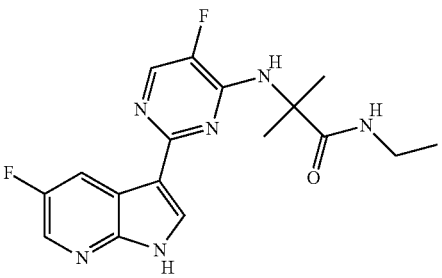
184
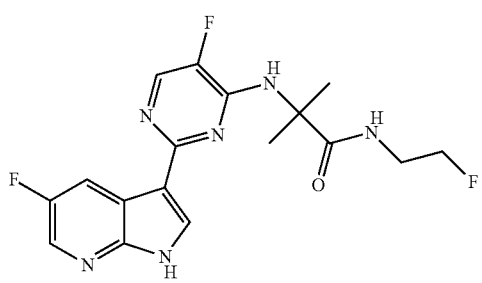
185
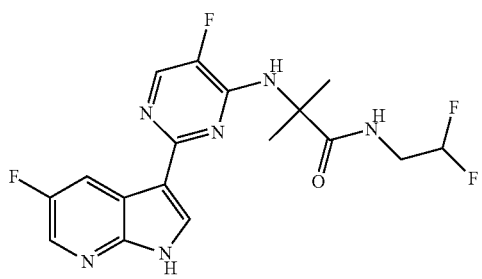
186
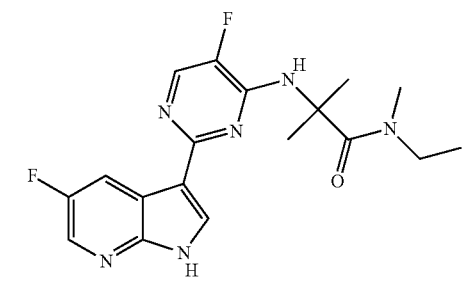
187

TABLE 2-continued
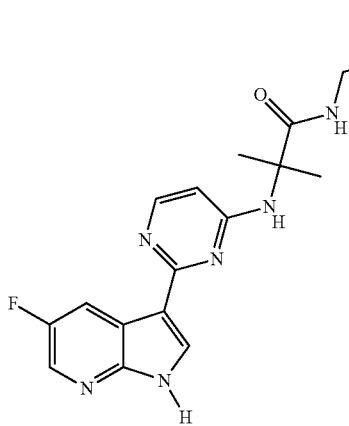
188
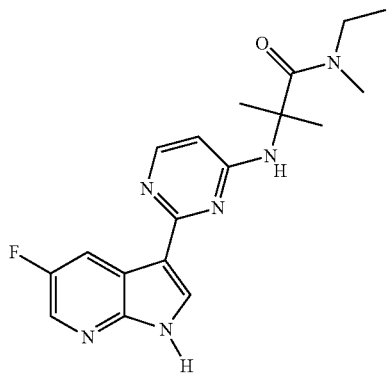
191
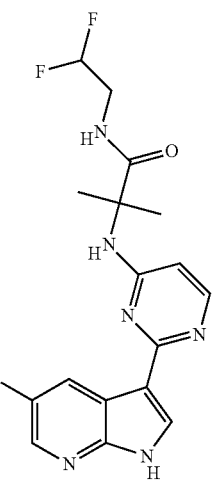
189
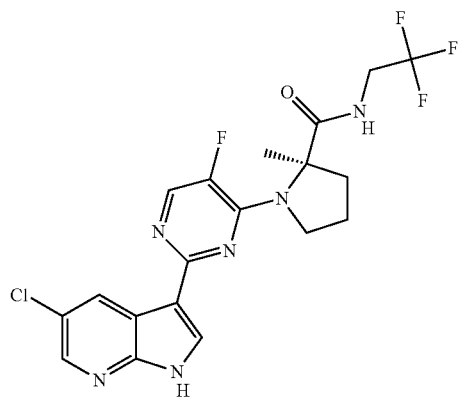
192
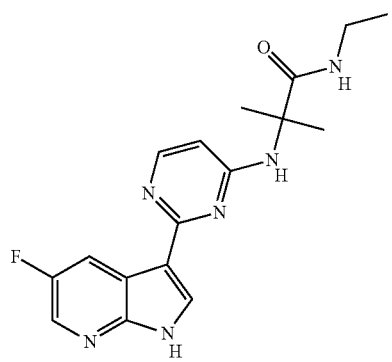
190
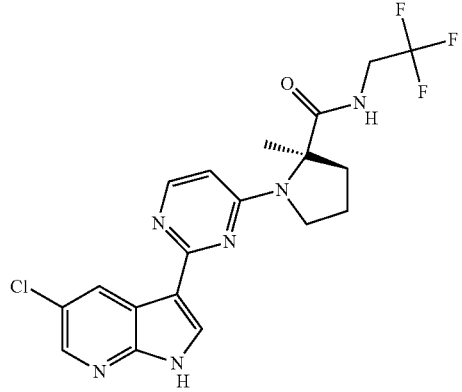
193

TABLE 2-continued
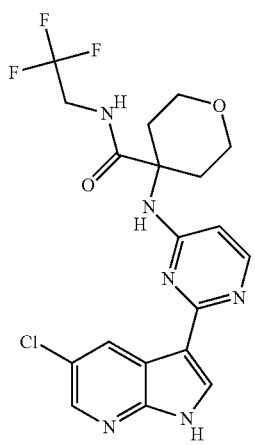
194
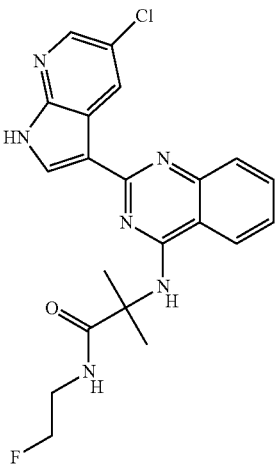
197
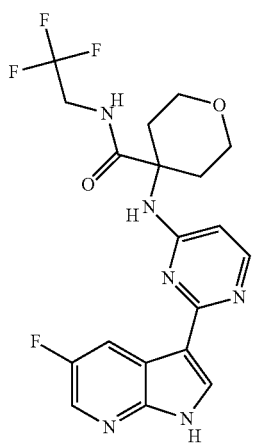
195
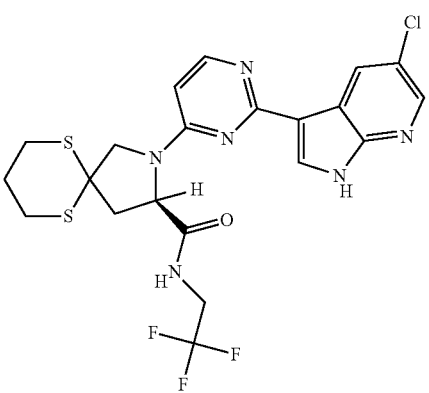
198
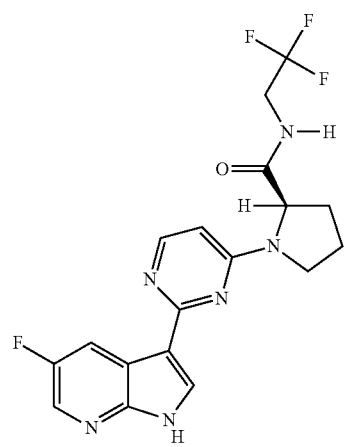
196
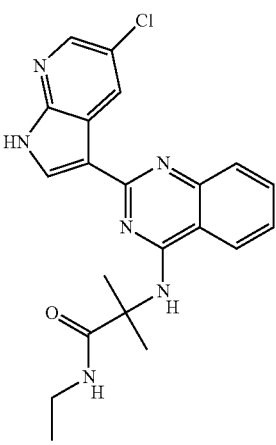
199

TABLE 2-continued
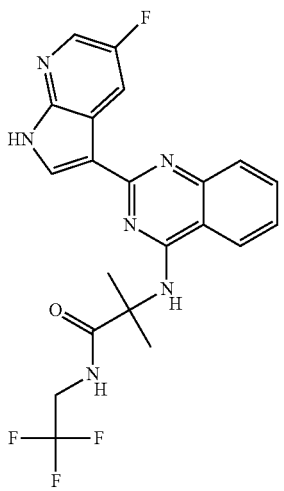
200
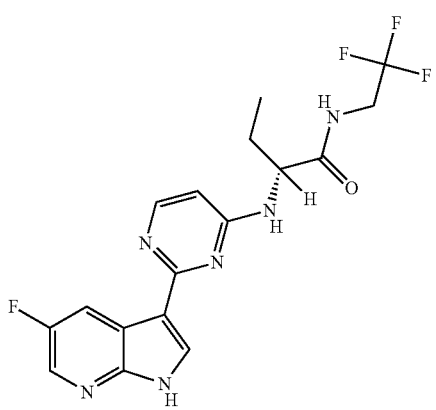
201
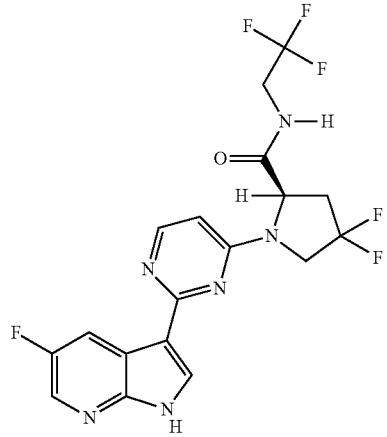
202
TABLE 2-continued
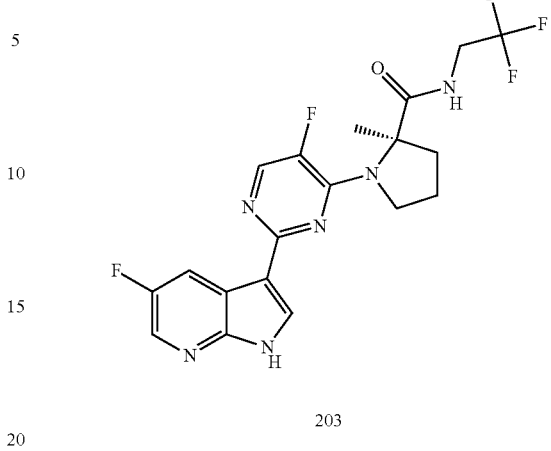
203
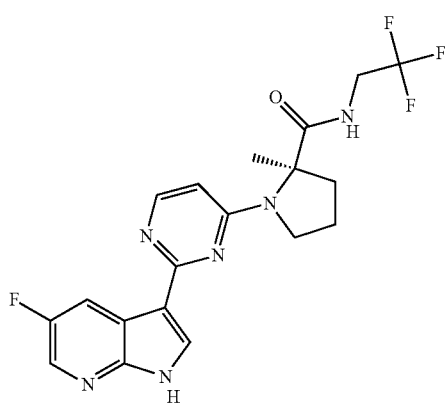
204
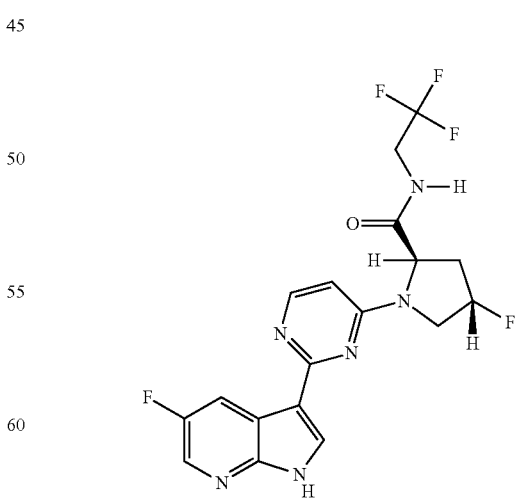
205

TABLE 2-continued
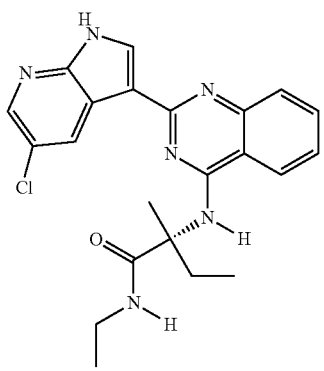
206
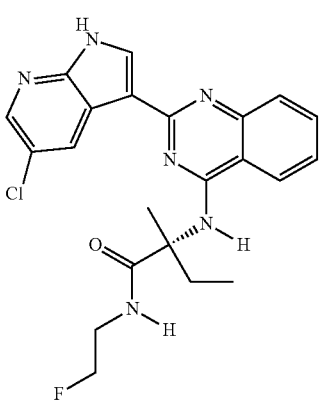
207
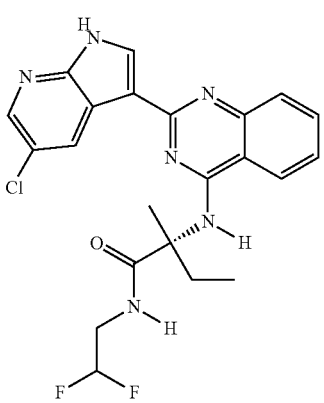
208
TABLE 2-continued
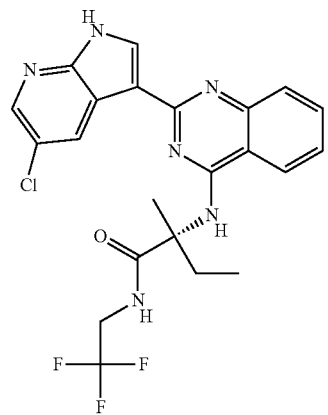
209
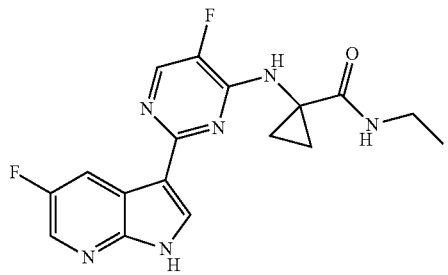
210
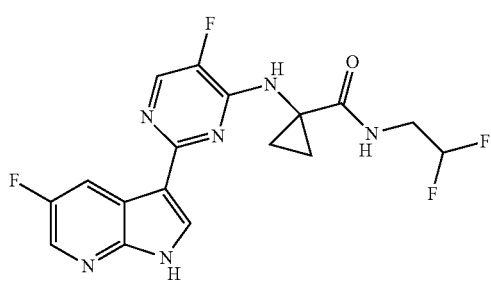
211
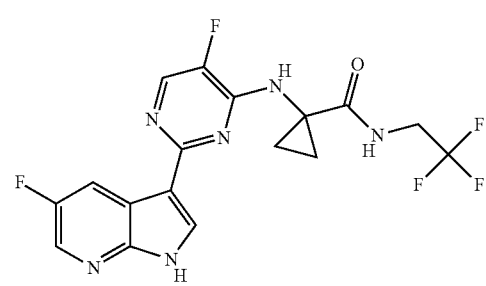
212

TABLE 2-continued
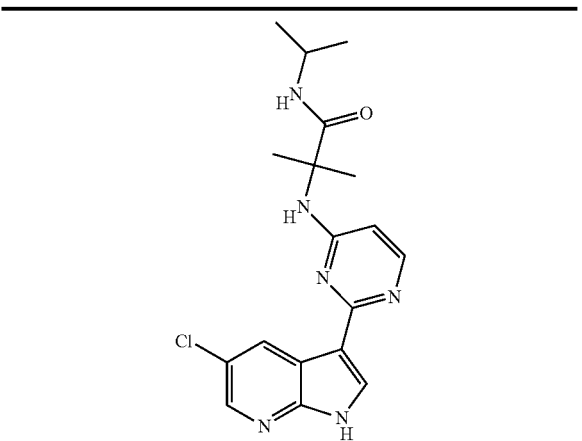
213
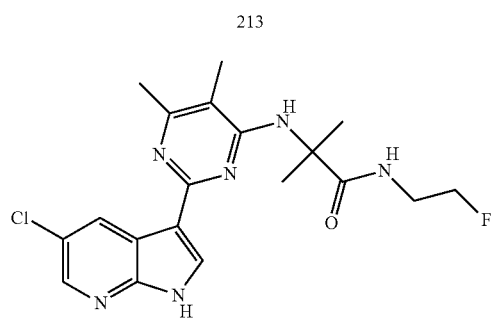
214
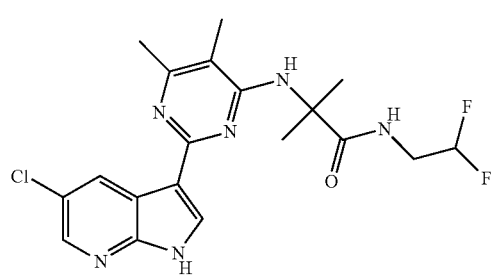
215
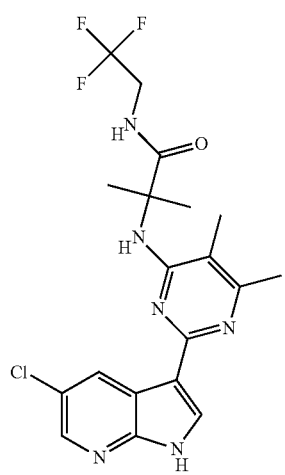
216
TABLE 2-continued
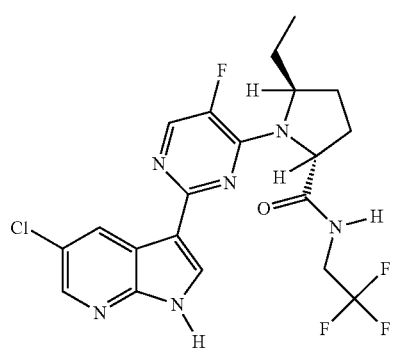
217
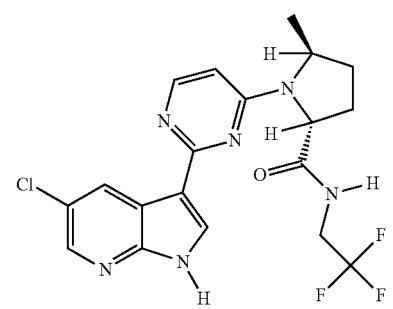
218
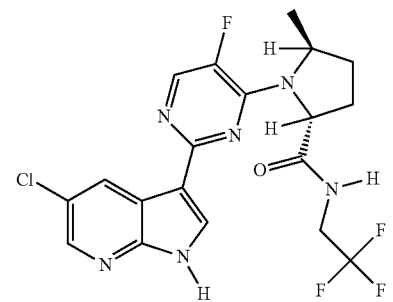
219
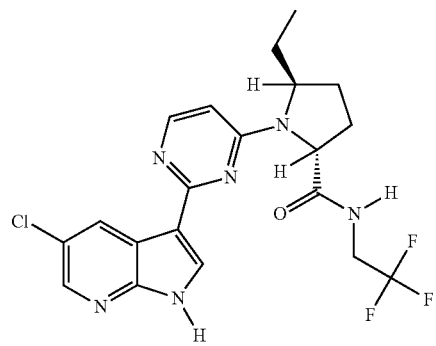
220

TABLE 2-continued
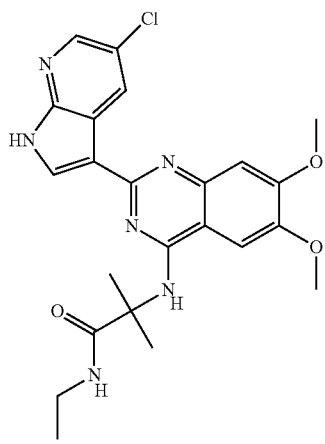
221
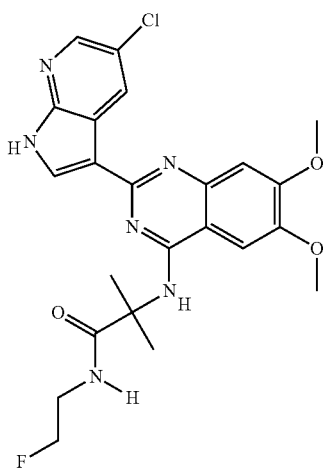
222
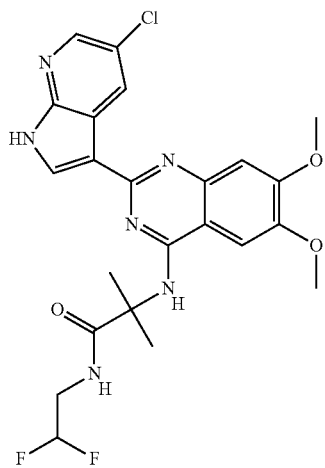
223
TABLE 2-continued
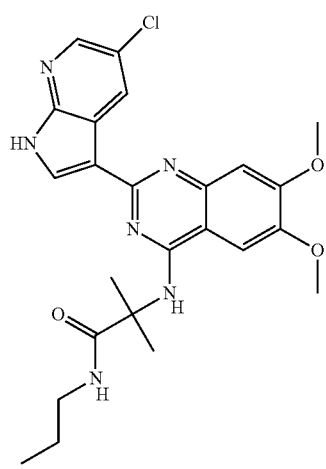
224
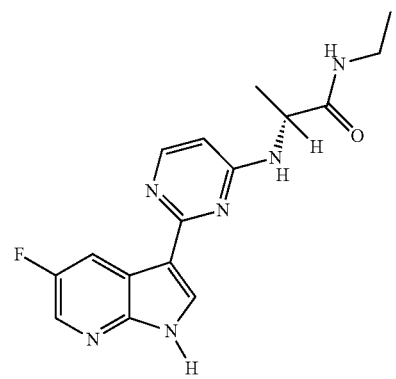
225
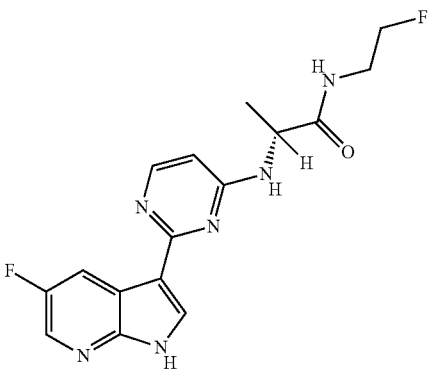
226

TABLE 2-continued
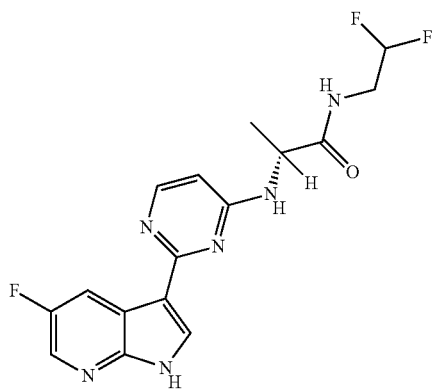
227
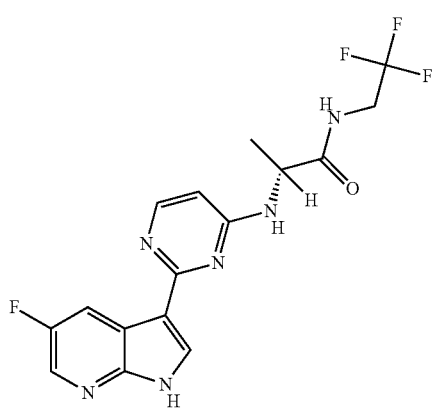
228
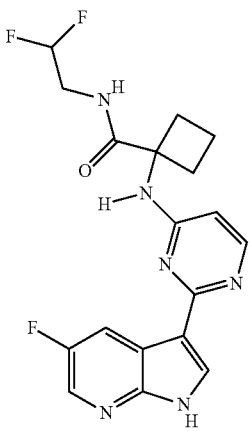
229
TABLE 2-continued
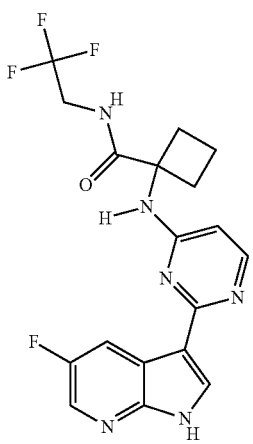
230
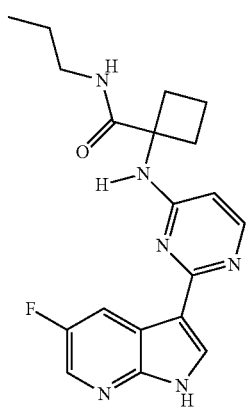
231
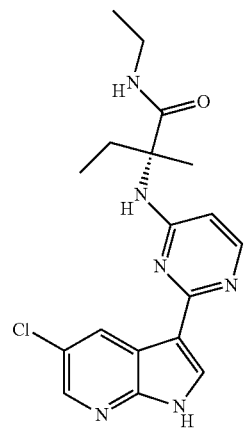
232

TABLE 2-continued
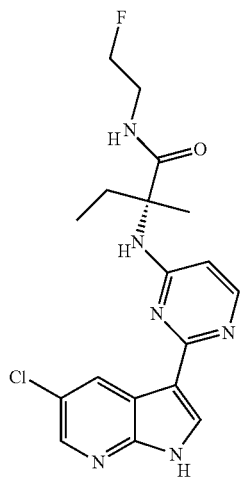
233
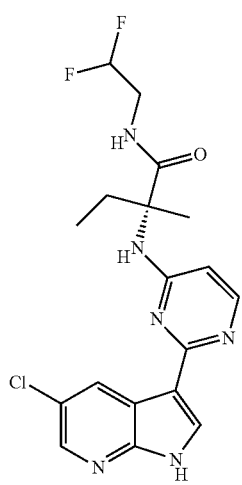
234
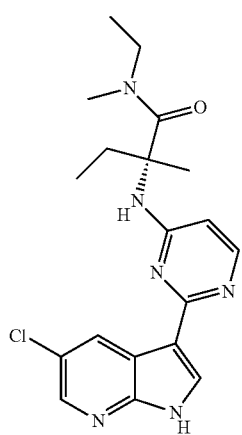
235
TABLE 2-continued
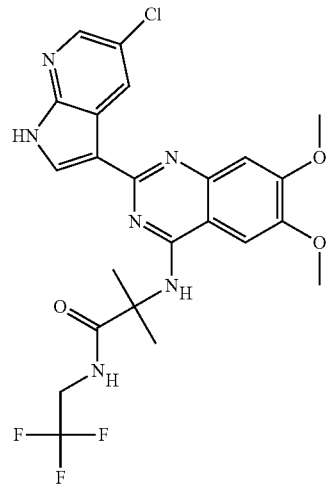
236
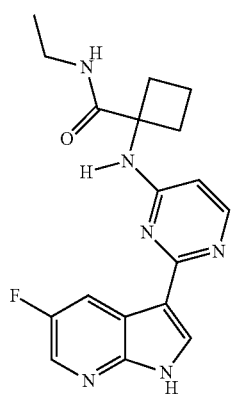
237
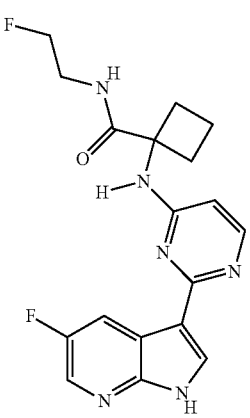
238

TABLE 2-continued
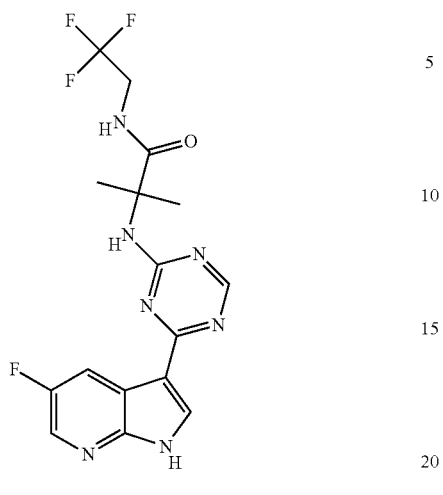
239
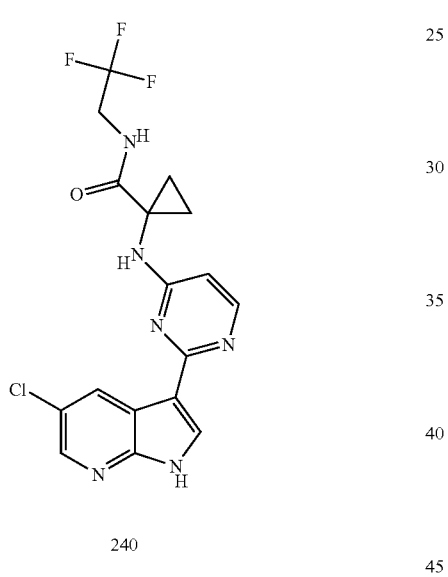
240
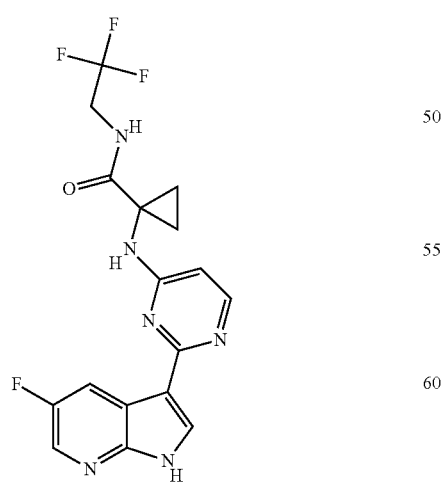
241
TABLE 2-continued
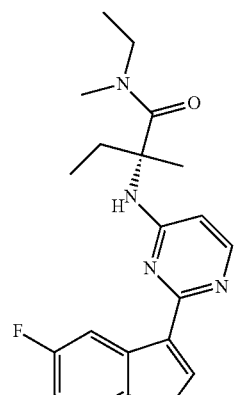
242
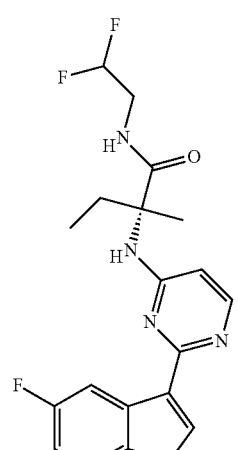
243
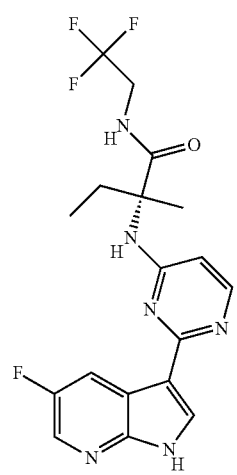
244

TABLE 2-continued
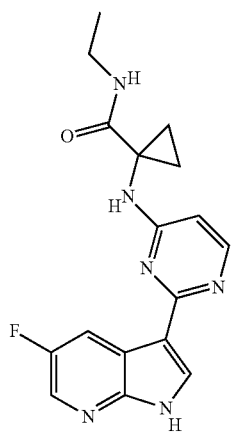
245
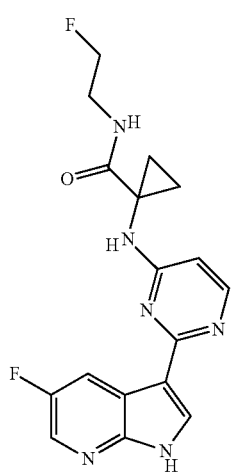
246
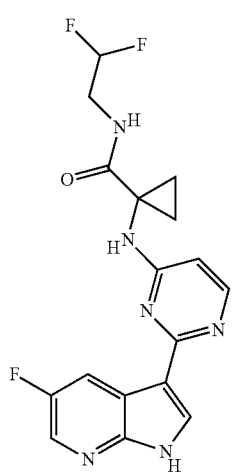
247
TABLE 2-continued
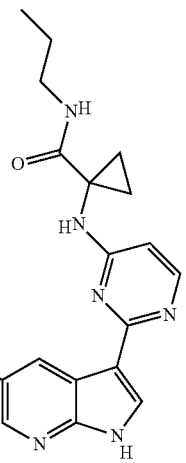
248
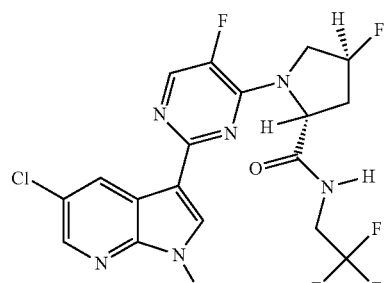
249
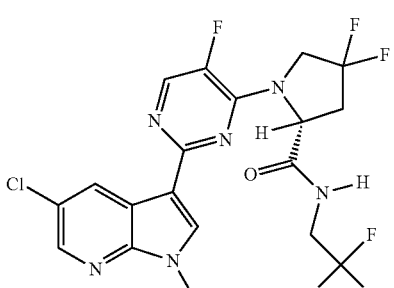
250
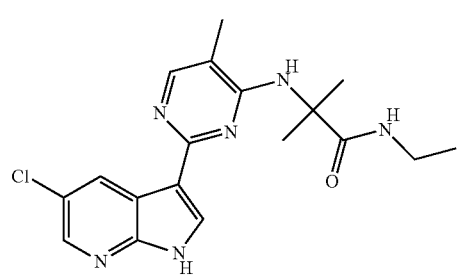
251

TABLE 2-continued
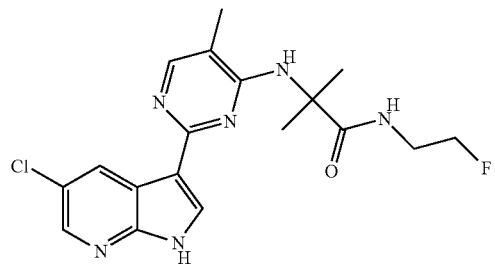
252
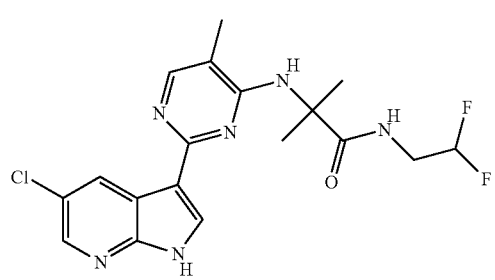
253
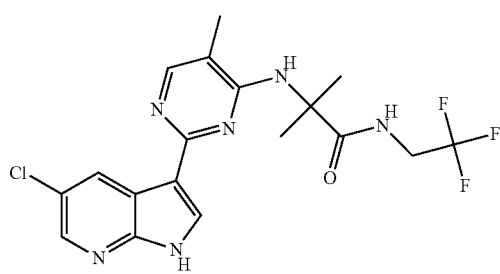
254
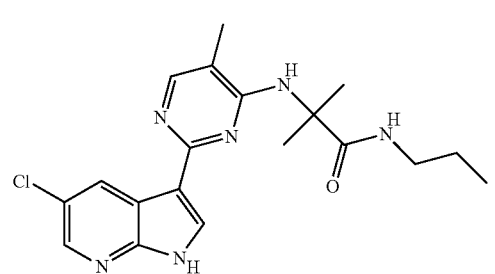
255
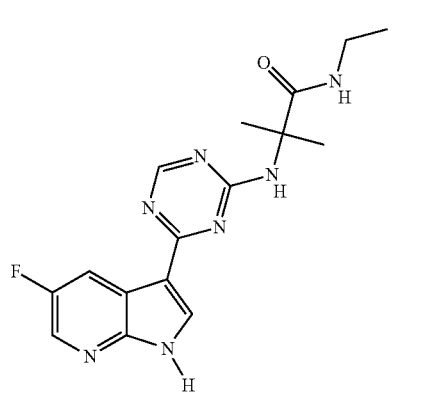
256
TABLE 2-continued
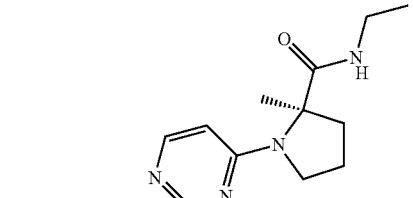
257
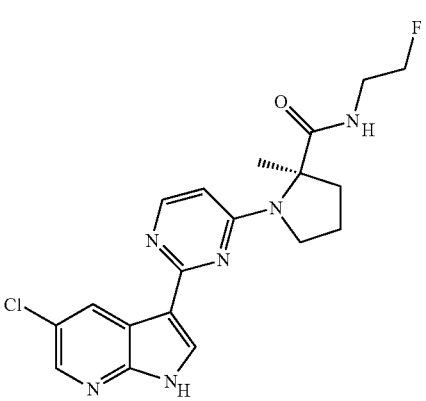
258
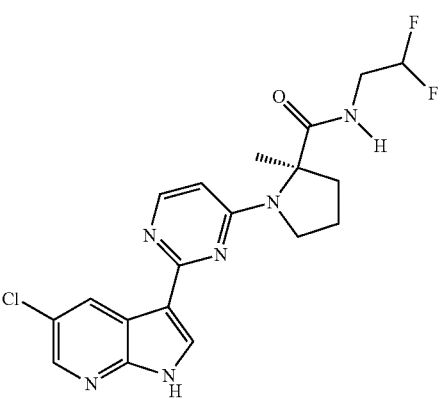
259

TABLE 2-continued
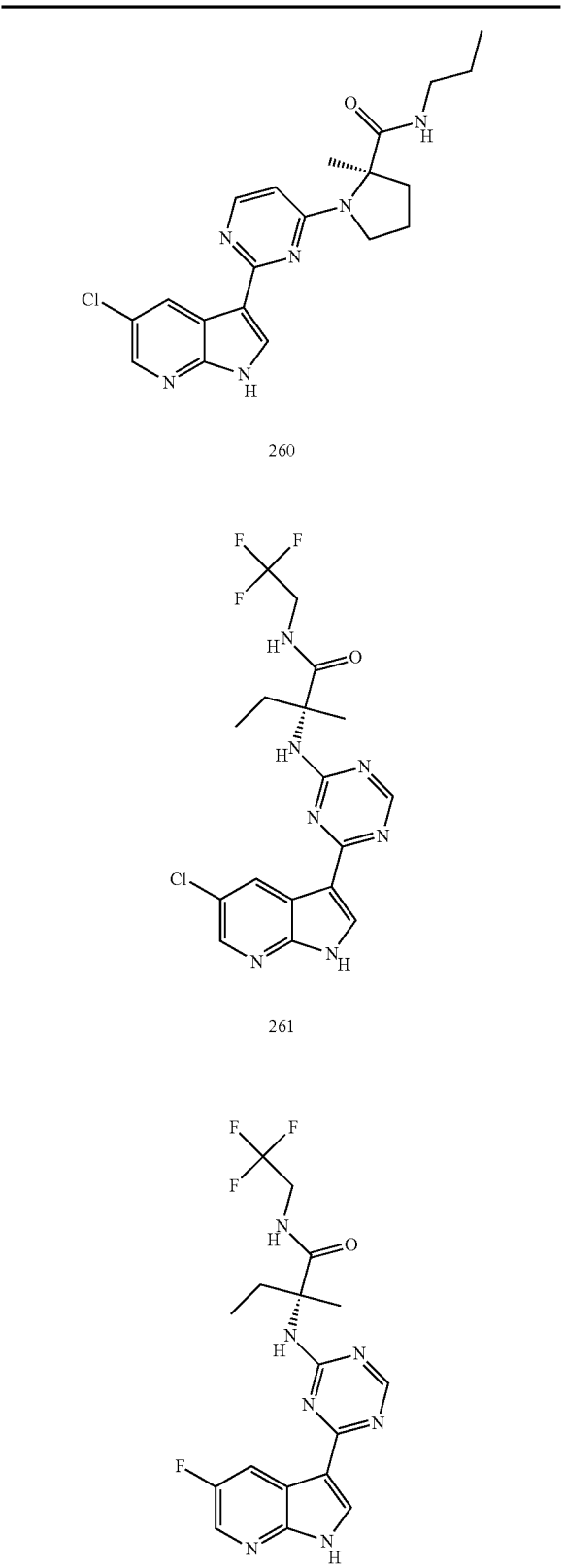
260
261
262
TABLE 2-continued
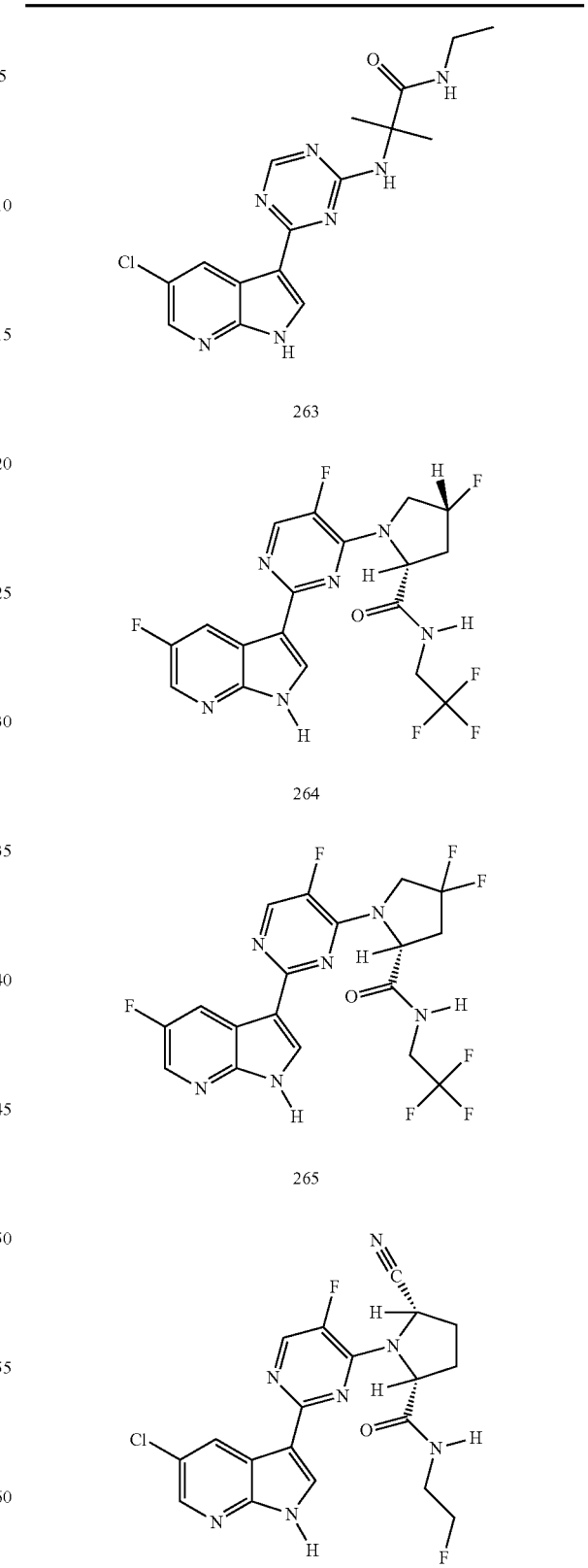
263
264
265
266

TABLE 2-continued
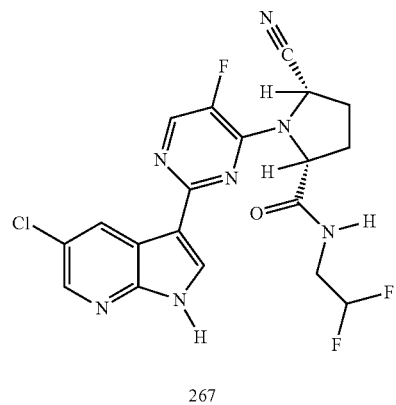
267
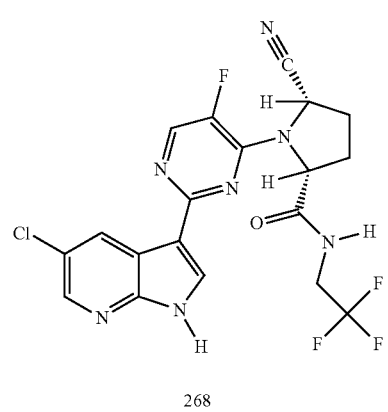
268
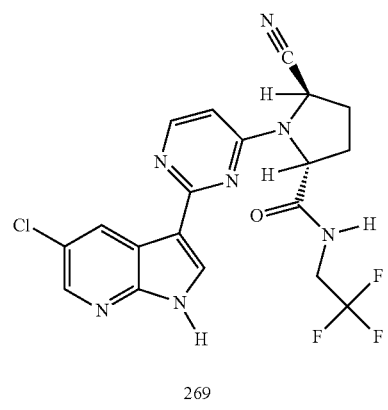
269
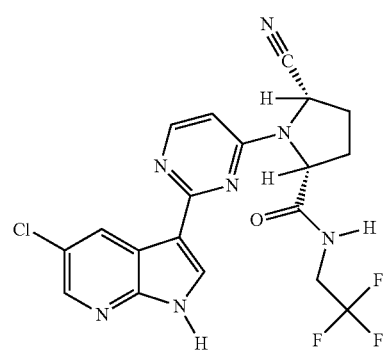
270
TABLE 2-continued
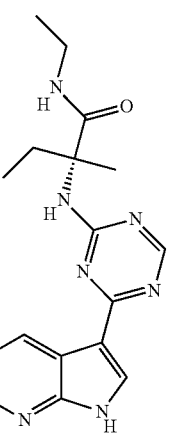
271
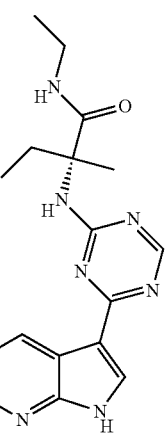
272
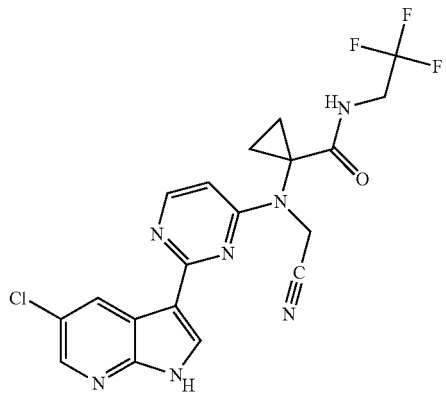
273

TABLE 2-continued
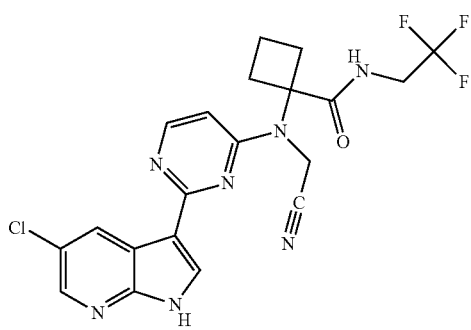
274
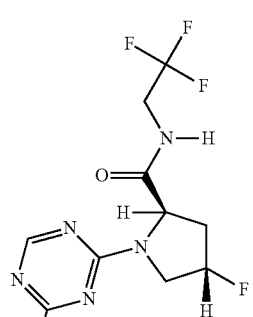
275
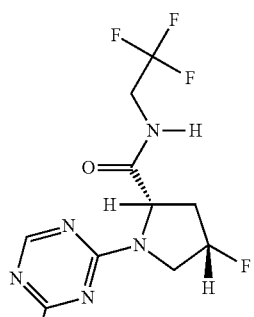
276
TABLE 2-continued
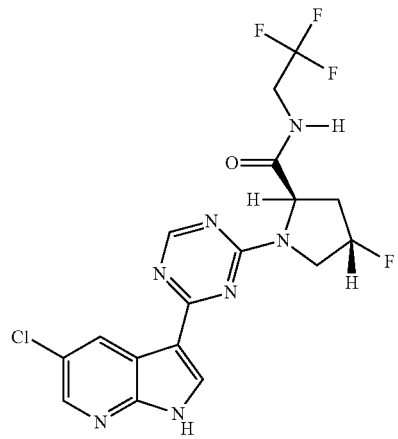
277
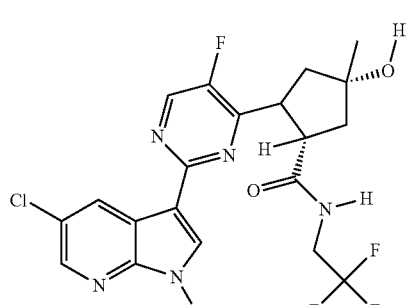
278
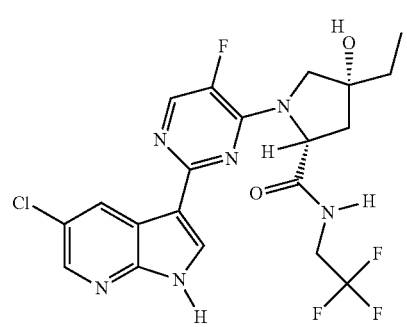
279
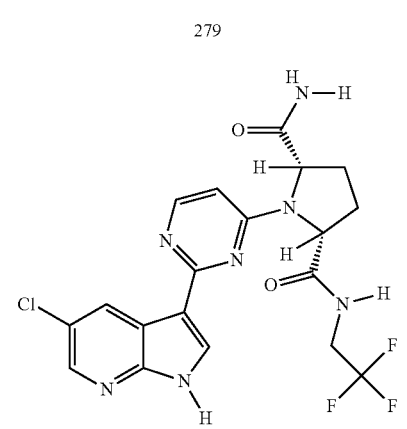
280

US 8,163,917 B2
TABLE 2-continued
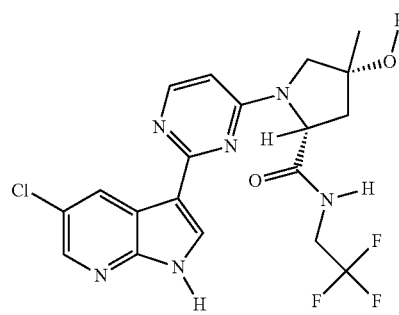
281
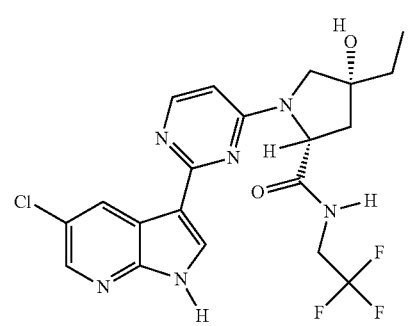
282
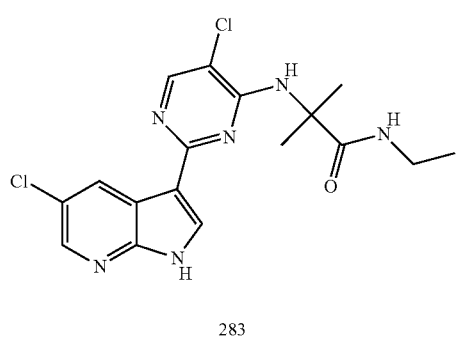
283
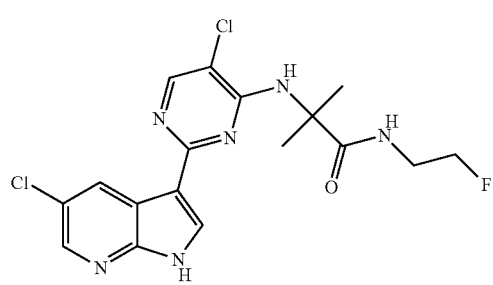
284
TABLE 2-continued
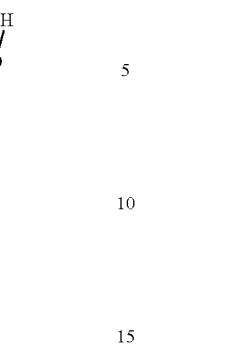
285
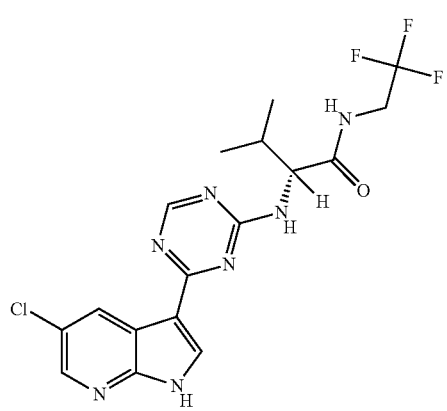
286
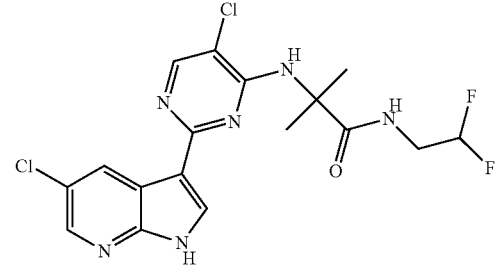
287
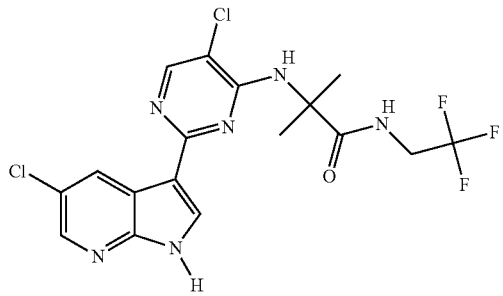
288

TABLE 2-continued
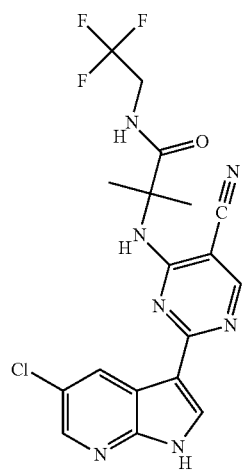
289
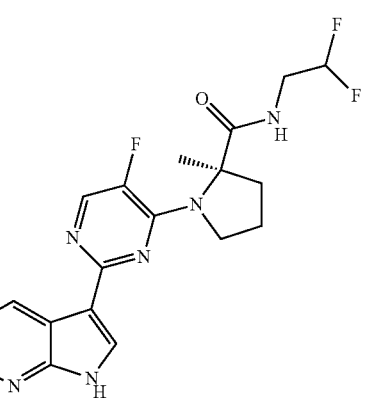
292
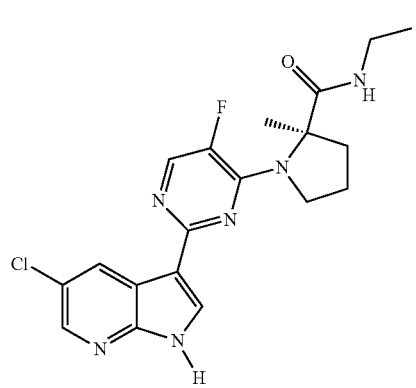
290
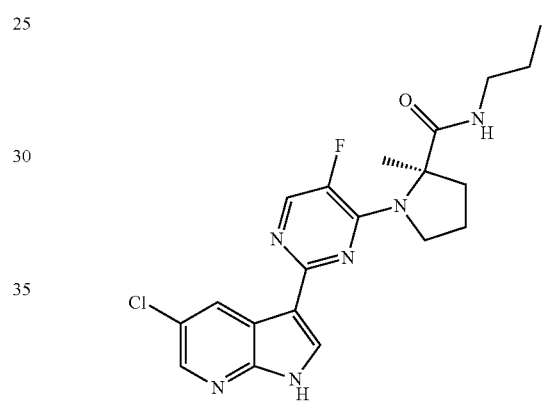
293
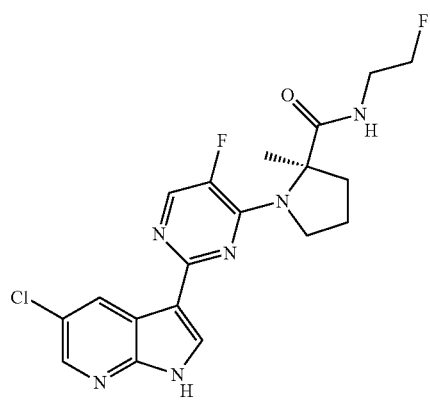
291
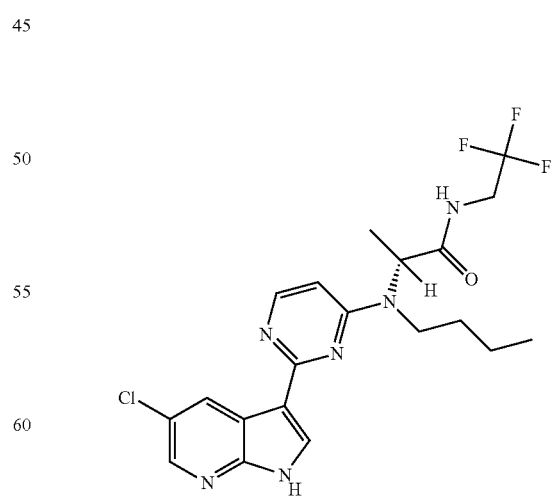
294

TABLE 2-continued
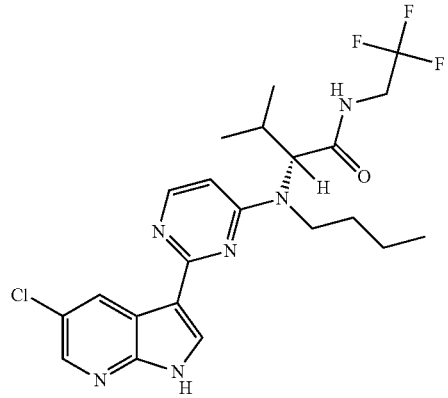
295
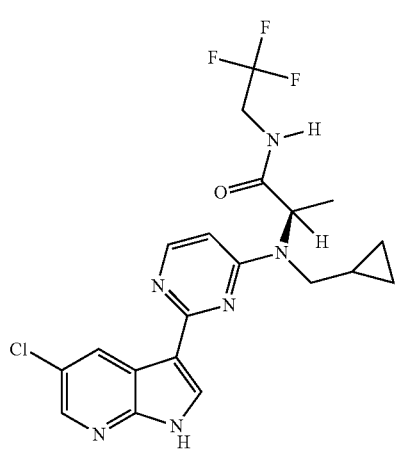
296
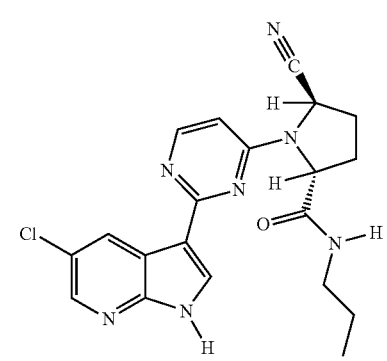
297
TABLE 2-continued
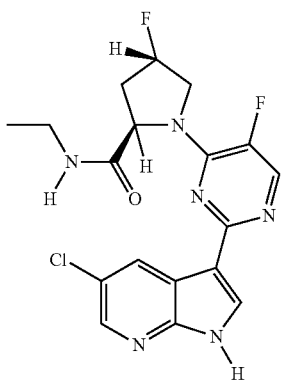
298
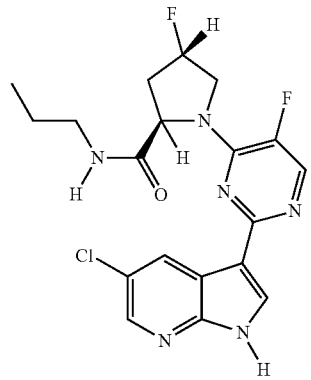
299
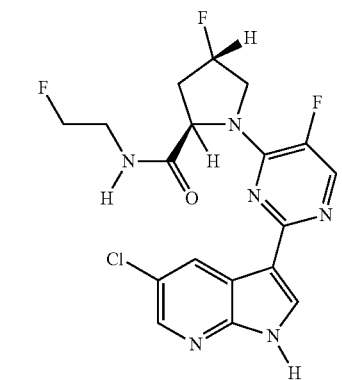
300
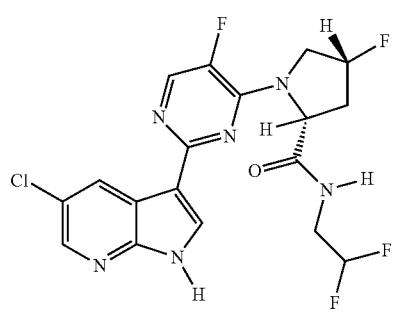
301

TABLE 2-continued
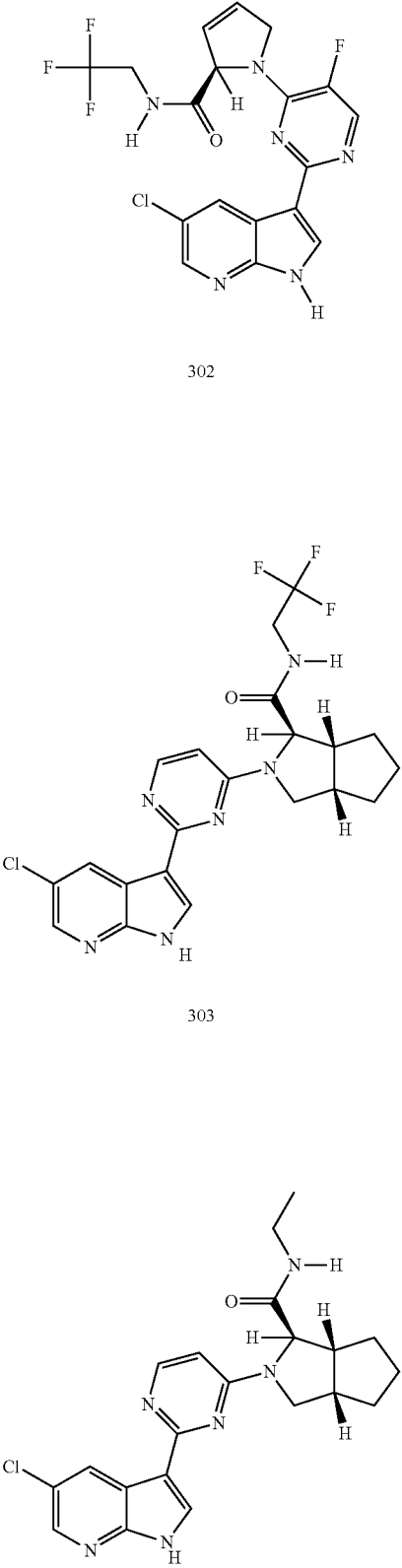
302
303
304
TABLE 2-continued
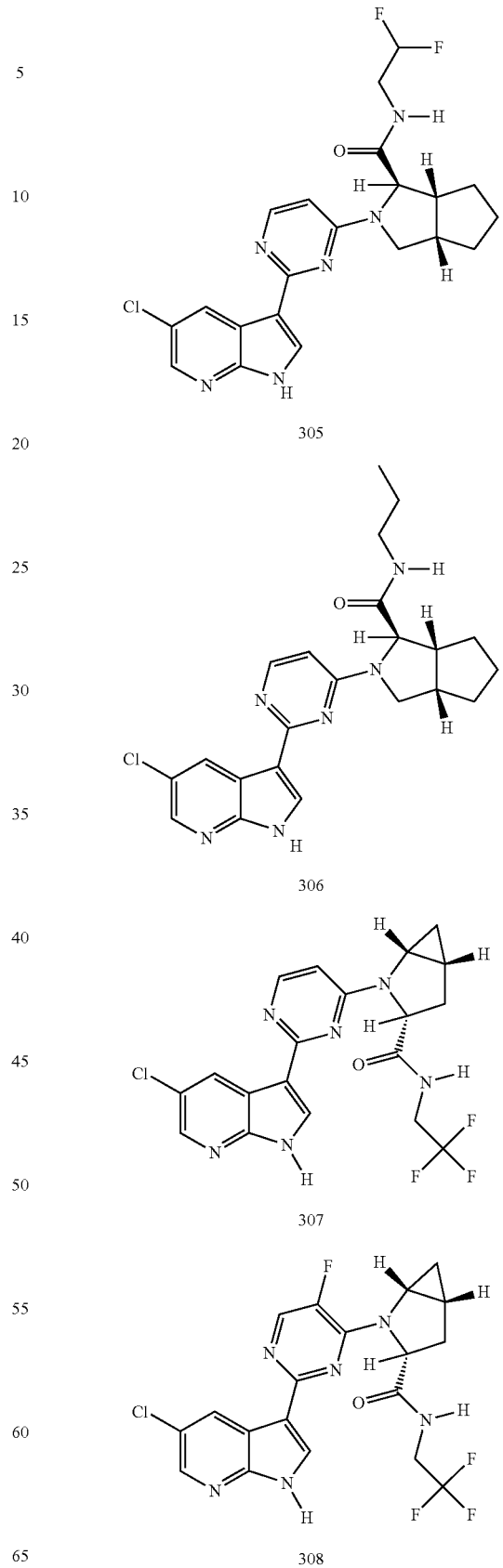
305
306
307
308

TABLE 2-continued
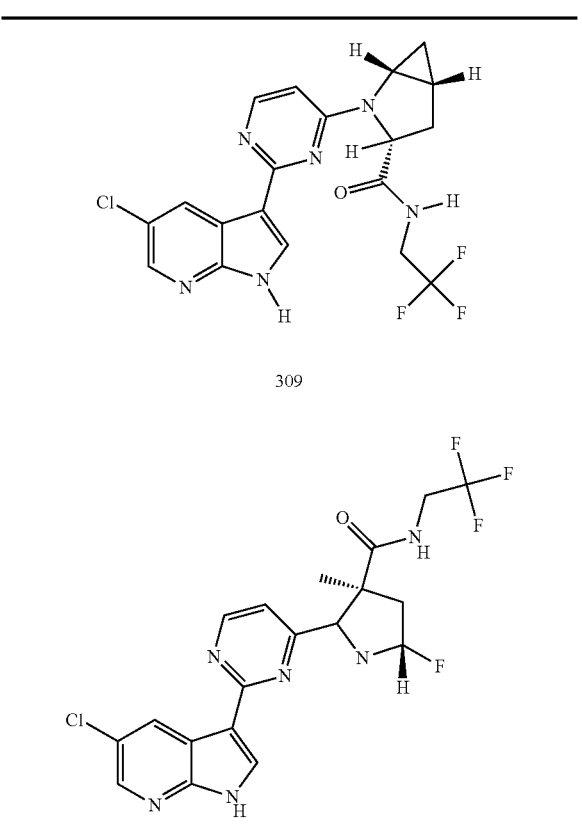
309
310
TABLE 3
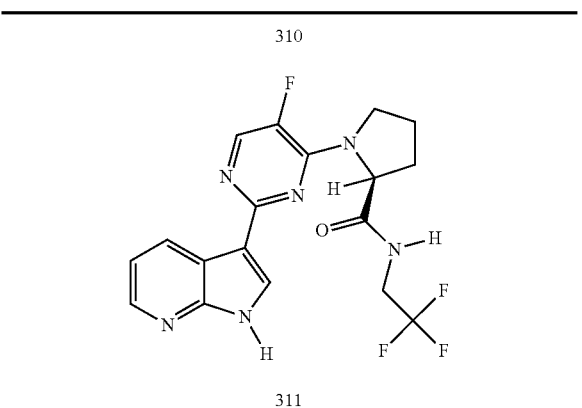
311
312
TABLE 3-continued
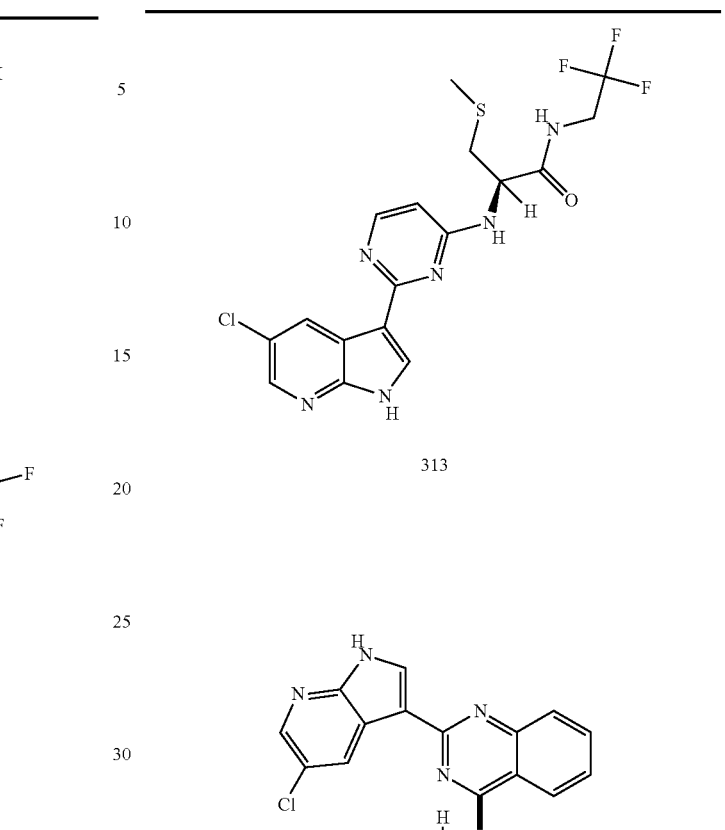
313
314
315

TABLE 3-continued
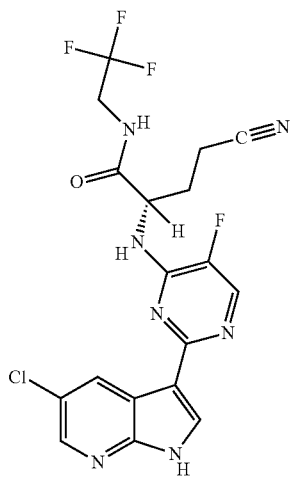
316
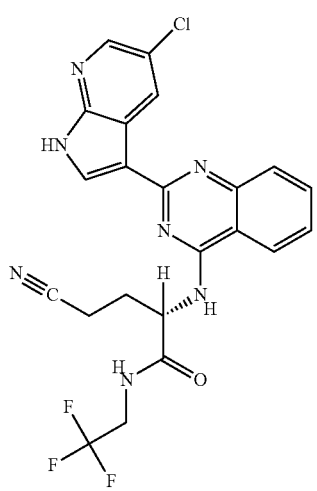
317
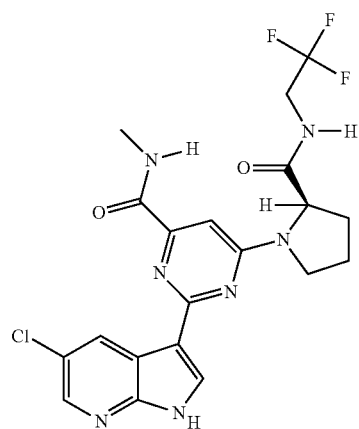
318
TABLE 3-continued
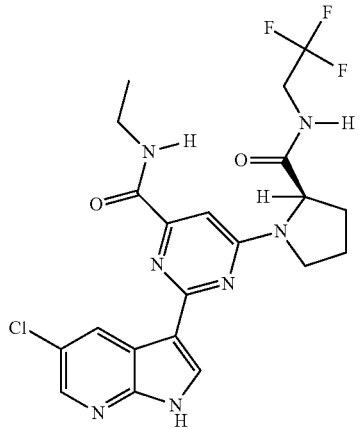
319
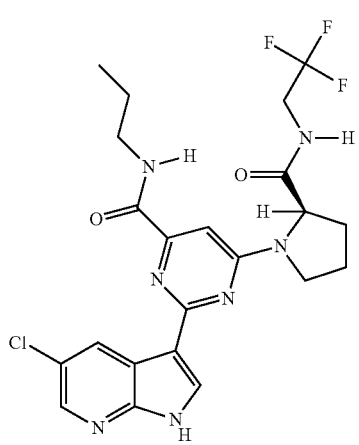
320
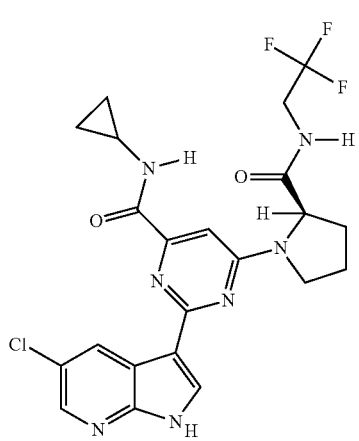
321

TABLE 3-continued
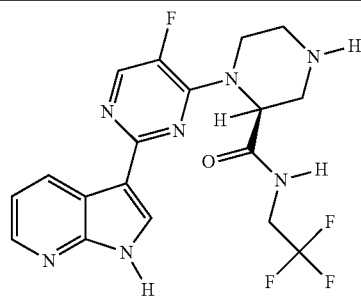
322
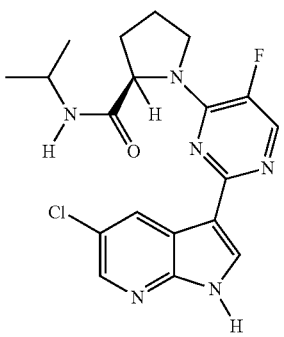
323
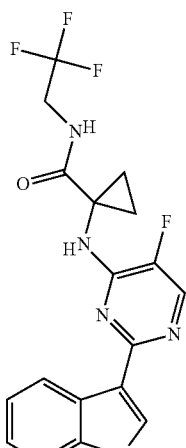
324
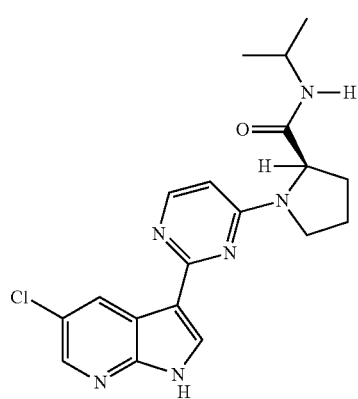
TABLE 3-continued
325
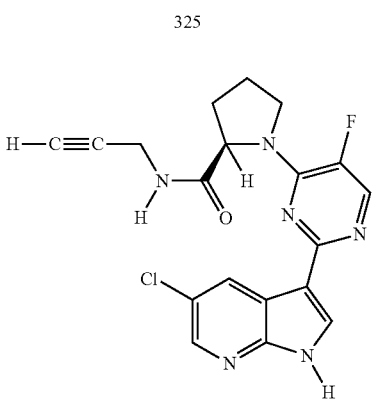
326
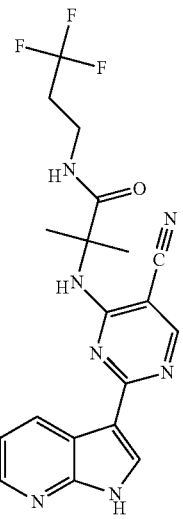
327
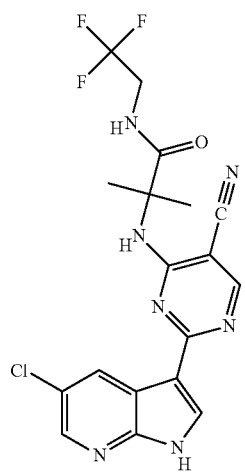
328

TABLE 3-continued
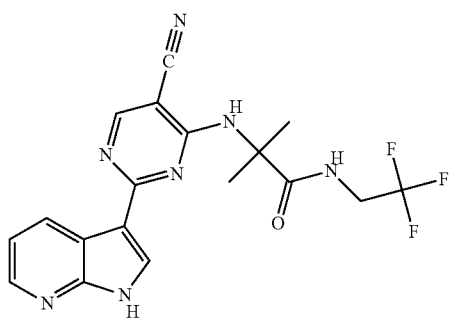
329
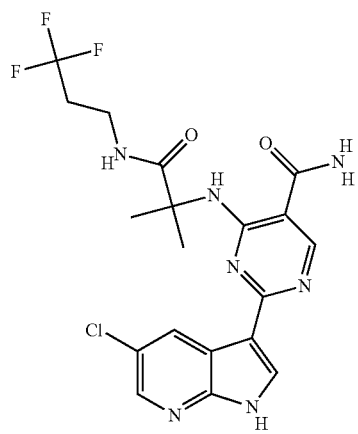
330
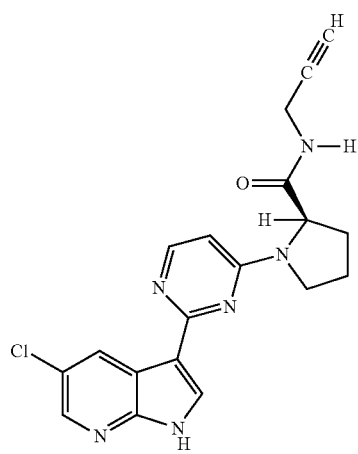
331
TABLE 3-continued
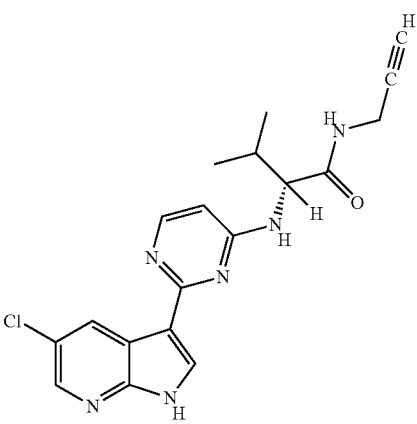
332
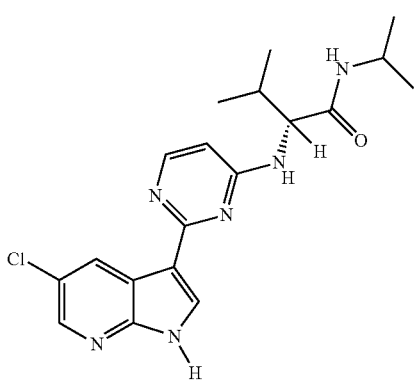
333
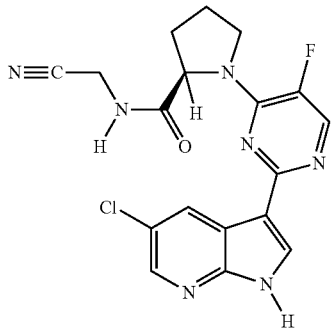
334

TABLE 3-continued
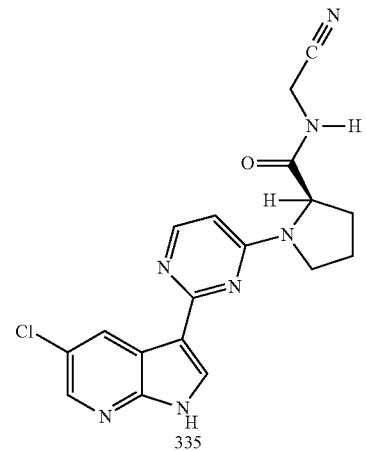
335
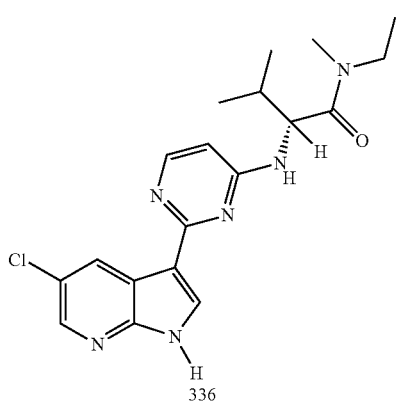
336
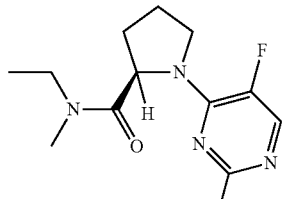
337
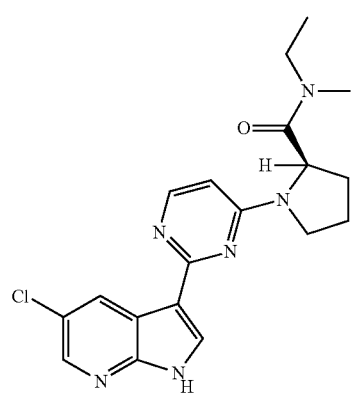
338
TABLE 3-continued
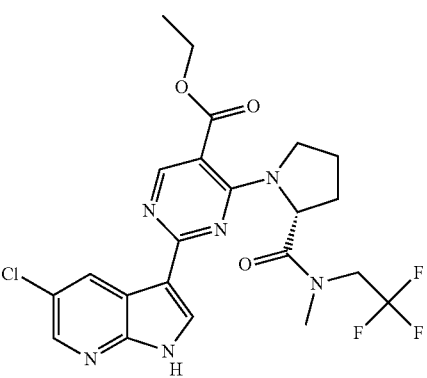
339
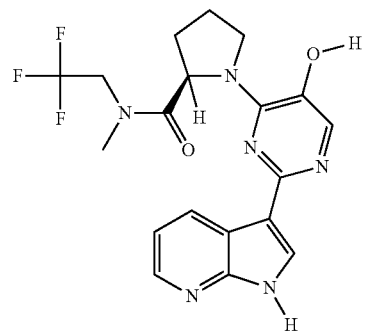
340
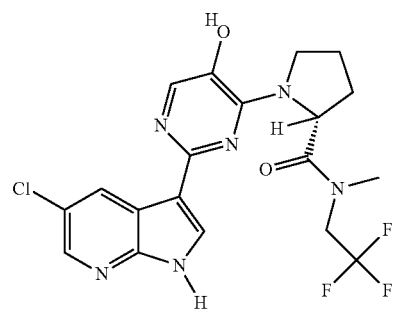
341

TABLE 3-continued
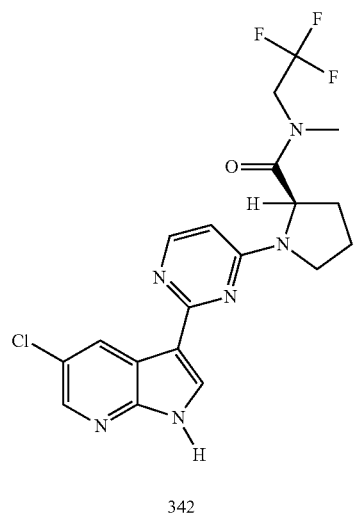
342
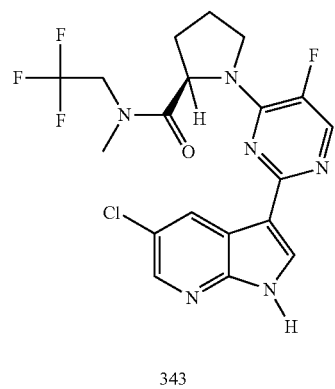
343
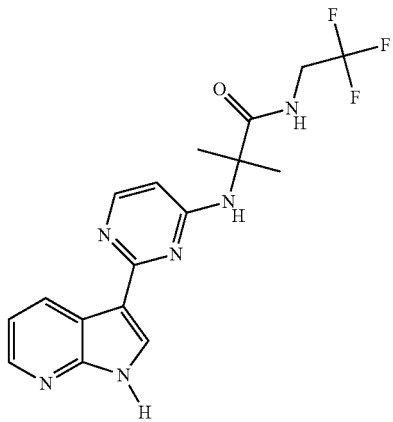
344
TABLE 3-continued
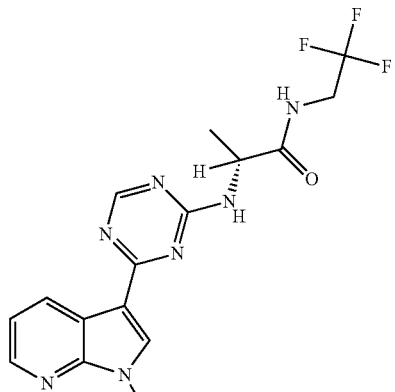
345
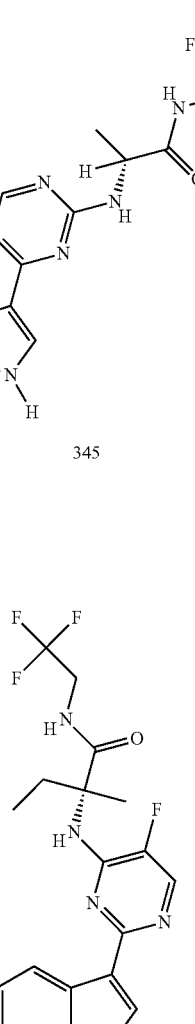
346
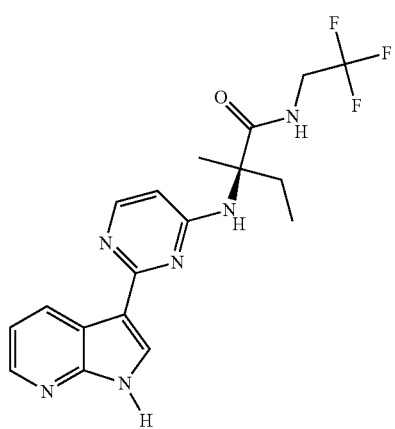
347

TABLE 3-continued
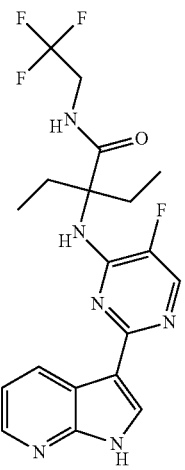
348
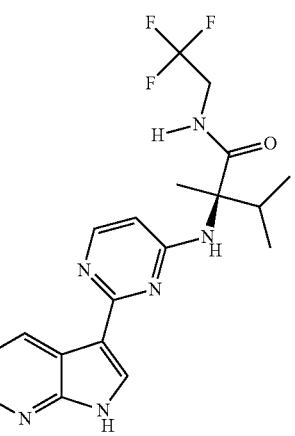
351
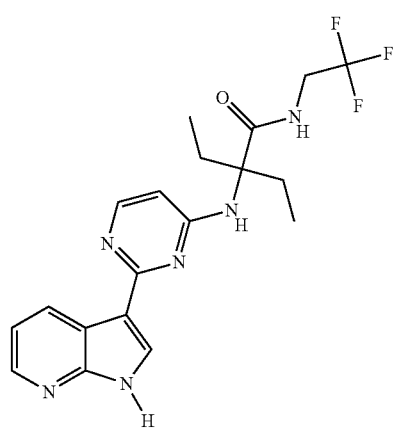
349
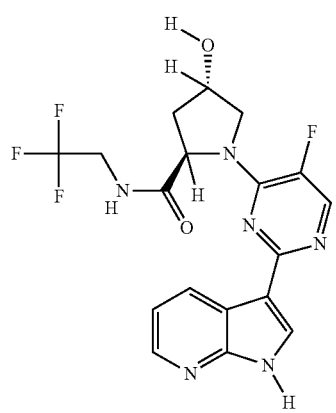
352
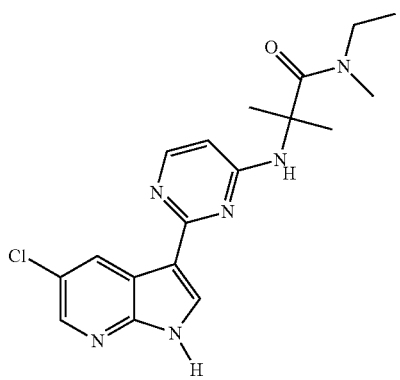
350
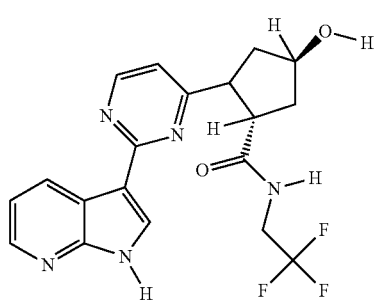
353

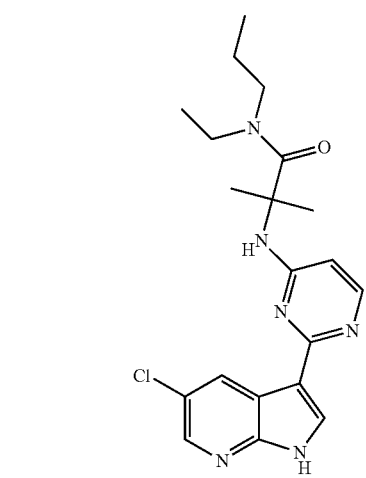
354
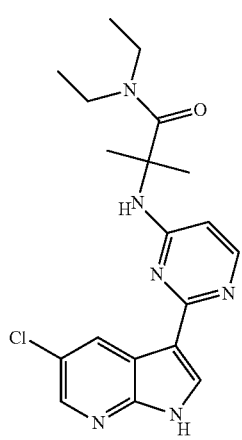
355
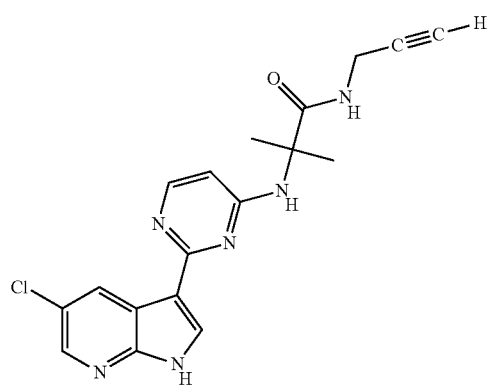
356
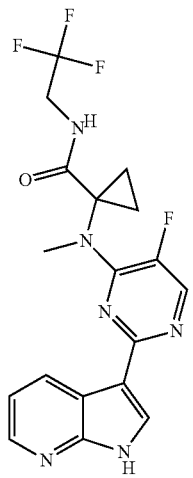
357
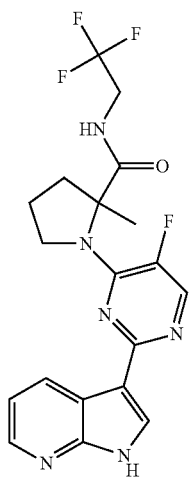
358
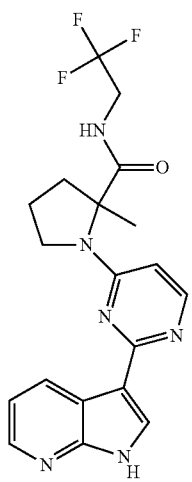
359

TABLE 3-continued
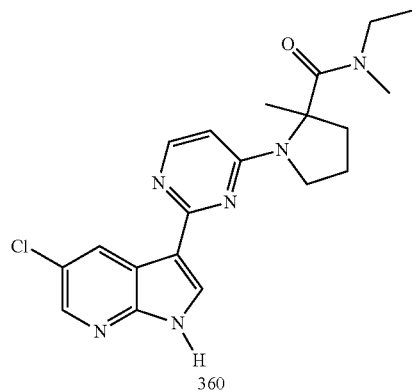
360
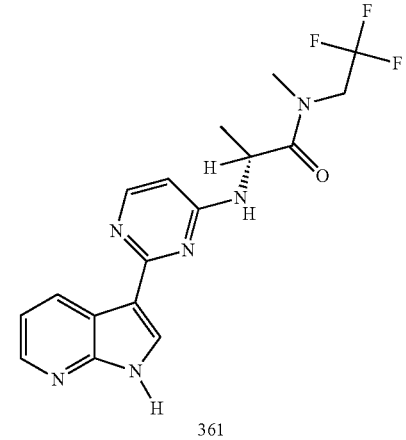
361
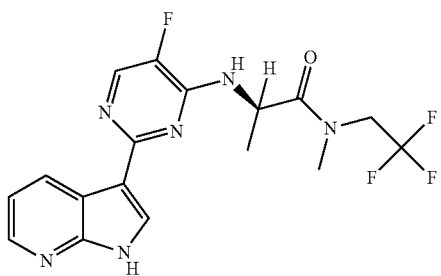
362
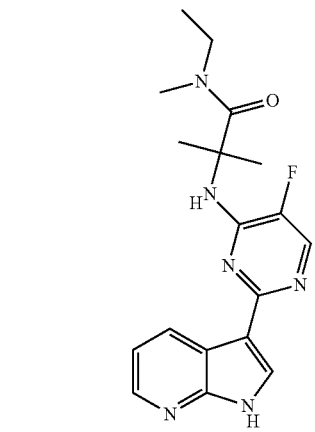
363
TABLE 3-continued
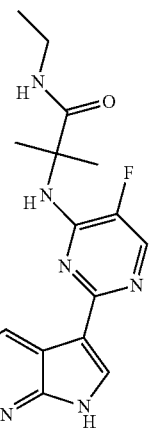
364
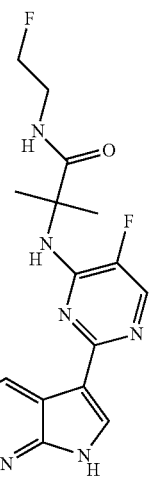
365
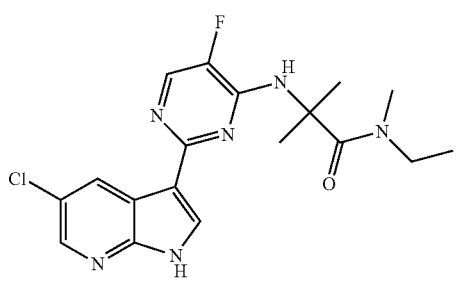
366

TABLE 3-continued
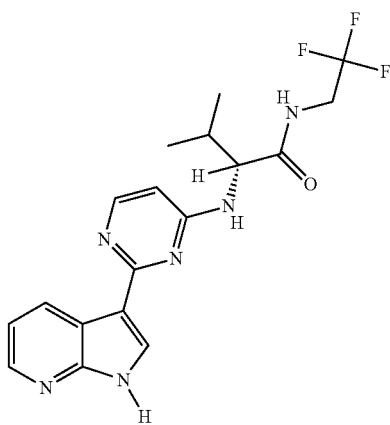
367
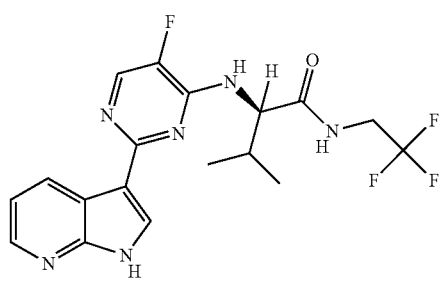
368
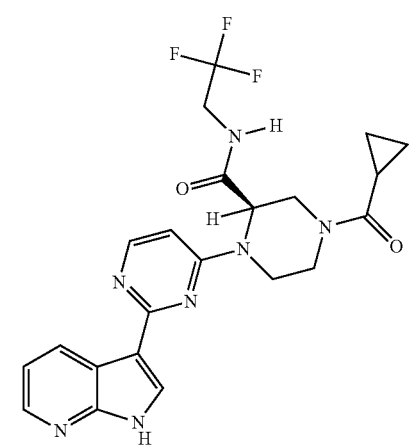
369
TABLE 3-continued
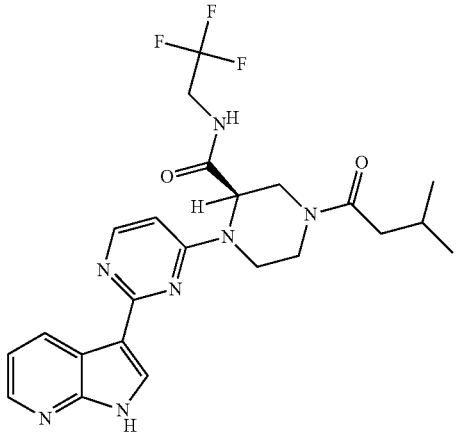
370
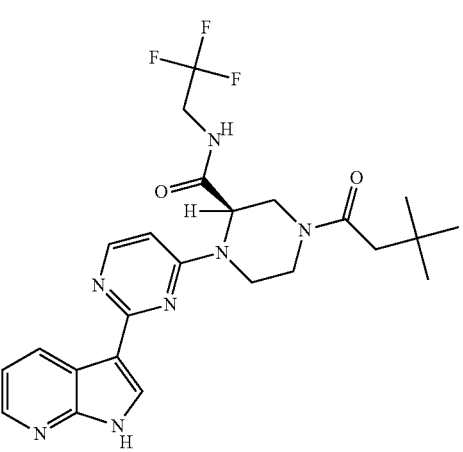
371
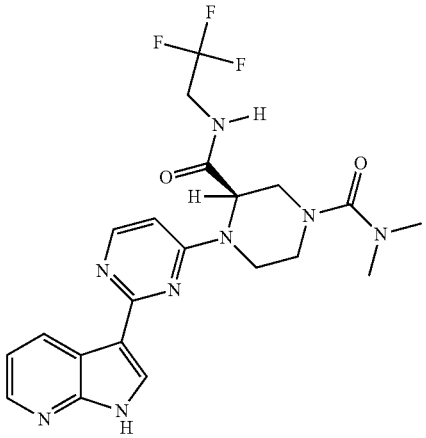
372

TABLE 3-continued
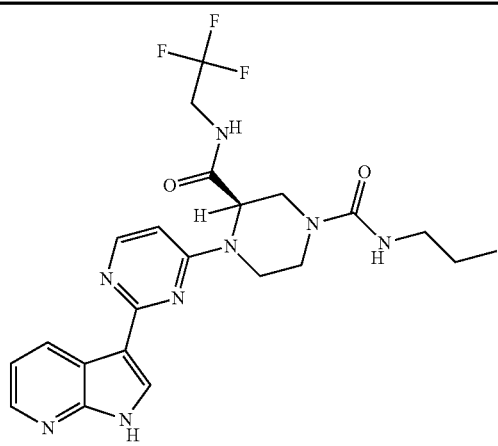
373
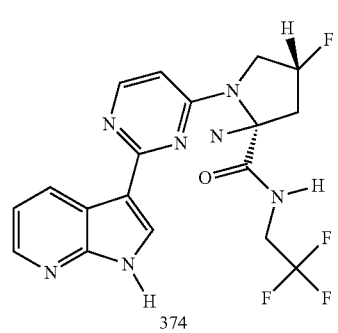
374
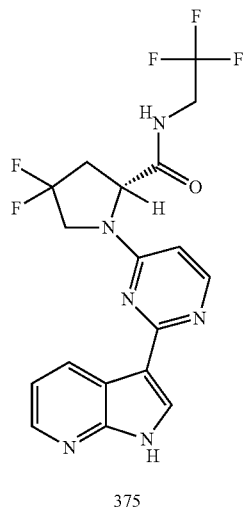
375
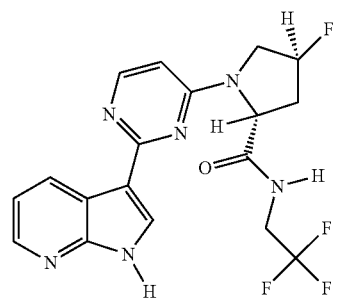
376
TABLE 3-continued
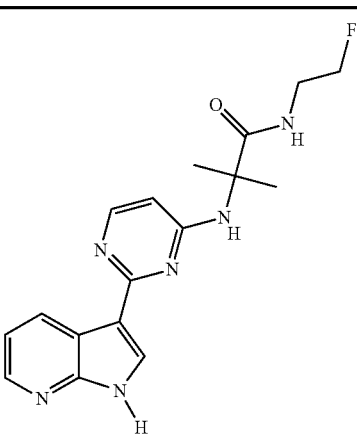
377
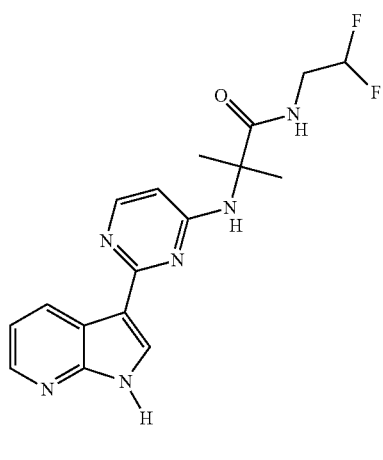
378
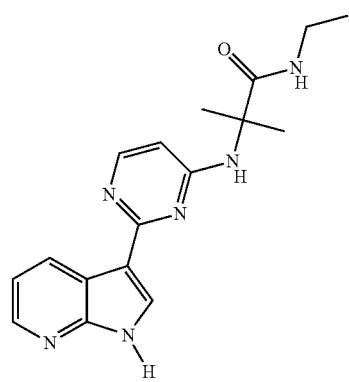
379

TABLE 3-continued
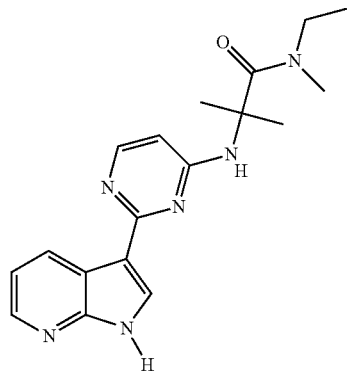
380
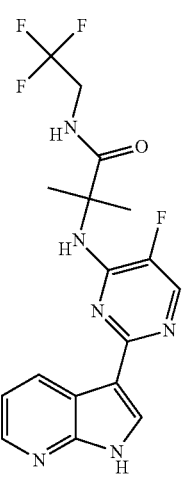
381
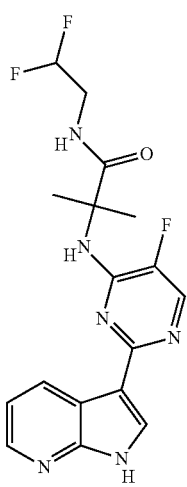
382
TABLE 3-continued
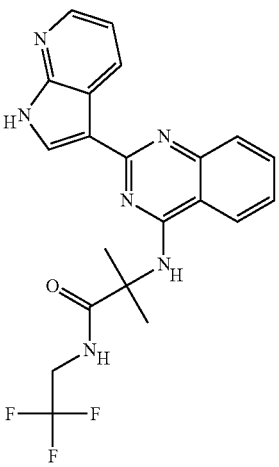
383
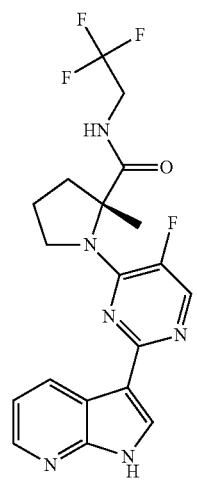
384
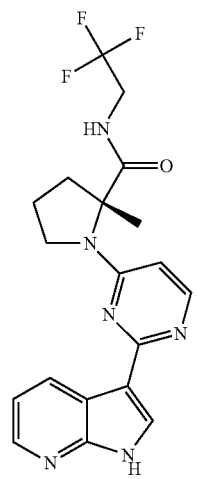
385

TABLE 3-continued
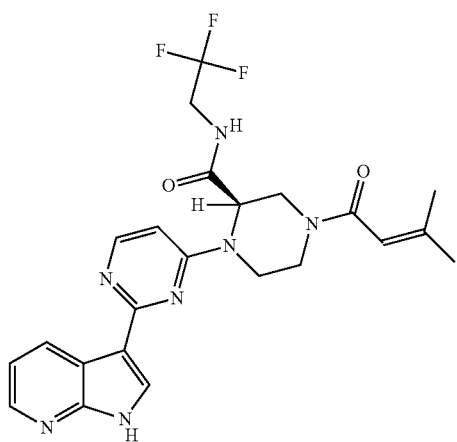
386
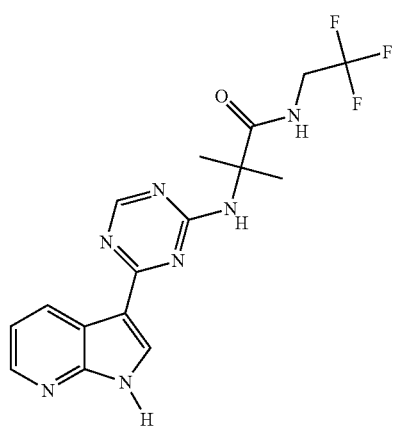
387
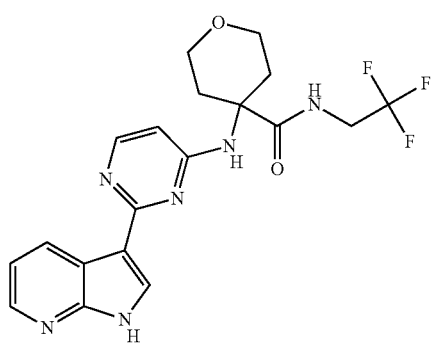
388
TABLE 3-continued
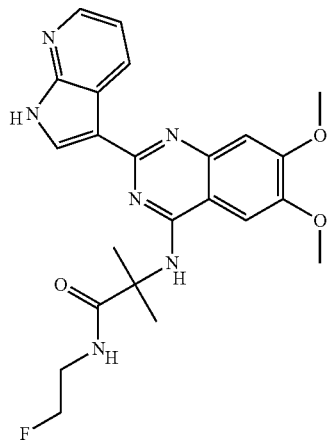
389
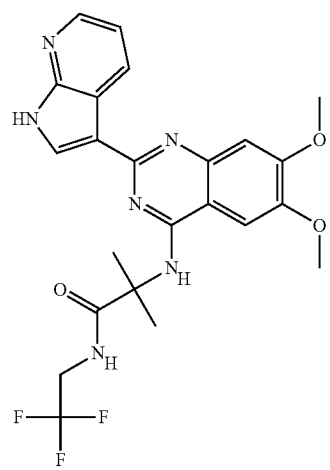
390
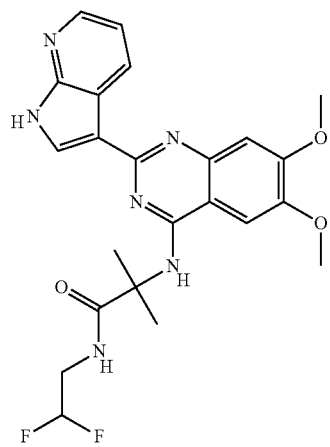
391

TABLE 3-continued
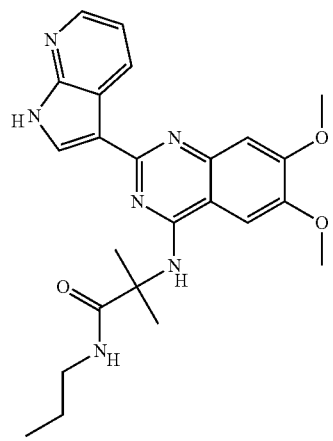
392
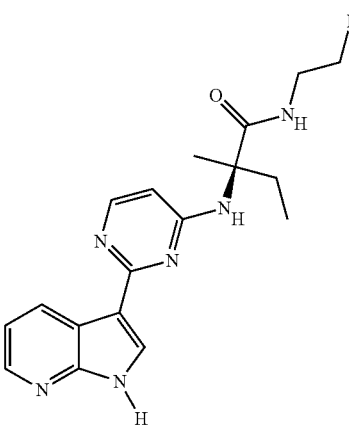
395
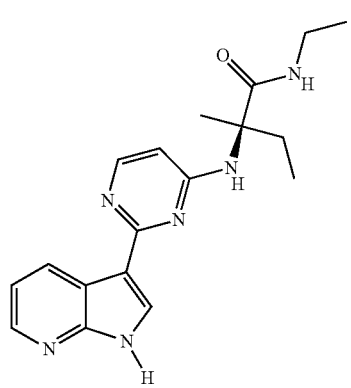
393
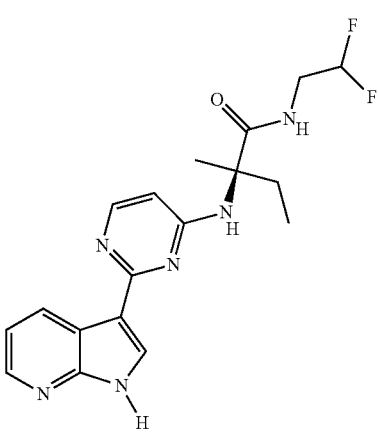
396
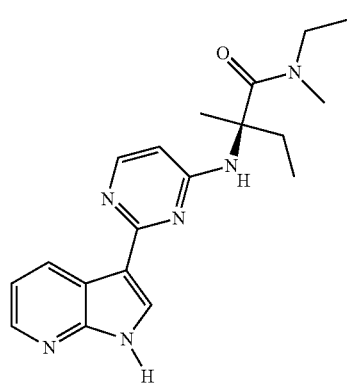
394
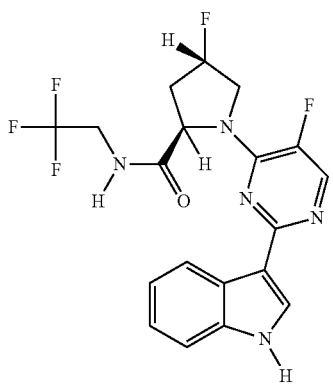
397

TABLE 3-continued
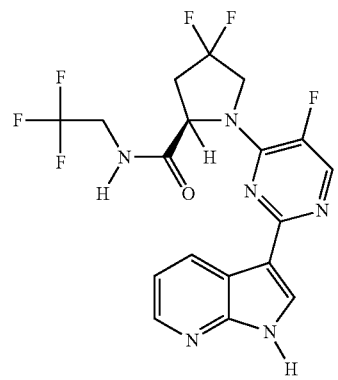
398
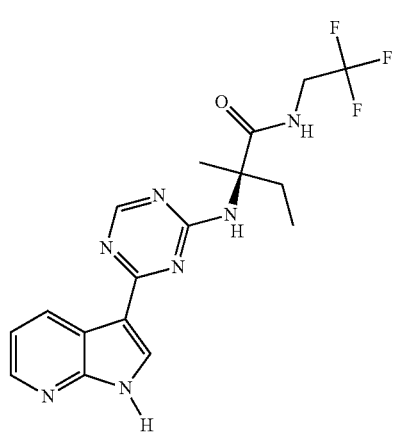
399
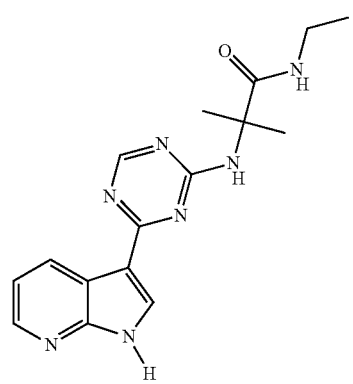
400
TABLE 3-continued
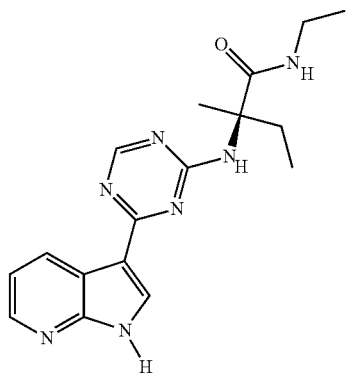
401
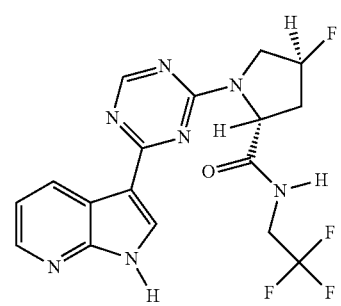
402
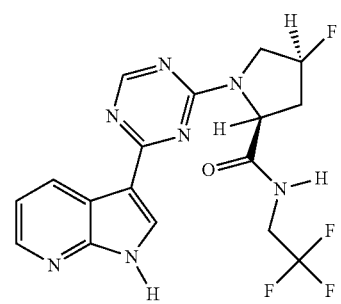
403
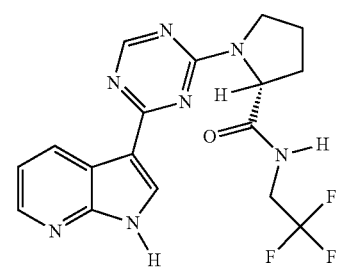
404

TABLE 3-continued

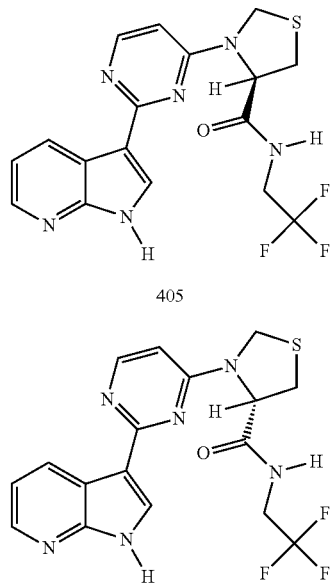

405

Uses, Formulation and Administration
Pharmaceutically Acceptable Compositions

In another embodiment, the invention provides a pharmaceutical composition comprising a compound of formulae I, IA, IB, II or III.

In a further embodiment, the composition additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly a JAK family kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitorily active metabolite or residue thereof" means that a metabolite or residue thereof is also an inhibitor of a JAK family kinase.

As used herein, the term "pharmaceutically acceptable salt" refers to those salts which are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly JAK kinase activity, between a sample comprising a compound of this invention and a JAK kinase and an equivalent sample comprising JAK kinase in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebit®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycopheno late mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In one embodiment, the invention provides a method of inhibiting JAK kinase activity in a patient, comprising administering to said patient a compound or composition of the invention.

In another embodiment, the invention comprises a method of treating or lessening the severity of a JAK-mediated condition or disease in a patient. The term "JAK-mediated disease", as used herein means any disease or other deleterious condition in which a JAK family kinase, in particular JAK2 or JAK3, is known to play a role. In a further embodiment, the invention comprises a method of treating a JAK3-mediated disease. Such conditions include, without limitation, immune responses such as allergic or type 1 hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas.

In another embodiment, the invention provides a method of treating or lessening the severity of a disease of condition selected from a proliferative disorder, a cardiac disorder, a neurodegenerative disorder, an autoimmune disorder, a condition associated with organ transplant, an inflammatory disorder, an immune disorder or an immunologically mediated disorder, comprising administering to said patient a compound or composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In one embodiment, the disease or disorder is allergic or type 1 hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection. In another embodiment, said disease or disorder is rheumatoid arthritis.

In another embodiment, a compound or composition of this invention may be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML or juvenile myelomonocytic leukemia.

In another embodiment, the invention provides for the use of a compound of formulae I, IA, IB, II or III to treat a JAK-mediated disease. In a further embodiment, the invention provides for the use of said compound to treat any of the diseases discussed above. In another embodiment, the invention provides for the use of a compound of formulae I, IA, IB, II or III for the manufacture of a medicament for treating a JAK-mediated disease. In a further embodiment, the invention provides for the use of said compound for the manufacture of a medicament for treating any of the diseases discussed above.

In another embodiment, the invention provides a method of inhibiting JAK kinase activity in a biological sample, comprising contacting said biological sample with a compound or composition of the invention.

The term "biological sample", as used herein, means an ex vivo sample, and includes, without limitation, cell cultures or extracts thereof; tissue or organ samples or extracts thereof; biopsied material obtained from a mammal or extracts thereof; and blood, saliva, urine, feces, semen, tears, or other body fluids or extracts thereof.

Inhibition of kinase activity, particularly JAK kinase activity, in a biological sample is useful for a variety of purposes that are known to one of skill in the art. Examples of such purposes include, but are not limited to, blood transfusion, organ-transplantation, biological specimen storage, and biological assays.

In certain embodiments of the present invention an "effective amount" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like.

In an alternate embodiment, the methods of this invention comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

Methodology for Synthesis and Characterization of Compounds

The compounds of this invention may be prepared in general by methods known to those skilled in the art for analogous compounds or by those methods depicted in the Examples below. See, e.g., the examples described in WO 2005/095400, which is herein incorporated by reference in its entirety.

All references provided in the Examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

EXAMPLES

Example 1

Preparation of Compounds of the Invention

General Synthetic Scheme

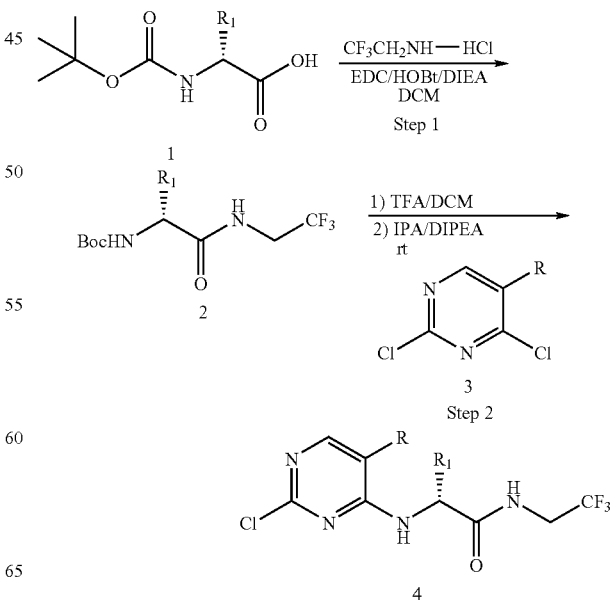

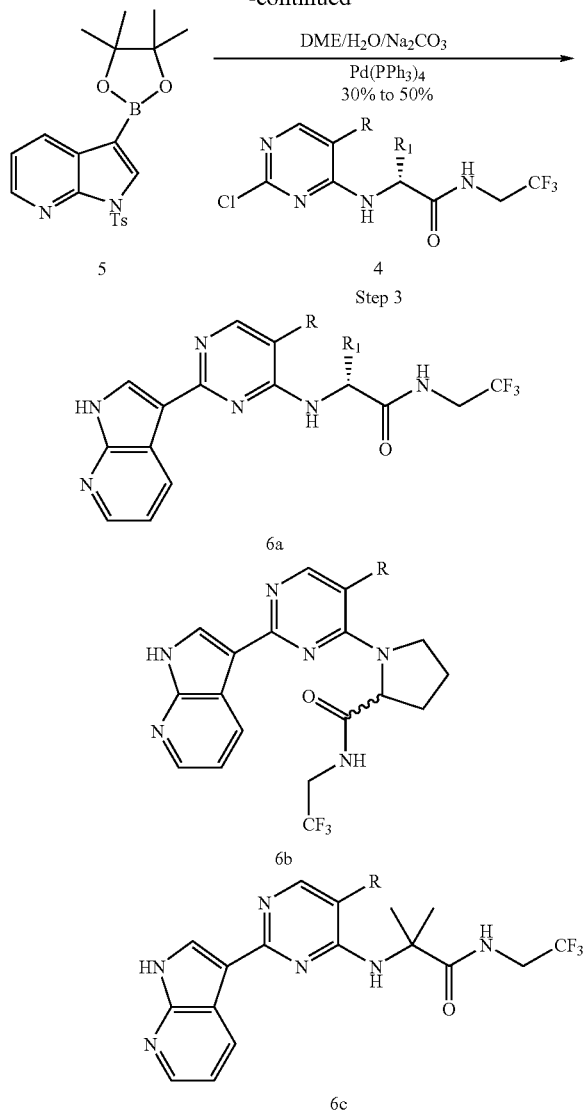

Step 1

To a stirred solution of Boc-valine (1; $R_1$ is Me; 3.8 g, 0.02 mol), EDC (4.63 g, 0.024 mol), HOBt (4.0 g, 0.026 mol), DIEA (10.5 mL, 0.06 mol) in 100 mL of DCM is added trifluoroethylamine HCl (2.92 g, 0.022 mol). The reaction mixture is stirred for 16 h. It is concentrated to dryness and redissolved in EtOAc, washed successively with 0.5N HCl, saturated aqueous solution of $NaHCO_3$ and brine. The organic layer is dried ($Na_2SO_4$) and concentrated in vacuo to give 5.4 g (98%) of 2 as a white solid.

Step 2

Compound 2 (5.32 g, 0.0197 mol) is deprotected with a 1:1 mixture of DCM/TFA at rt for 45 min. Concentration to dryness gives the intermediate amine that is used directly for the next step. A mixture of 5-fluoro-2,4-dichloropyrimidine (3; R is F; 3.28 g, 0.0197 mol), the crude amine TFA salt (5.25 g, 0.0197 mol) and DIEA (10.27 mL, 0.059 mol) are stirred in isopropanol at rt for 16 h. The reaction mixture is concentrated in vacuo and redissolved in EtOAc, washed successively with 0.5N HCl, saturated aqueous solution of $NaHCO_3$ and brine. The organic layer is dried ($Na_2SO_4$) and concentrated in vacuo to give a crude oil that is subjected to chromatography (50% EtOAc/50% hexanes) to yield the desired compound 4.

Step 3

A mixture of 5 (30 mg, 0.075 mmol; prepared according to WO 2005/095400), 4 (23 mg, 0.075 mmol), Pd($Ph_3P)_4$ (9 mg, 0.0078 mmol) and sodium carbonate 2M (115 uL, 0.23 mmol) in 1 mL of DME is microwaved at 150° C. for 10 minutes. The reaction mixture is filtered through a short pad of silica gel with 30% EtOAc-70% hexanes as eluent to provide, after concentration to dryness, the crude intermediate that is used directly for the next step.

The crude intermediate is dissolved in 1 mL of dry methanol and 200 uL of sodium methoxide in methanol 25% was added. The reaction mixture is stirred at 60° C. for 1 h and quenched with 6N HCl (154 uL). The mixture is dried under a flow of nitrogen and purified by reverse phase HPLC (10-60 MeCN/water w/0.5% TFA) to provide the desired material of formula 6a.

Compounds of formulae 6b and 6c may be prepared in an analogous manner using the appropriate starting reagents. For instance, a compound of formula 6b may generally be made by substituting Cert-butyl 2-(2,2,2-trifluoroethylcarbamoyl) pyrrolidine-1-carboxylate for compound 1, while a compound of formula 6c may generally be made by substituting tert-butyl 2-(2,2,2-trifluoroethylcarbamoyl)propan-2-ylcarbamate for compound 1.

Example 2

Analytical Results

Tables 4, 5 and 6 below depicts exemplary $^1$H-NMR data (NMR) and liquid chromatographic mass spectral data, reported as mass plus proton (M+H), as determined by electrospray, and retention time (RT) for certain compounds of the present invention, wherein compound numbers in Tables 4, 5 and 6 correspond to the compounds depicted in Tables 1, 2 and 3, respectively (empty cells indicate that the test was not performed):

TABLE 4

| Cmpd # | M + H | RT | NMR |
|---|---|---|---|
| 1 | 442.90 | 2.20 | DMSO-d6: 12.4 (br s, 1H); 8.7 (dd, 1H); 8.65 (s, 1H); 8.25 (m, 2H); 8.2 (m, 1H); 4.8 (d, 1H); 4.0-3.8 (m, 4H); 2.3 (m, 1H); 2.05-1.9 (m, 3H) |
| 2 | 442.90 | 2.20 | DMSO-d6: 12.4 (br s, 1H); 8.7 (dd, 1H); 8.65 (s, 1H); 8.25 (m, 2H); 8.2 (m, 1H); 4.8 (d, 1H); 4.0-3.8 (m, 4H); 2.3 (m, 1H); 2.05-1.9 (m, 3H) |
| 3 | 430.90 | 2.50 | (CD3OD) 1.7 (s, 6H), 3.8 (m, 2H), 8.15 (s, 1H), 8.2 (d, 1H), 8.25 (m, 1H), 8.5 (t, 1H), 8.85 (d, 1H) |
| 4 | 463.00 | 1.90 | (CD3OD) 1.9 (s, 6H), 3.8 (m, 2H), 7.75 (t, 1H), 7.9 (d, 1H), 8.05 (t, 1H), 8.35 (d, 1H), 8.55 (d + t, 2H), 8.7 (s, 1H), 8.85 (d, 1H) |
| 5 | 399.00 | 1.70 | DMSO-d6: 8.92 (m, 1H); 8.60 (m, 2H); 8.32 (s, 1H); 8.18 (m, 1H); 6.65 (m, 1H); 6.72 (m, 1H); 4.80 (m, 1H); 4.00 (m, 2H); 1.42 9d, 3H) |
| 6 | 417.00 | 2.40 | DMSO-d6: 8.70 (dd, 1H); 8.65 *s, 1H); 8.28 (m, 2H); 8.20 (m, 1H); 7.90 (m, 1H); 4.62 (m, 1H); 3.88 (m, 2H); 1.41 (d, 3H) |
| 7 | 449.00 | 2.10 | DMSO-d6: 8.86 (m, 1H); 8.76 (m, 1H); 8.55 (m, 1H); 8.40 (m, 1H); 7.96 (m, 1H); 7.85 (m, 1H); 7.70 (m, 1H); 5.00 (m, 1H); 3.98 (m, 2H); 1.58 (d, 3H) |

TABLE 4-continued

| Cmpd # | M + H | RT | NMR |
|---|---|---|---|
| 8 | 459.30 | 1.70 | DMSO-d6: 12.3 (br s, 1H); 8.7 (s, 1H); 8.6 (t, 1H); 8.3 (m, 2H); 8.2 (m, 1H); 4.75 (m, 1H); 4.4 (m, 1H); 4.05-3.7 (m, 5H); 1.9 (m, 1H) |
| 9 | 457.30 | 2.20 | DMSO-d6: 12.3 (br s, 1H); 8.8 (m, 1H); 8.7 (s, 1H); 8.3 (m, 2H); 8.2 (m, 1H); 4.3 (m, 1H); 4.05-3.8 (m, 4H); 2.25 (m, 1H); 2.1 (m, 1H); 1.7 (m, 1H); 1.15 (m, 3H) |
| 10 | 459.30 | 1.80 | DMSO-d6: 12.35 (br s, 1H); 8.8 (m, 1H); 8.65 (s, 1H); 8.25 (m, 2H); 8.15 (m, 1H); 4.6 (m, 1H); 4.3 (m, 1H); 4.05 (m, 1H); 3.9-3.8 (m, 1H); 1.95 (m, 2H) |
| 11 | 455.30 | 2.10 | DMSO-d6: 12.35 (br s, 1H); 8.95 (m, 1H); 8.7 (s, 1H); 8.3 (m, 2H); 8.2 (m, 1H); 4.9 (m, 1H); 4.1-3.9 (m, 4H); 1.8-1.6 (m, 2H); 0.75 (m, 1H); 0.4 (m, 1H) |
| 12 | 459.30 | 1.70 | DMSO-d6: 12.3 (br s, 1H); 8.7 (s, 1H); 8.6 (t, 1H); 8.25 (m, 2H); 8.15 (m, 1H); 4.75 (m, 1H); 4.4 (m, 1H); 4.05-3.65 (m, 5H); 1.9 (m, 1H) |
| 13 | 459.30 | 1.70 | DMSO-d6: 12.3 (br s, 1H); 8.8 (m, 1H); 8.7 (s, 1H); 8.3 (m, 2H); 8.2 (m, 1H); 4.8 (m, 1H); 4.45 (m, 1H); 4.05-3.65 (m, 4H); 2.25 (m, 1H); 1.9 (m, 1H) |
| 14 | 425.00 | 1.70 | DMSO-d6: 12.9 (br s, 1H); 8.9 (m, 1H); 8.6 (m, 2H); 8.4 (s, 1H); 8.35 (m, 1H); 6.7 (m, 1H); 4.9 (m, 1H); 4.1-3.9 (m, 2H); 3.8 (m, 1H); 3.65 (m, 1H); 2.4 (m, 1H); 2.15-1.95 (m, 3H) |
| 15 | 461.30 | 2.10 | |
| 16 | 425.00 | 1.70 | DMSO-d6: 12.9 (br s, 1H); 8.85 (m, 1H); 8.6 (m, 2H); 8.35 (s, 1H); 8.3 (m, 1H); 6.7 (m, 1H); 4.9 (m, 1H); 4.1-3.9 (m, 2H); 3.75 (m, 1H); 3.6 (m, 1H); 2.4 (m, 1H); 2.15-1.95 (m, 3H) |
| 17 | 461.30 | 2.20 | |
| 18 | 427.20 | 1.90 | DMSO d6: 13.0 ppm (bs, 1H); 9.0 (t, 1H); 8.7 (s, 1H); 8.6 (s, 1H); 8.4 (s, 1H); 8.2 (d, 1H); 6.8 (bs, 1H); 4.8 (t, 1H); 4.1 (m, 1H); 3.8 (m, 2H); 2.3 (m, 1H); 1.05 (d, 3H); 1.0 (d, 3H) |
| 19 | 441.20 | 2.00 | DMSO d6: 13.0 ppm (bs, 1H); 9.0 (t, 1H); 8.7 (s, 1H); 8.4 (s, 1H); 8.1 (d, 1H); 6.6 (d, 1H); 4.8 (t, 1H); 3.8-4.2 (m, 4H); 1.7 (bs, 2H); 1.0 (d, 3H); 0.9 (d, 3H) |
| 20 | 445.20 | 2.90 | DMSO d6: 12.4 ppm (bs, 1H); 8.8 (t, 1H); 8.7 (s, 1H); 8.3 (s, 1H); 8.2 (d, 2H); 7.6 (d, 1H); 4.5 (t, 1H); 3.9-4.1 (m, 2H); 2.2 (m, 1H); 1.0 (d, 3H); 0.9 (d, 3H) |
| 21 | 459.20 | 3.00 | DMSO d6: 12.4 ppm (bs, 1H); 8.8 (t, 1H); 8.7 (s, 1H); 8.3 (m, 3H); 7.8 (d, 1H); 4.7 (t, 1H); 3.9 (m, 2H); 1.9 (m, 1H); 1.8 (m, 1H); 1.6 (m, 1H); 1.0 (d, 3H); 0.9 (d, 3H) |
| 22 | 473.20 | 3.40 | DMSO d6: 8.7 ppm (t, 1H); 8.6 (s, 1H); 8.4 (s, 1H); 8.35 (s, 1H); 8.3 (s, 1H); 7.9 (d, 1H); 4.7 (t, 1H); 4.0 (m, 2H); 3.9 (s, 3H); 1.9 (m, 1H); 1.8 (m, 1H); 1.7 (m, 1H); 1.0 (d, 3H); 0.9 (d, 3H) |
| 23 | 431.10 | 2.50 | DMSO d6: 12.4 (bs, 1H); 8.8 (t, 1H); 8.7 (s, 1H); 8.3 (s, 1H); 8.25 (dd, 2H); 7.7 (bs, 1H); 4.5 (q, 1H); 3.8-4.0 (m, 2H); 1.9 (q, 2H); 1.0 (t, 3H) |
| 24 | 413.10 | 1.80 | DMSO d6: 12.9 ppm (bs, 1H); 9.0 (t, 2H); 8.65 (s, 1H); 8.6 (s, 1H); 8.4 (s, 1H); 8.1 (d, 1H); 6.7 (bs, 1H); 4.7 (m, 1H); 3.8-4.2 (m, 2H); 1.9 (m, 2H); 1.0 (t, 3H) |
| 25 | 439.20 | 2.00 | 1H NMR (CD3OD, 500 MHz): 1.53-2.05 (m, 6H), 2.45-2.53 (m, 1H), 3.46-3.59 (m, 1H), 3.83-4.32 (m, 3H), 7.06 (s, br., 1H), 8.18 (d, 1H), 8.38 (d, 1H), 8.42 (s, 1H), 8.83 (s, br., 1H) |
| 26 | 457.10 | 3.20 | 1H NMR (CD3OD, 500 MHz): 1.57-2.03 (m, 6H), 2.37-2.44 (m, 1H), 3.50-3.57 (m, 1H), 3.90-4.09 (m, 2H), 4.49-4.57 (m, 1H), 5.38 (s, br, 1H), 8.26 (s, 1H), 8.28 (s, 1H), 8.31 (d, 1H), 8.60 (d, 1H) |
| 27 | 429.30 | 2.30 | (CD3OD) 1.3 (m, 2H), 1.8 (m, 2H), 3.9 (m, 2H), 8.25 (m, 3H), 8.6 (t, 1H), 8.8 (d, 1H) |
| 28 | 439.20 | 1.90 | DMSO d6: 13.0 ppm (bs, 1H), 9.0 (s, 1H), 8.7 (s, 1H), 8.6 (s, 1H), 8.4 (s, 1H), 8.2 (d, 1H), 6.7 (s, 1H), 4.9 (d, 1H), 3.9-4.1 (m, 3H), 1.9 (q, 1H), 1.6 (q, 1H), 0.9 (bs, 1H), 0.5 (m, 2H), 0.2 (m, 2H) |
| 29 | 457.10 | 2.80 | DMSO d6: 12.4 ppm (bs, 1H), 8.8 (t, 1H), 8.7 (s, 1H), 8.3 (s, 1H), 8.25 (m, 2H), 7.8 (bs, 1H), 4.7 (q, 1H), 3.8-4.0 (m, 3H), 1.9 (m, 1H), 1.6 (m, 1H), 0.9 (m, 1H), 0.4 (m, 2H), 0.2 (m, 2H) |
| 30 | 459.10 | 1.90 | DMSO d6: 12.9 ppm (bs, 1H), 9.0 (s, 1H), 8.7 (s, 1H), 8.6 (s, 1H), 8.4 (s, 1H), 8.2 (d, 1H), 6.7 (s, 1H), 4.9 (s, 1H), 3.9-4.1 (m, 2H), 2.5-2.7 (m, 2H), 2.1 (m, 3H), 2.0 (s, 3H) |
| 31 | 477.10 | 2.70 | DMSO d6: 12.4 ppm (bs, 1H), 8.8 (t, 1H), 8.7 (s, 1H), 8.3 (s, 2H), 8.25 (s, 1H), 7.9 (s, 1H), 4.8 (q, 1H), 3.8-4.0 (m, 2H), 2.5-2.7 (m, 2H), 2.2 (m, 2H), 2.1 (s, 3H) |
| 32 | 458.10 | 1.90 | (d4-methanol) 8.71 (s, 1H), 8.24 (d, 1H), 8.20 (s, 1H), 8.15 (s, 1H), 5.11 (br s, 1H), 4.32 (d, 1H), 4.01-3.55 (m, 4 H), 3.17 (dd, 1H), 3.11-2.95 (m, 2H) |
| 33 | 440.10 | 1.40 | (d4-methanol) 8.72 (d, 1H), 8.28 (d, 1H), 8.22 (s, 1H), 8.21 (d, 1H), 6.65 (d, 1H), 5.25 (br s, 1H), 4.12-3.87 (m, 3 H), 3.57 (d, 1H), 3.44 (dd, 1H), 3.14-2.82 (m, 3 H) |
| 34 | 457.00 | 3.00 | DMSO-d6: 12.4 (s, 1H); 8.65 (s, 1H); 8.35-8.25 (m, 3H); 8.1 (s, 1H); 3.95-3.8 (m, 2H); 3.7 (m, 2H); 2.05 (m, 4H); 1.65 (s, 3H). |
| 35 | 483.10 | 2.80 | |
| 36 | 469.10 | 2.50 | DMSO d6 12.5 (bs, 1H); 9.0 (m, 1H); 8.7 (m, 3H); 8.3 (m, 1H); 4.8 (bs, 1H); 4.0-3.5 (m, 4); 2.3 (m, 1H); 2.0 (m, 3H) |
| 37 | 411.10 | 2.10 | 1H NMR (CD3OD, 500 MHz): 2.42-2.52 (m, 1H), 2.80-2.93 (m, 1H), 3.89-4.14 (m, 2H), 4.27-4.37 (m, 2H), 5.09-5.16 (m, 1H), 7.34 (d, 1H), 8.18 (d, 1H), 8.30 (s, 1H), 8.50 (s, 1H), 8.66 (s, 1H) |
| 38 | 459.10 | 2.90 | 1H NMR (CD3OD, 500 MHz): 3.46-3.69 (m, 2H), 3.88-4.04 (m, 3H), 4.13-4.52 (m, 3H), 4.83-4.90 (m, 1H), 6.47 (d, 1H), 7.44 (d, 1H), 8.00 (d, 1H), 8.14 (d, 1H), 8.27-8.35 (m, 2H), 8.68 (s, 1H) |
| 39 | 458.10 | 1.80 | (d4-methanol) 8.74 (d, 1H), 8.42 (d, 1H), 8.25 (s, 1H), 8.23 (d, 1H), 5.62 (br s, 1H), 4.62 (d, 1H), 4.04-3.95 (m, 3H), 3.66 (ddd, 1H), 3.46 (dd, 1H), 3.41-3.34 (m, 2H) |
| 40 | 440.10 | 1.40 | (d4-methanol) 8.72 (d, 1H), 8.28 (d, 1H), 8.22 (s, 1H), 8.21 (d, 1H), 6.65 (d, 1H), 5.26 (br s, 1H), 4.10-2.84 (m, 8H) |
| 41 | 525.10 | 2.70 | (d4-methanol) 8.72 & 8.70 (2d, 1H), 8.31 & 8.27 (2d, 1H), 8.21 (d, 1H), 8.18 & 8.14 (2s, 1H), 7.35, 7.24 (2d, 1H), 5.36 (br s, 1H), 4.51-3.52 (m, 10 H) |
| 42 | 508.10 | 1.80 | (d4-methanol) 8.73 & 8.70 (2d, 1H), 8.36 & 8.33 (2d, 1H), 8.25 (s, 1H), 8.22 (d, 1H), 6.73, 6.61 (2d, 1H), 5.50, 5.22 (2 br s, 1H), 4.51-3.51 (m, 10 H) |
| 43 | 427.10 | 1.90 | DMSO d6: 13.0 ppm (bs, 1H), 9.0 (s, 1H), 8.6 (d, 2H), 8.4 (s, 1H), 8.2 (d, 1H), 6.7 (s, 1H), 4.8 (s, 1H), 3.8-4.2 (m, 3H), 1.9 (m, 2H), 1.4-1.5 (m, 2H), 0.9 (t, 3H) |
| 44 | 445.10 | 2.70 | DMSO d6: 12.4 ppm (s, 1H), 8.8 (t, 1H), 8.7 (s, 1H), 8.3 (m, 3H), 7.8 (bs, 1H), 4.6 (q, 1H), 3.8-4.0 (m, 2H), 1.8 (m, 2H), 1.3-1.5 (m, 2H), 0.9 (t, 3H) |
| 45 | 425.10 | 2.20 | DMSO-d6: 12.45 (s, 1H); 8.65 (s, 1H); 8.5 (m, 1H); 8.3 (m, 2H); 8.2 (m, 1H); 5.9 (t, 1H); 4.8 (d, 1H); 4.0 (m, 1H); 3.85 (m, 1H); 3.6-3.4 (m, 2H); 2.25 (m, 1H); 2.0 (m, 3H) |

TABLE 4-continued

| Cmpd # | M + H | RT | NMR |
|---|---|---|---|
| 46 | 443.10 | 2.50 | DMSO 1.9 (m, 2H), 2.3 (q, 2H), 2.75 (bq, 2H), 3.8 (m, 2H), 8 (d, 1H), 8.15 (overlap bt, bs, 2H), 8.25 (s, 1H), 8.3 (d, 1H), 8.7 (s, 1H), 12.3 (bs, 1H) |
| 47 | 407.10 | 1.60 | DMSO-d6: 13.0 (br s, 1H); 8.7-8.6 (m, 3H); 8.4 (m, 1H); 8.3 (m, 1H); 6.75 (d, 0.7H); 6.3 (d, 0.3H); 5.9 (t, 1H); 4.9 (d, 0.7H); 4.65 (0.3H); 4.05-3.6 (m, 2H); 2.35 (m, 1H); 2.05 (m, 3H). |
| 48 | 413.10 | 1.70 | (CD3OD) 1.75 (s, 6H), 3.85 (m, 2H), 6.75 (d, 1H), 8.05 (d, 1H), 8.3 (d, 1H), 8.5 (d, 1H), 8.65 (bt, 1H), 8.8 (s, 1H) |
| 49 | 389.10 | 2.00 | DMSO-d6: 12.4 (br s, 1H); 8.65 (s, 1H); 8.3 (m, 2H); 8.25 (m, 1H); 8.05 (m, 1H); 4.7 (d, 1H); 3.95 (m, 1H); 3.8 (m, 1H); 3.5 (m, 1H); 3.1 (m, 1H); 2.25 (m, 1H); 2.0 (m, 3H); 0.95 (m, 3H) |
| 50 | 457.10 | 2.70 | H NMR (500 MHz, Methanol-d4) 8.76 (d, J = 2.3 Hz, 1H), 8.48 (t, J = 6.2 Hz, 1H), 8.31-8.29 (m, 3H), 3.82 (m, 2H), 3.31 (qn, Methanol-d4), 2.55-2.53 (m, 2H), 2.27-2.24 (m, 2H), 1.88 (m, 4H) |
| 51 | 471.10 | 3.07 | |
| 52 | 371.20 | 1.50 | DMSO-d6: 13.0 (s, 1H); 8.75-8.6 (m, 2H); 8.4 (m, 1H); 8.3 (m, 1H); 8.2 (m, 1H); 6.75 (d, 0.7H) 6.35 (d, 0.3H); 4.85 (d, 0.7H); 4.55 (d, 0.3H); 3.8-3.6 (m, 2H); 3.2-3.0 (m, 2H); 2.35 (m, 1H); 2.05 (m, 3H); 1.05 (dd, 0.7H); 0.95 (dd, 2.3H) |
| 53 | 439.20 | 1.80 | DMSO-d6: 12.85 (br s, 1H); 8.7 (s, 1H); 8.5 (s, 1H); 8.4-8.35 (m, 2H); 8.3 (m, 1h); 6.7 (m, 1h); 3.95-3.7 (m, 4H); 2.15 (m, 4H); 1.7 (s, 3H) |
| 54 | 456.80 | 2.95 | DMSO-d6: 12.25 (br s, 1H); 8.7 (s, 1H); 8.3 (m, 3H); 8.0 (m, 1H); 4.1-3.7 (m, 4H); 2.05 (m, 4H); 1.6 (s, 3H) |
| 55 | 439.20 | 1.80 | DMSO-d6: 12.85 (br s, 1H); 8.7 (s, 1H); 8.5 (s, 1H); 8.4-8.35 (m, 2h); 8.3 (d, 1H); 6.7 (m, 1h); 3.95-3.7 (m, 4H); 2.15 (m, 4H); 1.7 (s, 3H) |
| 56 | 469.10 | 2.00 | DMSO-d6: 9.30 (m, 1H); 8.70 (s, 1H); 8.35 (m, 1H); 8.28 (m, 2H); 4.75 (m, 1H); 3.40 (m, 2H); 2.25 (m, 2H); 2.00 (m, 4H) |
| 57 | 497.10 | 2.70 | DMSO-d6: 8.80 (m, 2H); 8.55 (s, 1H); 8.28 (m, 2H); 4.80 (m, 1H); 4.24 (m, 2H); 3.80 (m, 4H); 2.20 (m, 1H); 1.90 (m, 23H); 1.20 (t, 2H) |
| 58 | 441.10 | 2.00 | H NMR (500 MHz, DMSO-d6) 12.9 (bs, 1H), 9.00 (s, 1H), 8.66 (s, 1H), 8.63 (s, 1H), 8.41 (d, J = 2.0 Hz, 1H), 8.16 (d, J = 6.2 Hz, 1H), 6.80 (s, 1H), 4.81 (s, 1H), 4.11-4.06 (m, 1H), 3.87 (m, 2H), 2.00 (m, 1H), 1.66 (m, 1H), 1.27-1.21 (m, 1H), 0.98 (d, J = 6.4 Hz, 3H), 0.92 (t, J = 7.2 Hz, 3H) |
| 59 | 459.10 | 3.10 | H NMR (500 MHz, DMSO-d6) 12.40 (s, 1H), 8.80 (t, J = 6.3 Hz, 1H), 8.71 (d, J = 2.4 Hz, 1H), 8.34 (d, J = 2.8 Hz, 1H), 8.29 (s, 1H), 8.27 (d, 1H), 7.58 (d, J = 6.2 Hz, 1H), 4.57 (t, J = 8.0 Hz, 1H), 4.04-3.98 (m, 1H), 3.89-3.83 (m, 1H), 2.05-1.99 (m, 1H), 1.65-1.60 (m, 1H), 1.33-1.23 (m, 1H), 0.96 (d, J = 3H), 0.88 (t, 3H) |
| 60 | 441.10 | 2.00 | H NMR (500 MHz, DMSO-d6) 13.0 (bs, 1H), 8.98 (s, 1H), 8.66 (s, 1H), 8.62 (s, 1H), 8.41 (d, J = 1.9 Hz, 1H), 8.17 (d, J = 6.3 Hz, 1H), 6.84 (s, 1H), 4.90 (s, 1H), 4.08-4.07 (m, 1H), 3.88 (m, 2H), 2.11-2.08 (m, 1H), 1.50 (t, J = 6.9 Hz, 1H), 1.27 (m, 1H), 1.00 (d, J = 6.9 Hz, 3H), 0.92 (q, J = 7.5 Hz, 3H) |
| 61 | 459.10 | 3.10 | H NMR (500 MHz, DMSO-d6) 12.38 (s, 1H), 8.76 (t, J = 6.3 Hz, 1H), 8.70 (d, J = 2.4 Hz, 1H), 8.28 (m, J = 4.2 Hz, 3H), 8.28 (s, 1H), 7.36 (d, J = 5.7 Hz, 1H), 4.72 (t, 1H), 4.02-3.85 (m, 2H), 2.05 (q, J = 6.8 Hz, 1H), 1.54-1.49 (m, 1H), 1.27-1.21 (m, 1H), 0.99 (d, J = 6.8 Hz, 3H), 0.92 (t, J = 7.4 Hz, 3H) |
| 62 | 441.10 | 2.00 | H NMR (500 MHz, DMSO-d6) 13.01 (s, 1H), 9.05 (s, 1H), 8.78 (s, 1H), 8.64 (s, 1H), 8.42 (d, J = 2.0 Hz, 1H), 8.16 (d, J = 6.4 Hz, 1H), 6.91 (s, 1H), 4.89 (d, J = 8.0 Hz, 1H), 4.15-4.07 (m, 1H), 3.82-3.85 (m, 1H), 1.08 (s, 9H) |
| 63 | 459.10 | 3.30 | H NMR (500 MHz, DMSO-d6) 12.41 (s, 1H), 8.85 (t, J = 6.3 Hz, 1H), 8.74 (d, J = 2.4 Hz, 1H), 8.31 (d, 1H), 8.29 (s, 2H), 6.86 (d, J = 7.8 Hz, 1H), 4.77 (d, J = 8.8 Hz, 1H), 4.09-4.02 (m, 1H), 3.88-3.82 (m, 1H), 1.08 (s, 9H) |
| 64 | 429.10 | 2.39 | 1H NMR (500 MHz, DMSO-d6): 2.45-2.52 (m, 1H), 2.91-3.00 (m, 1H), 3.89-4.14 (m, 2H), 4.50-4.61 (m, 2H), 5.25-5.30 (m, 1H), 8.23-8.30 (m, 3H), 8.63 (s, 1H) |
| 65 | 373.40 | 1.90 | DMSO-d6: 12.9 (br s, 1H); 8.7 (s, 1H); 8.6 (s, 1H); 8.4 (s, 1H); 8.3 (s, 1H); 8.15 (m, 1H); 6.8 (s, 1H); 4.6 (s, 1H); 3.1 (m, 1H); 2.7 (m, 1H); 2.25 (m, 1H); 1.1-0.95 (m, 9H) |
| 66 | 425.10 | 2.20 | H NMR (500 MHz, Methanol-d4) 8.73 (d, J = 2.0 Hz, 1H), 8.46 (s, 1H), 8.40 (s, 1H), 8.35 (d, J = 2.1 Hz, 1H), 8.10 (d, J = 7.2 Hz, 1H), 6.75 (d, J = 7.2 Hz, 1H), 3.85 (m, 2H), 3.01-2.97 (m, 2H), 2.44-2.39 (m, 2H), 2.16 (m, 2H) |
| 67 | 409.20 | 1.80 | DMSO-d6: 13.0 (br s, 1H); 8.75 (m, 1H); 8.65 (s, 1H); 8.6 (s, 1H); 8.4 (s, 1h); 8.15 (d, 1H); 6.8 (m, 1h); 6.05 (t, 1H); 4.75 (m, 1H); 3.75-3.5 (m, 2H); 2.25 (m, 1H); 1.1-0.95 (m, 6H) |
| 68 | 456.60 | 3.83 | 1H NMR (CD3OD, 500 MHz): 1.68-2.00 (m, 6H), 2.26-2.33 (m, 1H), 3.49-3.58 (m, 1H), 3.84-4.02 (m, 2H), 4.45-4.53 (m, 1H), 5.36-5.42 (m, 1H), 6.71 (d, 1H), 8.11-8.39 (m, 4H), 8.86-8.92 (m, 1H) |
| 69 | 497.80 | 1.79 | 1H NMR (CD3OD, 500 MHz): 3.38-4.35 (m, 10H), 4.67 (d, 1H), 5.19-5.54 (m, 1H), 6.80-7.07 (m, 1H), 8.23-8.80 (m, 4H) |
| 70 | 525.80 | 2.08 | 1H NMR (CD3OD, 500 MHz): 1.29 (d, 6H), 3.43-4.30 (m, 7H), 4.68 (d, 1H), 4.86-4.94 (m, 1H), 5.44 (m, br., 1H), 7.01 (s, br., 1H), 8.23-8.58 (m, 4H) |
| 71 | 523.80 | 2.05 | 1H NMR (CD3OD, 500 MHz): 3.40-4.30 (m, 7H), 4.53-4.74 (m, 3H), 5.19-5.54 (m, 3H), 5.92-6.01 (m, 1H), 6.98 (s, br., 1H), 8.24-8.57 (m, 4H) |
| 72 | 459.50 | 2.99 | 10.5 (s, 1H), 8.74 (d, 1H), 8.39 (s, 1H), 8.35 (d, 1H), 8.28 (d, 1H), 7.20 (m, 1H), 6.73 (s, 1H), 4.5-4.8 (s, 6H), 3.98 (m, 1H), 3.68 (m, 1H), 2.32 (m, 1H), 1.70 (s, 3H), 1.08 (dd, 6H) (CD3CN) |
| 73 | 441.20 | 1.80 | |
| 74 | 429.10 | 1.60 | H NMR (500 MHz, DMSO-d6) 12.95 (bs, 1H), 8.78 (s, 1H), 8.65 (s, 1H), 8.59 (s, 1H), 8.39 (d, J = 1.8 Hz, 1H), 8.17 (d, J = 4.8 Hz, 1H), 6.90 (s, 1H), 5.30 (s, 1H), 4.74 (s, 1H), 4.21 (s, 1H), 4.04-3.80 (m, 2H), 1.21 (d, J = 5.7 Hz, 3H) |
| 75 | 423.00 | 1.80 | H NMR (500 MHz, DMSO-d6) 12.95 (bs, 1H), 9.07 (s, 1H), 8.63 (s, 1H), 8.60 (s, 1H), 8.40 (d, J = 2.1 Hz, 1H), 8.20 (s, 1H), 6.75 (s, 1H), 4.99 (s, 1H), 4.05-3.83 (m, 2H), 2.98 (t, J = 2.4 Hz, 1H), 2.80 (d, J = 7.3 Hz, 2H) |
| 76 | 429.10 | 1.60 | H NMR (500 MHz, DMSO-d6) 12.96 (s, 1H), 8.79 (s, 1H), 8.65 (s, 1H), 8.61 (s, 1H), 8.40 (d, J = 2.1 Hz, 1H), 8.20-8.17 (m, 1H), 6.91 (s, 1H), 5.25 (bs, 1H), 4.75 (s, 1H), 4.21 (s, 1H), 4.04-3.88 (m, 2H), 1.22 (d, J = 6.2 Hz, 3H) |
| 77 | 482.40 | 1.69 | 1H NMR (CD3OD, 500 MHz): 2.08 (s, 3H), 3.18-4.97 (m, 9H), 6.87-7.08 (m, 1H), 8.24-8.59 (m, 4H) |
| 78 | 518.40 | 1.83 | 1H NMR (CD3OD, 500 MHz): 2.93 (s, 3H), 3.18-4.97 (m, 9H), 7.00-7.10 (m, 1H), 8.26-8.56 (m, 4H) |
| 79 | 526.50 | 2.00 | 1H NMR (CD3OD, 500 MHz): 0.98 (t, 3H), 1.67-1.74 (m, 2H), 3.18-4.90 (m, 11H), 6.86-7.00 (m, 1H), 8.24-8.59 (m, 4H) |
| 80 | 540.50 | 2.12 | 1H NMR (CD3OD, 500 MHz): 0.97 (d, 6H), 1.91-2.01 (m, 1H), 3.18-4.90 (m, 11H), 6.86-7.00 (m, 1H), 8.24-8.59 (m, 4H) |

TABLE 4-continued

| Cmpd # | M + H | RT | NMR |
|---|---|---|---|
| 81 | 482.50 | 1.61 | 1H NMR (CD3OD, 500 MHz): 2.08 (s, 3H), 3.18-4.97 (m, 9H), 6.87-7.08 (m, 1H), 8.24-8.59 (m, 4H) |
| 82 | 518.40 | 1.82 | 1H NMR (CD3OD, 500 MHz): 2.93 (s, 3H), 3.18-4.97 (m, 9H), 7.00-7.10 (m, 1H), 8.26-8.56 (m, 4H) |
| 83 | 441.20 | 1.50 | DMSO-d6: 12.85 (br s, 1H); 9.05 (s, 0.3H); 8.9 (s, 0.7H); 8.7 (m, 0.3H); 8.65-8.5 (m, 1.7H); 8.4-8.25 (m, 2H); 6.75 (m, 0.7H); 6.2 (m, 0.3H); 4.9 (m, 0.7H); 4.7 (m, 0.3H); 4.5 (m, 1H); 4.05-3.5 (m, 5H); 2.05 (m, 1H) |
| 84 | 473.10 | 2.20 | DMSO-d6: 12.35 (br s, 1H); 8.7 (s, 1H); 8.35-8.1 (m, 4H); 6.4 (m, 1H); 4.7 (dd, 1H); 4.0 (m, 2H); 3.8 (m, 2H); 3.15 (m, 1H); 2.25 (m, 1H); 2.0 (m, 1H) |
| 85 | 459.10 | 2.00 | DMSO-d6: 12.3 (br s, 1H); 8.8 (s, 1H); 8.7 (m, 1H); 8.3 (m, 2H); 8.15 (m, 1H); 4.85 (m, 1H); 4.45 (m, 1H); 4.05-3.7 (m, 5H); 1.9 (m, 1H) |
| 86 | 413.20 | 2.30 | H NMR (500 MHz, DMSO) 12.63 (s, 1H), 8.87-8.86 (bs, 1H), 8.61 (m, 2H), 8.35-8.31 (m, 2H), 7.25 (d, J = 4.8 Hz, 1H), 5.39 (q, J = 7.1 Hz, 1H), 3.95-3.81 (m, 2H), 3.18 (s, 3H), 1.43 (d, J = 6.9 Hz, 3H) |
| 87 | 431.20 | 2.70 | H NMR (500 MHz, DMSO) 12.38 (s, 1H), 8.70-8.65 (m, 2H), 8.32 (d, J = 6.9 Hz, 1H), 8.29 (dd, J = 2.4, 2.8 Hz, 2H), 5.16 (q, J = 7.0 Hz, 1H), 3.95-3.86 (m, 2H), 3.17 (d, J = 4.2 Hz, 3H), 1.46 (d, J = 7.0 Hz, 3H) |
| 88 | 400.10 | 2.30 | DMSO-d6: 12.6 (m, 1H); 8.60 (m, 1H); 8.50 (m, 1H); 8.30 (m, 1H); 8.25 (m, 1H); 4.50 (m, 1H); 3.80 (m, 2H); 1.42 (m, 3H) |
| 89 | 441.20 | 2.10 | H NMR (500 MHz, DMSO) 12.41 (s, 1H), 8.78 (t, J = 6.3 Hz, 1H), 8.71 (d, J = 2.4 Hz, 1H), 8.36 (d, 1H), 8.33 (d, 1H), 8.30 (d, J = 2.4 Hz, 1H), 4.86 (d, J = 10.4 Hz, 1H), 3.98-3.88 (m, 2H), 3.20 (d, J = 4.9 Hz, 3H), 2.44-2.40 (m, 1H), 1.04 (d, J = 6.5 Hz, 3H), 0.90 (d, J = 6.7 Hz, 3H) |
| 90 | 459.10 | 3.40 | H NMR (500 MHz, DMSO) 12.98 (s, 1H), 8.87 (bs, 1H), 8.70 (s, 2H), 8.42 (d, 1H), 8.38 (d, 1H), 5.4 (bs, 1H), 3.97-3.89 (m, 2H), 3.14 (bs, 3H), 2.51-2.42 (m, 1H), 1.03 (bs, 3H), 0.86 (d, J = 6.7 Hz, 3H) |
| 91 | 459.40 | 2.95 | 10.95 (s, 1H), 8.68 (s, 1H), 8.51 (s, 1H), 8.36 (s, 1H), 8.28 (d, 1H), 7.25 (m, 2H), 4.1-4.5 (s, 8H), 3.95 (m, 1H), 3.69 (m, 1H), 2.39 (m, 1H), 1.72 (s, 3H), 1.09 (dd, 6H) (CD3CN) |
| 92 | 445.40 | 2.70 | 10.69 (s, 1H), 8.70 (d, 1H), 8.48 (s, 1H), 8.41 (d, 1H), 8.28 (d, 1H), 7.34 (s, 1H), 7.23 (m, 1H), 3.75-4.2 (m, 26H), 2.20 (m, 2H), 1.72 (s, 3H), 0.93 (t, 3H) (CD3CN) |
| 93 | 487.30 | 2.10 | DMSO-d6: 12.3 (br s, 1H); 8.85 (s, 1H); 8.65 (s, 1H); 8.3 (m, 2H); 8.15 (s, 1H); 4.75 (dd, 1H); 4.25 (m, 1H); 4.05-3.8 (m, 4H); 3.6-3.45 (m, 3H); 2.0 (m, 1H); 1.1 (dd, 3H) |
| 94 | 499.40 | 2.20 | |
| 95 | 469.40 | 1.90 | DMSO-d6: 12.3 (br s, 1H); 9.1-8.3 (m, 5H); 6.75 (m, 0.7H); 6.2 (m, 0.3H); 4.85 (m, 0.7H); 4.6 (m, 0.3H); 4.3 (m, 1H); 4.1-3.5 (m, 7H); 2.1 (m, 1H); 1.1 (dd, 3H) |
| 96 | 481.40 | 2.00 | |
| 97 | 426.10 | 2.51 | DMSO-d6: 12.6 (m, 1H); 8.82 (m, 0.5H); 8.75 (s, 0.5H); 8.62 (m, 1H); 8.58 (s, 0.5H); 8.48 (m, 1H); 8.38 (m, 0.5H); 8.35 (m, 0.5H); 8.22 (m, 0.5H); 4.65-4.55 (m, 1H); 3.80-3.60 (m, 4H); 2.25 (m, 1H); 1.90 (m, 3H) |
| 98 | 414.10 | 2.52 | DMSO-d6: 12.6 (m, 1H); 8.95 (s, 0.5H); 8.70 (m, 0.5H); 8.50 (m, 0.5H); 8.40 (0.5H); 8.20 (m, 2.0H); 8.10-7.90 (m, 1H) |
| 99 | 427.10 | 1.80 | H NMR (500 MHz, DMSO-d6) 13.07 (s, 1H), 9.17 (s, 1H), 8.69-8.66 (m, 3H), 8.61 (m, 1H), 8.39 (d, J = 2.2 Hz, 1H), 8.20 (d, J = 7.1 Hz, 1H), 6.78 (d, J = 6.9 Hz, 1H), 3.83-3.78 (m, 2H), 2.14-2.07 (m, 1H), 2.01-1.94 (m, 1H), 1.61 (s, 3H), 0.88 (t, J = 7.5 Hz, 3H) |
| 100 | 445.10 | 2.70 | H NMR (500 MHz, DMSO-d6) 12.36 (s, 1H), 8.68 (d, J = 2.4 Hz, 1H), 8.41 (t, J = 6.4 Hz, 1H), 8.30-8.27 (m, 2H), 8.11 (s, 1H), 7.53 (s, 1H), 3.85-3.72 (m, 2H), 2.19-2.15 (m, 1H), 1.99-1.95 (m, 1H), 1.55 (s, 3H), 0.81 (t, J = 7.5 Hz, 3H) |
| 101 | 473.21 | 2.55 | DMSO-d6: 12.3 (br s, 1H); 8.8 (s, 1H); 8.7 (s, 1H); 8.3 (m, 2H); 8.15 (m, 1H); 8.75 (m, 1H); 4.15 (m, 1H); 4.1-3.75 (m, 4H); 3.45 (m, 4H); 2.0 (m, 1H) |
| 102 | 487.23 | 2.70 | DMSO-d6: 12.3 (br s, 1H); 8.8 (s, 1H); 8.7 (s, 1H); 8.3 (m, 2H); 8.15 (m, 1H); 4.75 (m, 1H); 4.2 (m, 1H); 4.05-4.75 (m, 4H); 3.5 (m, 3H); 2.0 (m, 1H); 1.1 (dd, 3H) |
| 103 | 455.10 | 1.70 | |
| 104 | 500.10 | 1.90 | |
| 105 | 499.10 | 2.90 | DMSO-d6: 12.35 (br s, 1H); 8.85 (s, 1H); 8.65 (s, 1H); 8.3 (m, 2H); 8.15 (m, 1H); 5.9 (m, 1H); 5.3 (d, 1H); 5.15 (d, 1H); 4.8 (m, 1H); 4.3 (m, 1H); 4.05 (m, 2H); 4.0-3.8 (m, 5H); 2.0 (m, 1H) |
| 106 | 455.10 | 1.70 | |
| 107 | 427.40 | 1.80 | 10.07 (s, 1H), 8.83 (d, 1H), 8.26 (d, 1H), 8.22 (d, 1H), 8.13 (d, 1H), 7.20 (m, 1H), 6.38 (d, 1H), 6.00 (s, 1H), 3.88 (m, 1H), 3.77 (m, 1H), 1.95 (m, 2H), 1.57 (s, 3H), 0.91 (t, 3H) (CD3CN) |
| 108 | 359.40 | 1.65 | |
| 109 | 395.40 | 1.77 | |
| 110 | 441.40 | 1.91 | 10.01 (s, 1H), 8.71 (d, 1H), 8.23 (d, 1H), 8.17 (d, 1H), 8.12 (d, 1H), 7.16 (m, 1H), 6.40 (d, 1H), 5.86 (s, 1H), 3.97 (m, 1H), 3.61 (m, 1H), 1.53 (s, 3H), 1.02 (dd, 6H) (CD3CN) |
| 111 | 414.10 | 2.50 | DMSO-d6: 12.65 (m, 1H); 8.95 (s, 0.5H);, 8.72 (m, 0.5H); 8.70 (m, 0.5H); 8.50 (m, 1H); 8.48 (m, 0.5H); 8.40 (m, 0.5H); 8.30 (m, 0.5H); 8.28 (m, 0.5H); 8.03 (m, 0.5H); 4.45 (m, 1H); 3.80 (m, 2H); 1.75 (m, 2H); 1.00 (m, 3H) |
| 112 | 440.10 | 2.70 | DMSO-d6: 12.68 (m, 1H); 8.98 (s, 0.5H); 8.68 (s, 0.5H); 8.58 (s, 0.5H); 8.48 (s, 0.5H); 8.43 (s, 0.5H); 8.35-8.15 (m, 3.5H); 3.75 (m, 2H); 2.15 (m, 2H); 2.02 (m, 2H); 1.65 (m, 4H) |
| 113 | 426.10 | 2.60 | DMSO-d6: 12.55 (m, 1H); 8.95 (m, 0.5H); 8.68 (m, 0.5H); 8.62 (m, 0.5H); 8.56 (m, 0.5H); 8.52 (m, 0.5H); 8.45 (m, 0.5H); 8.40 (m, 0.5H); 8.35 (m, 1H); 8.22 (0.5H); 8.16 (m, 1H); 3.80 (m, 2H); 2.70 (m, 1H); 2.40 (m, 2H); 2.25 (m, 2H); 1.88 (m, 2H) |
| 114 | 512.10 | 1.80 | DMSO-d6: 12.5 (bs, 1H); 8.95 (bs, 1H); 8.50 (m, 2H); 8.32 (m, 2H); 6.80 (m, 1H); 4.50 (m, 1H); 4.00-3.40 (m, 10H); 1.15 (t, 3H) |
| 115 | 540.10 | 2.10 | |
| 116 | 496.10 | 1.70 | DMSO-d6: 12.6 (m, 1H); 8.95 (m, 1H); 8.50 (m, 2H); 8.32 (m, 2H); 6.80 (m, 1H); 4.50 (m, 1H); 4.00-3.40 (m, 10): 1.15 (t, 3H) |
| 117 | 508.10 | 1.70 | |
| 118 | 522.20 | 1.90 | |
| 119 | 459.30 | 1.70 | DMSO-d6: 12.35 (br s, 1H); 8.8 (m, 1H); 8.65 (s, 1H); 8.3 (m, 2H); 8.15 (m, 1H); 4.8 (m, 1H); 4.4 (m, 1H); 4.05-3.7 (m, 4H); 2.3 (m, 1H); 1.95 (m, 1H) |
| 120 | 441.40 | 1.70 | DMSO-d6: 12.9 (br s, 1H); 9.05 (m, 0.3H); 8.9 (m, 0.7H); 8.7-8.5 (m, 2H); 8.4-8.25 (m, 2H); 6.75 (m, 0.7H); 6.2 (m, 0.3H); 4.95 (m, 0.7H); 4.7 (m, 0.3H); 4.5 (m, 1H); 4.05-3.5 (m, 4H); 2.4 (m, 1H); 2.05 (m, 1H) |
| 121 | 425.00 | 2.03 | 10.1 (s, 1H), 8.89 (s, 1H), 8.29 (m, 3H), 7.27 (s, 1H), 6.51 (d, 1H), 3.88 (m, 2H), 3.30 (s, 6H), 1.86 (m, 1H), 1.57 (m, 1H), 1.43 (m, 1H), 1.19 (m, 1H) (CD3CN) |

TABLE 4-continued

| Cmpd # | M + H | RT | NMR |
|---|---|---|---|
| 122 | 461.30 | 2.40 | |
| 123 | 443.30 | 1.90 | |
| 124 | 487.40 | 2.20 | |
| 125 | 479.40 | 2.30 | |
| 126 | 443.30 | 1.90 | |
| 127 | 439.17 | 1.84 | H NMR (500 MHz, MeOD) 8.79 (d, J = 2.3 Hz, 1H), 8.51 (t, J = 6.4 Hz, 1H), 8.48 (s, 1H), 8.35 (d, J = 2.3 Hz, 1H), 8.06 (d, J = 7.2 Hz, 1H), 6.73 (d, J = 7.2 Hz, 1H), 3.87-3.81 (m, 2H), 2.56-2.52 (m, 2H), 2.25-2.20 (m, 2H), 1.93-1.86 (m, 4H), 0.00 (TMS) |
| 128 | 441.40 | 2.20 | H NMR (500 MHz, DMSO) 8.66 (s, 1H), 8.62 (s, 1H), 8.58 (s, 1H), 8.38 (d, J = 2.0 Hz, 1H), 8.18 (d, J = 7.0 Hz, 1H), 6.81 (s, 1H), 4.09-3.78 (m, 2H), 2.18-2.16 (m, 2H), 2.10 (m, 2H), 0.77 (t, J = 7.4 Hz, 6H), 0.00 (TMS) |
| 129 | 459.40 | 2.40 | |
| 130 | 461.30 | 2.40 | |
| 131 | 377.30 | 1.67 | |
| 132 | 441.09 | 1.65 | H NMR (500 MHz, MeOD) 8.70 (d, J = 2.2 Hz, 1H), 8.48 (s, 1H), 8.36 (d, J = 2.3 Hz, H), 8.12 (d, J = 7.2 Hz, 1H), 7.59 (d, J = 8.2 Hz, 2H *0.7 equiv p-TsOH), 7.37 (d, J = 8.0 Hz, 2H*0.7 equiv p-TsOH), 6.76 (d, J = 7.2 Hz, 1H), 4.41 (d, J = 9.6 Hz, 1H), 4.22 (d, J = 9.5 Hz, 1H), 4.07-4.04 (m, 2H), 3.88-3.83 (m, 2H), 2.88-2.82 (m, 1H), 2.52-2.43 (m, 1H), 2.43 (s, 3H*0.7 equiv p-TsOH), 0.00 (TMS) |
| 133 | 443.30 | 2.86 | |
| 134 | 441.16 | 1.50 | |
| 135 | 455.10 | 1.80 | DMSO-d6: 12.8 (br s, 1H); 9.05-8.85 (m, 1H); 8.8-8.4 (m, 2H); 8.35 (m, 2H); 6.75 (m, 0.8H); 6.2 (m, 0.2H); 4.85 (m, 0.8H); 4.6 (m, 0.2H); 4.2 (m, 1H); 4.0 (m, 1H); 3.9-3.6 (m, 3H); 3.3 (s, 3H); 2.2 (m, 1H) |
| 136 | 455.10 | 1.80 | DMSO-d6: 12.9 (br s, 1H); 8.75-8.25 (m, 5H); 6.75 (m, 0.8H); 8.45 (m, 0.2H); 4.95 (m, 0.8H); 4.75 (m, 0.2H); 4.2 (m, 1H); 4.1-3.7 (m, 4H); 3.2 (s, 3H); 2.3 (m, 1H) |
| 137 | 473.10 | 2.00 | DMSO-d6: 12.35 (br s, 1H); 8.65 (m, 1H); 8.45 (dd, 1H); 8.25 (m, 2H); 8.15 (m, 1H); 4.8 (d, 1H); 4.1 (m, 1H); 4.0 (m, 1H); 3.9 (m, 1H); 3.85 (m, 1H); 3.2 (s, 3H); 2.2 (m, 1H) |
| 138 | 397.00 | 1.74 | (500 MHz, CD3OD) 8.57 (t, J = 6.2 Hz, 1H), 8.50 (s, 1H), 8.48 (d, J = 2.6 Hz, 1H), 8.3 (d, J = 1.2 Hz, 1H), 8.05 (d, J = 7.2 Hz, 1H), 6.7 (d, J = 7.2 Hz, 1H), 3.86-3.8 (m, 2H), 1.74 (s, 6H), 0 (TMS) |
| 139 | 445.10 | 3.30 | H NMR (500 MHz, DMSO) 12.24 (s, 1H), 8.69 (s, 1H), 8.32 (d, J = 6.9 Hz, 1H), 8.24 (m, 2H), 8.15 (s, 1H), 3.68-3.63 (m, 2H), 3.20 (m, 1H), 1.51 (s, 1H) |
| 140 | 427.10 | 1.80 | H NMR (500 MHz, DMSO) 12.7 (bs, 1H), 8.82 (s, 1H), 8.34-8.30 (m, 2H), 8.16 (s, 1H), 8.07 (d, J = 6.2 Hz, 1H), 6.63 (d, J = 6.2 Hz, 1H), 3.77-3.70 (m, 2H), 3.06 (s, 3H), 1.56 (s, 6H) |
| 141 | 431.10 | 2.50 | DMSO-d6: 12.2 (m, 1H); 8.60 (m, 1H); 8.22 (s, 1H); 8.18 (s, 1H); 8.10 (s, 1H); 7.70 (m, 1H); 5.16 (m, 1H); 4.18 (m, 2H); 3.3 (s, 2.5H); 2.9 (s, 0.5H); 1.35 (m, 3H) |
| 142 | 413.10 | 1.80 | DMSO-d6: 12.5 (m, 1H); 8.70 (m, 1H); 8.30 (m, 2H); 8.18 (m, 2H); 6.42 (m, 1H); 5.25 (m, 1H); 4.20 (m, 2H); 3.30 (s, 2.5H); 2.90 (s, 0.5H); 1.32 (m, 3H) |
| 143 | 413.10 | 1.84 | |
| 144 | 377.10 | 1.70 | |
| 145 | 395.10 | 1.74 | |
| 146 | 428.10 | 2.00 | |
| 147 | 411.10 | 2.00 | |
| 148 | 497.10 | 2.40 | |
| 149 | 554.00 | 2.20 | |
| 150 | 498.00 | 1.80 | DMSO-d6: 12.7 (m, 1H); 8.92 (m, 1H); 8.60 (m, 1H); 8.42 (m, 1H); 8.32 (m, 1H); 8.28 (m, 1H); 6.80 (m, 1H); 5.20 (m, 1H); 4.30-3.60 (m, 8H); 3.55 (m, 3H) |
| 151 | 512.00 | 1.90 | DMSO-d6: 12.5 (m, 1H); 8.90 (m, 1H); 8.55 (m, 1H); 8.42 (m, 1H); 8.32 (m, 1H); 8.30 (m, 1H); 6.70 (m, 1H); 5.20 (m, 1H); 4.35-3.55 (m, 10H); 1.15 (t, 3H) |
| 152 | 526.10 | 2.00 | |
| 153 | 526.00 | 2.00 | |
| 154 | 540.10 | 2.10 | |
| 155 | 540.10 | 2.10 | |
| 156 | 532.80 | 3.10 | DMSO-d6: 12.35 (br s, 1H); 8.9 (m, 1H); 8.7 (s, 1H); 8.4-8.1 (m, 3H); 4.85 (dd, 1H); 4.35-4.1 (m, 2H); 4.0-3.7 (m, 2H); 3.3 (m, 4H); 2.85 (m, 1H); 2.4 (m, 1H) |
| 157 | 546.90 | 3.20 | DMSO-d6: 12.35 (br s, 1H); 8.9 (m, 1H); 8.7 (s, 1H); 8.35-8.15 (m, 3H); 4.9 (dd, 1H); 4.1-3.75 (m, 4H); 3.1-2.9 (m, 5H); 2.15 (m, 1H); 1.95 (m, 2H) |
| 158 | 493.90 | 1.70 | |
| 159 | 522.00 | 1.90 | |
| 160 | 524.00 | 1.90 | |
| 161 | 538.00 | 2.10 | |
| 162 | 511.00 | 1.70 | DMSO-d6: 12.8 (m, 1H); 8.90 (m, 1H); 8.55 z9m, 2H); 8.35 (, 2H); 6.80 (m, 1H); 5.25 (, 1H); 4.20-3.60 (m, 8H); 2.62 (s, 6H) |
| 163 | 525.00 | 1.80 | |
| 164 | 560.00 | 2.20 | |
| 165 | 508.00 | 1.80 | |
| 166 | 443.00 | 1.60 | DMSO-d6: 12.8 (br s, 1H); 8.95-8.65 (m, 1H); 8.65-8.45 (m, 2H); 8.4-8.25 (m, 2H); 6.75 (m, 0.7H); 6.25 (m, 0.3H); 5.5 (d, 1H); 5.05 (m, 0.7H); 4.85 (m, 0.3H); 4.2-3.7 (m, 4H); 2.8-2.55 (m, 1H); 2.5-2.35 (m, 1H) |
| 167 | 460.90 | 1.80 | DMSO-d6: 12.75 (br s, 1H); 9.0 (m, 1H); 8.65-8.3 (m, 4H); 6.7 (m, 1H); 5.15 (m, 1H); 4.2 (m, 2H); 4.0 (m, 1H); 3.85 (m, 1H); 3.1 (m, 1H); 2.6 (m, 1H) |
| 168 | 443.00 | 1.60 | DMSO-d6: 12.8 (br s, 1H); 9.2-8.9 (m, 1H); 8.7-8.45 (m, 2H); 8.4-8.3 (m, 2H); 6.75 (m, 0.7H); 6.25 (m, 0.3H); 5.55 (d, 1H); 5.0 (m, 0.7H); 4.8 (m, 0.3H); 4.2-3.7 (m, 4H); 2.9-2.7 (m, 1H); 2.3-2.1 (m, 1H) |
| 169 | 403.10 | 2.20 | DMSO-d6: 12.45 (s, 1H); 8.7 (s, 1H); 8.3 (m, 2H); 8.25 (m, 1H); 8.0 (dd, 1H); 4.7 (m, 1H); 3.95 (m, 1H); 3.8 (m, 1H); 3.05 (m, 1H); 2.95 (m, 1H); 2.25 (m, 1H); 2.0 (m, 3H); 1.4 (m, 2H); 0.75 (m, 3H). |
| 170 | 385.10 | 1.70 | DMSO-d6: 12.9 (br s, 1H); 8.7-8.6 (m, 2H); 8.4 (m, 1H); 8.3 (m, 1H); 8.15 (m, 1H); 6.7 (d, 0.7H); 6.3 (d, 0.3H); 4.85 (d, 0.7H); 4.5 (0.3H); 4.05-3.6 (m, 2H); 3.2-3.05 (m, 1H); 2.9 (m, 1H); 2.35 (m, 1H); 2.05 (m, 3H); 1.5-1.3 (m, 2H); 0.8 (m, 1H); 0.7 (m, 2H). |
| 171 | 387.40 | 2.00 | DMSO-d6: 12.95 (br s, 1H); 8.7 (s, 1H); 8.6 (s, 1H); 8.4 (m, 1H); 8.3 (s, 1H); 8.15 (m, 1H); 6.8 (s, 1H); 4.65 (s, 1H); 3.2 (m, 1H); 3.0 (m, 1H); 2.25 (m, 1H); 1.45 (m, 2H); 1.1-0.95 (m, 6H); 0.85 (m, 3H). |
| 172 | 457.10 | 2.40 | DMSO-d6: 12.35 (br s, 1H); 8.7 (m, 1H); 8.3-8.25 (m, 3H); 8.2 (m, 1H); 4.65 (d, 1H); 4.0 (m, 1H); 3.8 (m, 1H); 3.5-3.3 (m, 2H); 2.4-2.2 (m, 3H); 2.0 (m, 3H). |
| 173 | 439.20 | 1.70 | DMSO-d6: 12.9 (br s, 1H); 8.7-8.65 (m, 2H); 8.45-8.25 (m, 3H); 6.75 (d, 0.8H); 6.3 (d, 0.2H); 4.85 (d, 0.8H); 4.55 (d, 0.2H); 4.05-3.55 (m, 4H); 2.4-2.25 (m, 3H); 2.1-2.0 (m, 3H). |
| 174 | 441.40 | 2.00 | |
| 175 | 373.40 | 1.74 | |
| 176 | 427.30 | 1.87 | |
| 177 | 401.10 | 2.00 | DMSO-d6: 12.45 (s, 1H); 8.7 (s, 1H); 8.3 (m, 2H); 8.25 (s, 1H); 8.15 (s, 1H); 4.6 (d, 1H); 3.9 (m, 1H); 3.8 (m, 1H); 2.6 (m, 1H); 2.25 (m, |

TABLE 4-continued

| Cmpd # | M + H | RT | NMR |
|---|---|---|---|
| | | | 1H); 1.95 (m, 3H); 0.6 (m, 2H); 0.4 (m, 1H); 0.35 (m, 1H). |
| 178 | 383.10 | 1.60 | DMSO-d6: 13.0 (br s, 1H); 8.65 (m, 1H); 8.6 (s, 1H); 8.4 (m, 1H); 8.35-8.2 (m, 2H); 6.75 (d, 0.7H); 6.3 (d, 0.3H); 4.8 (d, 0.7H); 4.5 (0.3H); 4.05-3.6 (m, 2H); 2.7-2.55 (m, 1H); 2.35 (m, 1H); 2.05 (m, 3H); 0.7-0.2 (m, 4H). |
| 179 | 385.40 | 1.90 | DMSO-d6: 12.95 (br s, 1H); 8.7 (s, 1H); 8.6 (s, 1H); 8.4 (s, 1H); 8.35 (s, 1H); 8.15 (m, 1H); 6.8 (s, 1H); 4.6 (s, 1H); 2.7 (m, 1H); 2.25 (m, 1H); 1.05-0.95 (m, 6H); 0.65 (m, 2H); 0.45 (m, 2H). |
| 180 | 371.40 | 1.65 | |

TABLE 5

| Cmpd # | M + H | RT | NMR |
|---|---|---|---|
| 181 | 473.1 | 1.9 | |
| 182 | 415.1 | 1.8 | (500 MHz, DMSO) 12.22 (s, 1H), 8.42 (dd, J = 2.8, 9.9 Hz, 1H), 8.37 (t, J = 6.4 Hz, 1H), 8.26-8.25 (m, 2H), 8.10 (d, J = 2.5 Hz, 1H), 3.78-3.71 (m, 2H), 1.57 (s, 6H), 0.00 (TMS) |
| 183 | 361.1 | 1.6 | (500 MHz, DMSO) 12.27 (s, 1H), 8.47 (dd, J = 2.8, 9.8 Hz, 1H), 8.25 (d, J = 3.0 Hz, 2H), 8.19 (d, J = 2.2 Hz, 1H), 7.75 (t, J = 5.6 Hz, 1H), 7.56 (bs, 1H), 3.02-2.99 (m, 2H), 1.56 (s, 6H), 0.77 (t, J = 7.1 Hz, 3H), 0.00 (TMS) |
| 184 | 379.1 | 1.6 | (500 MHz, DMSO) 12.3 (s, 1H), 8.45 (dd, J = 2.8, 9.8 Hz, 1H), 8.25 (m, 2H), 8.19 (bs, 1H), 8.05 (t, 1H), 7.7 (bs, 1H), 4.2 (dt, 2H, under water), 3.2 (dq, 2H), 1.6 (s, 6H), 0.00 (TMS) |
| 185 | 397.1 | 1.7 | (500 MHz, DMSO) 12.28 (s, 1H), 8.44 (dd, J = 2.8, 9.9 Hz, 1H), 8.27 (d, J = 4.4 Hz, 2H), 8.19 (t, J = 5.9 Hz, 1H), 8.15 (d, J = 2.5 Hz, 1H), 7.69 (bs, 1H), 5.7 (tt, J = 48 Hz, J = 4.3 Hz, 1H), 3.39-3.31 (m, 2H), 1.57 (s, 6H), 0.00 (TMS) |
| 186 | 375.1 | 1.7 | |
| 187 | 361.1 | 2.04 | |
| 188 | 379.1 | 2.21 | |
| 189 | 343.1 | 2.04 | |
| 190 | 357.1 | 2.3 | |
| 191 | 457 | 2.9 | (DMSO-d6) 12.35 (s, 1H); 8.7 (d, 1H); 8.4-8.25 (m, 3H); 8.1 (s, 1H); 4.1 (m, 1H); 3.95 (m, 1H); 3.85 (m, 1H); 3.7 (m, 1H); 2.05 (m, 4H); 1.65 (s, 3H). |
| 192 | 439 | 1.7 | (DMSO-d6) 12.9 (s, 1H); 8.75-8.65 (m, 1.1H); 8.55 (m, 0.9H); 8.45-8.15 (m, 3H); 6.7 (m, 0.9H); 6.1 (m, 0.1H); 4.15 (m, 0.1H); 3.95 (m, 0.9H); 3.8 (m, 3H); 2.2-2.05 (m, 4H); 1.75-1.6 (m, 3H). |
| 193 | 455.1 | 1.8 | (500 MHz, DMSO) 12.95 (s, 1H), 8.71 (s, 1H), 8.59 (bd, 2H), 8.36 (d, J = 2.2 Hz, 1H), 8.23 (d, J = 6.9 Hz, 1H), 6.82 (s, 1H), 3.82-3.77 (m, 4H), 3.66 (t, J = 10.5 Hz, 4H), 2.27-2.20 (m, 2H), 2.20-2.08 (m, 2H), 0.00 (TMS) |
| 194 | 439.1 | 1.7 | (500 MHz, DMSO) 12.89 (s, 1H), 8.61 (m, 2H), 8.46 (d, J = 9.6 Hz, 1H), 8.36 (s, 1H), 8.22 (d, J = 6.9 Hz, 1H), 6.82 (bd, 1H), 3.81-3.79 (m, 4H), 3.67-3.63 (m, 2H), 2.23 (t, J = 10.2 Hz, 2H), 2.12 (m, 2H), 0.00 (TMS) |
| 195 | 409.1 | 1.8 | |
| 196 | 427.08 | 1.7 | |
| 197 | 528.9 | 2 | (DMSO-d6) 12.5 (br s, 1H); 8.9 (m, 1H); 8.65 (m, 1H); 8.4-8.3 (m, 3H); 6.75 (m, 0.5H); 6.5 (m, 0.5H); 4.9 (m, 1H); 4.1-3.7 (m, 4H); 3.1-2.9 (m, 2H, 1H); 1.95 (m, 2H). |
| 198 | 409.1 | 1.9 | (500 MHz, MeOD) 8.91 (d, J = 2.2 Hz, 1H), 8.72 (s, 1H), 8.55 (d, J = 8.3 Hz, 1H), 8.38 (d, J = 2.2 Hz, 1H), 8.03 (t, J = 7.6 Hz, 2H), 7.88 (d, J = 8.3 Hz, 1H), 7.74 (t, J = 7.8 Hz, 1H), 3.21-3.15 (m, 2H), 1.87 (s, 6H), 0.89 (t, J = 7.2 Hz, 3H). |
| 199 | 447.1 | 1.79 | (500 MHz, MeOD) 8.73 (s, 1H), 8.63 (d, J = 9.5 Hz, 1H), 8.57 (m, 2H), 8.33 (s, 1H), 8.03 (m, 1H), 7.89 (d, J = 8.4 Hz, 1H), 7.74 (t, J = 7.7 Hz, 1H), 3.82 (m, 2H), 2.66 (s, 1.3H), 1.88 (s, 6H). (Peak at 2.66 is unidentified.) |
| 200 | 397.1 | 1.65 | (500 MHz, DMSO-d6) 12.90 (s, 1H), 9.05 (s, 1H), 8.66 (s, 1H), 8.40 (s, 1H), 8.37 (s, 1H), 8.16 (d, J = 6.4 Hz, 1H), 6.73 (s, 1H), 4.75 (s, 1H), 4.08-4.01 (m, 2H), 3.87 (d, J = 6.5 Hz, 1H), 1.93-1.83 (m, 2H), 1.00 (t, J = 7.4 Hz, 3H), 0.00 (TMS) |
| 201 | 445 | 1.7 | (DMSO-d6) 12.75 (br s, 1H); 9.0 (dd, 1H); 8.55 (s, 1H); 8.45-8.25 (m, 3H); 6.7 (m, 1H); 5.2 (m, 1H); 4.2 (m, 2H); 4.05-3.7 (m, 2H); 3.1 (m, 1H); 2.6 (m, 1H). |
| 202 | 441 | 2.7 | (DMSO-d6) 12.25 (br s, 1H); 8.4 (d, 1H); 8.35 (dd, 1H); 8.3 (d, 1H); 8.25 (s, 1H); 8.1 (s, 1H); 4.1 (m, 1H); 3.95 (m, 1H); 3.8 (m, 1H); 3.7 (m, 1H); 2.1-2.0 (m, 4H); 1.65 (s, 3H). |
| 203 | 423 | 1.7 | (DMSO-d6) 12.8 (br s, 1H); 8.5-8.2 (m, 5H); 6.7 (m, 1H); 4.0-3.7 (m, 4H); 2.2-2.0 (m, 4H); 1.7 (s, 3H). |
| 204 | 427 | 1.5 | (DMSO-d6) 12.85 (br s, 1H); 9.2-9.0 (m, 1H); 8.7-8.6 (m, 1H); 8.4 (m, 3H); 6.85 (m, 0.8H); 6.25 (m, 0.2H); 5.55 (d, 1H); 5.05 (dd, 0.8H); 4.8 (m, 0.2H); 4.2-3.6 (m, 4H); 2.8 (m, 1H); 2.3-2.15 (m, 1H). |
| 205 | 423.1 | 2 | |
| 206 | 441.1 | 2 | |
| 207 | 459.1 | 2.1 | (500 MHz, DMSO) 13.17 (s, 1H), 8.87 (s, 1H), 8.80-8.60 (m, 2H), 8.40-8.30 (m, 2H), 8.05-7.94 (m, 1H), 7.89 (d, J = 8.3 Hz, 1H), 7.70 (m, 1H), 5.70 (tt, J = 15.1, 3.9 Hz, 1H), 3.40-3.30 (m, 2H), 2.38-2.31 (m, 1H), 2.07 (m, 1H), 1.70 (s, 3H), 0.89 (t, J = 7.5 Hz, 3H). |
| 208 | 477.1 | 2.2 | (500 MHz, DMSO) 8.85 (s, 1H), 8.67-8.55 (m, 3H), 8.39 (s, 1H), 7.99 (m, 1H), 7.89 (d, J = 8.1 Hz, 1H), 7.69 (m, 1H), 3.86-3.71 (m, 2H), 2.40-2.34 (m, 1H), 2.10-2.06 (m, 1H), 1.70 (s, 3H), 0.89 (t, J = 7.5 Hz, 3H). |
| 209 | 359.1 | 1.6 | (500 MHz, MeOD) 8.48 (dd, J = 2.8, 9.3 Hz, 1H), 8.43 (s, 1H), 8.35-8.33 (m, 1H), 8.28-8.27 (m, 1H), 3.21 (q, J = 7.2 Hz, 2H), 1.77-1.75 (m, 2H), 1.29 (m, 2H), 0.97 (t, J = 7.2 Hz, 3H). |
| 210 | 395.1 | 1.7 | (500 MHz, DMSO) 12.35 (s, 1H), 8.57 (s, 1H), 8.39 (d, J = 6.1 Hz, 2H), 8.31 (d, J = 3.9 Hz, 1H), 8.27-8.25 (m, 2H), 5.95-5.71 (m, 1H), 3.45-3.37 (m, 2H), 1.53 (br, 2H), 1.16 (br, 2H). |
| 211 | 413 | 1.8 | (500 MHz, MeOD) 8.46-8.43 (m, 2H), 8.37 (t, J = 4.8 Hz, 1H), 8.27-8.26 (m, 1H), 3.90-3.83 (m, 2H), 1.82 (m, 2H), 1.38 (m, 2H). Multiplet (0.47H) at 8.71, identified as an exchangeable proton that did not fully exchange, which decreased to 0.38H after 1 h. |
| 212 | 373.1 | 1.72 | (500 MHz, DMSO-d6) 13.04 (s, 1H), 9.16 (d, J = 3.2 Hz, 1H), 8.82 (s, 1H), 8.66 (d, J = 3.0 Hz, 1H), 8.39 (d, J = 2.0 Hz, 1H), 8.15 (d, J = 7.0 Hz, 1H), 7.64 (d, J = 7.2 Hz, 1H), 6.68 (d, J = 7.1 Hz, 1H), 3.88-3.84 (m, 1H), 1.60 (s, 6H), 0.84 (d, J = 6.2 Hz, 6H), 0.00 (TMS) |
| 213 | 405.1 | 1.6 | (500 MHz, MeOD) 8.83 (d, J = 2.3 Hz, 1H), 8.58 (s, 1H), 8.35 (d, J = 2.3 Hz, 1H), 8.18 (m, 1H), 4.21 (t, J = 4.8 Hz, 1H), 4.11 (t, J = 4.8 Hz, 1H), 3.37-3.32 (m, 2H), 2.58 (s, 3H), 2.27 (s, 3H), 1.79 (s, 6H). |
| 214 | 423 | 1.71 | (500 MHz, MeOD) 8.79 (d, J = 2.3 Hz, 1H), 8.58 (s, 1H), 8.36 (d, J = 2.3 Hz, 1H), 8.29 (m, 1H), 5.67-5.43 (m, 1H), 3.48-3.38 (m, 2H), 2.58 (s, 3H), 2.27 (s, 3H), 1.79 (s, 6H). |
| 215 | 441 | 1.8 | (500 MHz, MeOD) 8.77 (d, J = 2.3 Hz, 1H), 8.56 (s, 1H), 8.44-8.34 (m, 1H), 8.34 (d, J = 2.2 Hz, 1H), 3.86-3.79 (m, 2H), 2.58 (s, 3H), 2.28 (s, 3H), 1.79 (s, 6H). |

TABLE 5-continued

| Cmpd # | M + H | RT | NMR |
|---|---|---|---|
| 216 | 471 | 2.9 | (500 MHz, DMSO) 12.32 (s, 1H), 8.69 (m, 2H), 8.28-8.13 (m, 3H), 4.9-4.75 (m, 1H), 4.7-4.5 (m, 1H), 3.95-3.75 (m, 3H), 2.15-1.95 (m, 1H), 1.87 (m, 2H), 1.6 (s, 1H), 1.44-1.41 (m, 1H), 1.1-0.85 (m, 3H) |
| 217 | 439 | 1.8 | (500 MHz, MeOD) 8.77 (s, 1H), 8.22-8.19 (m, 3H), 6.40 (s, 1H), 4.69 (s, 1H), 4.32 (bs, 1H), 4.01-3.91 (m, 2H), 2.43-2.38 (m, 1H), 2.27-2.16 (m, 2H), 1.86-1.82 (m, 1H), 1.45 (d, J = 6.0 Hz, 3H) |
| 218 | 457 | 2.7 | (500 MHz, MeOD) 8.78-8.77 (m, 1H), 8.20 (d, J = 2.1 Hz, 1H), 8.15-8.10 (m, 2H), 4.90 (d, J = 9.4 Hz, 1H), 3.94-3.82 (m, 2H), 2.58-2.40 (m, 1H), 2.24-2.21 (m, 1H), 2.0-2.1 (m, 1H), 1.82 (m, 1H), 1.50 (d, 1H), 1.4-1.23 (m, 3H) |
| 219 | 452.9 | 2 | (500 MHz, MeOD) 8.76 (s, 1H), 8.21-8.17 (m, 3H), 6.40 (d, J = 5.9 Hz, 1H), 4.90 (d, J = 9.1 Hz, 1H), 4.04-3.88 (m, 2H), 3.63 (s, 1H), 2.53-2.39 (m, 1H), 2.22-2.11 (m, 3H), 2.01-1.92 (m, 1H), 1.60-1.45 (m, 1H), 1.08 (t, J = 7.2 Hz, 2H), 1.01 (t, J = 7.1 Hz, 3H), |
| 220 | 469.1 | 1.84 | (500 MHz, DMSO) 13.52-13.35 (br, 1H), 13.12-12.96 (br, 1H), 9.07-8.61 (br, 1H), 8.93 (s, 1H), 8.37 (s, 1H), 8.07-7.54 (m, 2H), 7.40-7.27 (br, 1H), 3.02-2.97 (m, 2H), 1.71 (s, 6H), 0.72 (t, J = 7.1 Hz, 3H). |
| 221 | 487.1 | 1.85 | (500 MHz, MeOD) 8.93 (d, J = 2.3 Hz, 1H), 8.61 (s, 1H), 8.37 (d, J = 2.2 Hz, 1H), 8.21 (m, 1H), 7.98 (s, 1H), 7.31 (s, 1H), 4.20 (t, J = 4.8 Hz, 1H), 4.11 (t, J = 4.9 Hz, 1H), 4.07 (s, 3H), 4.06 (s, 3H), 3.36-3.35 (m, 2H), 1.87 (s, 6H). |
| 222 | 505.1 | 1.9 | (500 MHz, MeOD) 8.89 (d, J = 2.3 Hz, 1H), 8.61 (s, 1H), 8.37 (d, J = 2.3 Hz, 1H), 8.33 (m, 1H), 7.99 (s, 1H), 7.32 (s, 1H), 5.67-5.43 (m, 1H), 4.07 (s, 3H), 4.06 (s, 3H), 3.35-3.33 (m, 2H), 1.87 (s, 6H). |
| 223 | 483 | 1.9 | (500 MHz, MeOD) 8.91 (d, J = 2.3 Hz, 1H), 8.62 (s, 1H), 8.37 (d, J = 2.3 Hz, 1H), 7.98 (s, 1H), 7.31 (s, 1H), 4.07 (s, 3H), 4.07 (s, 3H), 3.12-3.08 (m, 2H), 1.86 (s, 6H), 1.33-1.25 (m, 2H), 0.62 (t, J = 7.5 Hz, 3H). |
| 224 | 329.05 | 1.4 | (500 MHz, MeOD) 8.49 (d, J = 3.2 Hz, 1H), 8.45-8.40 (m, 1H), 8.33 (d, J = 1.5 Hz, 1H), 8.03 (d, J = 7.1 Hz, 1H), 6.69 (d, J = 6.9 Hz, 1H), 4.77-4.75 (m, 1H), 3.3 (m overlap with meoh signal, 2H), 1.61 (d, 7.1 Hz, 3H), 1.10 (t, J = 7.2 Hz, 3H), 0.00 (TMS) |
| 225 | 346.93 | 1.4 | |
| 226 | 365 | 1.4 | (500 MHz, MeOD) 8.49 (s, 1H), 8.41 (d, J = 7.9 Hz, 1H), 8.33-8.32 (m, 1H), 8.04 (d, J = 6.9 Hz, 1H), 6.70 (d, J = 6.6 Hz, 1H), 5.84 (t, J = 55.8 Hz, 1H), 3.74-3.44 (2m, 2H), 1.63 (d, J = 7.2 Hz, 3H), 0.00 (TMS) |
| 227 | 383 | 1.6 | |
| 228 | 391.1 | 2.3 | (500 MHz, DMSO) 12.96 (s, 1H), 8.65 (s, 1H), 8.42-8.38 (m, 2H), 8.25 (s, 1H), 8.20 (d, J = 7.0 Hz, 1H), 6.68 (d, J = 6.8 Hz, 1H), 5.76 (t, J = 56.1 Hz, 1H), 3.43-3.37 (m, 2H), 2.81-2.78 (m, 2H), 2.30 (dd, J = 8.6, 18.9 Hz, 2H), 2.01 (qn, J = 8.1 Hz, 2H), 0.00 (TMS) |
| 229 | 409.1 | 2.4 | (500 MHz, DMSO) 12.91 (s, 1H), 8.62 (s, 1H), 8.46 (s, 1H), 8.41 (d, J = 8.8 Hz, 1H), 8.36 (s, 1H), 8.20 (d, J = 6.7 Hz, 1H), 6.66 (d, J = 6.6 Hz, 1H), 3.82-3.79 (m, 2H), 2.84 (m, 2H), 2.32-2.28 (m, 2H), 2.02-1.95 (m, 2H), 0.00 (TMS) |
| 230 | 369.2 | 1.6 | (500 MHz, DMSO) 12.92 (s, 1H), 8.63 (s, 1H), 8.47 (d, J = 8.5 Hz, 1H), 8.37 (s, 1H), 8.18 (d, J = 6.8 Hz, 1H), 7.84 (s, 1H), 6.65 (d, J = 6.5 Hz, 1H), 2.97 (m, 2H), 2.79 (m, 2H), 2.26 (m, 2H), 2.00 (m, 2H), 1.23 (dd, J = 6.9, 14.1 Hz, 2H), 0.54 (t, J = 7.1 Hz, 3H), 0.00 (TMS) |
| 231 | 373.1 | 1.76 | (500 MHz, DMSO-d6) 13.02 (s, 1H), 8.99 (s, 1H), 8.76 (s, 1H), 8.63 (s, 1H), 8.39 (d, J = 2.3 Hz, 1H), 8.16 (d, J = 6.7 Hz, 1H), 7.92 (s, 1H), 6.75 (d, J = 4.9 Hz, 1H), 3.07-3.05 (m, 2H), 2.10-1.93 (m, 2H), 1.58 (s, 3H), 0.86 (t, J = 7.5 Hz, 3H), 0.81 (s, 3H), 0.00 (TMS) |
| 232 | 391.1 | 1.77 | (500 MHz, DMSO-d6) 13.66-13.49 (m, 1H), 12.96-12.93 (m, 1H), 8.76 (s, 1H), 8.57 (d, J = 10.2 Hz, 1H), 8.37 (s, 1H), 8.16-8.13 (m, 2H), 6.68 (d, J = 9.6 Hz, 1H), 4.21 (d, J = 51.9 Hz, 2H), 3.28 (q, J = 5.4 Hz, 2H), 2.10-1.94 (m, 2H), 1.57 (s, 3H), 0.87 (t, J = 7.5 Hz, 3H), 0.00 (TMS) |
| 233 | 409.1 | 1.87 | (500 MHz, DMSO-d6) 13.02 (s, 1H), 9.05 (s, 1H), 8.70 (s, 1H), 8.62 (s, 1H), 8.39 (d, J = 2.2 Hz, 1H), 8.35 (s, 1H), 8.18 (d, J = 7.0 Hz, 1H), 6.75 (d, J = 5.6 Hz, 1H), 5.86-5.64 (m, 1H), 3.43-3.37 (m, 2H), 2.12-1.93 (m, 2H), 1.59 (s, 3H), 0.88 (t, J = 7.5 Hz, 3H), 0.00 (TMS) |
| 234 | 387.1 | 1.87 | (500 MHz, DMSO-d6) 13.56 (s, 1H), 12.89 (s, 1H), 8.89 (s, 1H), 8.57 (s, 1H), 8.36 (s, 1H), 8.16 (d, J = 6.8 Hz, 1H), 6.63 (s, 1H), 3.24 (s, 3H), 2.94 (s, 2H), 2.20-1.87 (m, 2H), 1.57 (s, 3H), 0.87 (t, J = 7.4 Hz, 3H), 0.75 (s, 3H), 0.00 (TMS) |
| 235 | 523.1 | 1.9 | |
| 236 | 355.2 | 1.8 | |
| 237 | 373.1 | 1.8 | |
| 238 | 398 | 2.6 | (DMSO-d6) 12.56 (m, 1H); 8.80 (m, 0.5H); 8.55 (s, 0.5H); 8.50 (s, 0.5H); 8.45 (m, 1.0H); 8.40-8.30 (m, 1.5H); 8.28 (m, 1.5H); 8.10 (m, 0.5H); 3.80 (m, 2H); 1.42 (m, 6H). |
| 239 | 410.9 | 1.7 | (500 MHz, DMSO) (warmed at 100 C.) 12.26 (s, 1H), 8.84 (d, J = 2.2 Hz, 1H), 8.43 (bs, 1H), 8.38 (s, 1H), 8.29 (d, J = 2.4 Hz, 1H), 8.23 (d, J = 6.3 Hz, 1H), 8.13 (bt, 1H), 6.46 (d, J = 6.3 Hz, 1H), 3.93-3.83 (m, 2H), 1.62-1.60 (m, 2H), 1.23-1.17 (m, 2H), 0.0 (TMS) |
| 240 | 395 | 1.6 | (500 MHz, CD3OD, RT) 8.8 (m, 0.6 H); 8.65 (bt, 1H); 8.5 (s, 1H), 8.45 (bd, 1H); 8.25 (m, 1.3H); 8.1 (d, 0.8 H); 6.7 (d, 1H); 3.9 (m, 2H), 1.8 (bm, 2H), 1.35 (bm, 2H), 0 (TMS) |
| 241 | 371.1 | 1.76 | |
| 242 | 393.1 | 1.77 | |
| 243 | 411.1 | 1.86 | |
| 244 | 341.1 | 1.5 | (500 MHz, MeOD, rt, contains conformers) 8.77 (dd, J = 2.8, 9.2 Hz, 0.29H), 8.54-8.49 (m, 1.66H), 8.31 (d, J = 1.5 Hz, 1H), 8.26-8.24 (m, 0.3H), 8.10 (dd, J = 4.3, 7.2 Hz, 0.82H), 6.70 (d, J = 7.3 Hz, 0.29H), 6.66 (dd, J = 4.3, 7.2 Hz, 0.71H), 3.27-3.18 (m, 2H), 1.77-1.72 (m, 2H), 1.28-1.24 (m, 2H), 1.09 (t, J = 7.1 Hz, 0.98H), 0.96 (t, J = 7.1 Hz, 2.2H). |
| 245 | 359.1 | 1.6 | (500 MHz, MeOD, rt, contains conformers) 8.82-8.72 (m, 0.26H), 8.50 (m, 1.67H), 8.43-8.31 (m, 1.84H), 8.25 (br, 0.26H), 8.10 (d, J = 6.4 Hz, 0.72H), 6.70-6.65 (m, 1H), 4.48-4.25 (m, 2H), 3.49-3.37 (m, 2H), 1.80 (m, 2H), 1.27 (br, 2H). |
| 246 | 377.1 | 1.65 | (500 MHz, MeOD, rt, contains conformers) 8.77 (dd, J = 2.8, 9.1 Hz, 0.28H), 8.57-8.45 (m, 2.29H), 8.32 (d, J = 1.5 Hz, 1H), 8.27-8.26 (m, 0.29H), 8.11 (dd, J = 4.0, 7.1 Hz, 0.74H), 6.72 (d, J = 7.3 Hz, 0.29H), 6.68 (d, J = 7.1 Hz, 0.73H), 5.89-5.60 (m, 1H), 3.59-3.47 (m, 2H), 1.80-1.76 (m, 2H), 1.34-1.30 (m, 2H). |
| 247 | 355.1 | 1.6 | (500 MHz, MeOD, rt, contains conformers) 8.77 (dd, J = 2.8, 9.3 Hz, 0.28H), 8.56-8.50 (m, 1.68H), 8.31 (d, J = 1.5 Hz, 1H), 8.26 (m, 2H), 8.10 (dd, J = 4.4, 7.2 Hz, 0.75H), 6.72-6.70 (m, 0.29H), 6.67 (m, 0.72H), 3.18-3.12 (m, 2H), 1.77-1.72 (m, 2H), 1.50 (m, 0.6H), 1.38 (m, 1.57H), 1.29-1.24 (m, 2H), 0.87 (t, J = 7.4 Hz, 0.92H), 0.67 (t, J = 7.3 Hz, 2.2H). |
| 248 | 460.9 | 2.7 | (DMSO-d6) 12.4 (s, 1H); 8.9 (m, 1H); 8.65 (s, 1H); 8.35 (d, 1H); 8.3 (s, 1H); 8.2 (m, 1H); 5.5 (d, 1H); 4.9 (m, 1H); 4.3-3.8 (m, 4H); 2.7 (m, 1H); 2.2-2.0 (m, 1H). |
| 249 | 478.9 | 2.9 | (DMSO-d6) 12.4 (s, 1H); 8.9 (m, 1H); 8.65 (s, 1H); 8.4 (d, 1H); 8.3 (m, 1H); 8.2 (m, 1H); 5.05 (m, 1H); 4.3 (m, 2H); 3.9 (m, 2H); 3.0 (m, 1H); 2.5 (m, 1H). |
| 250 | 373 | 1.59 | (500 MHz, MeOD) 8.81 (d, J = 2.1 Hz, 1H), 8.45 (s, 1H), 8.36 (d, J = 2.1 Hz, 1H), 7.99 (s, 1H), 3.98 (s, 1H), 3.19 (q, J = 7.2 Hz, 2H), 2.31 (s, 3H), 1.79 (s, 6H), 0.90 (t, J = 7.2 Hz, 3H). |

TABLE 5-continued

| Cmpd # | M + H | RT | NMR |
|---|---|---|---|
| 251 | 391 | 1.61 | (500 MHz, DMSO) 13.07-12.73 (br, 1H), 8.83 (d, J = 2.0 Hz, 1H), 8.55 (s, 1H), 8.36 (d, J = 1.8 Hz, 1H), 8.12 (s, 1H), 8.09 (br, 1H), 4.18 (t, J = 5.1 Hz, 1H), 4.08 (t, J = 5.1 Hz, 1H), 3.27 (q, J = 5.3 Hz, 1H), 3.22 (q, J = 5.3 Hz, 1H), 2.24 (s, 3H), 1.65 (s, 6H). |
| 252 | 409.1 | 1.69 | (500 MHz, MeOD) 8.79 (d, J = 2.1 Hz, 1H), 8.44 (s, 1H), 8.37 (d, J = 2.0 Hz, 1H), 8.32 (br, 1H), 8.01 (s, 1H), 5.58 (m, 1H), 3.48-3.42 (m, 2H), 2.31 (s, 3H), 1.79 (s, 6H). |
| 253 | 427.1 | 1.77 | (500 MHz, MeOD) 8.78 (s, 1H), 8.46 (br, 1H), 8.42 (s, 1H), 8.35 (s, 1H), 8.01 (s, 1H), 3.85-3.82 (m, 2H), 2.32 (s, 3H), 1.79 (s, 6H). Unidentified peak at d 1.94. |
| 254 | 387 | 1.66 | (500 MHz, MeOD) 8.81 (d, J = 2.0 Hz, 1H), 8.45 (s, 1H), 8.36 (d, J = 2.0 Hz, 1H), 8.00 (s, 1H), 3.98 (s, 1H), 3.12-3.09 (m, 2H), 2.31 (s, 3H), 1.79 (s, 6H), 1.33 (m, 2H), 0.67 (t, J = 7.4 Hz, 3H). |
| 255 | 344 | 2 | (500 MHz, MeOD) 8.79 (br, 0.27H), 8.59 (d, J = 8.9 Hz, 0.69H), 8.53 (s, 1H), 8.47 (s, 1H), 8.24 (s, 1H), 3.17 (m, 2H), 1.66 (s, 6H), 1.08 (br, 0.93H), 0.91 (m, 2.14H). |
| 256 | 385 | 1.9 | |
| 257 | 403 | 1.8 | |
| 258 | 421 | 2 | |
| 259 | 399.1 | 2 | |
| 260 | 428 | 2.7 | (500 MHz, MeOD) 9.07 (s, 0.33H), 8.78 (s, 0.56H), 8.57-8.31 (m, 3.58H), 3.88 (m, 2H), 2.18 (m, 1H), 2.05-2.03 (m, 1H), 1.66 (m, 3H), 0.96 (t, J = 7.4 Hz, 3H). |
| 261 | 412 | 2.5 | (500 MHz, MeOD) 8.80 (m, 0.35H), 8.56-8.47 (m, 3.2H), 8.40 (m, 0.36H), 8.26 (m, 1H), 3.85 (m, 2H), 2.18 (m, 1H), 2.04 (m, 1H), 1.66 (m, 3H), 0.96 (t, J = 7.5 Hz, 3H). |
| 262 | 360 | 2.1 | |
| 263 | 445 | 2.4 | (DMSO-d6) 12.3 (br s, 1H); 8.9 (m, 1H); 8.4 (d, 1H); 8.35 (d, 1H); 8.25 (s, 1H); 8.2 (s, 1H); 5.5 (d, 1H); 4.9 (dd, 1H); 4.3-3.75 (m, 4H); 2.7 (m, 1H); 2.2-2.0 (m, 1H). |
| 264 | 463 | 2.8 | (DMSO-d6) 12.3 (br s, 1H); 8.9 (dd, 1H); 8.4-8.3 (m, 2H); 8.25-8.2 (m, 2H); 5.05 (d, 1H); 4.35 (m, 2H); 3.9 (m, 2H); 3.0 (m, 1H); 2.5 (m, 1H). |
| 265 | 432.2 | 2.6 | (CD3CN) 10.40 (s, 1H), 8.80 (s, 1H), 8.29 (m, 3H), 6.97 (m, 1H), 5.22 (m, 1H), 4.79 (m, 1H), 4.43 (dt, 2H), 3.49 (dt, 2H), 2.54 (m, 1H), 2.43 (m, 1H), 2.39 (m, 1H), 2.22 (m, 1H). |
| 266 | 450.2 | 2.7 | (CD3CN) 10.48 (s, 1H), 8.79 (s, 1H), 8.30 (m, 3H), 7.01 (t, 1H), 5.90 (tt, 1H), 5.24 (m, 1H), 5.83 (m, 1H), 3.60 (m, 2H), 2.53 (m, 1H), 2.42 (m, 1H), 2.36 (m, 1H), 2.21 (m, 1H) |
| 267 | 468.2 | 2.86 | (CD3CN) 10.38 (s, 1H), 8.79 (s, 1H), 8.29 (m, 3H), 7.21 (t, 1H), 5.21 (m, 1H), 4.83 (m, 1H), 3.99 (m, 1H), 3.86 (m, 1H), 2.51 (m, 1H), 2.45 (m, 1H), 2.35 (m, 1H), 2.20 (m, 1H) |
| 268 | 450.1 | 1.88 | |
| 269 | 450.1 | 1.93 | |
| 270 | 374.1 | 2.3 | (500 MHz, MeOD) 9.05 (s, 0.32H), 8.84 (s, 0.65H), 8.53 (s, 1H), 8.43 (s, 1H), 8.29 (s, 1H), 3.27-3.17 (m, 2H), 2.18-2.10 (m, 1H), 2.07-2.00 (m, 1H), 1.64 (m, 3H), 1.08 (m, 1H), 0.95 (t, J = 7.4 Hz, 5H). |
| 271 | 358 | 2.1 | (500 MHz, MeOD) 8.78 (br, 0.33H), 8.58 (d, J = 8.6 Hz, 0.81H), 8.53 (s, 1H), 8.46 (s, 1H), 8.24 (s, 1H), 3.26-3.16 (m, 2H), 2.17-2.13 (m, 1H), 2.01 (m, 1H), 1.71-1.57 (m, 3H), 0.95 (t, J = 7.5 Hz, 6H). |
| 272 | 450 | 2.4 | (500 MHz, MeOD) 8.87 (s, 1H), 8.56 (bt, 1H), 8.53 (s, 1H), 8.43 (d, J = 6.9 Hz, 1H), 8.35 (d, J = 2.2 Hz, 1H), 6.91 (d, J = 6.7 Hz, 1H), 5.09 (apparent d, 1H), 4.86 (apparent d, 1H), 4.02-3.96 (m, 1H), 3.87-3.81 (m, 1H), 2.03 (m, 1H), 1.88-1.80 (m, 2H), 1.48-1.43 (m, 1H), 0.00 (TMS) |
| 273 | 464.1 | 2.5 | (500 MHz, MeOD) 8.86 (d, J = 2.1 Hz, 1H), 8.44 (t, 1H), 8.40 (s, 1H), 8.37 (d, J = 6.6 Hz, 1H), 8.31 (d, J = 2.2 Hz, 1H), 6.52 (bs, 1H), 4.85 (s, 2H), 3.93 (m, 2H), 2.86 (m, 2H), 2.72 (m, 2H), 2.25 (m, 1H), 2.06 (m, 1H), 0.00 (TMS) |
| 274 | 428 | 2.4 | (DMSO-d6) (rotational mixture about 1.3:1): 12.6 (m, 1H); 9.0 (dd, 0.6H); 8.8 (dd, 0.4H); 8.65-8.3 (m, 4H); 5.6-5.35 (m, 1H); 4.8 (t, 0.6H); 4.7 (t, 0.4H); 4.35 (m, 0.4H); 4.2 (m, 0.6H) 4.1-3.7 (m, 4H); 2.75-2.6 (m, 1H); 2.25-2.05 (m, 1H). |
| 275 | 428 | 2.3 | (DMSO-d6) (rotational mixture about 1.3:1): 12.6 (m, 1H); 8.7-8.25 m, 5H); 5.5-5.3 (m, 1H); 4.9 (d, 0.6H); 4.75 (d, 0.4H); 4.1-3.7 (m, 4H); 2.75-2.6 (m, 1H); 2.4-2.3 (m, 1H). |
| 276 | 444 | 2.5 | (DMSO-d6) (rotational mixture about 1.3:1): 12.7 (m, 1H); 9.0-8.3 (m, 5H); 5.6-5.4 (m, 1H); 4.8 (t, 0.6H); 4.7 (t, 0.4H); 4.4-3.75 (m, 4H); 2.8-2.6 (m, 1H); 2.25-2.05 (m, 1H). |
| 277 | 473 | 2.3 | (DMSO-d6) 12.35 (m, 1H); 8.75-8.6 (m, 2H); 8.35-8.15 (m, 3H); 4.75 (m, 1H); 4.0-3.7 (m, 4H); 2.3 (m, 1H); 2.0 (m, 1H); 1.35 (s, 3H). |
| 278 | 487 | 2.5 | (DMSO-d6) 12.35 (m, 1H); 8.75-8.6 (m, 2H); 8.35-8.15 (m, 3H); 4.75 (m, 1H); 4.0-3.7 (m, 4H); 2.3 (m, 1H); 2.0 (m, 1H); 1.6 (m, 2H); 1.0 (m, 3H). |
| 279 | 468.1 | 1.59 | |
| 280 | 455 | 1.5 | (DMSO-d6) 13.05-12.9 (m, 1H); 8.8-8.25 (m, 5H); 6.75 (m, 0.7H); 6.35 (m, 0.3H); 4.95 (m, 0.7H); 4.75 (m, 0.3H); 4.05-3.6 (m, 4H); 2.4-2.1 (m, 2H); 1.4 (m, 3H). |
| 281 | 469 | 1.6 | (DMSO-d6) 13.0-12.9 (m, 1H); 8.8-8.25 (m, 5H); 6.7 (m, 0.7H); 6.3 (m, 0.3H); 5.05-4.8 (m, 1H); 4.1-3.6 (m, 4H); 2.4-2.05 (m, 2H); 1.75-1.6 (m, 2H); 1.05-0.9 (m, 3H). |
| 282 | 392.9 | 2.7 | (500 MHz, MeOD) 8.80 (d, J = 2.3 Hz, 1H), 8.35 (s, 1H), 8.33 (s, 1H), 8.28 (d, J = 2.3 Hz, 1H), 3.19 (q, J = 7.2 Hz, 2H), 1.74 (s, 6H), 0.93 (t, J = 7.2 Hz, 3H). |
| 283 | 410.9 | 2.7 | (500 MHz, MeOD) 8.81 (d, J = 2.3 Hz, 1H), 8.35 (s, 1H), 8.33 (s, 1H), 8.28 (d, J = 2.2 Hz, 1H), 8.19-8.17 (m, 0.33H), 4.23 (dt, J = 47.4, 5.1 Hz, 2H), 3.42 (dt, J = 25.5, 5.1 Hz, 2H), 1.75 (s, 6H). |
| 284 | 439.9 | 1.9 | (500 MHz, MeOD) 8.72 (s, 1H), 8.57-8.53 (m, 2H), 8.45 (s, 1H), 8.26 (s, 1H), 3.85-3.78 (m, 2H), 1.75 (s, 6H). |
| 285 | 428 | 2.8 | (500 MHz, MeOD) 9.07 (d, J = 1.9 Hz, 0.53H), 8.81-8.78 (m, 0.84H), 8.55 (d, J = 10.5 Hz, 1H), 8.45 (d, J = 15.6 Hz, 1H), 8.30 (s, 1H), 4.56-4.52 (m, 1H), 4.06-4.00 (m, 1H), 3.89-3.84 (m, 1H), 2.34-2.24 (m, 1H), 1.12-1.06 (m, 6H). |
| 286 | 428.9 | 2.9 | (500 MHz, MeOD) 8.79 (d, J = 2.3 Hz, 1H), 8.36 (s, 1H), 8.33-8.28 (m, 2.8H), 5.64 (tt, J = 56.5, 4.2 Hz, 1H), 3.51-3.43 (m, 2H), 1.74 (s, 6H). |
| 287 | 446.9 | 3 | (500 MHz, MeOD) 8.78 (d, J = 2.3 Hz, 1H), 8.45 (t, J = 6.1 Hz, 1H), 8.34 (s, 1H), 8.25 (d, J = 3.3 Hz, 2H), 3.86-3.44 (m, 2H), 1.73 (s, 6H). |
| 288 | 437.96 | 2.9 | (500 MHz, MeOD) 9.24 (m, 0.5H), 8.87-8.73 (m, 0.27H), 8.62-8.29 (m, 2.7H), 7.76-7.37 (m, 0.46H), 3.86-3.76 (m, 2H), 1.80-1.50 (m, 6H). |
| 289 | 403.5 | 2.9 | (DMSO-d6) 12.3 (br s, 1H); 8.7 (s, 1H); 8.3-8.2 (m, 2H); 8.1 (s, 1H); 7.65 (m, 1H); 4.1-3.85 (m, 2H); 3.15-2.9 (m, 2H); 2.1-1.9 (m, 4H); 1.6 (s, 3H); 0.8 (m, 3H). |
| 290 | 421.5 | 2.9 | (DMSO-d6) 12.3 (br s, 1H); 8.7 (s, 1H); 8.25 (m, 2H); 8.1 (s, 1H); 7.95 (m, 1H); 4.35-4.05 (m, 3H); 3.95 (m, 1H); 3.35-3.2 (m, 2H); 2.1-1.9 (m, 4H); 1.6 (s, 3H). |
| 291 | 439.5 | 3 | (DMSO-d6) 12.3 (br s, 1H); 8.7 (s, 1H); 8.3 (m, 2H); 8.15-8.05 (m, 2H); 5.8 (dd, 1H); 4.1 (m, 1H); 3.9 (m, 1H); 3.4 (m, 2H); 2.1-1.9 (m, 4H); 1.6 (s, 3H). |
| 292 | 417.1 | 2.7 | (DMSO-d6) 12.3 (s, 1H); 8.7 (s, 1H); 8.25 (m, 2H); 8.1 (s, 1H); 7.7 (dd, 1H); 4.1 (m, 1H); 3.9 (m, 1H); 3.1-2.8 (m, 2H); 2.1-1.9 (m, 4H); 1.6 (s, 3H); 1.35-1.15 (m, 2H); 0.6 (m, 3H). |
| 293 | 455.1 | 2.09 | |
| 294 | 483.1 | 2.42 | |

TABLE 5-continued

| Cmpd # | M + H | RT | NMR |
|---|---|---|---|
| 295 | 453 | 2.02 | |
| 296 | 410.3 | 1.75 | |
| 297 | 407.1 | 2.3 | (DMSO-d6): 12.45 (br s, 1H); 8.7 (s, 1H); 8.4-8.2 (m, 4H); 5.5 (d, 1H); 4.75 (t, 1H); 4.25-3.9 (m, 2H); 3.2-3.0 (m, 2H); 2.6-2.0 (m, 2H); 1.0 (m, 3H). |
| 298 | 421.2 | 2.5 | (DMSO-d6) 12.4 (br s, 1H); 8.7 (s, 1H); 8.4-8.2 (m, 4H); 5.5 (d, 1H); 4.75 (t, 1H); 4.25-3.9 (m, 2H); 3.8 (m, 1H); 3.0 (m, 1H); 2.3-2.0 (m, 2H); 1.45-1.2 (m, 2H); 0.75 (m, 3H). |
| 299 | 425.1 | 2.3 | (DMSO-d6) 12.4 (br s, 1H); 8.7 (s, 1H); 8.6 (m, 1H); 8.35-8.2 (m, 3H); 5.5 (d, 1H); 4.8 (t, 1H); 4.45 (m, 1H); 4.3-3.9 (m, 3H); 3.3 (m, 1H); 2.7 (m, 1H); 2.3-2.0 (m, 2H). |
| 300 | 443.1 | 2.5 | (DMSO-d6) 12.4 (br s, 1H); 8.8-8.6 (m, 2H); 8.4-8.2 (m, 3H); 5.9 (dd, 1H); 5.5 (d, 1H); 4.85 (t, 1H); 4.3-3.9 (m, 2H); 2.75-2.0 (m, 4H). |
| 301 | 441.1 | 2.6 | |
| 302 | 465.2 | 1.9 | |
| 303 | 411.2 | 1.8 | |
| 304 | 447.2 | 1.8 | |
| 305 | 425.2 | 1.9 | |
| 306 | 437.2 | 1.8 | |
| 307 | 455.2 | 2 | |
| 308 | 437.2 | 1.9 | |
| 309 | 457.1 | 1.8 | (DMSO-d6) 12.3 (br s, 1H); 8.75 (s, 1H); 8.35-8.2 (m, 3H); 8.1 (s, 1H); 6.45 (m, 1H); 5.55 (m, 1H); 4.2-3.7 (m, 4H); 2.4-2.2 (m, 2H); 1.7 (s, 3H). |

TABLE 6

| Cmpd # | M + H | RT | NMR |
|---|---|---|---|
| 310 | 409.00 | 1.80 | DMSO-d6: 12.25 (br s, 1H); 8.8 (m, 1H); 8.7 (m, 1H); 8.35-8.3 (m, 2H); 8.2 (m, 1H); 7.2 (m, 1H); 4.85 (d, 1H); 4.0 (m, 1H); 3.95-3.8 (m, 3H); 2.35 (m, 1H); 2.1-1.85 (m, 3H). |
| 311 | 409.00 | 1.80 | DMSO-d6: 12.25 (br s, 1H); 8.8 (m, 1H); 8.7 (m, 1H); 8.35-8.3 (m, 2H); 8.2 (m, 1H); 7.2 (m, 1H); 4.85 (d, 1H); 4.0 (m, 1H); 3.95-3.8 (m, 3H); 2.35 (m, 1H); 2.1-1.85 (m, 3H). |
| 312 | 444.90 | 2.20 | 500 MHz DMSO-d @60 C.: 12.8 (br m, 1H), 8.85 (m, 1H), 8.8 (m, 1H), 8.65 (s, 1H), 8.3 (d, 1H), 8.25 (1H), 7.75 (br m, 1H), 7.3 (d, 1H), 4.85 (m, 1H), 3.9 (m, 2H), 3.0 (d m, 2H), 2.2 (s, 3H) |
| 313 | 495.00 | 2.30 | |
| 314 | 438.00 | 2.00 | 500 MHz MeOD-d4: 8.68 (m, 1H), 8.5 (s, 1H), 8.35 (s, 1H), 8.1 (d.1H), 6.71 (d, 1H), 4.04 (m, 1H), 3.99m, 1H), 2.7 (t, 2H), 2.4 (m, 1H), 2.24 (m, 1H) |
| 315 | 456.00 | 2.80 | 500 MHz MeOD-d4: 8.66 (s, 1H), 8.4 (s, 1H), 8.35 (d, 1H), 8.3 (d.1H), 5.45 (m, 1H, parially ex), 5.04 (m, 1H), 4.01m, 1H), 3.93 (m, 1H), 2.73 (t, 2H), 2.5 (m, 1H), 2.32 (m, 1H) |
| 316 | 488.00 | 2.10 | 500 MHz MeOD-d4: 8.77 (s, 1H), 8.71 (s, 1H), 8.5 (d, 1H), 8.35 (s.1H), 8.02 (t, 1H), 7.88 (d, 1H), 7.71 (t, 1 H), 5.25 (m, 1H), 4.02 (m, 1H), 3.90 (m, 1H)2.73 (t, 2H), 2.6 (m, 1H), 2.5 (m, 1H) |
| 317 | 482.00 | 2.70 | DMSO d5 12.8 (bs, 1H); 8.7 (bs, 1H); 8.5 (m, 2H); 8.4 (s, 1H); 7.7 (s, 1H); 6.9 (s, 1H); 4.8 (m, 1H); 3.8 (m, 2H); 3.6 (m, 3H); 29 (m, 2H); 2.0 (m, 2H); 1.2 (m, 2H) |
| 318 | 496.10 | 2.90 | DMSO d5 12.6 (bs, 1H); 8.8 (m, 1H); 8.7 (m, 2H); 8.4 (s, 1H); 7.7 (s, 1H); 6.9 (s, 1H); 4.8 (m, 1H); 3.8 (m, 2H); 3.6 (m, 2H); 3.5 (m, 5H); 2.0 (m, 2H); 1.2 (m, 3H) |
| 319 | 510.10 | 3.10 | DMSO d5 12.6 (bs, 1H); 8.9 (bs, 1H); 8.6 (m, 2H); 8.4 (s, 1H); 7.8 (s, 1H); 4.7 (m, 1H); 3.9 (m, 2H); 3.7 (m, 2H); 3.3 (m, 2H); 2.0 (m, 2H); 1.5 (m, 2H); 0.9 (t, 3H) |
| 320 | 508.10 | 3.00 | DMSO d5 12.6 (bs, 1H); 8.8 (bs, 1H); 8.6 (m, 2H); 8.4 (s, 1H); 7.7 (s, 1H); 4.7 (m, 1H); 4.0 (m, 2H); 3.8 (m, 2H); 2.9 (s, 1H); 2.0 (m, 2H); 1.9 (m, 3H); 0.8 (t, 2H); 0.6 (m, 1H) |
| 321 | 424.20 | 1.50 | (d4-methanol) 8.86 (d, 1H); 8.40 (d, 1H); 8.29 (d, 1H); 8.25 (s, 1H); 7.30 (dd, 1H); 5.65 (br s, 1H); 4.62 (d, 1H); 4.03-3.35 (m, 7H) |
| 322 | 403.10 | 2.10 | DMSO-d6: 12.5 (s, 1H); 8.7 (s, 1H); 8.3 (m, 3H); 7.9 (d, 1H); 4.65 (d, 1H); 3.95 (m, 1H); 3.85 (m, 2H); 2.25 (m, 1H); 2.0 (m, 3H); 1.05 (m, 3H). |
| 323 | 395.10 | 1.70 | (500 MHz, DMSO-d6) d 12.31 (s, 1H), 8.79 (s, 1H), 8.65 (d, J = 7.8 Hz, 1H), 8.61 (t, J = 6.3 Hz, 1H), 8.38 (d, J = 4.1 Hz, 1H), 8.29 (dd, J = 4.7, 1.5 Hz, 1H), 8.24 (s, 1H), 7.15 (dd, J = 7.9, 4.7 Hz, 1H),, 3.81 (m, 2H), 1.57 (t, 2H), 1.19 (t, 2H) |
| 324 | 385.20 | 1.70 | DMSO-d6: 13.0 (br s, 1H); 8.7-8.6 (m, 2H); 8.4 (m, 1H); 8.3 (m, 1H); 8.15 (d, 0.3H); 8.0 (d, 0.7H); 6.3 (d, 0.3H); 4.85 (d, 0.7H); 4.5 (0.3H); 4.0-3.85 (m, 1H); 3.8-3.6 (m, 2H); 2.35 (m, 1H); 2.05 (m, 3H); 1.1 (dd, 2H); 0.95 (dd, 4H). |
| 325 | 399.10 | 2.10 | DMSO-d6: 12.4 (br s, 1H); 8.65 (s, 1H); 8.55 (m, 1H); 8.3 (m, 2H); 8.25 (s, 1H); 4.7 (d, 1H); 3.95 (m, 1H); 3.85 (m, 2H); 3.8 (m, 1H); 3.0 (s, 1H); 2.25 (m, 1H); 2.0 (m, 3H). |
| 326 | 452.39 | 3.60 | CD3OD/CDCl3: 1.68 (6H, s), 2.14 (2H, m), 3.38 (2H, m), 7.98 (1H, t), 8.22 (1H, s), 8.28 (1H, s), 8.54 (1H, s), 8.83 (1H, s) |
| 327 | 438.41 | 3.56 | CD3OD/CDCl3: 1.70 (6H, s), 3.81 (2H, m), 7.59 (1H, t), 8.22 (1H, s), 8.26 (1H, s), 8.45 (1H, t), 8.58 (1H, s), 8.81 (1H, s) |
| 328 | 404.34 | 3.23 | DMSO-d6/CD3OD/CDCl3: 1.58 (6H, s), 3.12 (1H, s), 3.75 (2H, m), 7.21 (1H, m), 8.19 (1H, s), 8.28 (1H, m), 8.45 (1H, t), 8.69 (1H, s), 8.71 (1H, d) |
| 329 | 470.35 | 3.24 | MeOD: 1.75 (6H, s), 2.16 (2H, m), 3.35 (2H, m), 8.34 (2H, s), 8.48 (1H, s), 8.75 (1H, s), 8.85 (1H, s) |
| 330 | 381.20 | 1.50 | DMSO-d6: 12.8 (s, 1H); 8.7-8.5 (m, 3H); 8.4-8.25 (m, 2H); 6.7 (m, 0.7H) 6.3 (m, 0.3H); 4.8 (m, 0.7H); 4.6 (m, 0.3H); 4.0-3.6 (m, 4H); 2.95 (m, 1H); 2.35 (m, 1H); 2.05 (m, 3H). |
| 331 | 383.20 | 1.70 | DMSO-d6: 12.9 (br s, 1H); 8.8 (m, 1H); 8.7 (s, 1H); 8.6 (s, 1H); 8.4 (s, 1H); 8.15 (m, 1H); 6.8 (s, 1H); 4.7 (s, 1H); 4.05-3.85 (m, 2H); 3.1 (s, 1H); 2.25 (m, 1H); 1.1-0.95 (m, 6H). |
| 332 | 387.40 | 2.00 | DMSO-d6: 12.95 (br s, 1H); 8.7 (s, 1H); 8.6 (s, 1H); 8.4 (s, 1H); 8.15 (m, 2H); 6.8 (s, 1H); 4.6 (s, 1H); 3.9 (m, 1H); 2.25 (m, 1H); 1.1-0.95 (m, 12H). |
| 333 | 400.20 | 2.00 | DMSO-d6: 12.35 (br s, 1H); 8.77 (dd, 1H); 8.65 (s, 1H); 8.3 (m, 2H); 8.2 (m, 1H); 4.7 (d, 1H); 4.1 (m, 2H); 3.95 (m, 1H); 3.8 (m, 1H); 2.25 (m, 1H); 2.0 (m, 3H). |
| 334 | 382.20 | 1.50 | DMSO-d6: 12.9 (br s, 1H); 8.95 (dd, 1H); 8.75 (m, 0.4H); 8.6 (m, 1.6H); 8.4-8.3 (m, 2H); 6.75 (d, 0.8H); 6.35 (d, 0.2H); 4.9 (d, 0.8H); 4.65 (d, 0.2H); 4.2-4.0 (m, 2H); 3.8 (m, 1H); 3.6 (m, 1H); 2.35 (m, 1H); 2.1-2.0 (m, 3H). |
| 335 | 387.40 | 2.00 | |
| 336 | 403.40 | 1.90 | |
| 337 | 385.40 | 1.80 | |
| 338 | 511.20 | 2.50 | DMSO-d6: 8.60 (m, 2H); 8.30 (s, 1H); 8.23 (bs, 1H); 5.50 (m, 1H); 4.38 (m, 2H); 4.10 (m, 2H); 3.38 (m, 4H); 2.50 (m, 1H); 1.90-2.00 (m, 3H); 1.32 (t, 3H) |
| 339 | 421.30 | 2.00 | |
| 340 | 455.20 | 2.10 | |
| 341 | 439.20 | 1.90 | DMSO-d6: 13.0 (bs, 1H); 8.55 (m, 1H); 8.45 (m, 1H); 8.35 (m, 1H); 6.72 (m, 1H); 5.60 (m, 1H); 4.20-3.70 (m, 5H); 3.30 (s, 3H); 2.00 (m, 3H) |
| 342 | 457.10 | 2.40 | DMSO-d6: 8.30 (m, 2H); 8.30 (m, 1H); 7.70 (m, 1H); 5.40 (m, 1H); 4.20-3.70 (m, 5H); 3.30 (s, 3H); 2.00 (m, 3H) |
| 343 | 379.20 | 2.04 | (500 MHz, DMSO) 12.83 (s, 1H), 9.30 (s, 1H), 8.61 (t, J = 7.6 Hz, 2H), 8.37 (d, J = 4.5 Hz, 1H), 8.17 (d, J = 7.1 Hz, 1H), 7.27 (dd, J = 4.7, 7.7 Hz, |

TABLE 6-continued

| Cmpd # | M + H | RT | NMR |
|---|---|---|---|
| 344 | 366.10 | 1.87 | 1H), 6.69 (d, J = 6.9 Hz, 1H), 3.79-3.76 (m, 2H), 1.63 (s, 6H) DMSO-d6: 12.5 (m, 1H); 8.95 (m, 0.5 H) 8.78 (m, 0.5H); 8.65 (m, 0.5H); 8.52 (m, 0.5H); 8.48 (s, 1H); 8.32-8.25 (m, 2H); 8.30 (m, 1.5H); 8.12 (m, 1H); 7.20 (m, 1H); 4.54 (m, 1H); 3.80 (m, 2H); 1.32 (m, 3H) |
| 345 | 411.20 | 1.90 | (500 MHz, DMSO-d6) 12.20 (s, 1H), 8.67 (dd, J = 1.4, 7.9 Hz, 1H), 8.43 (t, J = 6.2 Hz, 1H), 8.32-8.28 (m, 2H), 8.10 (s, 1H), 7.5 (bs, 1H), 7.20 (dd, J = 4.7, 7.9 Hz, 2H), 3.81-3.73 (m, 2H), 2.20-2.16 (m, 1H), 1.99-1.95 (m, 1H), 1.56 (s, 3H), 0.82 (t, J = 7.5 Hz, 3H) |
| 346 | 393.20 | 1.60 | (DMSO-d6, 300 MHz) 11.95 (bs, 1H), 8.7 (d, 1H), 8.25 (m, 2H), 8.12 (d, 1H), 8.02 (d, 1H), 7.28 (s, 1H), 7.13 (dd, 1H), 6.38 (bd, 1H), 3.75 (m, 2H), 2.06 (m, 1H), 1.83 (m, 1H), 1.46 (s, 3H), 0.8 (t, 3H); |
| 347 | 425.27 | 2.25 | (500 MHz, MeOD) 8.87 (d, J = 8.1 Hz, 1H), 8.60 (t, 1H), 8.36 (d, 1H), 8.27-8.26 (m, 2H), 7.39 (dd, J = 5.0, 8.0 Hz, 1H), 3.86 (m, 2H), 2.29 (t, J = 7.5 Hz, 4H), 0.87 (t, J = 7.5 Hz, 6H) |
| 348 | 407.20 | 1.67 | (500 MHz, DMSO-d6) d 12.81 (s, 1H), 8.92 (s, 1H), 8.68-8.57 (m, 3H), 8.38 (d, J = 3.3 Hz, 1H), 8.17 (d, 1H), 7.30-7.27 (m, 1H), 6.82 (d, 1H), 3.82-3.74 (m, 2H), 2.26-2.12 (m, 2H), 2.12-2.05 (m, 2H), 0.82-0.78 (m, 6H) |
| 349 | 373.40 | 1.74 | |
| 350 | 407.40 | 1.72 | CD3CN: 9.89 (s, 1H), 8.79 (d, 1H), 8.27 (m, 1H), 8.19 (d, 1H), 8.10 (d, 1H), 7.18 (m, 2H), 6.49 (d, 1H), 5.80 (s, 1H), 3.97 (m, 1H), 3.59 (m, 1H), 1.53 (s, 3H), 1.02 (dd, 6H) |
| 351 | 425.40 | 1.40 | DMSO-d6: 12.2 (br s, 1H); 8.85 (m, 1H); 8.7 (d, 1H); 8.3 (m, 2H); 8.15 (m, 1H); 7.2 (m, 1H); 4.9 (dd, 1H); 4.45 (m, 1H); 4.05-3.7 (m, 4H); 2.3 (m, 1H); 1.95 (m, 1H). |
| 352 | 407.40 | 1.40 | DMSO-d6: 12.8 (br s, 1H); 9.1 (m, 1H); 8.7-8.6 (m, 2H); 8.45-8.3 (m, 2H); 7.4 (m, 0.3H); 7.3 (m, 0.7H); 6.85 (d, 0.7H); 6.35 (d, 0.3H); 5.1 (dd, 0.7H); 4.8 (dd, 0.3H); 4.5 (m, 4H); 2.4 (m, 1H); 2.1 (m, 1H). |
| 353 | 401.40 | 1.95 | |
| 354 | 387.40 | 1.87 | |
| 355 | 369.30 | 1.69 | |
| 356 | 409.40 | 2.25 | |
| 357 | 423.30 | 1.90 | |
| 358 | 405.40 | 1.80 | |
| 359 | 399.10 | 1.80 | DMSO-d6: 12.7 (br, 1H); 8.8 (s, 1H); 8.7-8.2 (s, 3H); 6.5 (m, 0.8H); 6.2 (m, 0.2H); 4.2 (m, 0.3H); 4.0 (m, 0.7H); 3.8-3.6 (m, 2H); 3.4 (m, 1H); 3.2-3.05 (m, 1H); 2.7 (m, 2H); 2.2 (m, 3H); 2.05 (m, 1H); 1.7 (s, 2.7H); 1.6 (s, 0.3H); 1.0 (m, 0.3H); 0.7 (m, 2.7H). |
| 360 | 379.20 | 1.60 | DMSO-d6: 11.92 (m, 1H); 8.72 (bs, 1H); 8.22 (m, 1H); 8.05 (m, 2H); 7.42 (m, 1H); 7.18 (m, 1H); 6.32 (bs, 1H); 5.22 (m, 1H); 4.20 (m, 2H); 3.32 (s, 3H); 1.35 (m, 3H) |
| 361 | 397.10 | 1.90 | DMSO-d6: 11.9 (m, 1H); 8.55 (m, 1H); 8.25 (m, 1H); 8.18 (m, 1H); 7.98 (m, 1H); 7.65 (m, 1H); 7.15 (m, 1H); 5.15 (m, 1H); 4.18 (m, 2H); 3.30 (s, 2.5H); 2.90 (s, 0.5H); 1.35 (m, 3H) |
| 362 | 357.10 | 1.51 | |
| 363 | 343.10 | 1.40 | |
| 364 | 361.10 | 1.41 | |
| 365 | 391.10 | 1.85 | |
| 366 | 393.10 | 1.60 | (500 MHz, DMSO) 12.83 (s, 1H), 9.2 (bs, 1H), 9.07 (s, 1H), 8.68 (d, J = 7.8 Hz, 1H), 8.61 (s, 1H), 8.42 (d, J = 4.6 Hz, 1H), 8.15 (d, J = 7.1 Hz, 1H), 7.35 (dd, J = 4.8, 7.8 Hz, 1H), 6.86 (d, J = 7.2 Hz, 1H), 4.86 (t, J = 6.3 Hz, 1H), 4.12-4.04 (m, 1H), 3.90-3.85 (m, 1H), 2.31 (t, J = 6.6 Hz, 1H), 1.02 (d, 6H) |
| 367 | 410.91 | 2.10 | (500 MHz, DMSO) 12.36 (s, 1H), 8.86 (t, J = 6.3 Hz, 1H), 8.72 (dd, J = 1.4, 7.9 Hz, 1H), 8.35-8.31 (m, 3H), 7.86 (s, 1H), 7.26 (dd, J = 4.7, 7.9 Hz, 1H), 4.60 (t, J = 7.6 Hz, 1H), 4.04-3.96 (m, 1H), 3.90-3.83 (m, 1H), 2.28 (td, J = 13.8, 6.9 Hz, 1H), 1.02 (t, 6H), |
| 368 | 474.00 | 1.60 | |
| 369 | 490.00 | 1.80 | |
| 370 | 504.10 | 1.90 | |
| 371 | 477.00 | 1.50 | |
| 372 | 491.00 | 1.60 | |
| 373 | 409.00 | 1.40 | DMSO-d6: 12.9 (m, 1H); 8.95-8.85 (m, 1H); 8.8-8.65 (m, 2H); 8.55-8.3 (m, 2H); 7.4 (m, 0.3H); 7.3 (m, 0.7H); 6.85 (d, 0.7H); 6.5 (d, 0.3H); 5.55 (d, 1H); 5.2 (d, 0.7H); 5.0 (d, 0.3H); 4.3-3.8 (m, 4H); 2.8-2.6 (m, 1H); 2.5-2.4 (m, 1H). |
| 374 | 427.00 | 1.60 | DMSO-d6: 12.8 (br s, 1H); 9.1 (m, 1H); 8.7-8.35 (m, 4H); 7.3 (m, 1H); 6.8 (m, 0.7H); 6.5 (m, 0.3H); 5.3 (m, 0.7H); 5.1 (m, 0.3H); 4.3 (m, 2H); 3.9 (m, 2H); 3.15 (m, 1H); 2.65 (m, 1H). |
| 375 | 409.00 | 1.40 | DMSO-d6: 12.9 (m, 1H); 9.25-9.1 (m, 1H); 8.75-8.6 (m, 2H); 8.45-8.35 (m, 2H); 7.4 (m, 0.3H); 7.3 (m, 0.7H); 6.9 (m, 0.7H); 6.3 (d, 0.3H); 5.6 (d, 1H); 5.1 (dd, 0.7H); 4.9 (dd, 0.3H); 4.5 (m, 0.3H); 4.2 (m, 0.7H); 4.3-3.6 (m, 3H); 2.8 (m, 1H); 2.3-2.1 (m, 1H). |
| 376 | 343.10 | 1.37 | |
| 377 | 361.10 | 1.48 | |
| 378 | 325.10 | 1.37 | |
| 379 | 339.10 | 1.49 | |
| 380 | 397.10 | 1.60 | |
| 381 | 379.10 | 1.99 | |
| 382 | 429.35 | 1.70 | (500 MHz, MeOD) 8.83 (d, J = 8 Hz, 2H), 8.68 (s, 1H), 8.59-8.57 (m, 2H), 8.42-8.41 (m, 1H), 8.07-8.03 (m, 1H), 7.90 (dd, J = 4.4, 8.2 Hz, 1H), 7.77-7.73 (m, 1H), 7.41 (m, 1H), 3.83-3.76 (m, 2H), 1.88 (s, 6H). |
| 383 | 423.00 | 2.10 | DMSO-d6: 12.3 (s, 1H); 8.7 (d, 1H); 8.45-8.25 (m, 3H); 8.15 (s, 1H); 7.25 (m, 1H); 4.15 (m, 1H); 4.0 (m, 1H); 3.85 (m, 1H); 3.7 (m, 1H); 2.05 (m, 4H); 1.75 (s, 3H). |
| 384 | 405.10 | 1.50 | DMSO-d6: 12.8 (s, 1H); 8.8-8.2 (m, 5H); 7.4 (m, 0.2H); 7.25 (m, 0.8H); 6.8 (d, 0.8H); 6.15 (d, 0.2H); 4.2 (m, 0.2H); 3.95 (m, 0.8H); 3.8 (m, 3H); 2.2-2.0 (m, 4H); 1.8-1.6 (m, 3H). |
| 385 | 488.00 | 1.70 | |
| 386 | 380.00 | 1.90 | DMSO-d6: 12.4 (bs, 1H); 8.92 (m, 0.5H); 8.62 (m, 0.5H); 8.50 (s, 0.5H); 8.42 (s, 0.5H); 8.40-8.20 (m, 4H); 7.20 (m, 0.5H); 7.15 (m, 0.5H); 3.72 (m, 2H); 1.45 (m, 6H) |
| 387 | 421.10 | 1.50 | (500 MHz, DMSO) 12.81 (s, 1H), 8.65-8.56 (m, 3H), 8.36 (d, J = 4.4 Hz, 1H), 8.22 (d, J = 6.9 Hz, 1H), 7.26 (dd, J = 4.7, 7.9 Hz, 1H), 6.85 (d, J = 6.4 Hz, 1H), 3.80 (bm, 1H), 3.66-3.62 (m, 1H), 2.26-2.22 (m, 2H), 2.15 (m, 2H), 0.00 (TMS) |
| 388 | 453.30 | 1.68 | (500 MHz, MeOD) 8.88 (dd, J = 1.5, 8.1 Hz, 1H), 8.60 (s, 1H), 8.40 (d, J = 3.1 Hz, 1H), 8.32-8.26 (m, 1H), 7.99 (s, 1H), 7.40 (dd, J = 4.7, 8.0 Hz, 1H), 7.31 (s, 1H), 4.19 (t, J = 4.8 Hz, 1H), 4.11-4.09 (m, 1H), 4.07 (s, 3H), 4.07 (s, 3H), 3.35-3.32 (m, 2H), 1.87 (s, 6H), 1.38-1.29 (m, 2H, impurity). |
| 389 | 489.00 | 1.78 | (500 MHz, MeOD) 8.82 (dd, J = 1.4, 8.1 Hz, 1H), 8.58 (s, 1H), 8.52 (m, 1H), 8.40 (d, J = 3.2 Hz, 1H), 8.00 (s, 1H), 7.39 (dd, J = 4.7, 8.0 Hz, 1H), 7.32 (s, 1H), 4.08 (s, 3H), 4.07 (s, 3H), 3.80-3.77 (m, 2H), 1.87 (s, 6H). |
| 390 | 471.10 | 1.70 | (500 MHz, MeOD) 8.85 (dd, J = 1.4, 8.1 Hz, 1H), 8.60 (s, 1H), 8.42-8.40 (m, 1H), 8.37-8.30 (m, 1H), 8.00 (s, 1H), 7.40 (dd, J = 4.7, 8.0 Hz, 1H), 7.32 (s, 1H), 5.64-5.41 (m, 1H), 4.08 (s, 3H), 4.07 (s, 3H), 3.44 (m, 2H), 1.87 (s, 6H). |

TABLE 6-continued

| Cmpd # | M + H | RT | NMR |
|---|---|---|---|
| 391 | 449.20 | 1.70 | (500 MHz, MeOD) 8.88-8.87 (m, 1H), 8.59 (s, 1H), 8.40 (d, J = 3.3 Hz, 1H), 8.03-8.02 (m, 1H), 7.99 (s, 1H), 7.40 (dd, J = 4.7, 8.1 Hz, 1H), 7.31 (s, 1H), 4.07 (s, 3H), 4.07 (s, 3H), 3.07 (m, 2H), 1.86 (s, 6H), 1.29 (m, 2H), 0.61 (t, J = 7.5 Hz, 3H). |
| 392 | 339.10 | 1.45 | |
| 393 | 353.10 | 1.56 | |
| 394 | 357.10 | 1.47 | |
| 395 | 375.10 | 1.56 | |
| 396 | 427.00 | 1.90 | DMSO-d6: 12.25 (s, 1H); 8.95 (m, 1H); 8.7 (d, 1H); 8.35 (d, 1H); 8.3 (m, 1H); 8.2 (m, 1H); 7.25 (dd, 1H); 5.5 (d, 1H); 4.95 (dd, 1H); 4.3-3.75 (m, 4H); 2.7 (m, 1H); 2.2-2.0 (m, 1H). |
| 397 | 445.00 | 2.30 | DMSO-d6: 12.15 (s, 1H); 8.9 (m, 1H); 8.65 (d, 1H); 8.35 (d, 1H); 8.3 (m, 1H); 8.15 (m, 1H); 7.2 (m, 1H); 5.1 (m, 1H); 4.3 (m, 2H); 3.9 (m, 2H); 3.0 (m, 1H); 2.5 (m, 1H). |
| 398 | 394.00 | 2.10 | (500 MHz, MeOD) 9.14 (m, 0.25H), 8.95 (d, J = 6.7 Hz, 0.66H), 8.59-8.41 (m, 3.64H), 7.45 (m, 1H), 3.84 (m, 2H), 2.21-2.18 (m, 1H), 2.05-2.02 (m, 1H), 1.67 (m, 3H), 0.97 (t, J = 7.3 Hz, 3H). |
| 399 | 325.90 | 1.60 | |
| 400 | 340.00 | 1.80 | (500 MHz, MeOD) 9.07 (br, 0.24H), 8.54 (s, 1H), 8.46 (s, 1H), 8.36 (d, J = 4.3 Hz, 1H), 7.39-7.36 (m, 1H), 3.25-3.15 (m, 2H), 2.19-2.00 (m, 2H), 1.65 (m, 3H), 0.97-0.90 (m, 6H). |
| 401 | 410.10 | 2.10 | DMSO-d6 (rotational mixture about 1.3:1): 12.45 (m, 1H); 9.05-8.3 (m, 5H); 7.3-7.2 (m, 1H); 5.6-5.4 (m, 1H); 4.8 (t, 0.6H); 4.7 (t, 0.4H); 4.45 3.75 (m, 4H); 2.8-2.6 (m, 1H); 2.25-2.1 (m, 1H). |
| 402 | 410.10 | 2.00 | DMSO-d6 (rotational mixture about 1.3:1): 12.45 (m, 1H); 8.8-8.3 (m, 5H); 7.3-7.15 (m, 1H); 5.5-5.35 (m, 1H); 4.9 (d, 0.6H); 4.75 (d, 0.4H); 4.15-3.8 (m, 4H); 2.75-2.6 (m, 1H); 2.4-2.3 (m, 1H). |
| 403 | 392.10 | 2.00 | |
| 404 | 409.10 | 1.50 | |
| 405 | 409.00 | 1.50 | |

Example 3

JAK3 Inhibition Assay

Compounds were screened for their ability to inhibit JAK3 using the assay shown below. Reactions were carried out in a kinase buffer containing 100 mM HEPES (pH 7.4), 1 mM DTT, 10 mM MgCl$_2$, 25 mM NaCl, and 0.01% BSA. Substrate concentrations in the assay were 5 µM ATP (200 uCi/µmole ATP) and 1 µM poly(Glu)$_4$Tyr. Reactions were carried out at 25° C. and 1 nM JAK3.

To each well of a 96 well polycarbonate plate was added 1.5 µl of a candidate JAK3 inhibitor along with 50 µl of kinase buffer containing 2 poly(Glu)$_4$Tyr and 10 µM ATP. This was then mixed and 50 µl of kinase buffer containing 2 nM JAK3 enzyme was added to start the reaction. After 20 minutes at room temperature (25° C.), the reaction was stopped with 50 µl of 20% trichloroacetic acid (TCA) that also contained 0.4 mM ATP. The entire contents of each well were then transferred to a 96 well glass fiber filter plate using a TomTek Cell Harvester. After washing, 60 µl of scintillation fluid was added and $^{33}$P incorporation detected on a Perkin Elmer TopCount.

Example 4

JAK2 Inhibition Assay

The assays were as described above in Example 3 except that JAK-2 enzyme was used, the final poly(Glu)$_4$Tyr concentration was 15 µM, and final ATP concentration was 12 µM.

All compounds depicted in Tables 1, 2 and 3 were found to inhibit JAK3 with a Ki of less than 0.1 µM except for compounds 22, 35, 56, 68, 177, 223, 310, 317, 318, 319, 320, 321, 322, 326, 336, 337, 338, 339, 340, 351, 356, 367, 369, 370, 388, and 390. All Table 1, 2 and 3 compounds inhibited JAK3 with a Ki of less than 2.0 µM except for compounds 68 and 319. All Table 1, 2 and 3 compounds were found to inhibit JAK2 with a Ki of less than 0.5 µM except for compounds 9, 22, 35, 56, 57, 68, 310, 317, 38, 319, 320, 321, 336, 338, 339, 340, 348, 351, 356, 367 and 372. All Table 1, 2 and 3 compounds inhibited JAK2 with a Ki of less than 5.0 µM except for compounds 68, 318 and 319.

Example 5

JAK3 Cellular Inhibition Assay

HT-2 clone A5E cells (ATCC Cat. # CRL-1841) were grown and maintained at 37° C. in a humidified incubator in cell culture medium (RPMI 1640 supplemented with 2 mM L-glutamine adjusted to contain 1.5 g/L sodium bicarbonate, 4.5 g/L glucose, 10 mM HEPES, 1.0 mM sodium pyruvate, 0.05 mM 2-mercaptoethanol, 10% fetal bovine serum, and 10% by volume rat T-STIM factor [Fisher Scientific Cat # CB40115] with Con A). On the day of the experiment, HT-2 cells were washed, resuspended at a density of 5×10$^6$ cells per ml in fresh cell culture medium without T-STIM and incubated for 4 hours without T-STIM. After four hours, 50 µl (0.25×10$^6$ cells) of the resuspended cells were added to each well of a 96 well plate. Serial dilutions of compounds were made in DMSO and then added to RPMI. 100 µl of the diluted compounds were added to each well and the plates were incubated for 1 hour at 37° C. 50 µl of recombinant murine interleukin-2 (rmIL-2) at 40 ng/ml (R & D systems Inc. Cat # 402-ML) was added and the plates were incubated for 15 minutes at 37° C.

The plates were then centrifuged for 5 minutes at 1000 rpm, the supernatant was aspirated and 50 µl of 3.7% formaldehyde in phosphate buffered saline (PBS) was added per well. The plates were incubated for 5 minutes at room temperature on a plate shaker. The plates were again centrifuged at 1000 rpm for 5 minutes. The supernatant was aspirated, 50 µl of 90% methanol was added to each well, and the plate was incubated on ice for 30 minutes. The supernatant was aspirated and the plate washed with PBS. 25 µl per well of 1:10 diluted Phospho STAT-5 (Y694) PE conjugated antibody (PS-5 PE antibody, Becton-Dickinson Cat. # 61256) was added to the plates and the plates were incubated for 45 minutes at room temperature on a plate shaker. 100 µl PBS was added and the plates were centrifuged. The supernatant was aspirated and the cells resuspended in 100 µPBS. The plate was then read on a 96 well FACS reader (Guava PCA-96).

Compounds of the invention were found to inhibit JAK3 in this assay.

Example 6

JAK2 Cellular Inhibition Assay

TF-1 cells (ATCC Cat. # CRL-2003) were grown and maintained at 37° C. in a humidified incubator in cell culture medium (RPMI 1640 supplemented with 2 mM L-glutamine adjusted to contain 1.5 g/L sodium bicarbonate, 4.5 g/L glucose, 10 mM HEPES, 1.0 mM sodium pyruvate, 10% fetal bovine serum and recombinant human granulocyte-macrophage colony stimulating factor [rhGMCSF, R&D Systems Inc.

Cat. # 215-GM]). On the day of the experiment, TF-1 cells were washed, resuspended at a density of 5×10⁶ cells per ml in fresh cell culture medium without rhGMCSF and incubated for 4 hours without rhGMCSF. After four hours, 50 μl (0.25×10⁶ cells) of the resuspended cells were added to each well of a 96 well plate. Serial dilutions of compounds were made in DMSO and then added to RPMI. 100 μl of the diluted compounds were added to each well and the plates were incubated for 1 hour at 37° C. 50 μl of rhGMCSF at 10 ng/ml was added and the plates were incubated for 15 minutes at 37° C. The plates were then processed for FACS analysis as detailed above in Example 5. Compounds of the invention were found to inhibit JAK2 in this cellular assay.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:

1. A compound of formula (I):

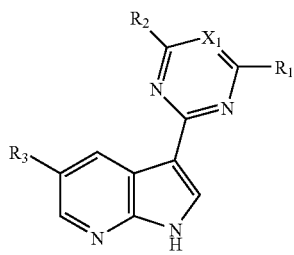

I or a pharmaceutically acceptable salt thereof, wherein:
$R^3$ is Cl or F;
$X^1$ is $CR^4$;
$R^2$ is H, F, R', OH, OR', COR', COOH, COOR', CONH$_2$, CONHR', CON(R')$_2$, or CN;
$R^4$ is H, F, R', OH, OR', COR', COOH, COOR', CONH$_2$, CONHR', CON(R')$_2$, or CN; or $R^2$ and $R^4$, taken together, form a 5-7-membered aryl or heteroaryl ring optionally substituted with 1-4 occurrences of $R^{10}$;
R' is a $C_{1-3}$ aliphatic optionally substituted with 1-4 occurrences of $R^5$;
each $R^5$ is independently selected from halogen, $CF_3$, $OCH_3$, OH, SH, $NO_2$, $NH_2$, $SCH_3$, $NCH_3$, CN or unsubstituted $C_{1-2}$ aliphatic, or two $R^5$ groups, together with the carbon to which they are attached, form a cyclopropyl ring or C=O;
each $R^{10}$ is independently selected from halogen, $OCH_3$, OH, $NO_2$, $NH_2$, SH, $SCH_3$, $NCH_3$, CN or unsubstituted $C_{1-2}$ aliphatic;
$R^1$ is

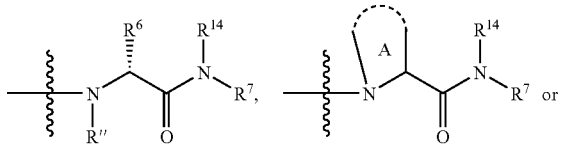

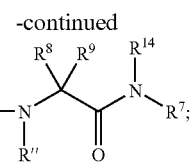

R" is H or is a —$C_{1-2}$ aliphatic optionally substituted with 1-3 occurrences of $R^{11}$;
each $R^{11}$ is independently selected from halogen, $OCH_3$, OH, SH, $NO_2$, $NH_2$, $SCH_3$, $NCH_3$, CN, $CON(R^{15})_2$ or unsubstituted $C_{1-2}$ aliphatic, or two $R^{11}$ groups, together with the carbon to which they are attached, form a cyclopropyl ring or C=O;
$R^6$ is a $C_{1-4}$ aliphatic optionally substituted with 1-5 occurrences of $R^{12}$;
each $R^{12}$ is independently selected from halogen, $OCH_3$, OH, $NO_2$, $NH_2$, SH, $SCH_3$, $NCH_3$, CN or unsubstituted $C_{1-2}$ aliphatic, or two $R^{12}$ groups, together with the carbon to which they are attached, form a cyclopropyl ring;
Ring A is a 4-8 membered saturated nitrogen-containing ring comprising up to two additional heteroatoms selected from N, O or S and optionally substituted with 1-4 occurrences of $R^{13}$;
each $R^{13}$ is independently selected from halogen, R', $NH_2$, NHR', N(R')$_2$, SH, SR', OH, OR', $NO_2$, CN, $CF_3$, COOR', COOH, COR', OC(O)R' or NHC(O)R'; or any two $R^{13}$ groups, on the same substituent or different substituents, together with the atom(s) to which each $R^{13}$ group is bound, form a 3-7 membered saturated, unsaturated, or partially saturated carbocyclic or heterocyclic ring optionally substituted with 1-3 occurrences of $R^5$;
$R^8$ is $C_{1-4}$ aliphatic optionally substituted with 1-5 occurrences of $R^{12}$;
$R^9$ is $C_{1-2}$ alkyl; or
$R^8$ and $R^9$ are taken together to form a 3-7 membered carbocyclic or heterocyclic saturated ring optionally substituted with 1-5 occurrences of $R^{12}$;
$R^{14}$ is H or unsubstituted $C_{1-2}$ alkyl;
$R^{15}$ is H or unsubstituted $C_{1-2}$ alkyl; and
$R^7$ is a $C_{2-3}$ aliphatic or cycloaliphatic optionally substituted with up to 6 occurrences of F.

2. The compound according to claim 1, wherein the compound has formula I-A:

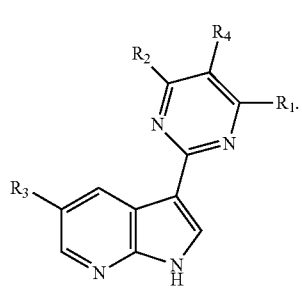

I-A

3. The compound according to claim 2, wherein $R^3$ is Cl.
4. The compound according to claim 3, wherein $R^2$ is H, F, R', OH or OR'.
5. The compound according to claim 4, wherein $R^2$ is H or F.
6. The compound according to claim 2, wherein the compound is of formula I-A and $R^4$ is H, F, R', OH or OR', or $R^2$ and $R^4$ are taken together to form a 6-membered aryl ring.

7. The compound according to claim 6, wherein R⁴ is H or F.

8. The compound according to claim 7, wherein if R⁴ is F, then R² is H and if R² is F, then R⁴ is H.

9. The compound according to claim 7, wherein R² and R⁴ are both H.

10. The compound according to claim 2, wherein R⁷ is CH₂CH₃, CH₂CF₃, CH₂CHF₂, CH₂CH₂F, CH₂CH₂CH₃, CH₂CH₂CF₃, CH₂CH₂CH₂F or CH₂CH₂CHF₂.

11. The compound according to claim 10, wherein R⁷ is CH₂CH₃, CH₂CF₃, CH₂CH₂CH₃ or CH₂CH₂CF₃.

12. The compound according to claim 11, wherein R⁷ is CH₂CF₃.

13. The compound according to claim 1, wherein R" is H or CH₃.

14. The compound according to claim 13, wherein R" is H.

15. The compound according to claim 2, wherein R¹⁴ is H.

16. The compound according to claim 2, wherein R¹⁵ is H.

17. The compound according to claim 1, wherein the compound is of formula II:

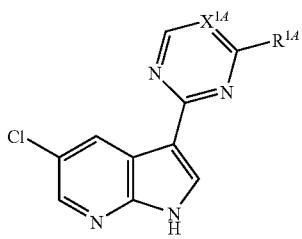

wherein X¹·⁴ is CH or CF and R¹·⁴ is

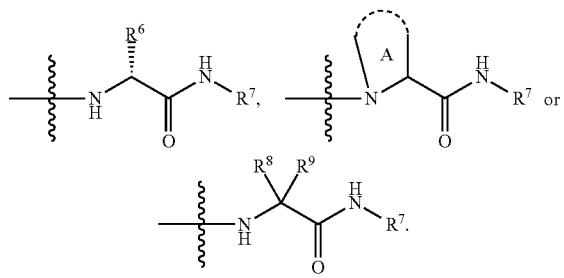

18. The compound according to claim 17, wherein R⁷ is CH₂CH₃, CH₂CF₃, CH₂CH₂CH₃ or CH₂CH₂CF₃.

19. The compound according to claim 18, wherein R⁷ is CH₂CF₃.

20. The compound according to claim 17, wherein R¹·⁴ is

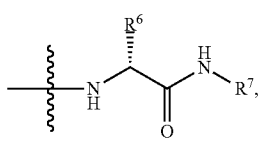

and R⁶ and the carbon atom to which it is attached form

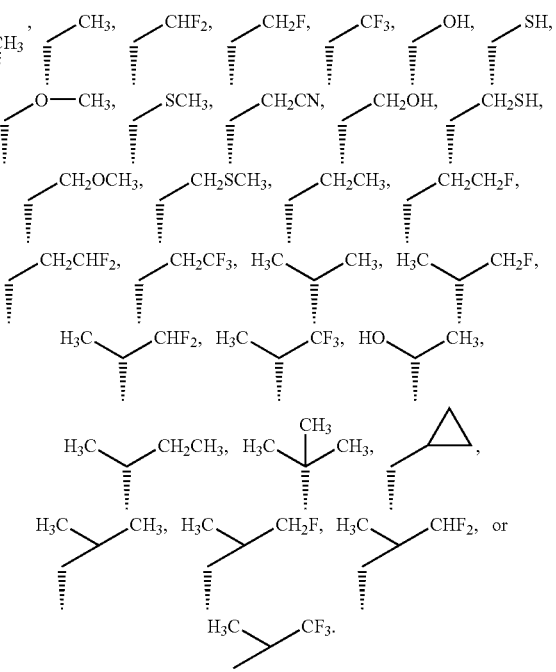

21. The compound according to claim 20, wherein R¹·⁴ is

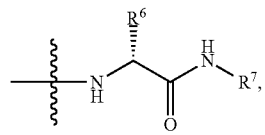

and R⁶ and the carbon atom to which it is attached form

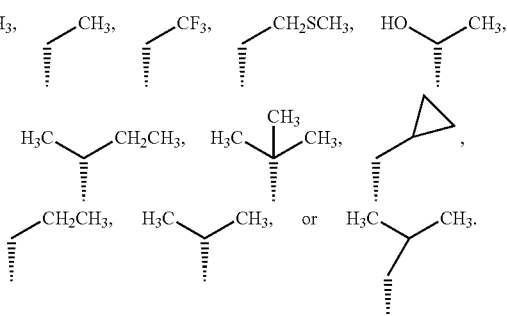

22. The compound according to claim 21, wherein R¹·⁴ is

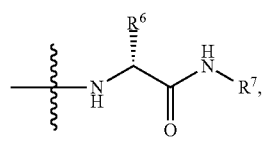

and $R^6$ and the carbon atom to which it is attached form,

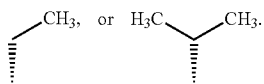

23. The compound according to claim 17, wherein $R^{1A}$ is

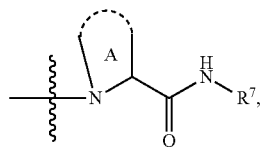

and Ring A is

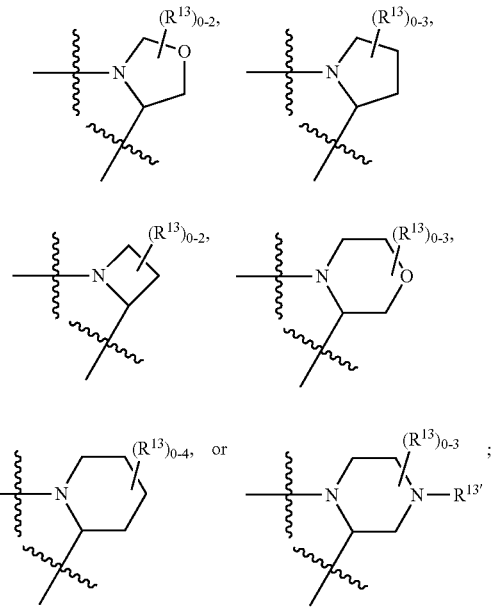

and $R^{13'}$ is H or $R^{13}$.

24. The compound according to claim 23, wherein $R^{1A}$ is

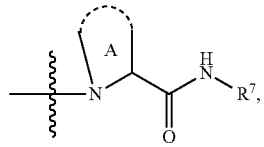

and Ring A is

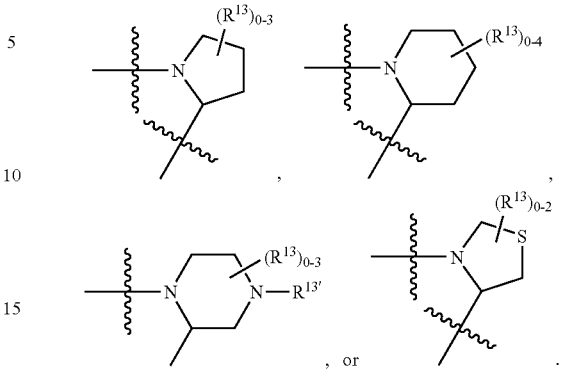

25. The compound according to claim 24, wherein $R^{1A}$ is

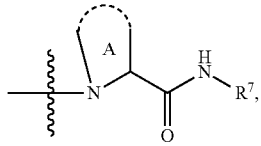

and Ring A is

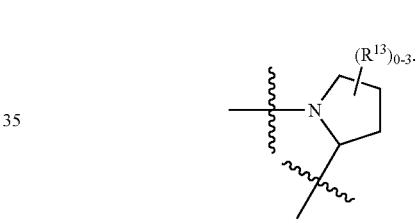

26. The compound according to claim 25, wherein $R^{13}$ is absent.

27. The compound according to claim 25, wherein Ring A is substituted with one occurrence of $R^{13}$.

28. The compound according to claim 27, wherein $R^{13}$ is OH, $CH_3$, F, OR' or NHR'.

29. The compound according to claim 28, wherein R' is $C_{1-2}$ alkyl or $C_{2-3}$ alkenyl.

30. The compound according to claim 28, wherein $R^{13}$ is OH.

31. The compound according to claim 17, wherein $R^{1A}$ is

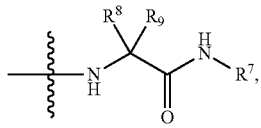

and $R^8$ and $R^9$ are taken together to form a ring selected from

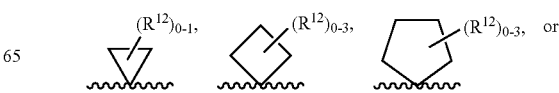

-continued

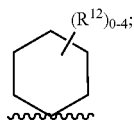

wherein one or more carbon atoms in of said ring are optionally and independently replaced by N, O or S.

32. The compound according to claim 17, wherein $R^{1A}$ is

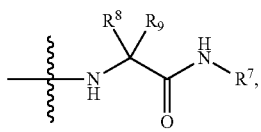

and $R^8$, $R^9$, and the carbon to which they are attached form

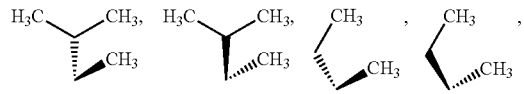

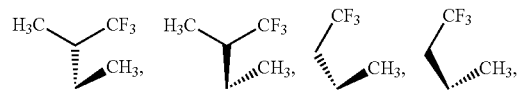

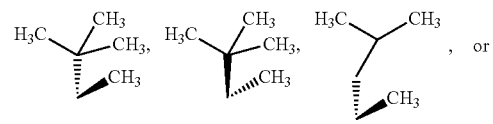

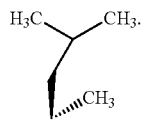

33. The compound according to claim 32, wherein $R^{1A}$ is

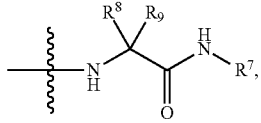

and $R^8$, $R^9$, and the carbon atom to which they are attached form

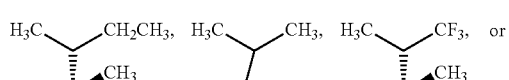

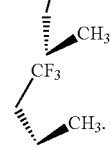

34. The compound according to claim 33, wherein $R^{1A}$ is

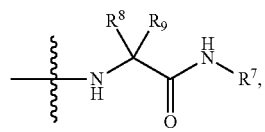

and $R^8$, $R^9$, and the carbon atom to which they are attached form

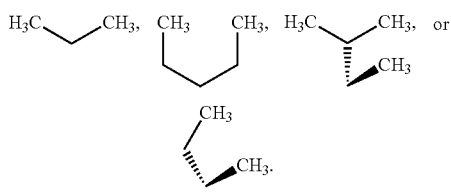

35. The compound according to claim 17, wherein $X^{1A}$ is CH or CF.

36. A compound selected from

1
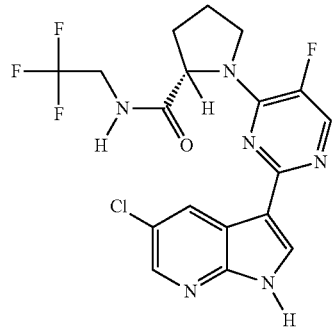

2
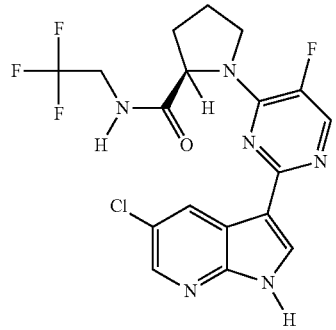

3
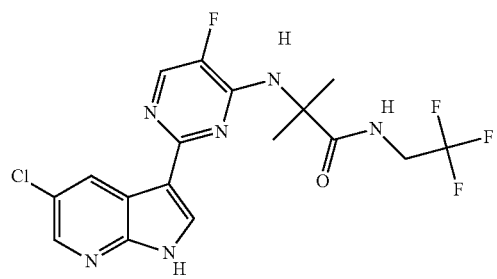

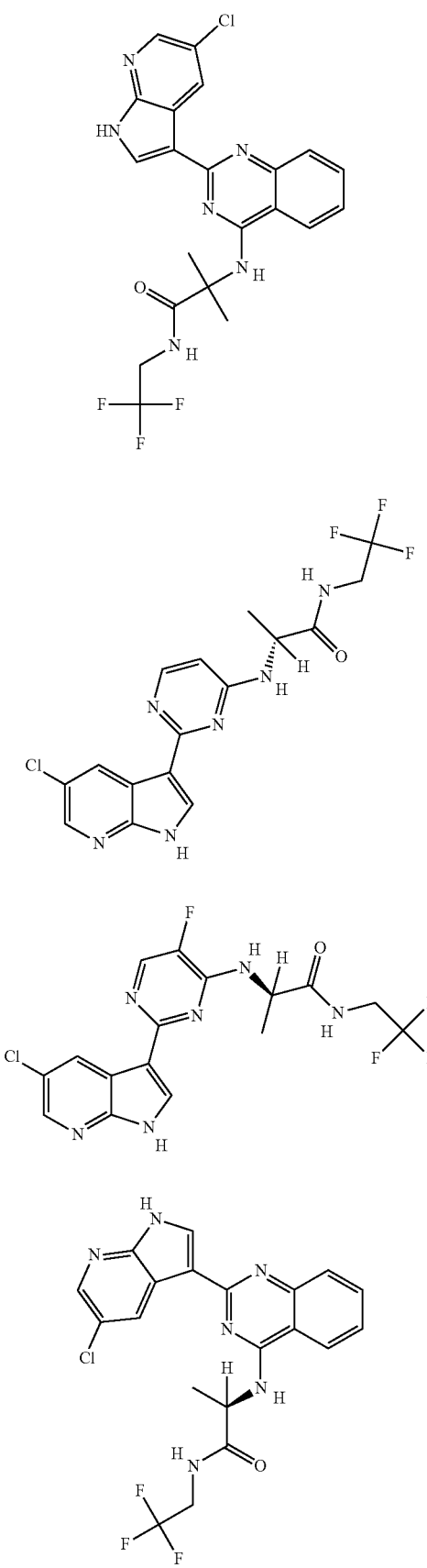
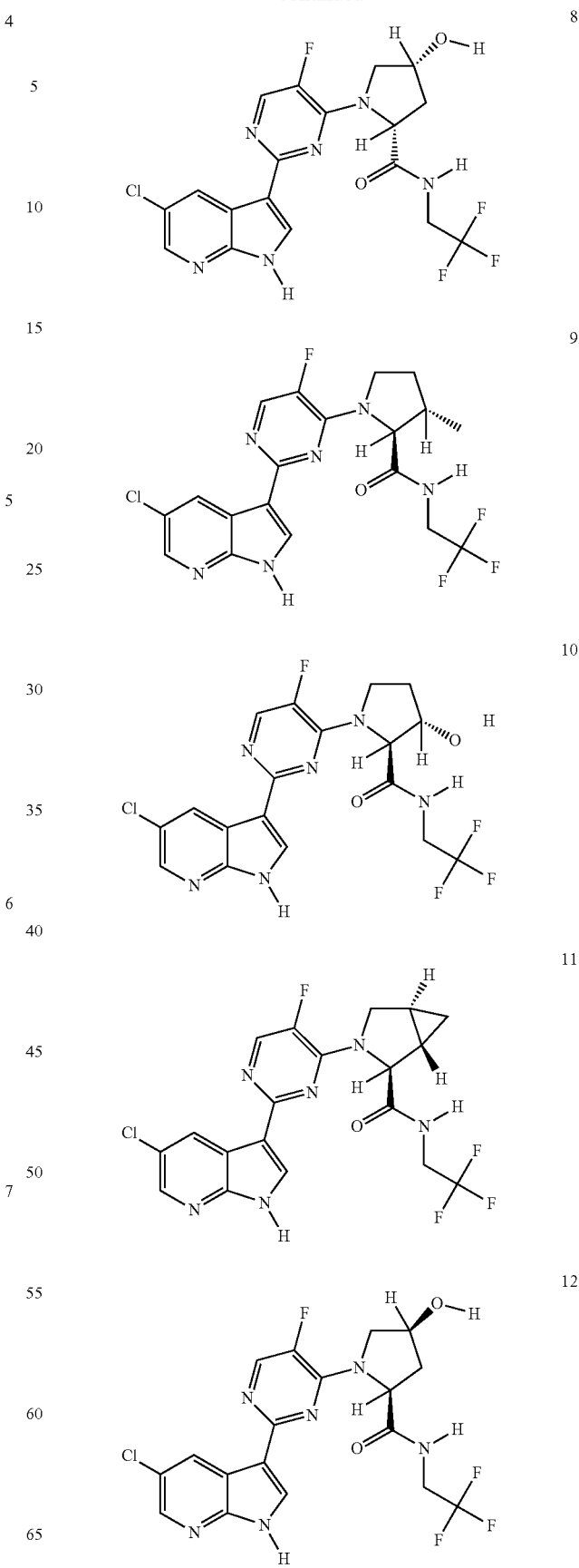

-continued
13
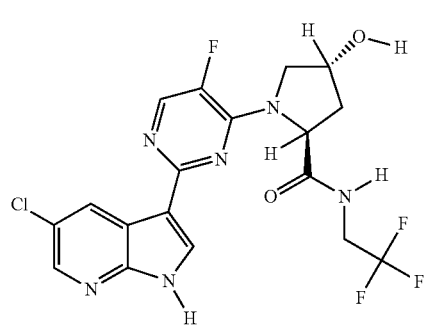
14
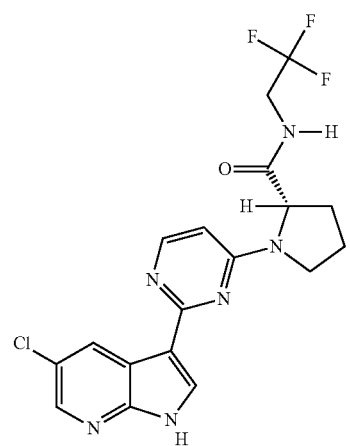
15
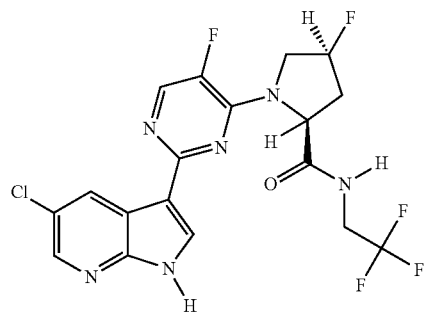
16
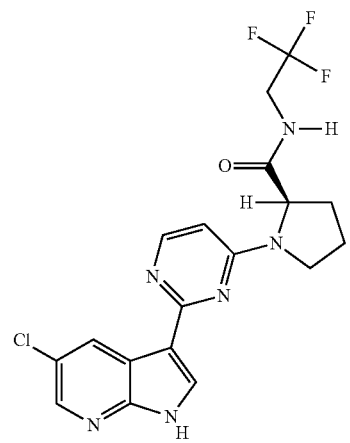
-continued
17
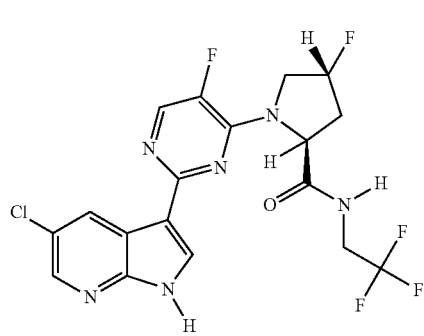
18
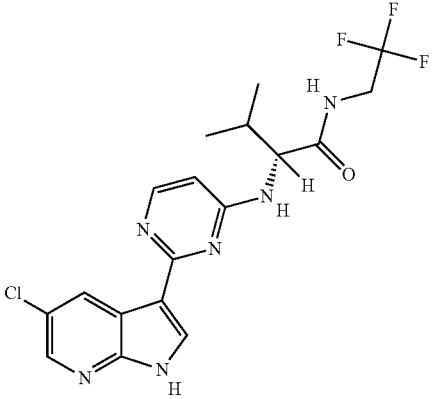
19
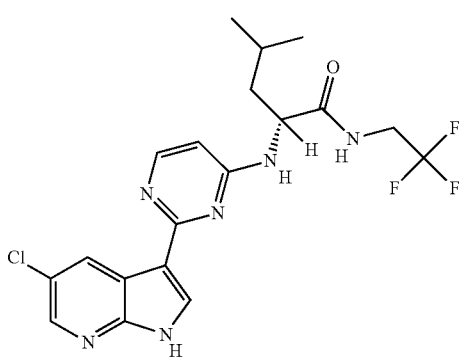
20
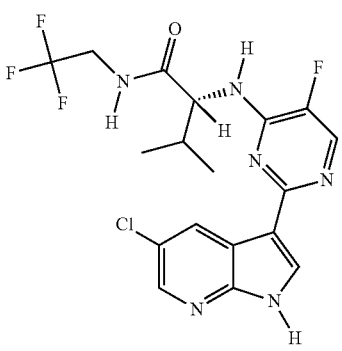

| 21 | 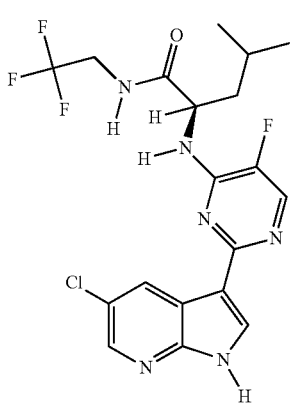 | 25 | 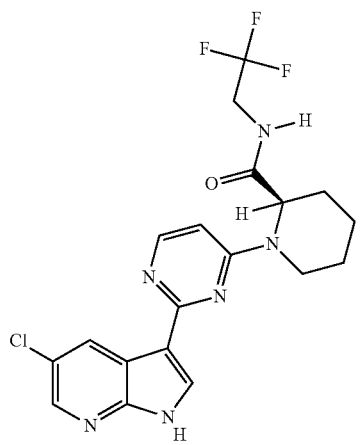 |
| 22 | 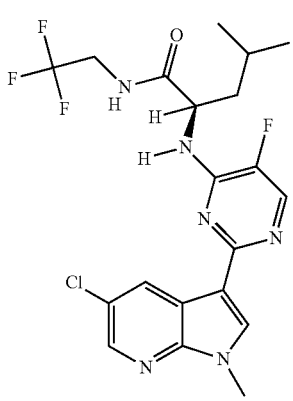 | 26 | 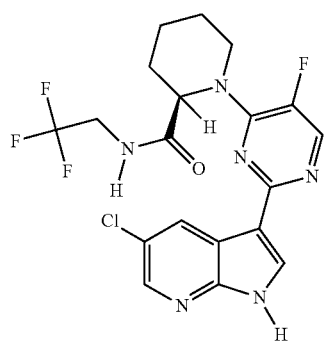 |
| 23 | 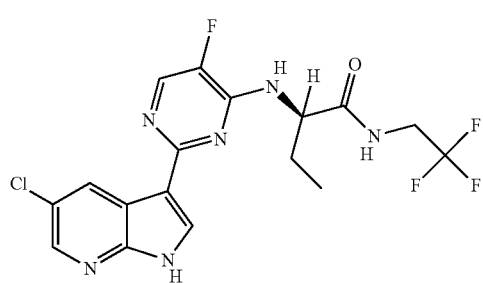 | 27 | 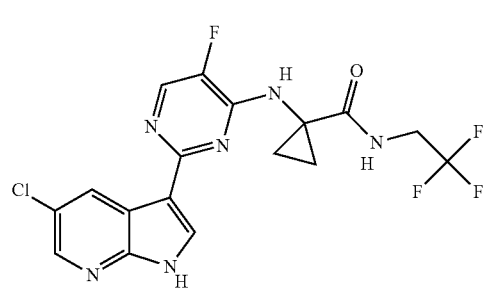 |
| 24 | 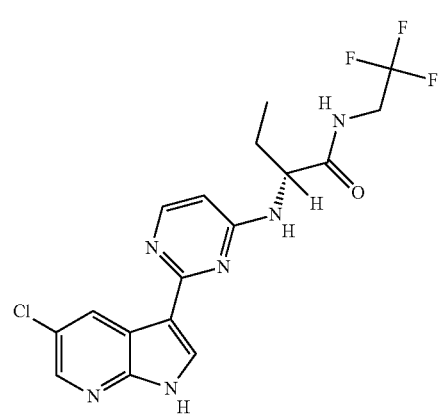 | 28 | 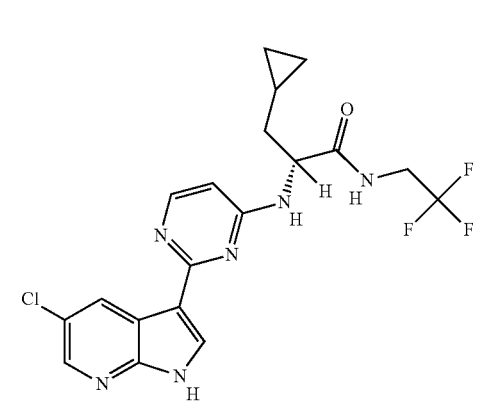 |

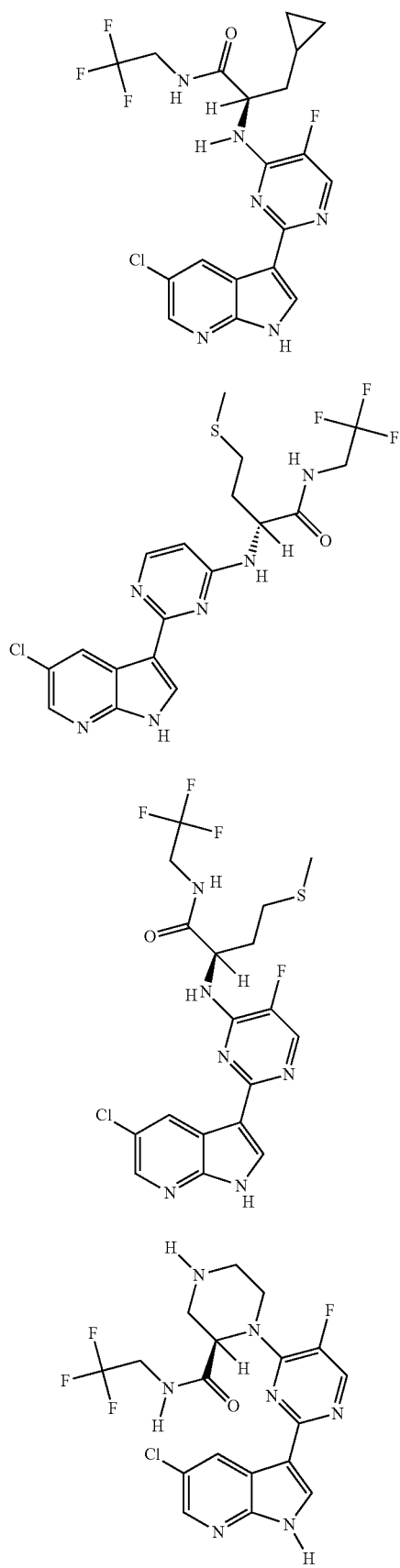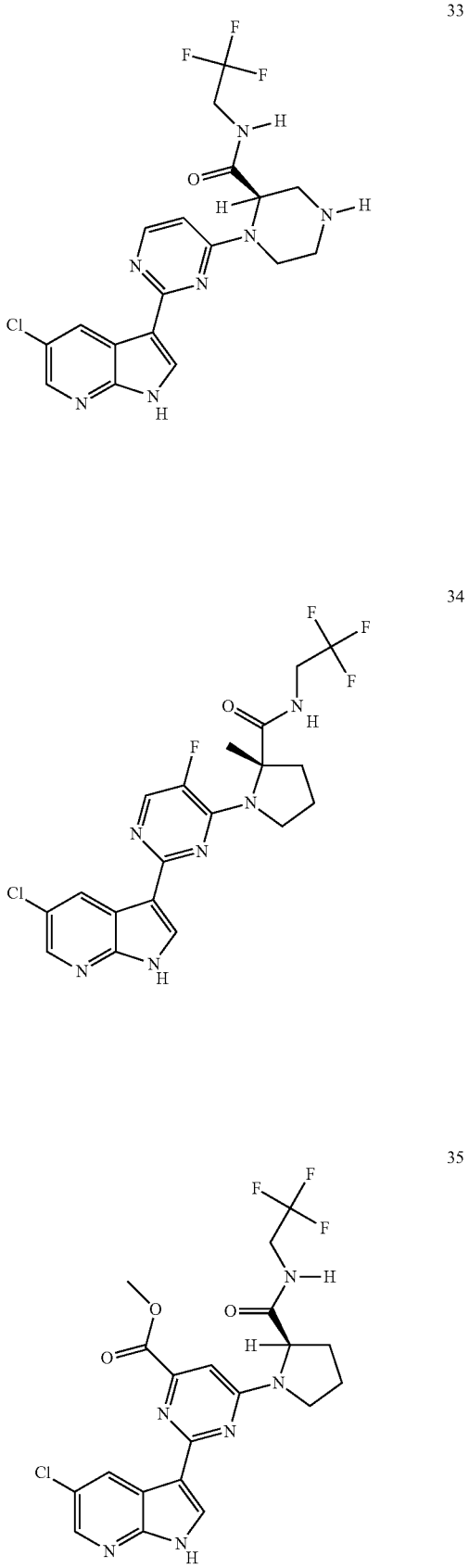

183
-continued
36
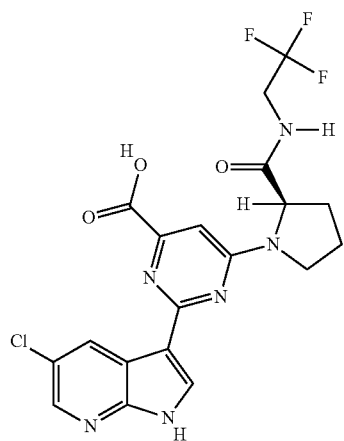
37
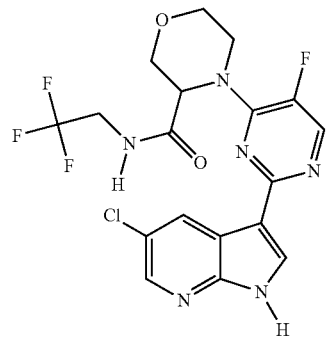
38
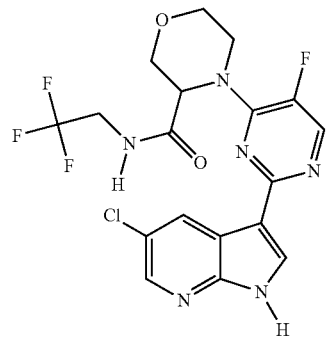
39
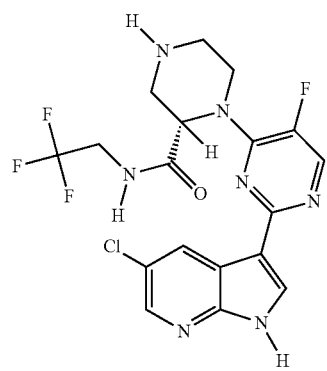
184
-continued
40
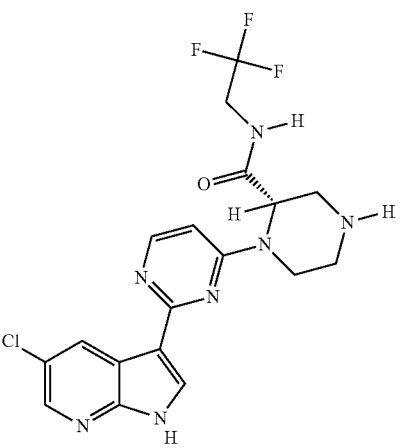
41
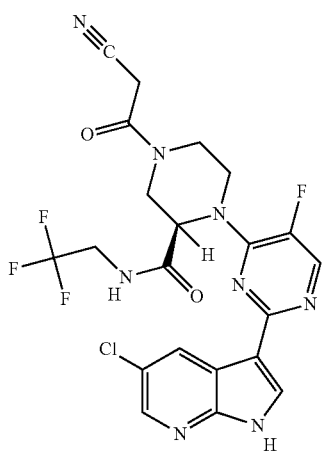
42
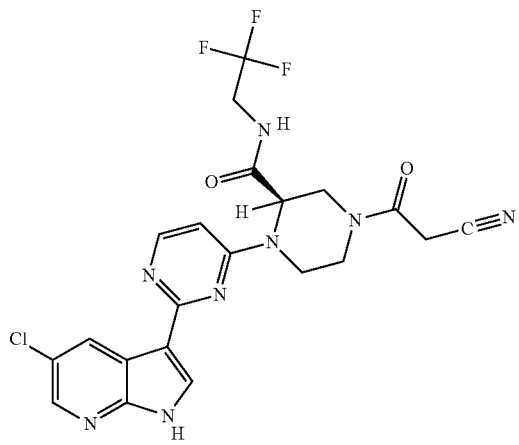

43
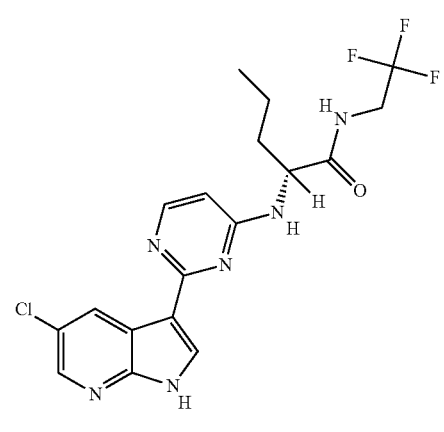
44
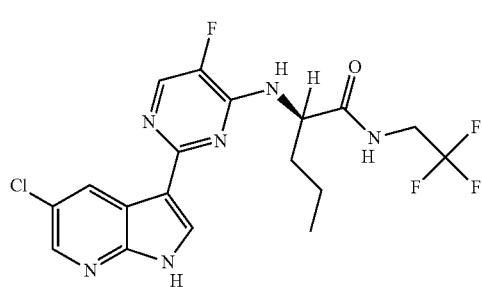
45
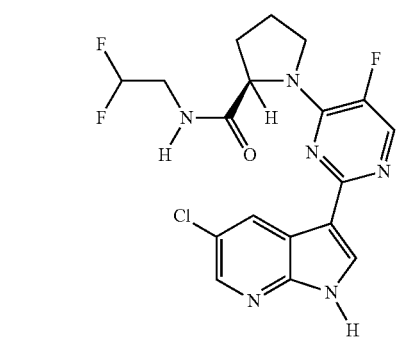
46
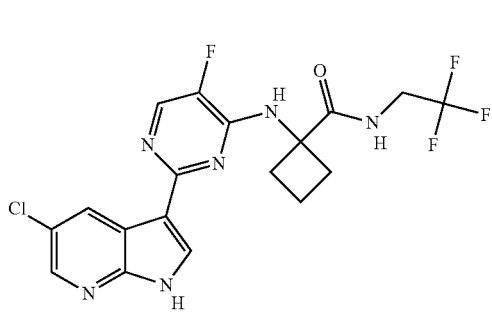
47
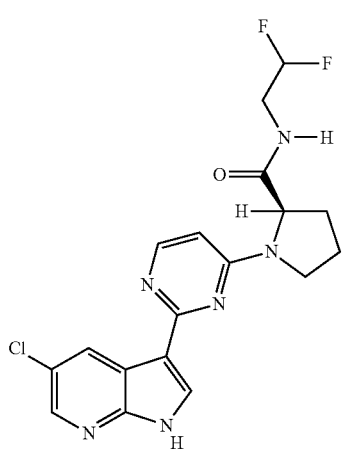
48
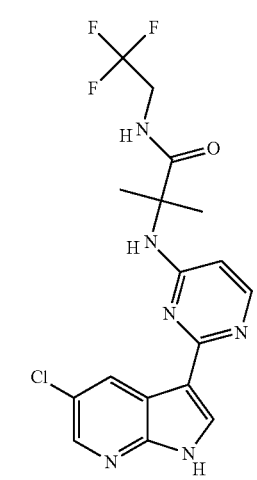
49
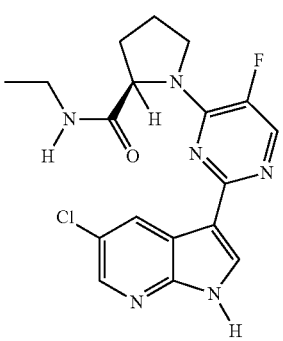
50
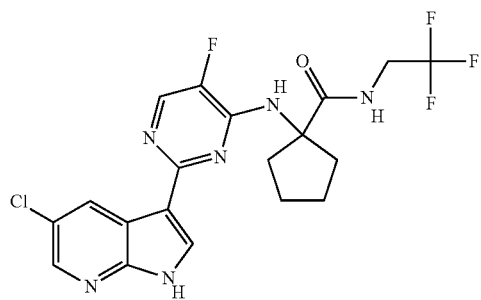

51 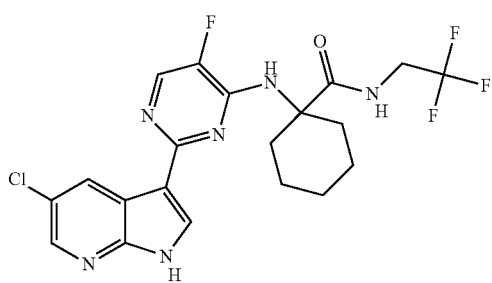
52 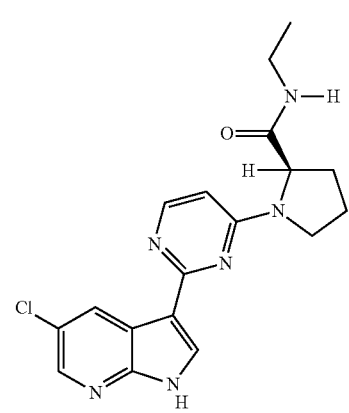
53 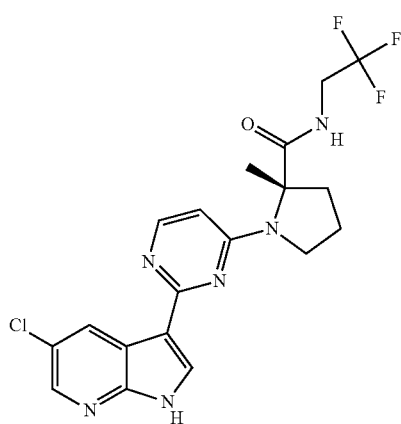
54 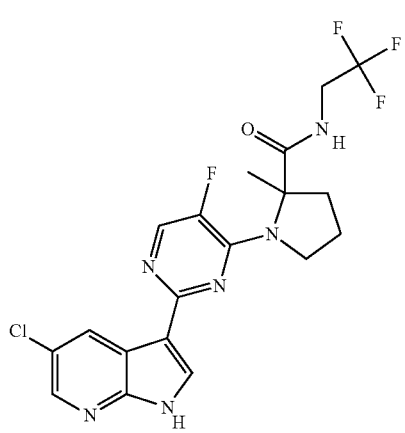
55 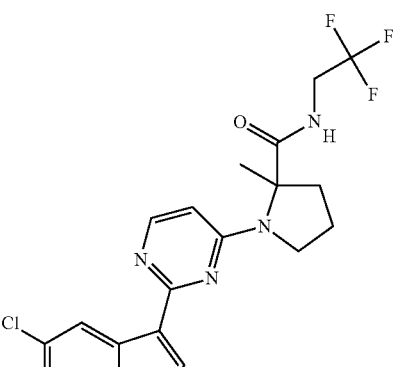
56 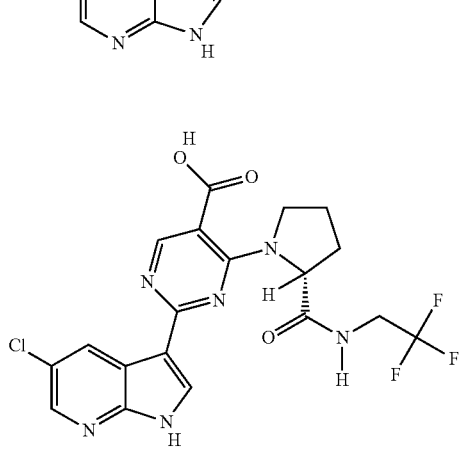
57 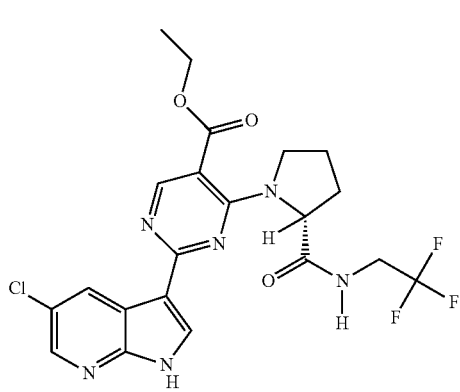
58 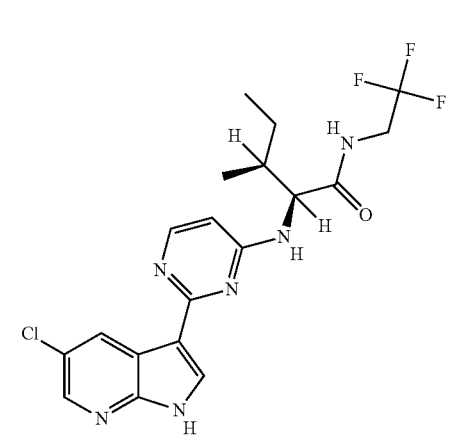

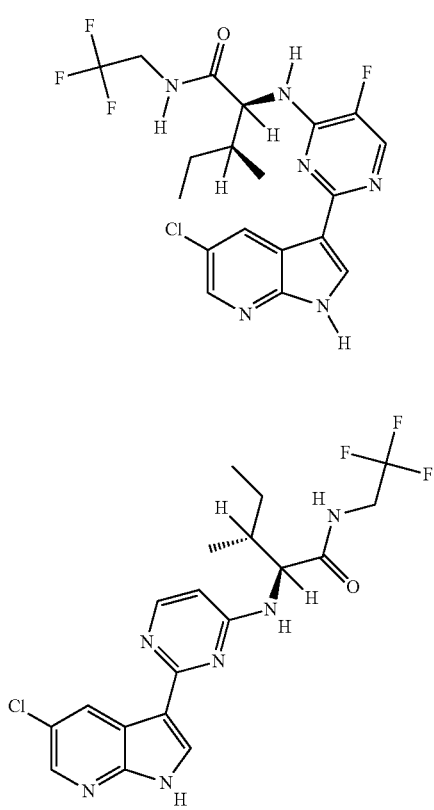
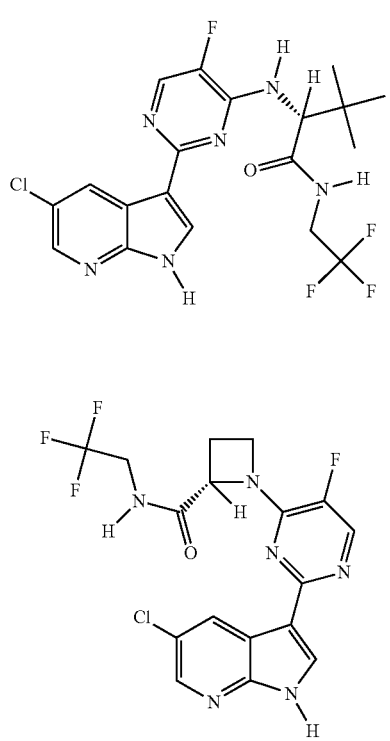
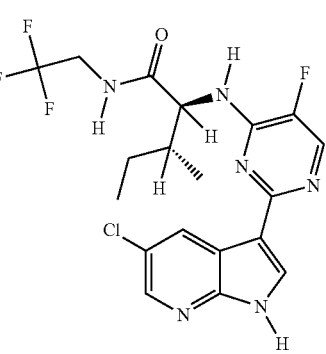
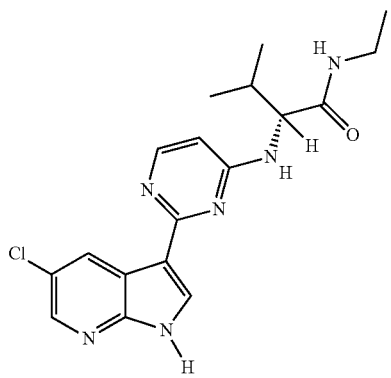
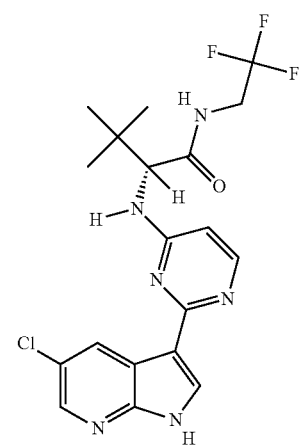
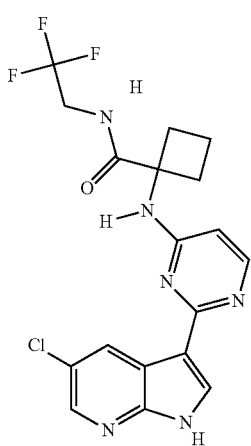

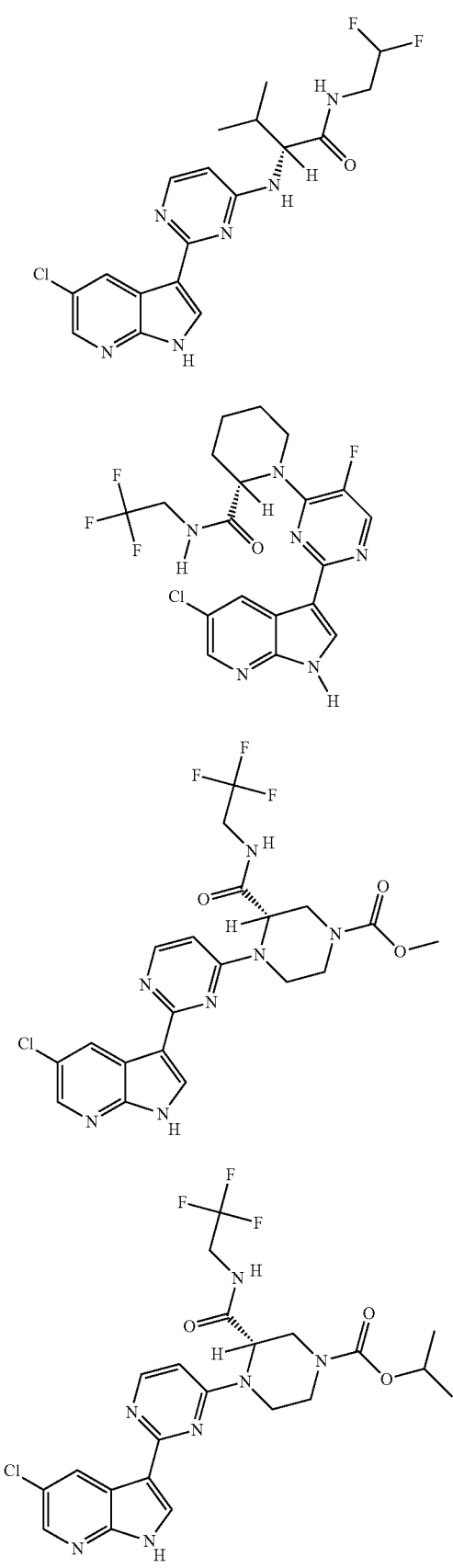
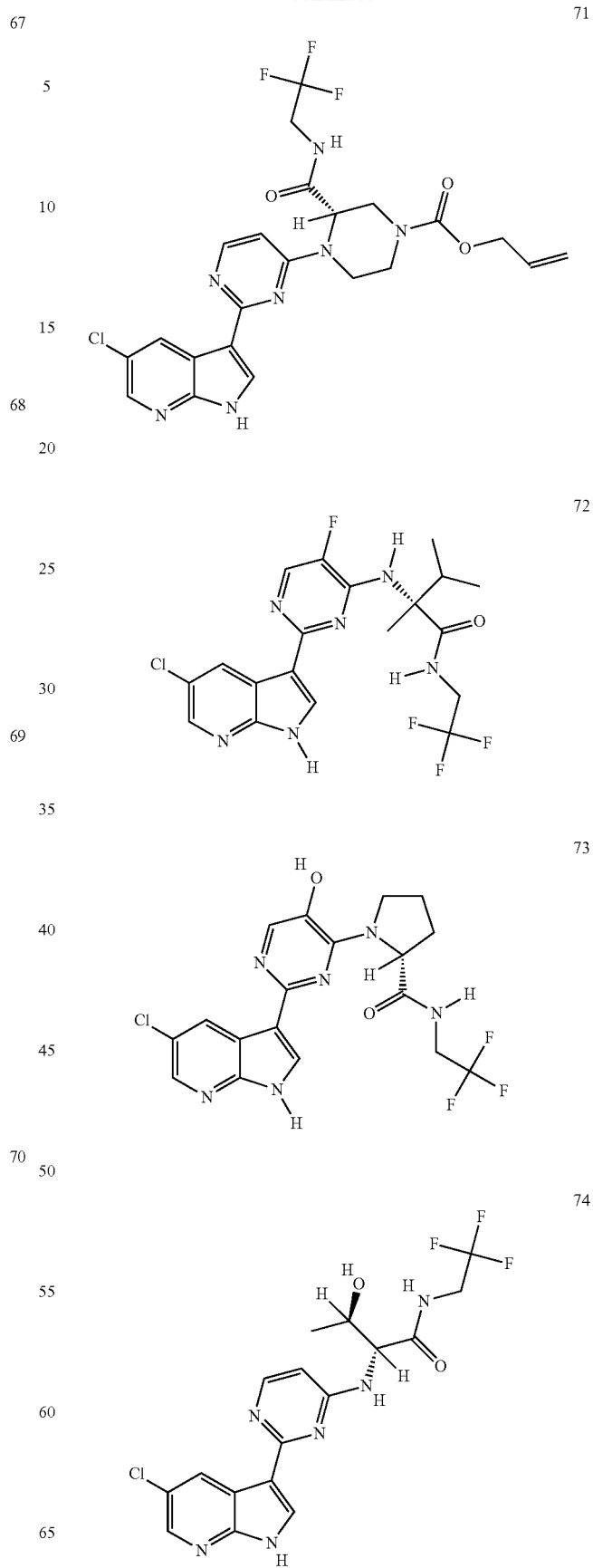

75
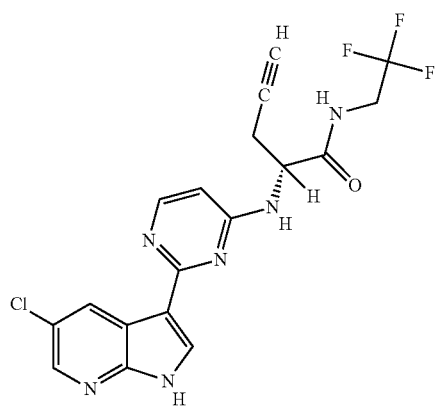
78
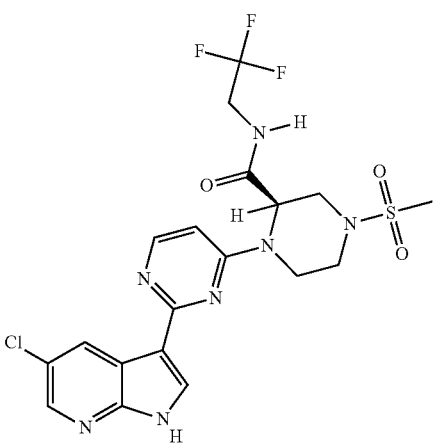
76
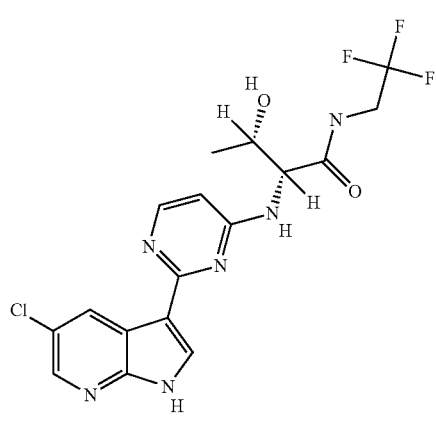
79
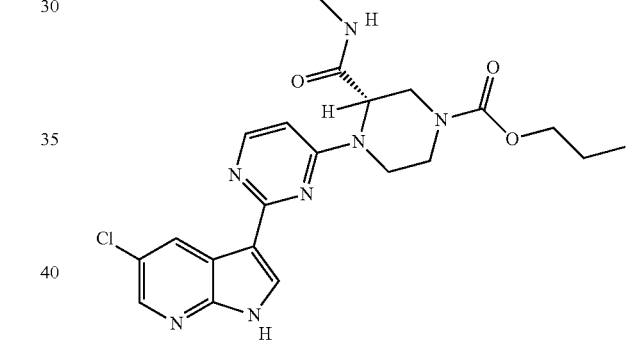
77
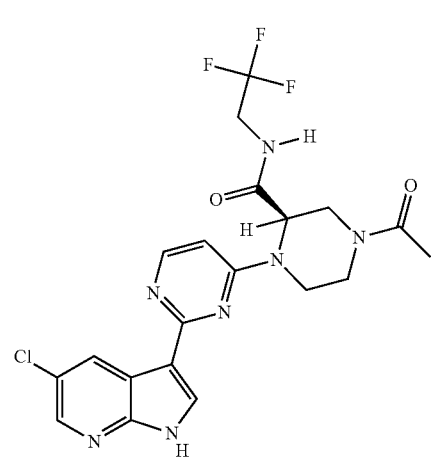
80
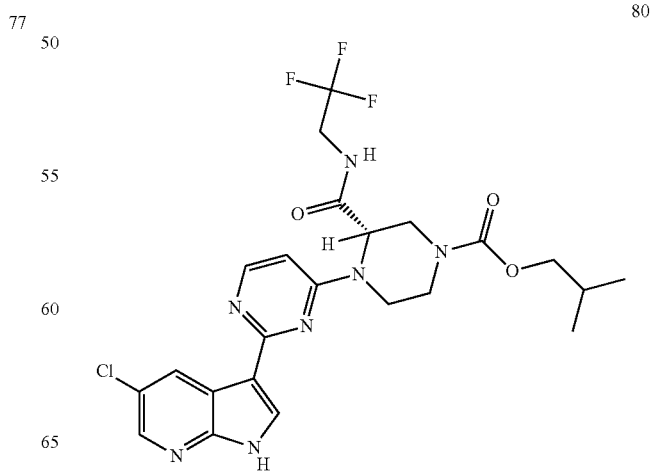

81
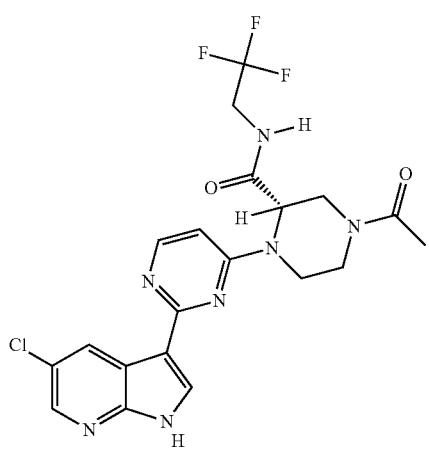
82
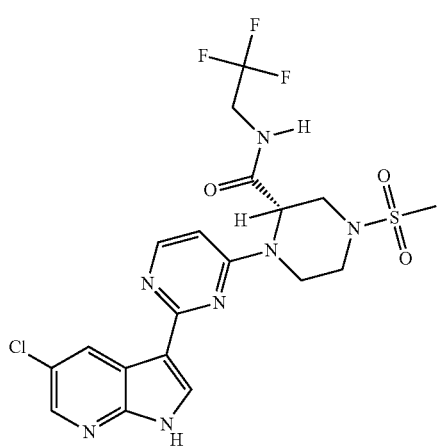
83
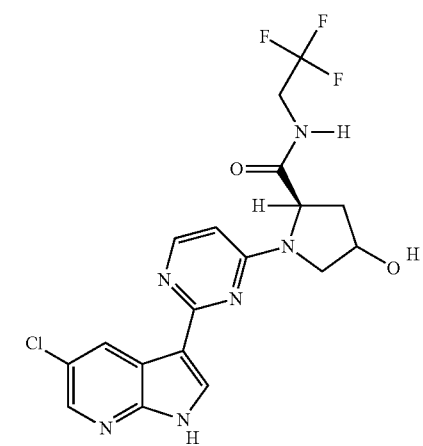
84
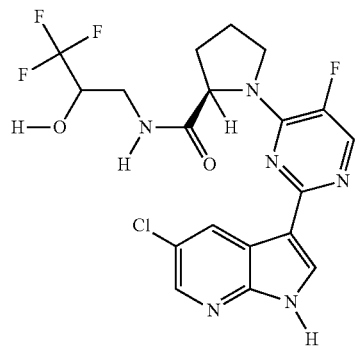
85
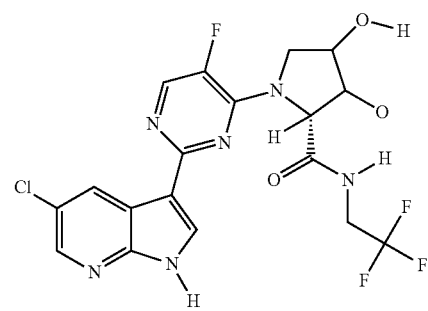
86
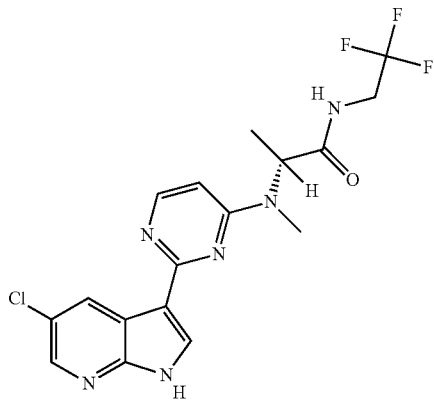
87
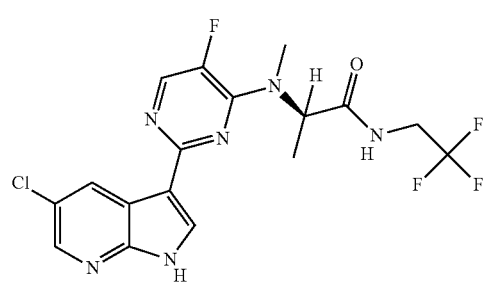

88
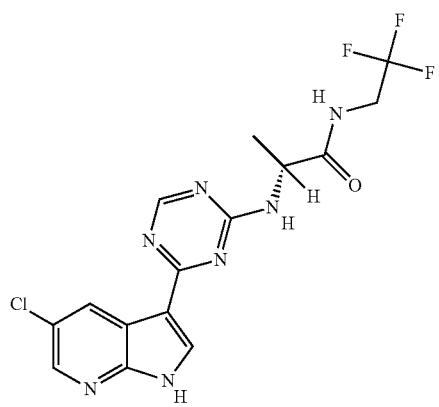
89
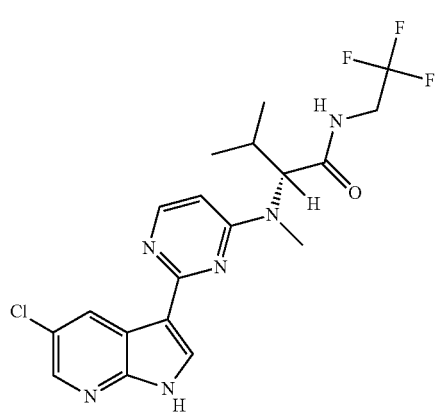
90
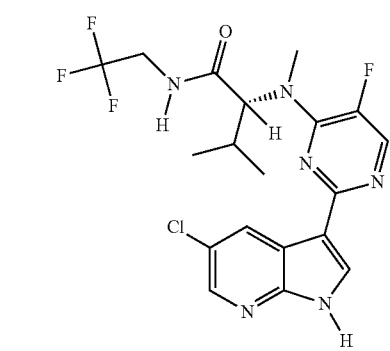
91
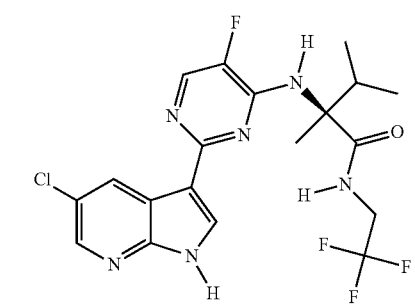
92
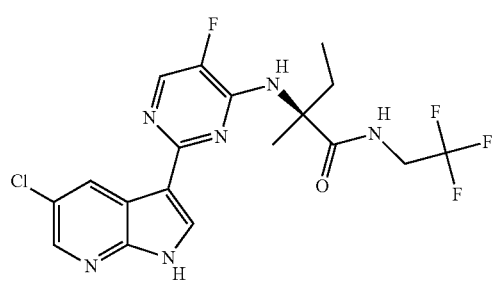
93
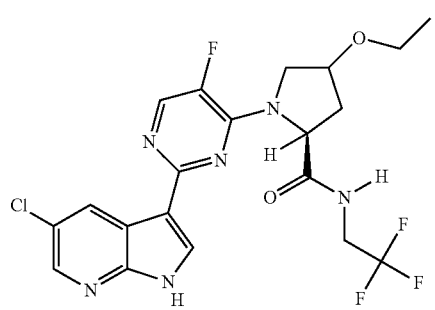
94
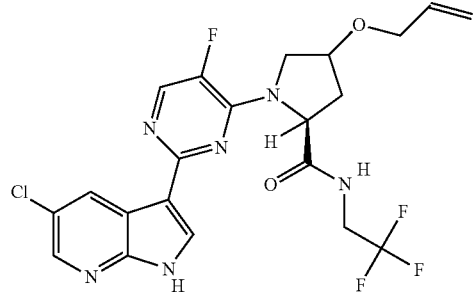
95
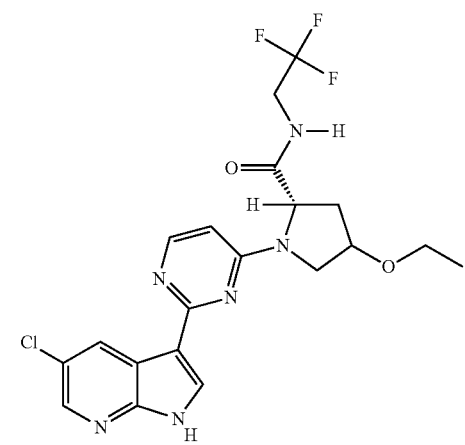

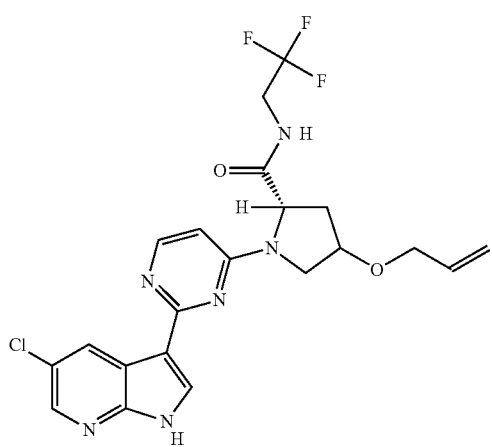
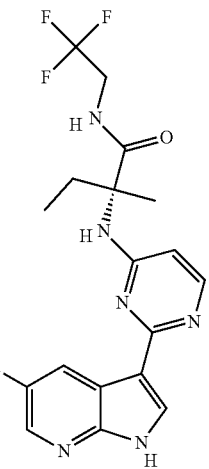
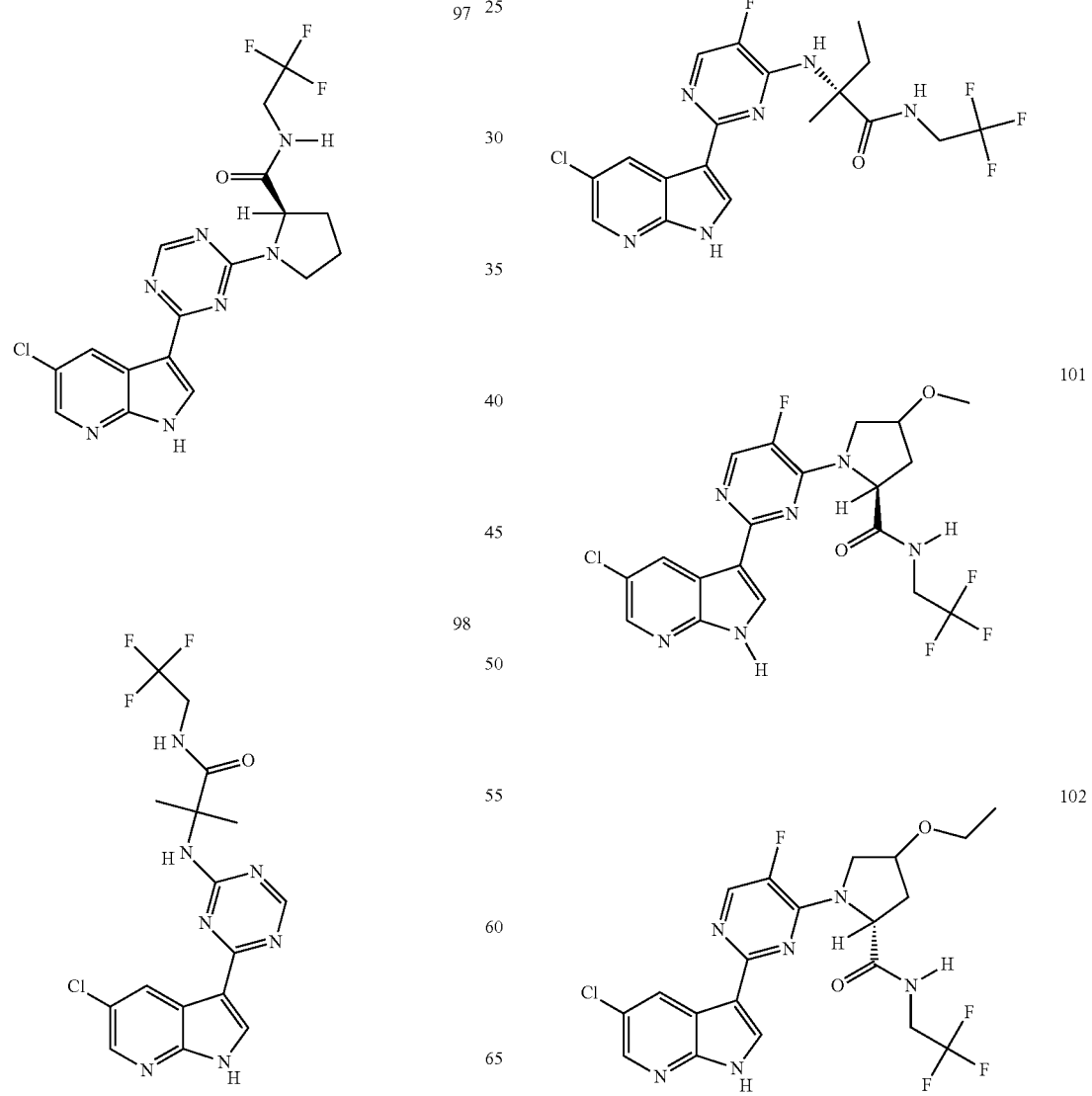

-continued
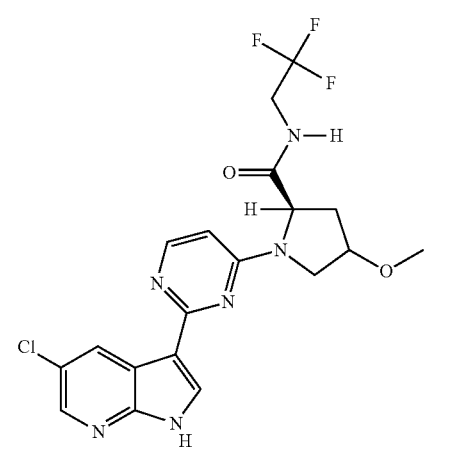
103
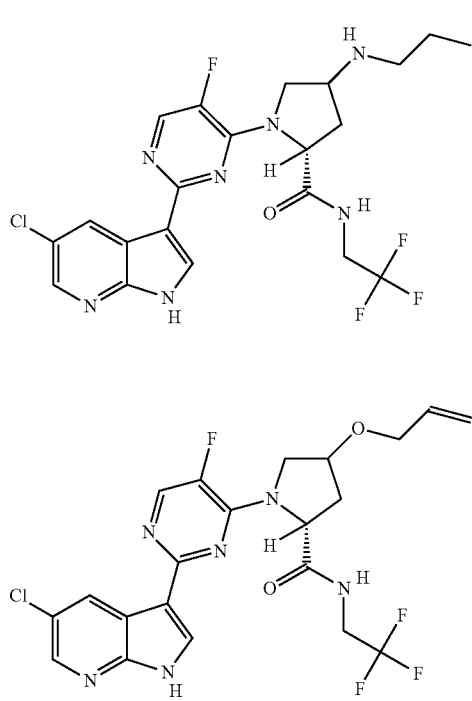
104
105
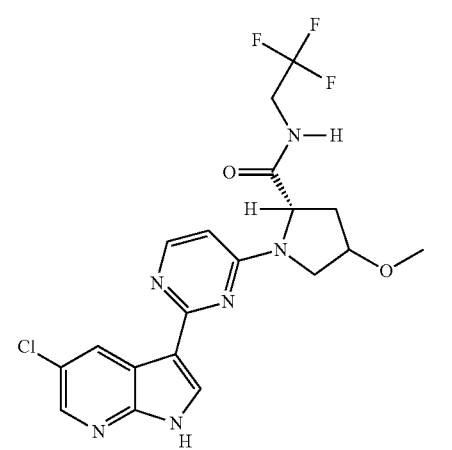
106
-continued
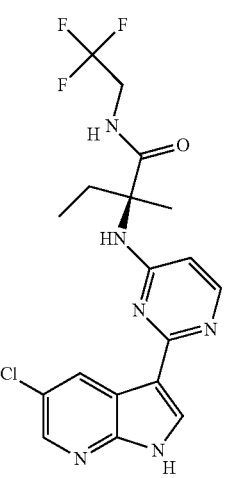
107
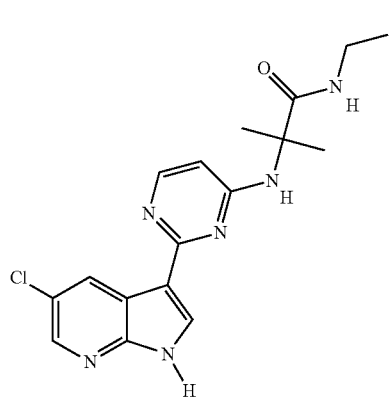
108
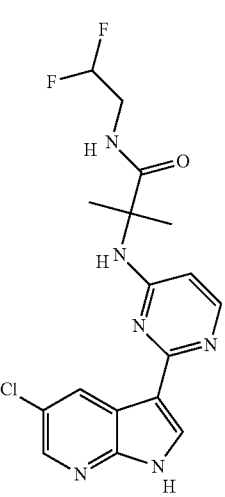
109

-continued
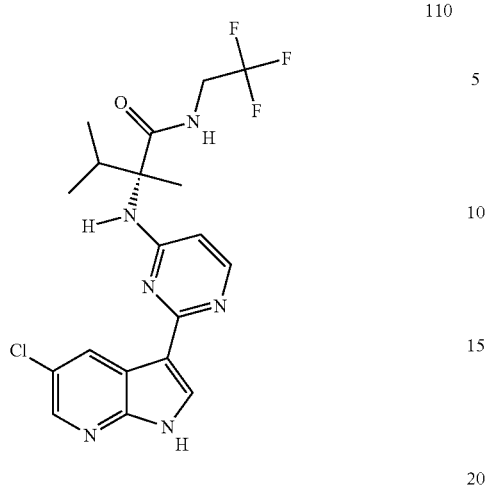
110
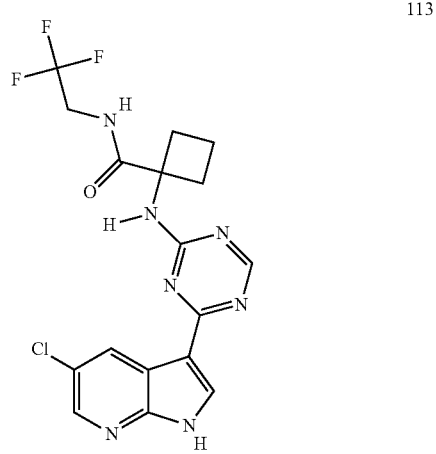
113
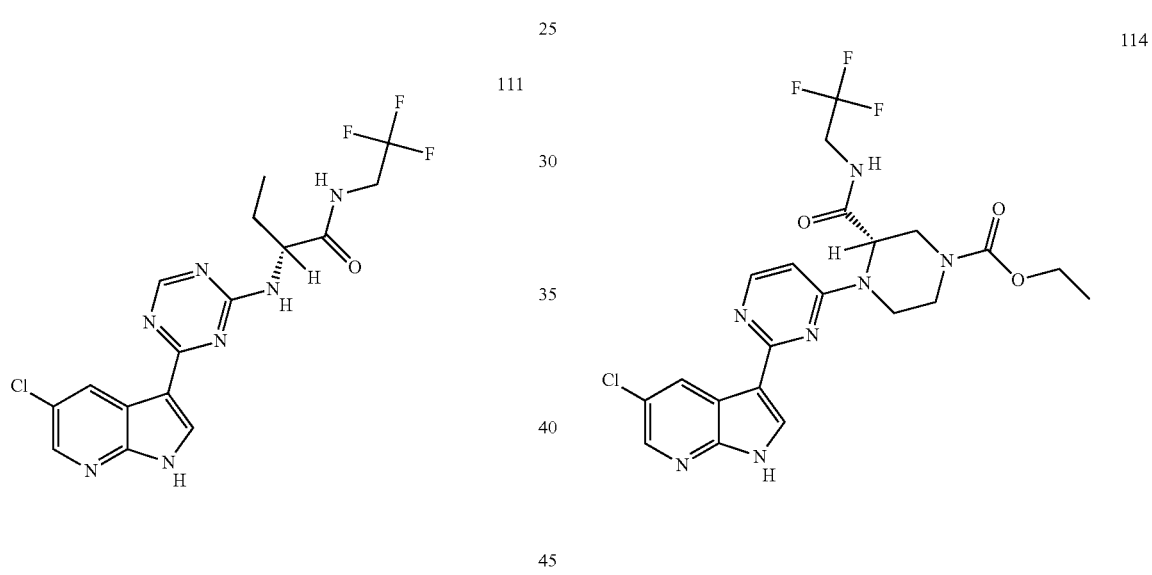
111
114
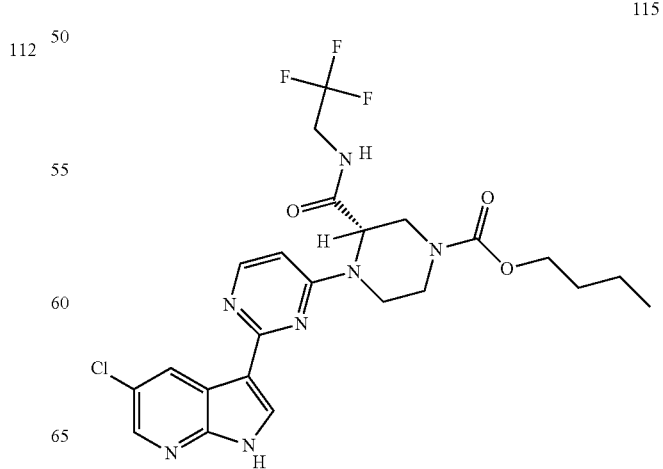
112
115

116
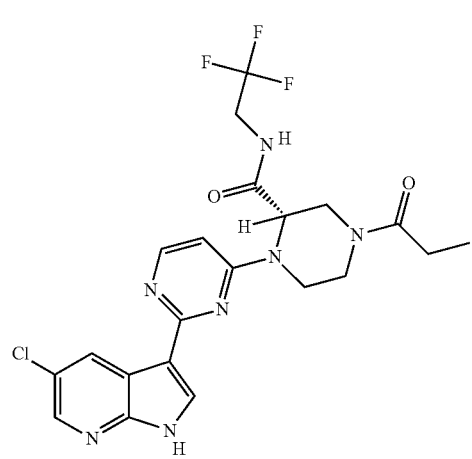
117
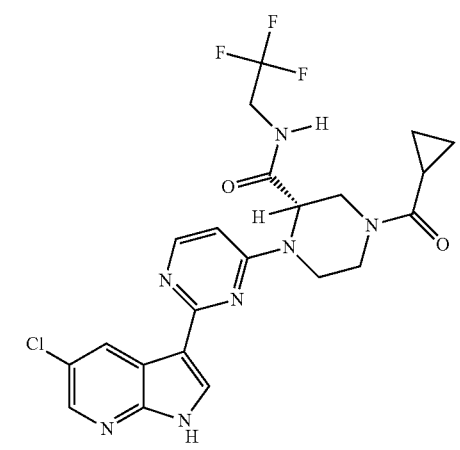
118
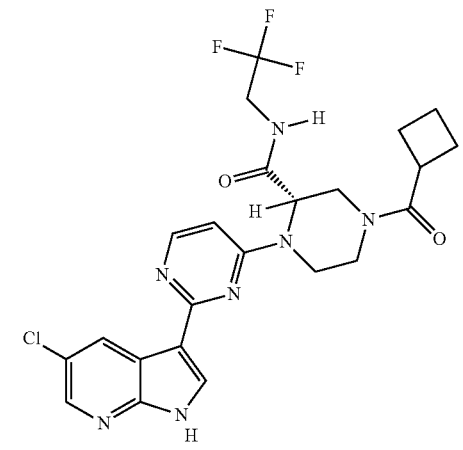
119
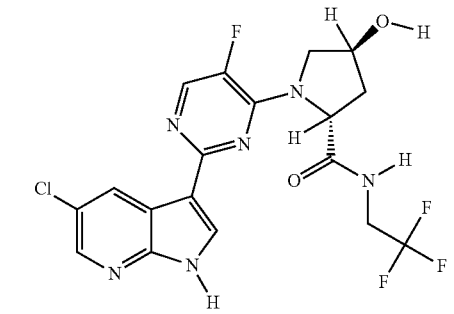
120
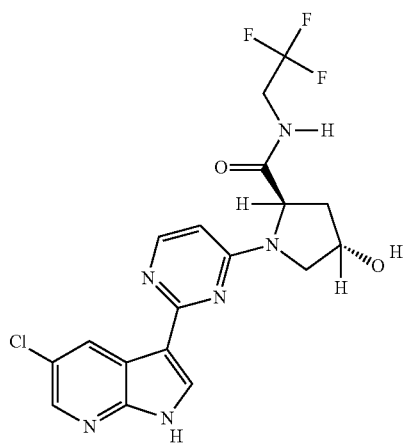
121
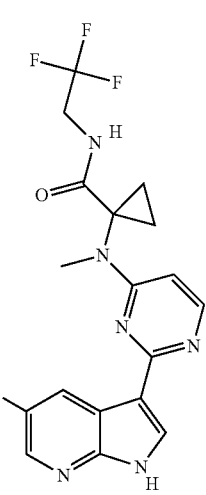
122
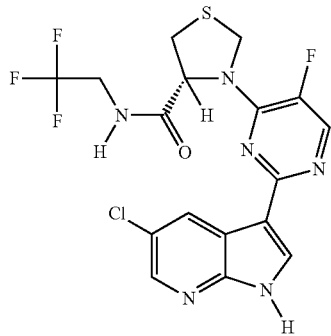

| 123 | 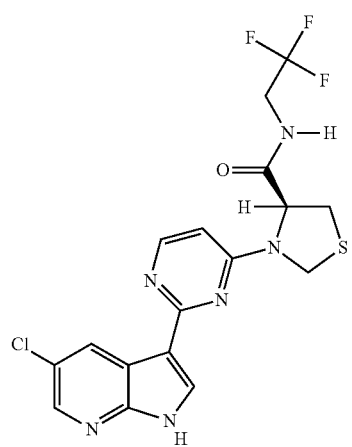 | 126 | 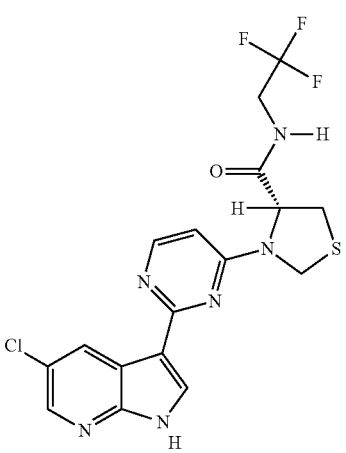 |
| 124 | 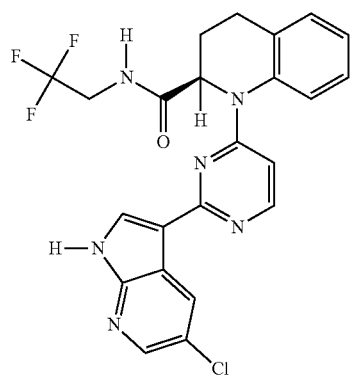 | 127 | 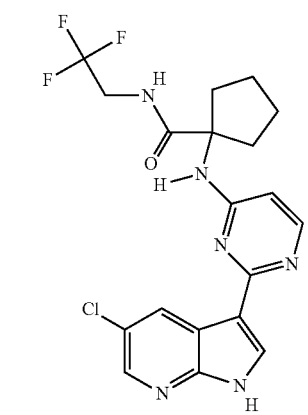 |
| | | 128 | 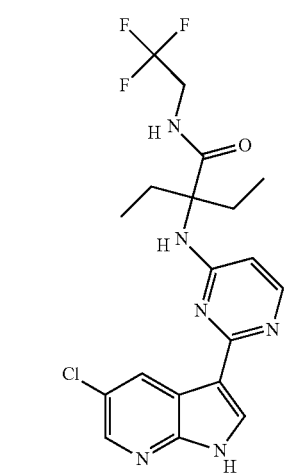 |
| 125 | 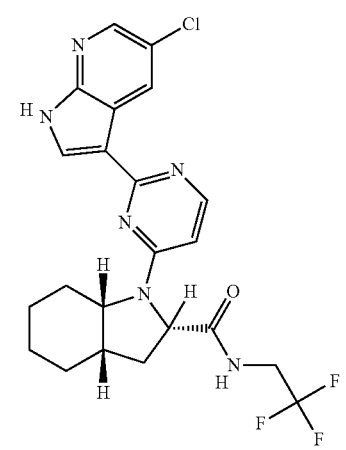 | 129 | 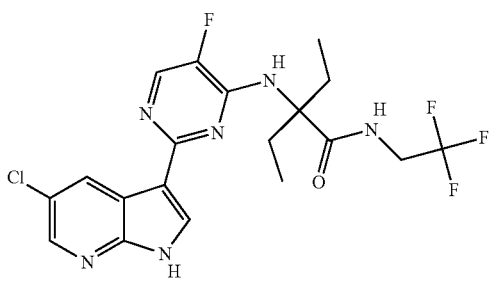 |

-continued
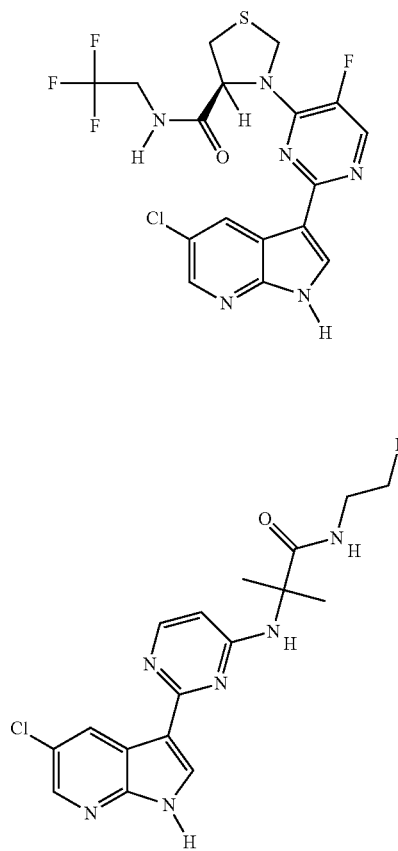
130
131
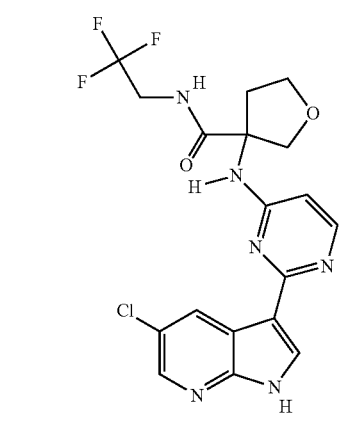
132
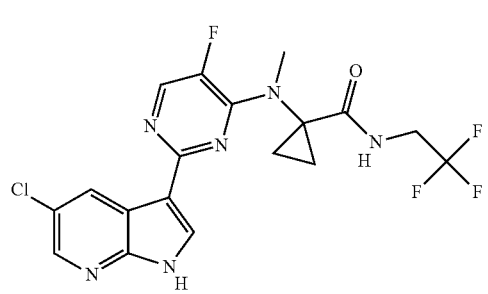
133
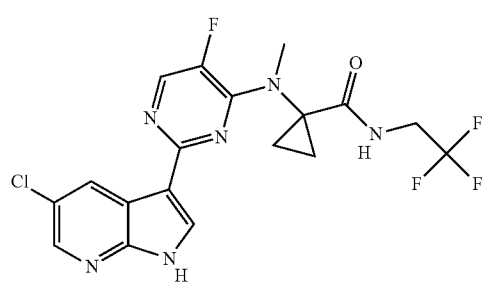
-continued
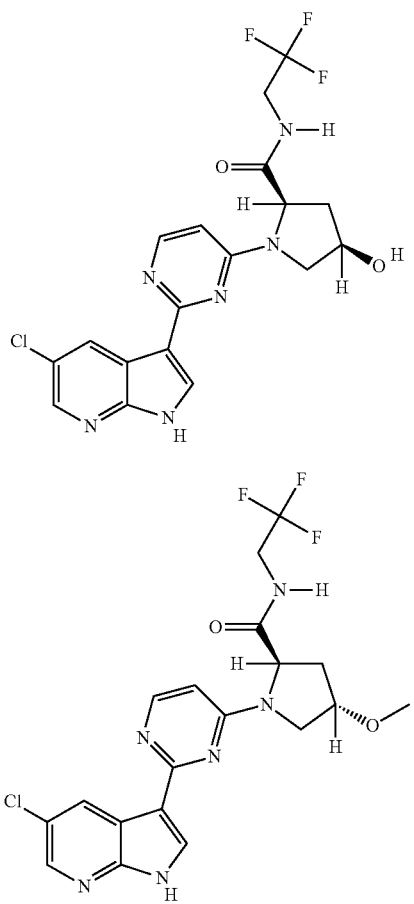
134
135
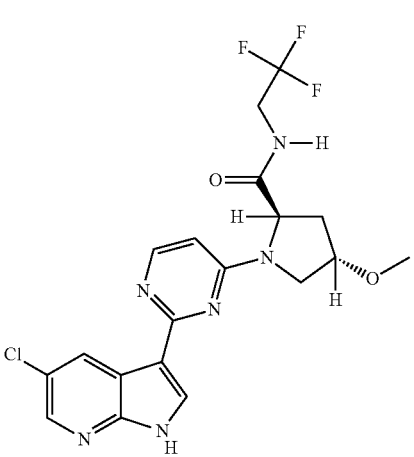
136
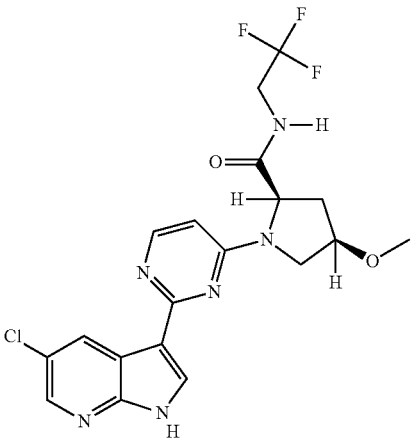
137
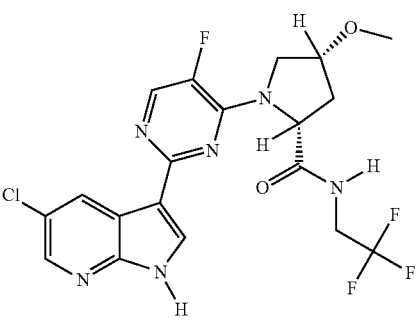

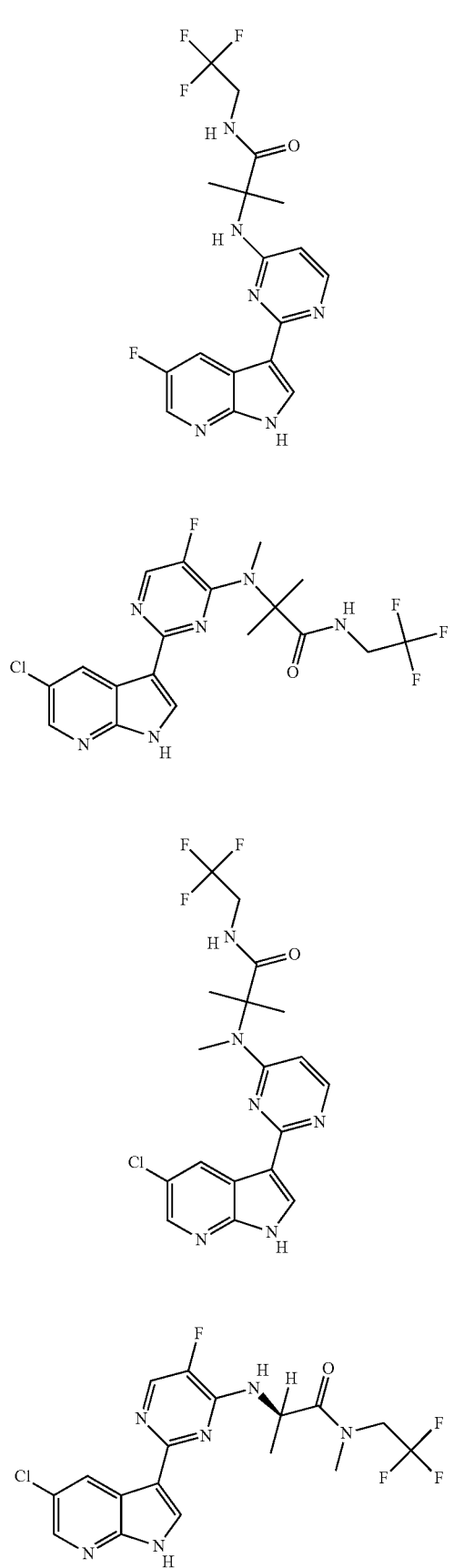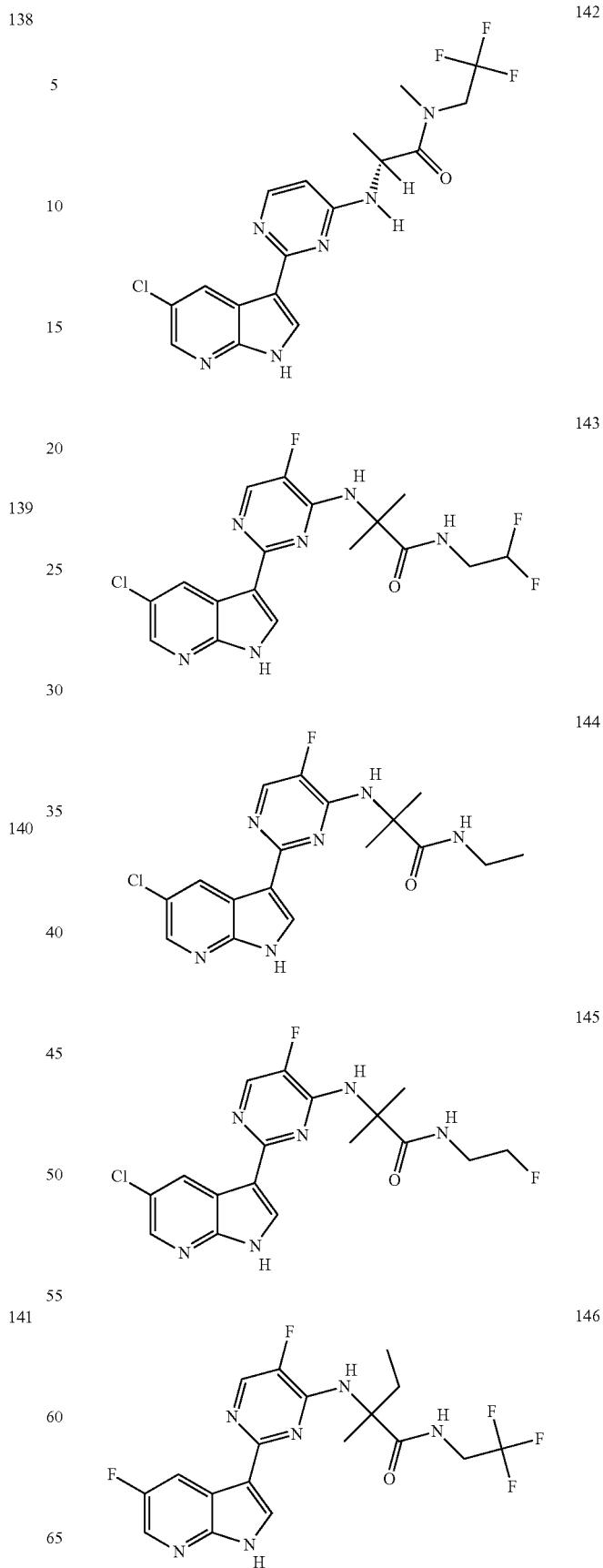

213
-continued
214
-continued
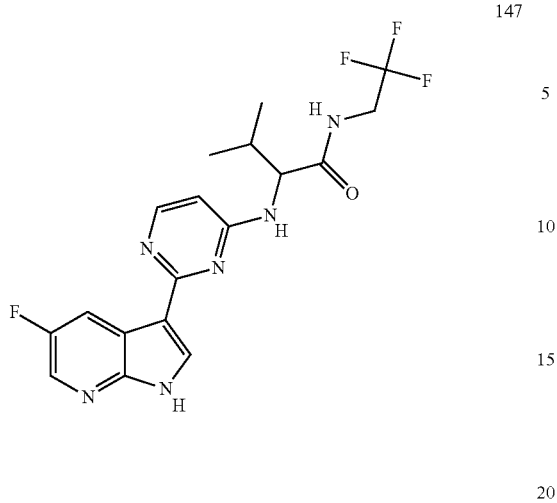
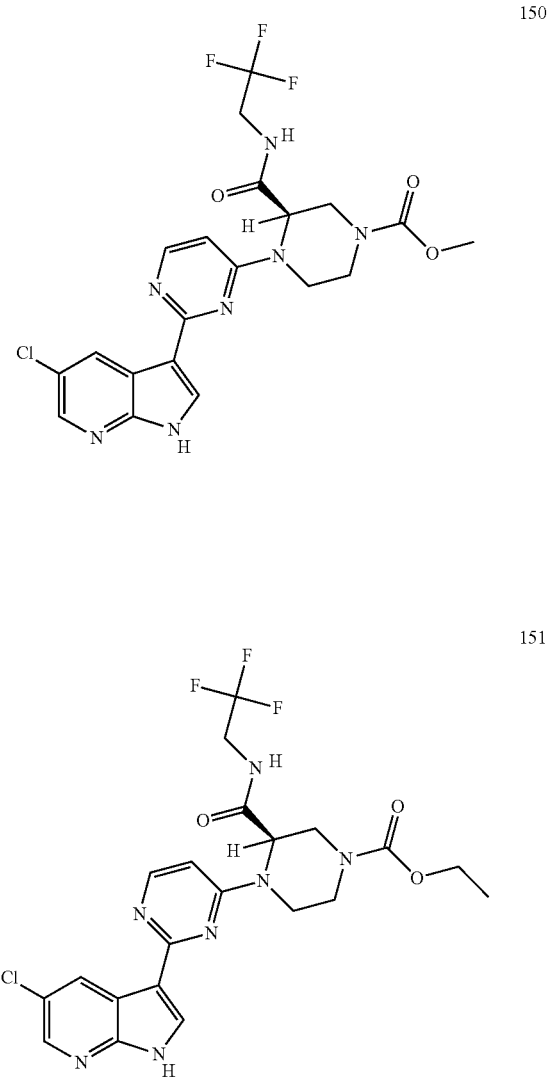
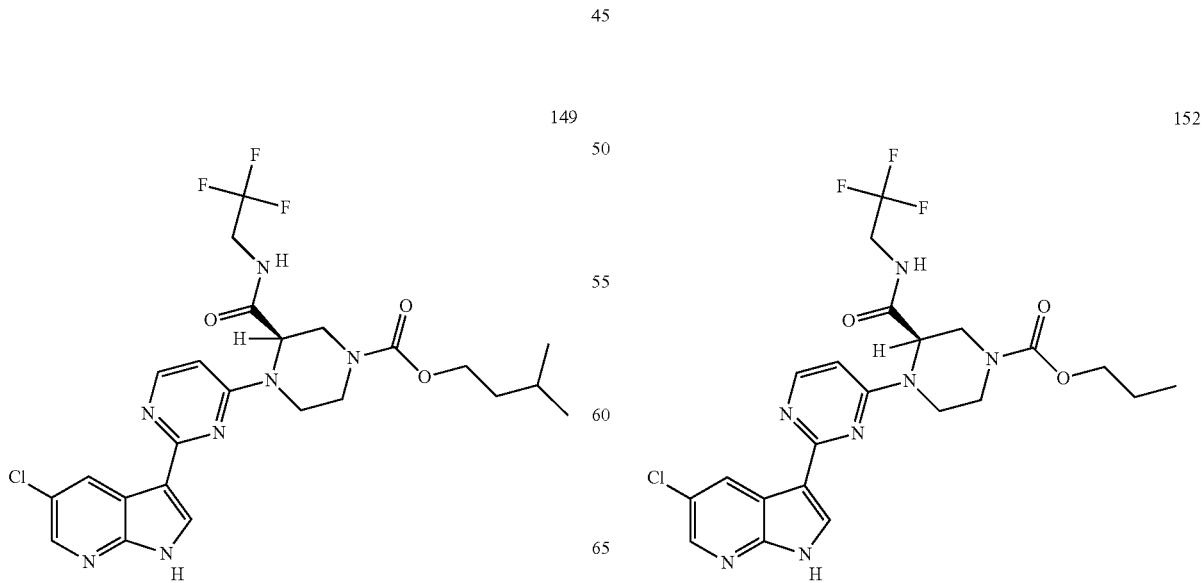

153
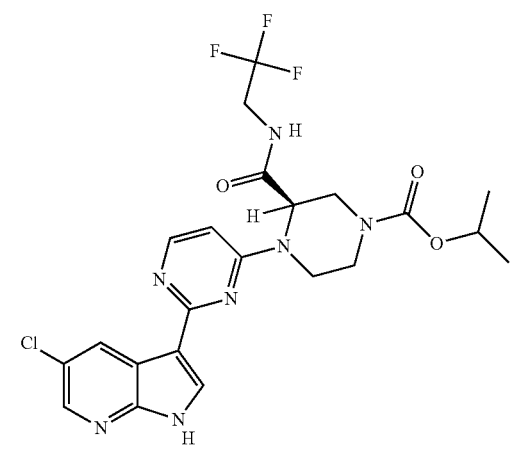
154
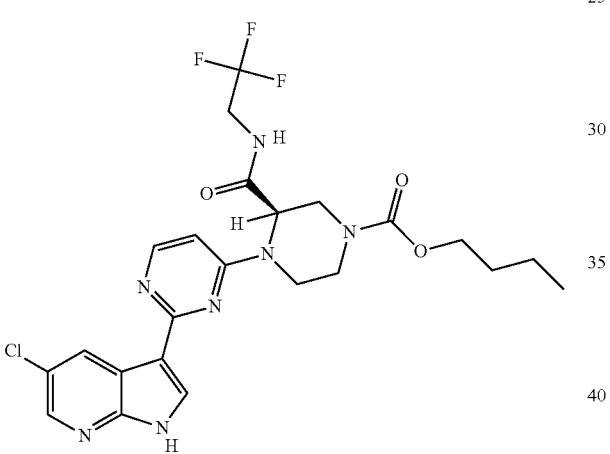
155
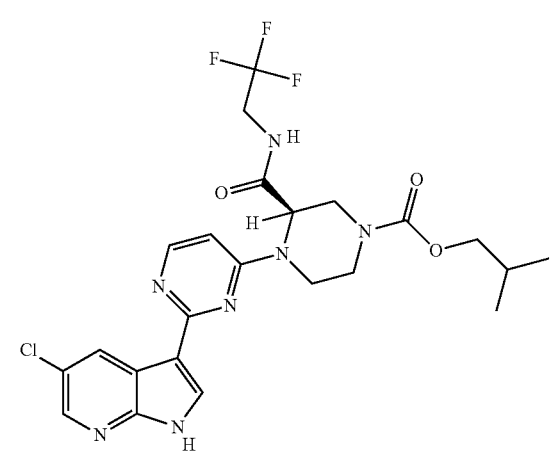
156
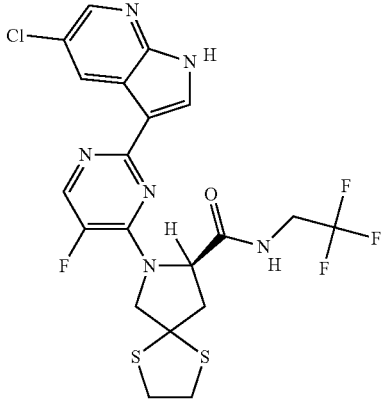
157
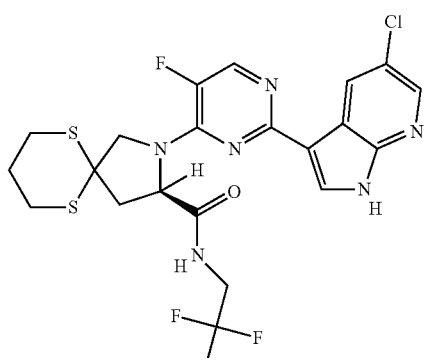
158
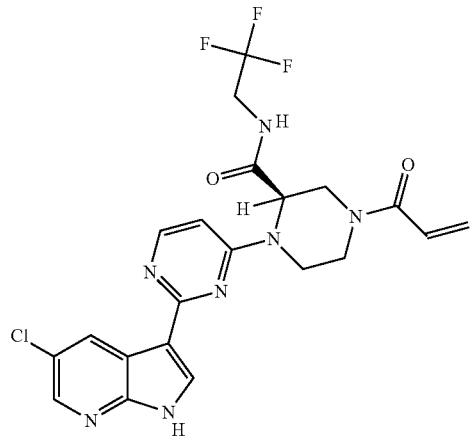
159
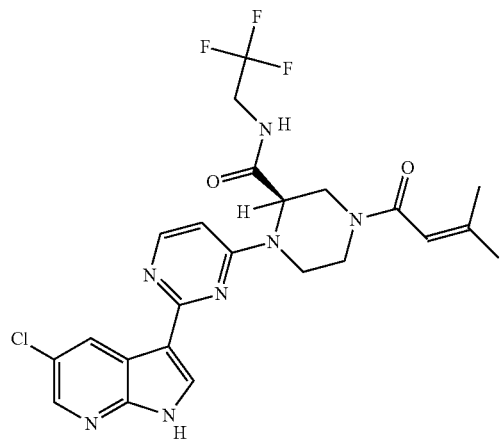

160
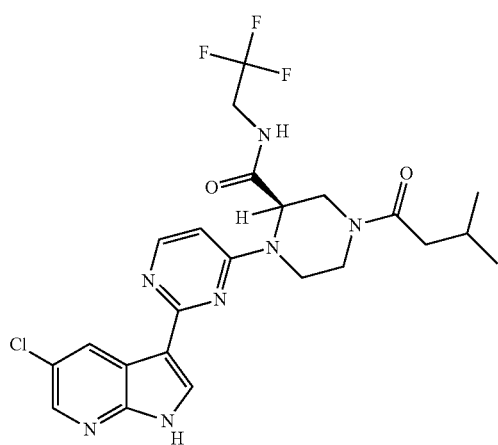
161
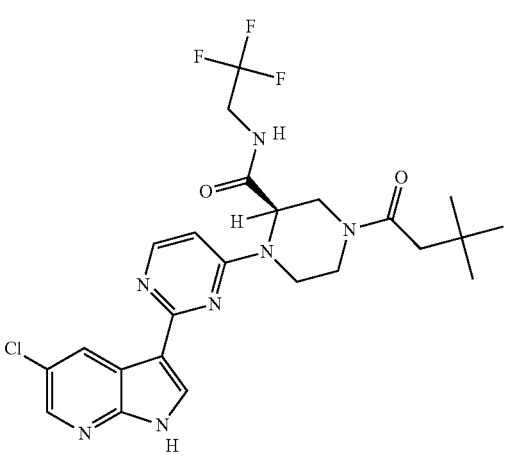
162
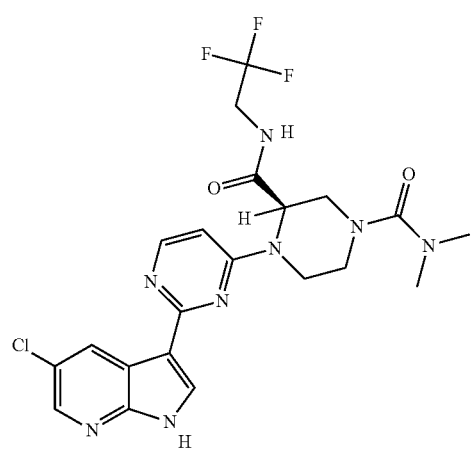
163
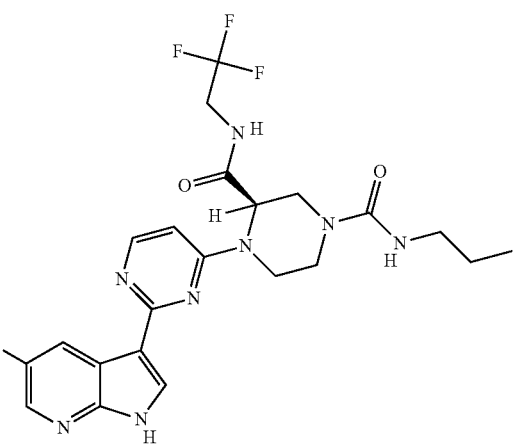
164
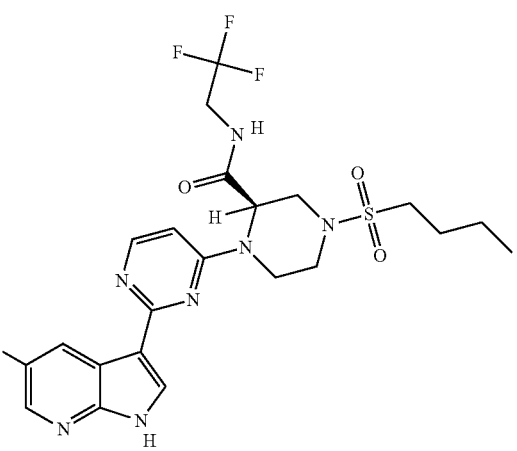
165
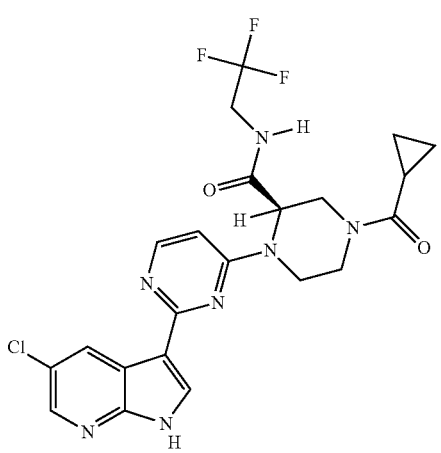

166
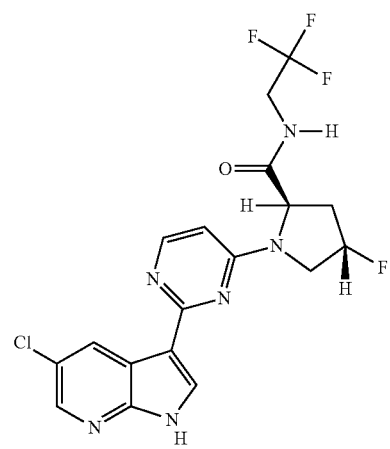
167
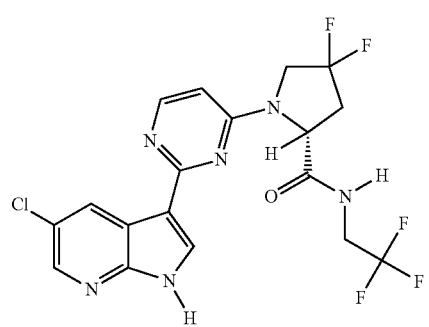
168
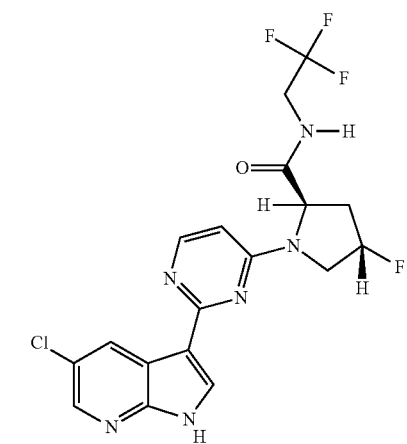
169
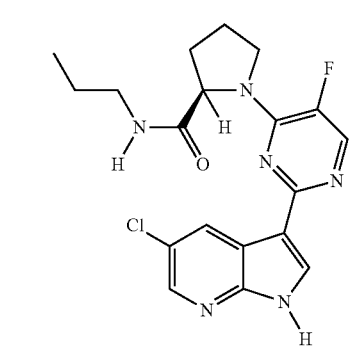
170
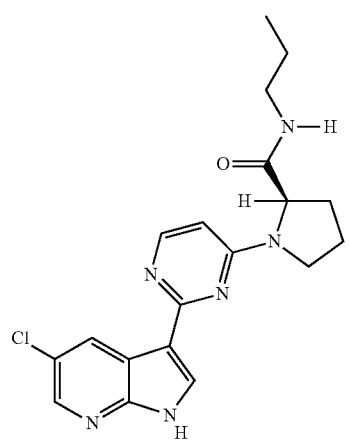
171
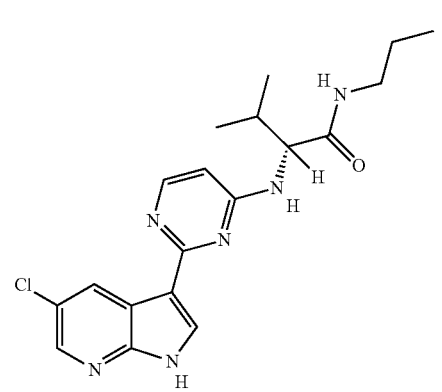
172
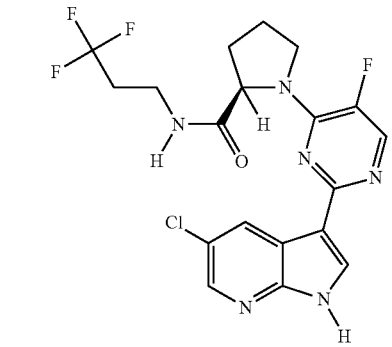
173
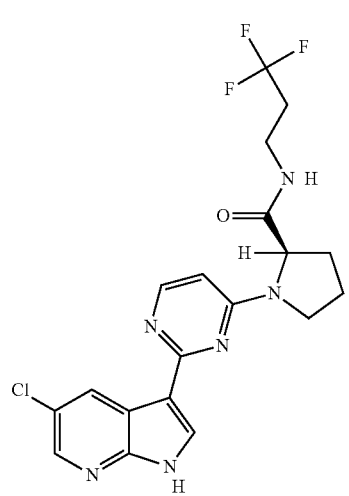

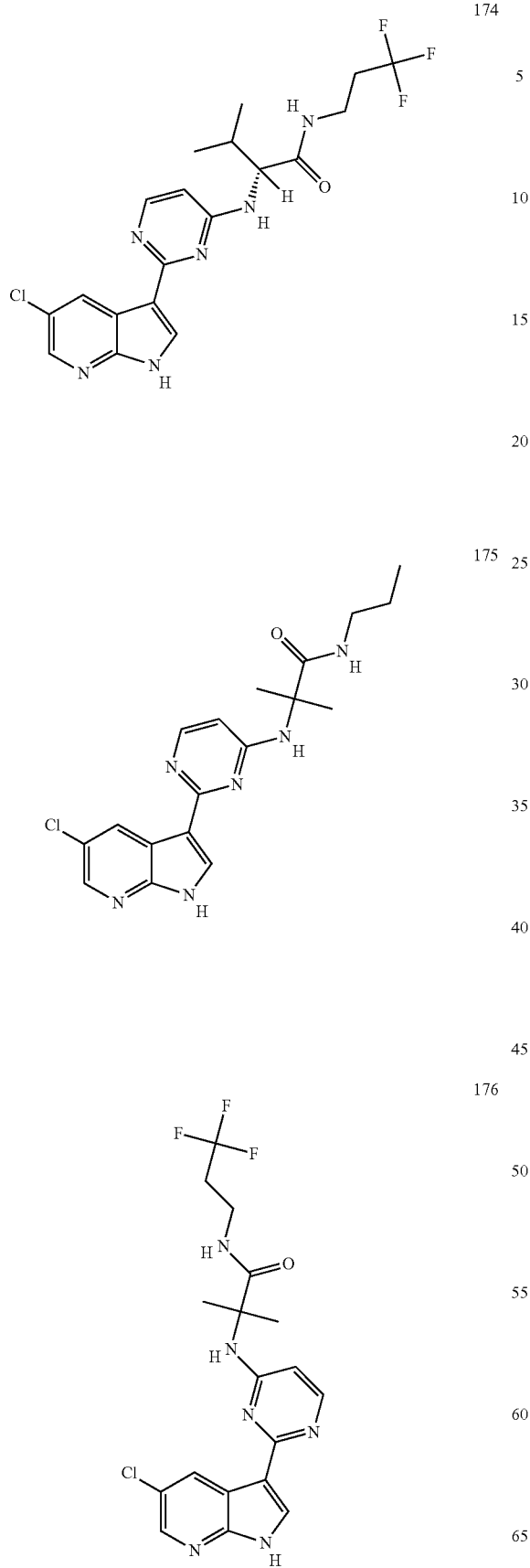
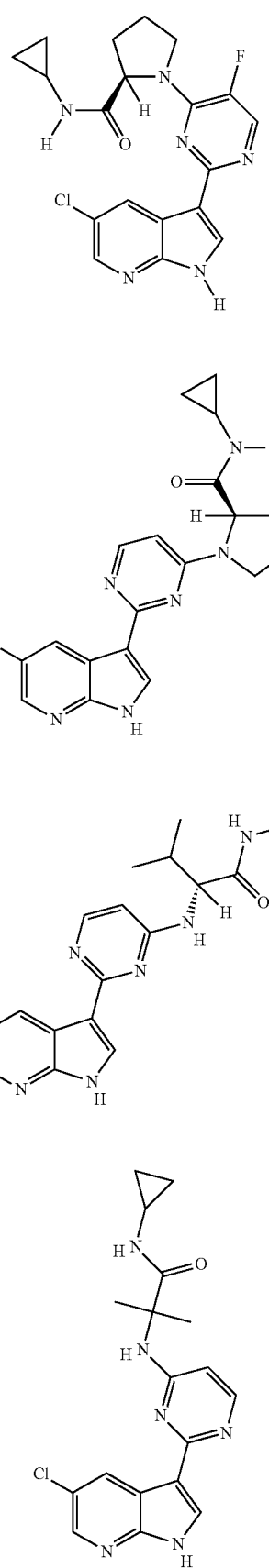

| 181 | 186 |
|---|---|
| 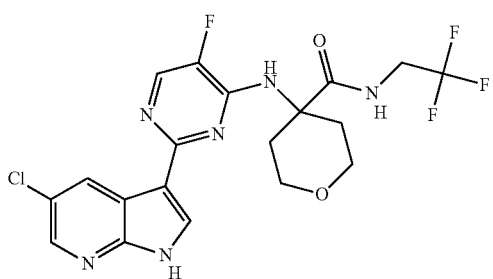 | 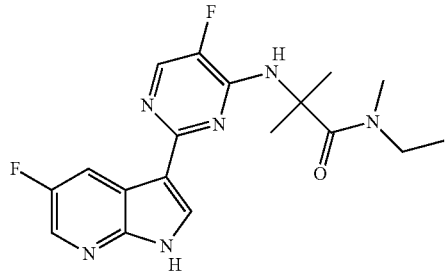 |
| 182 | 187 |
| 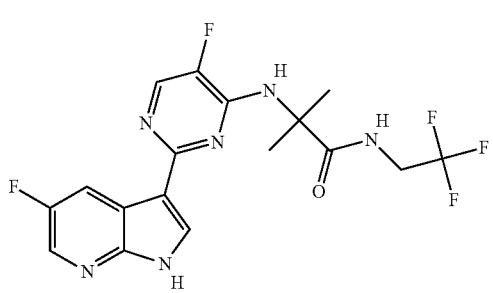 | 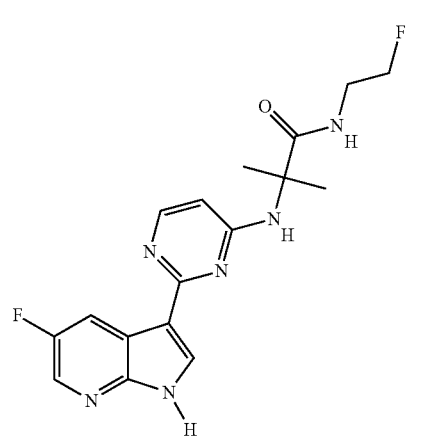 |
| 183 | 188 |
| 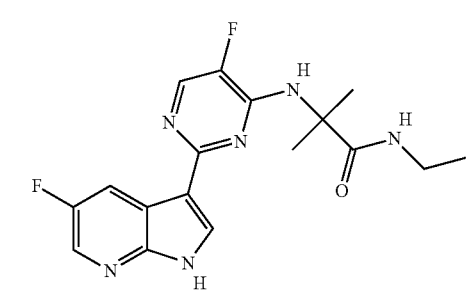 | 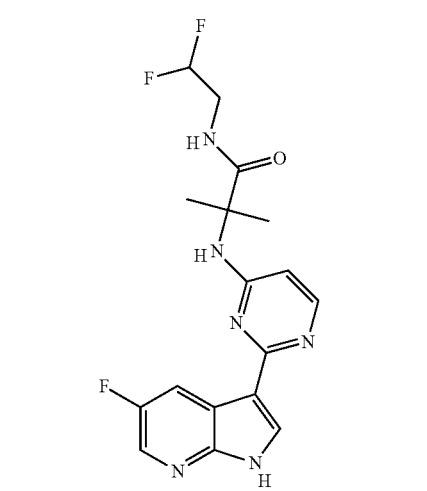 |
| 184 | 189 |
| 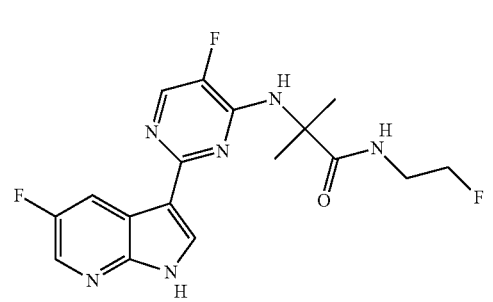 | 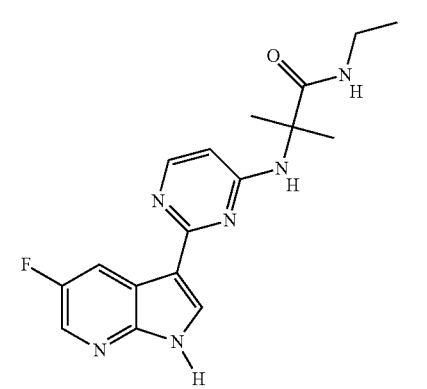 |
| 185 | |
| 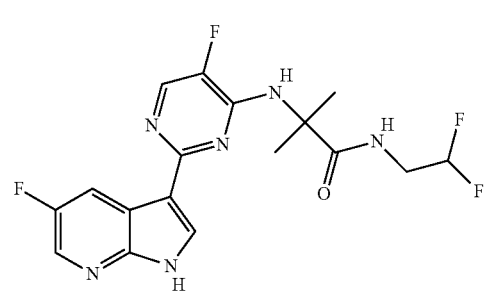 | |

225
-continued
226
-continued
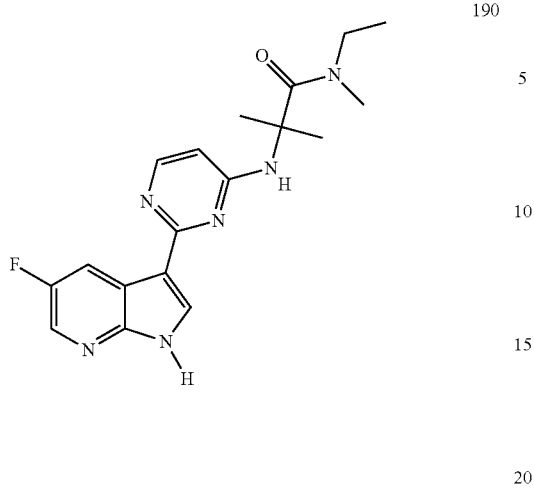
190
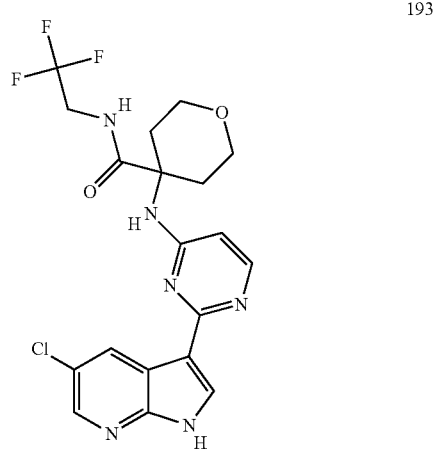
193
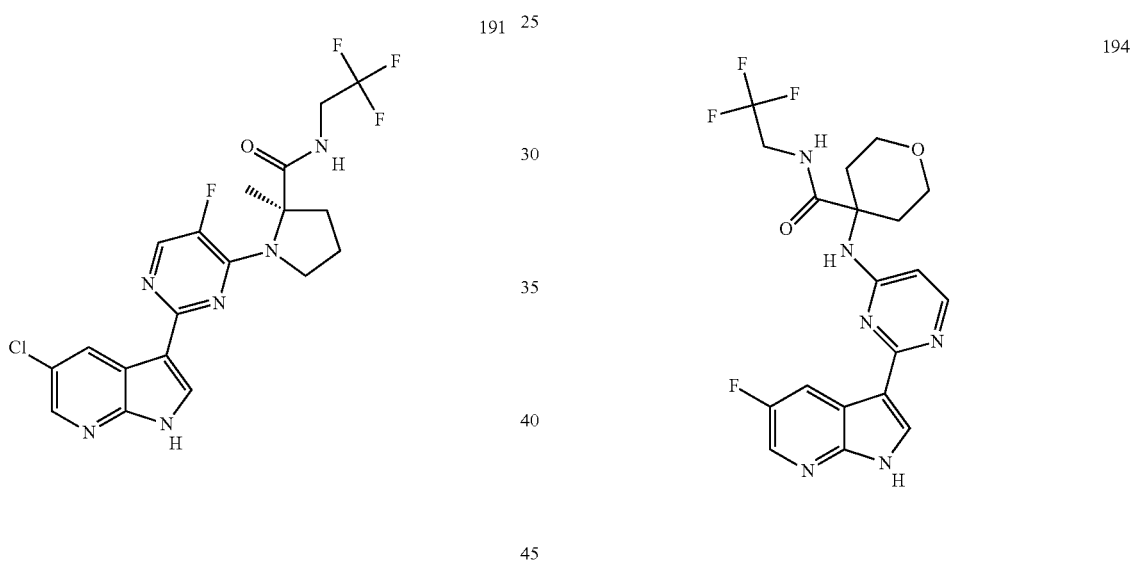
191
194
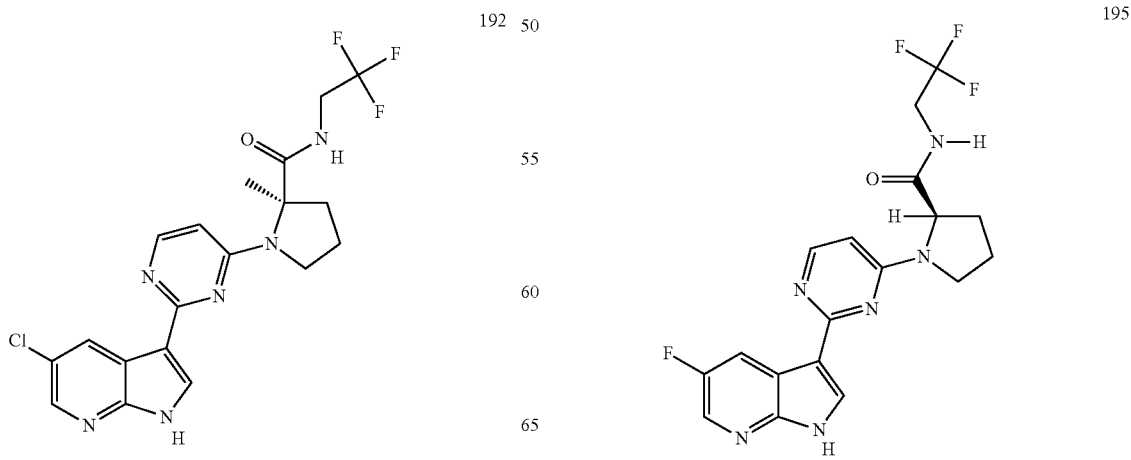
192
195

227
-continued
196
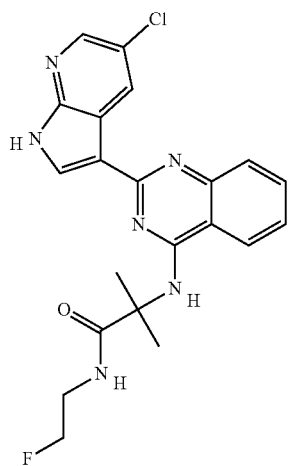
197
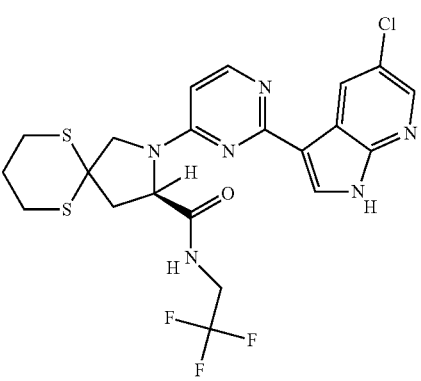
198
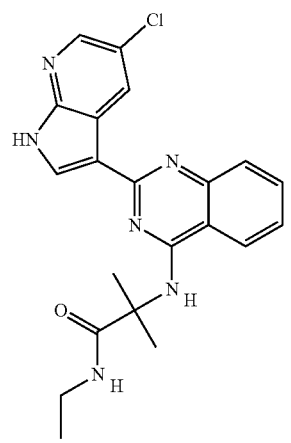
228
-continued
199
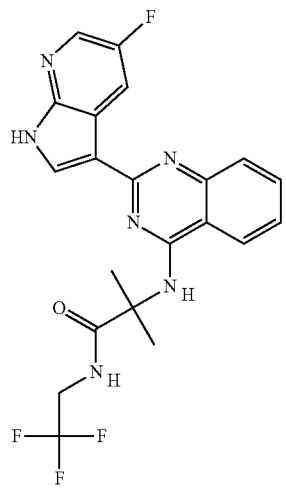
200
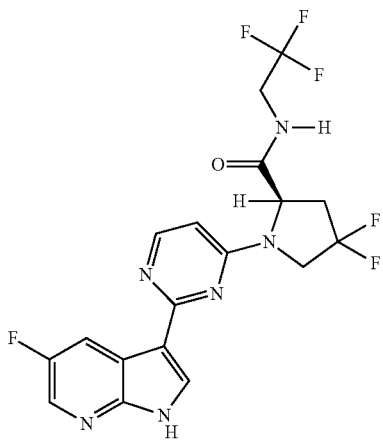
201

-continued
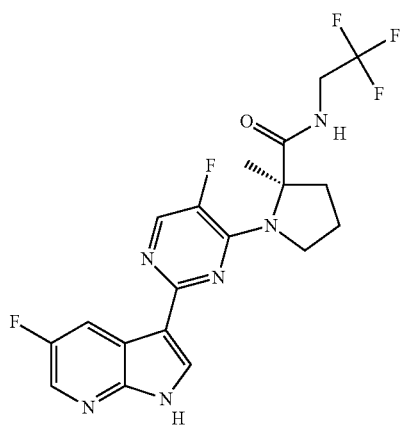
202
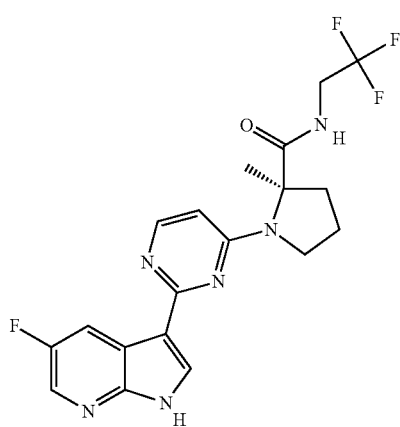
203
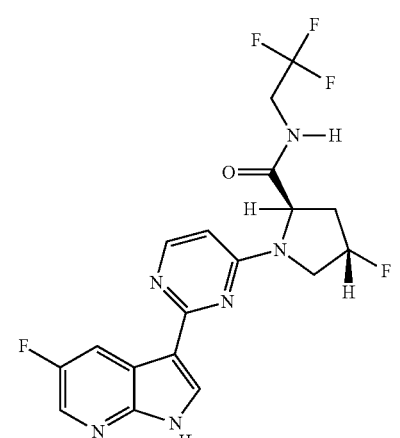
204
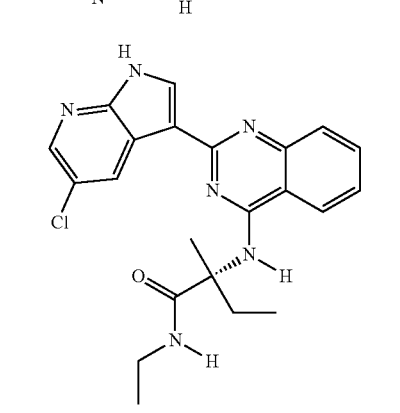
205
-continued
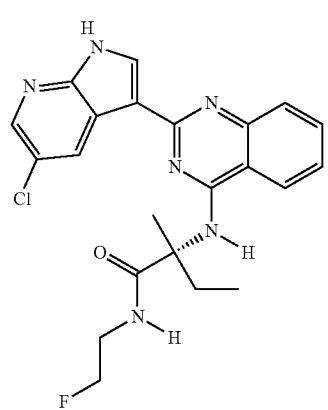
206
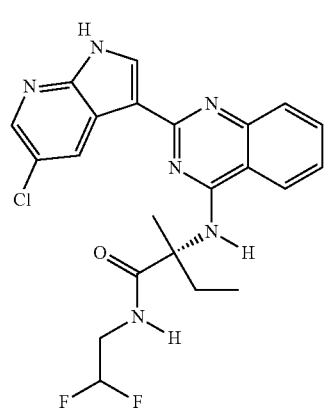
207
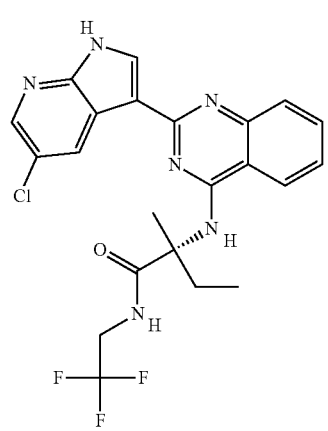
208
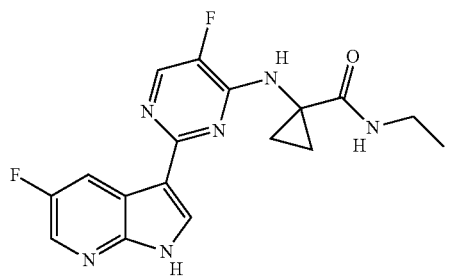
209

231
-continued
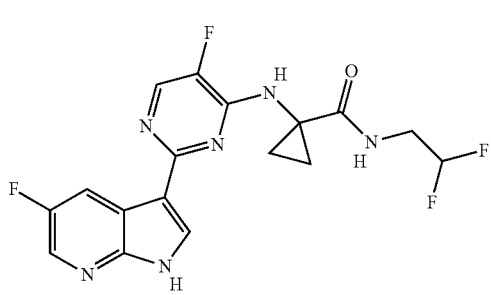
210
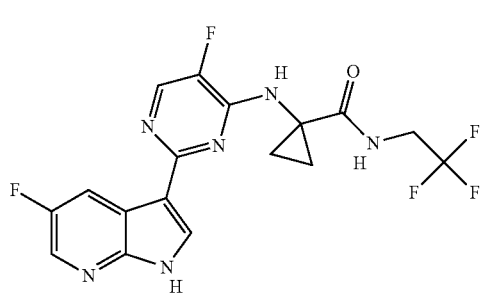
211
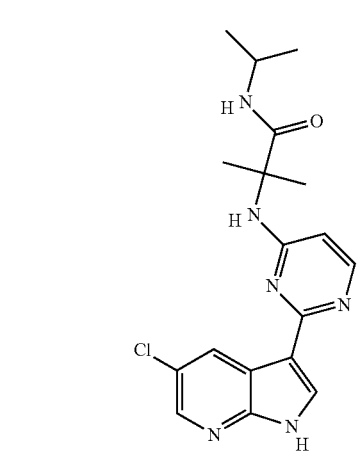
212
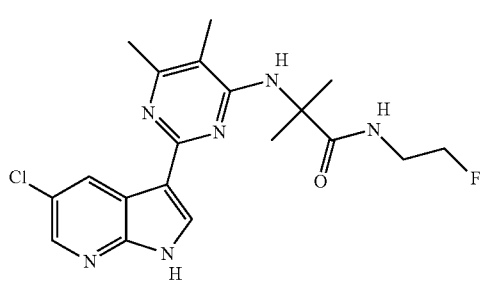
213
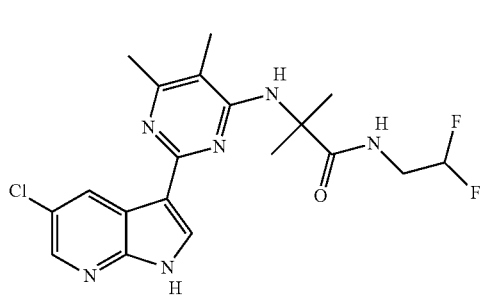
214
232
-continued
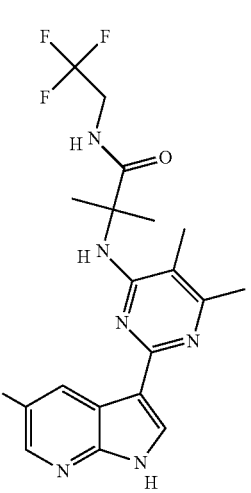
215
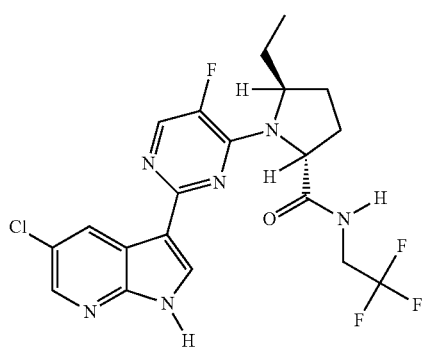
216
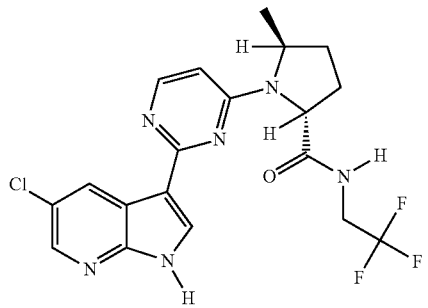
217
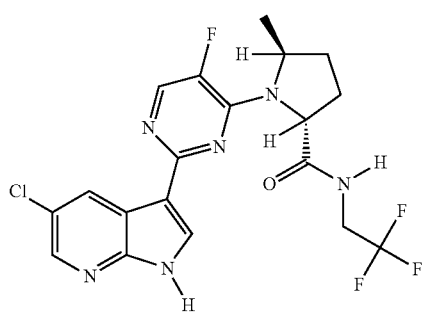
218

-continued
219
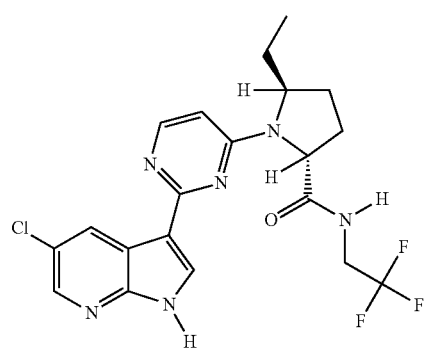
220
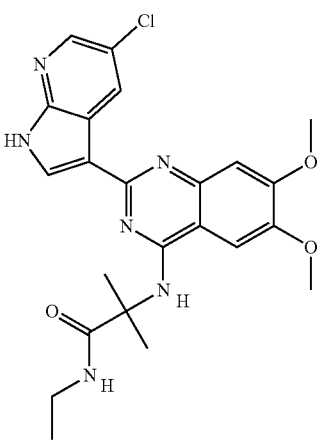
221
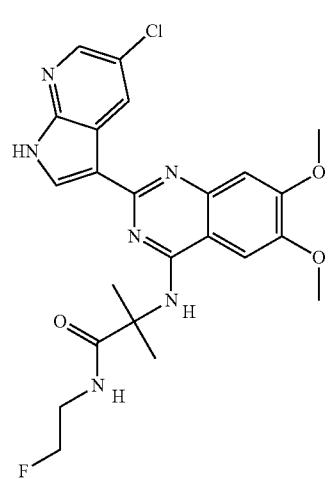
-continued
222
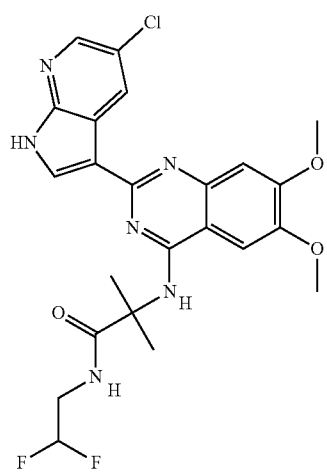
223
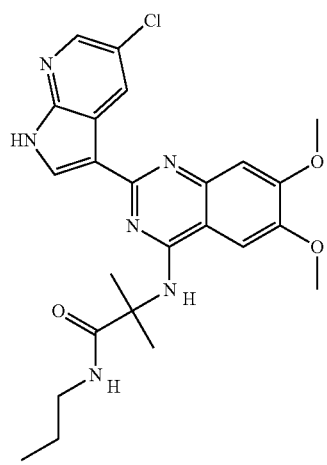
224
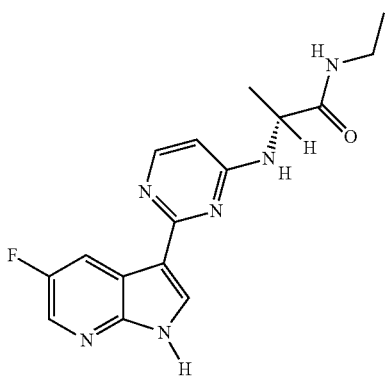

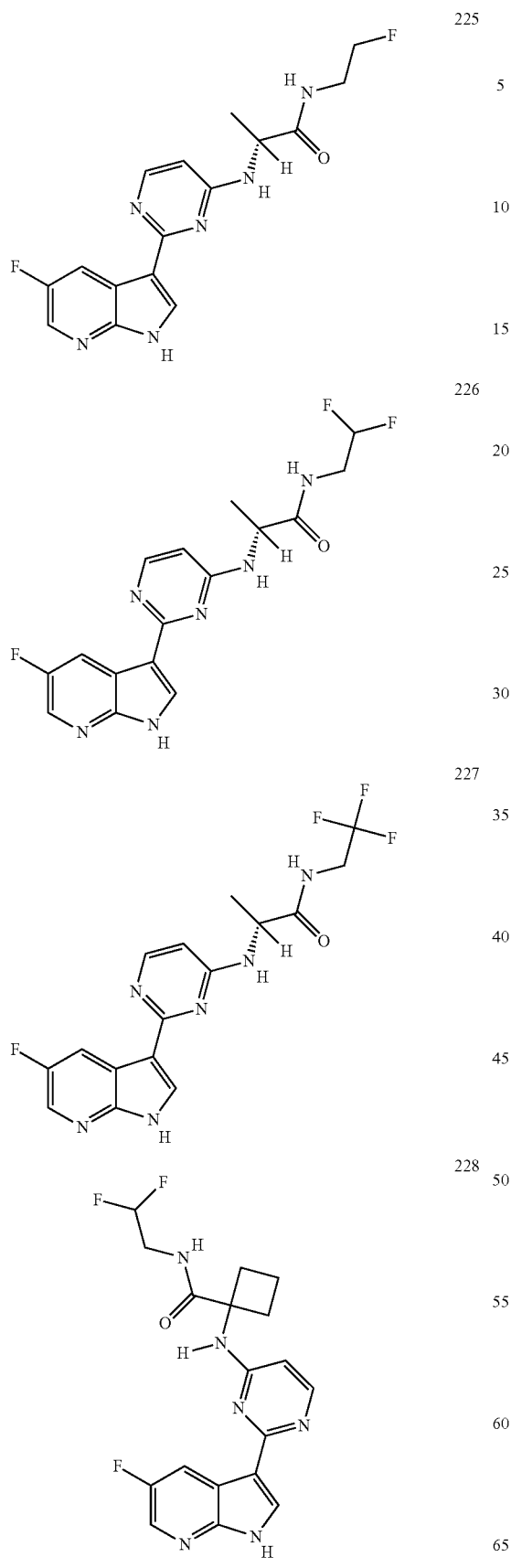

232 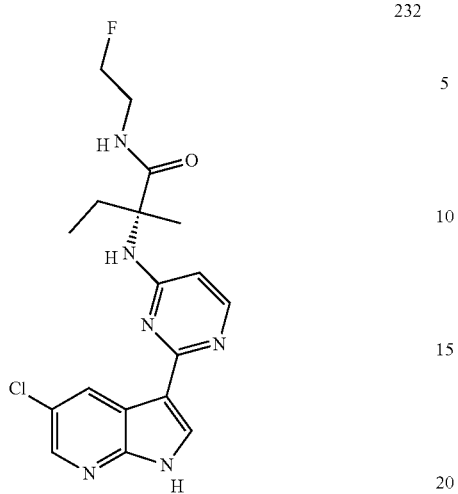
233 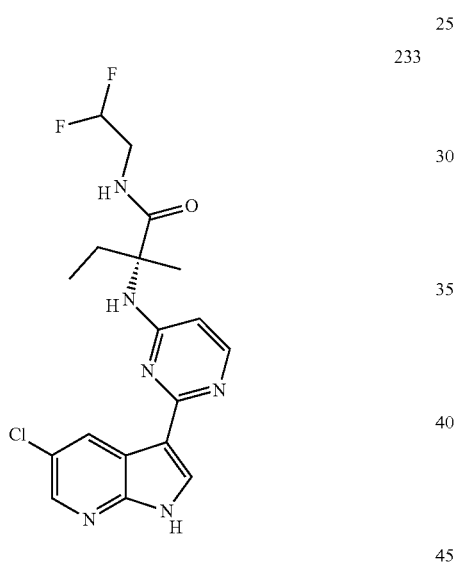
234 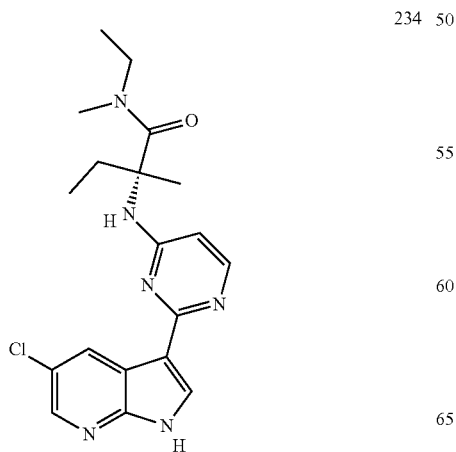
235 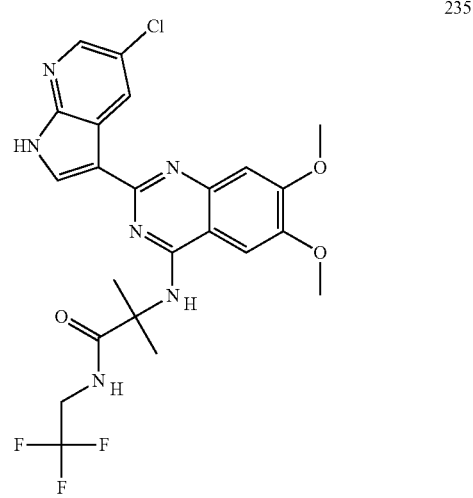
236 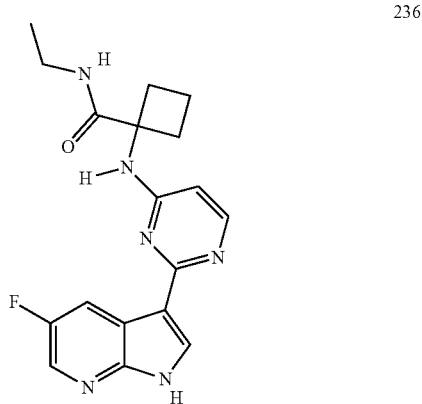
237 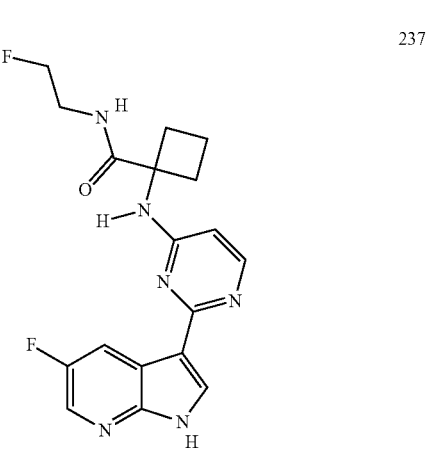

238
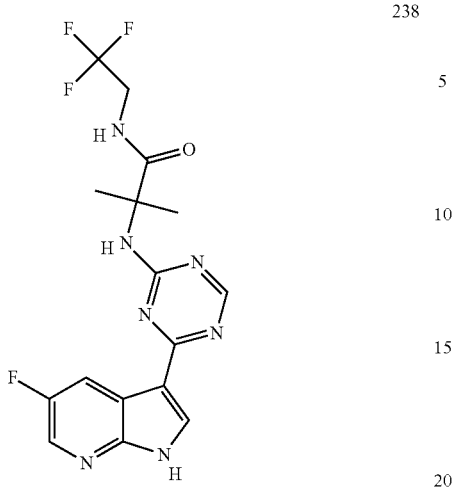
239
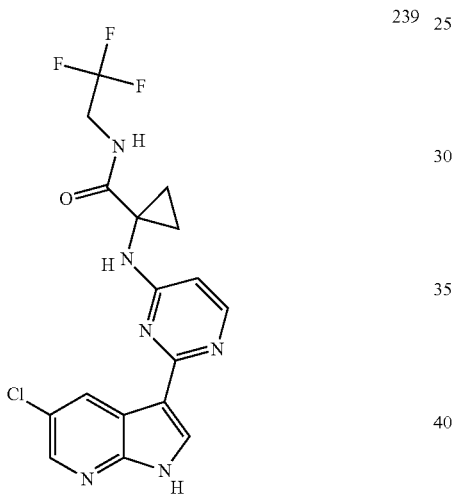
240
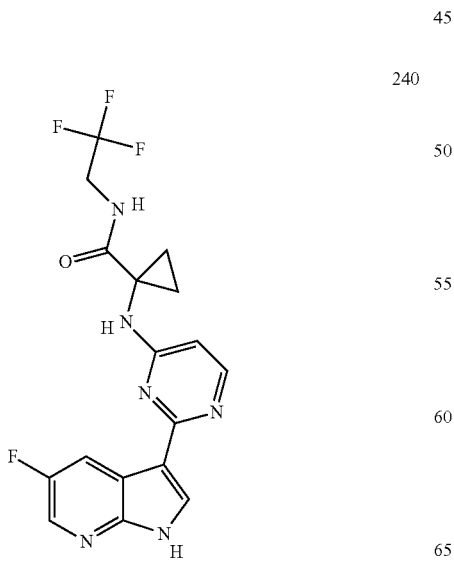
241
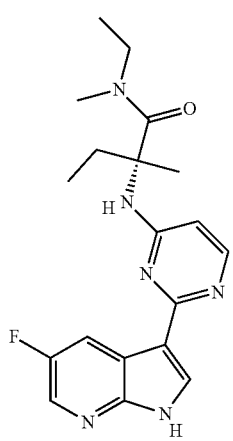
242
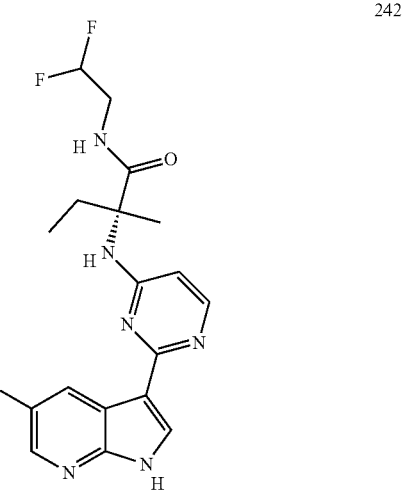
243
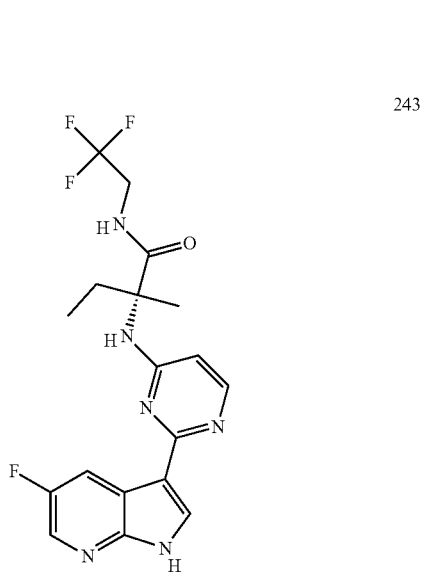

244
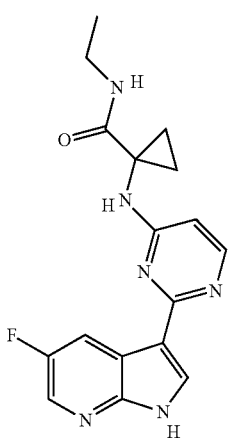
245
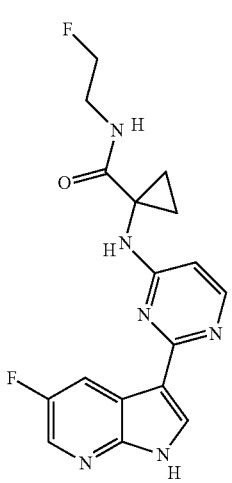
246
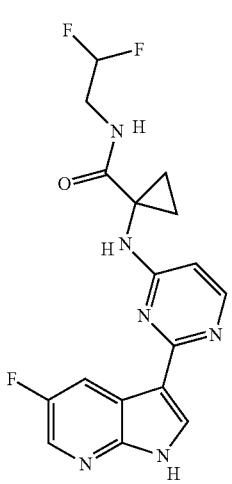
247
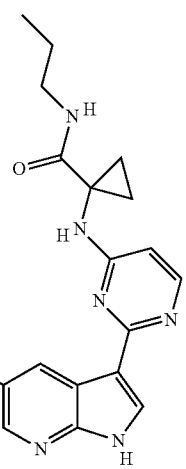
248
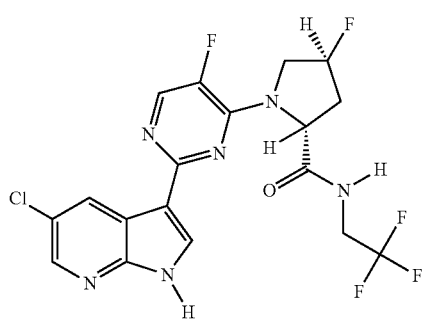
249
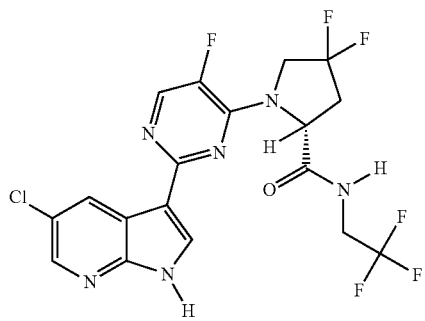
250
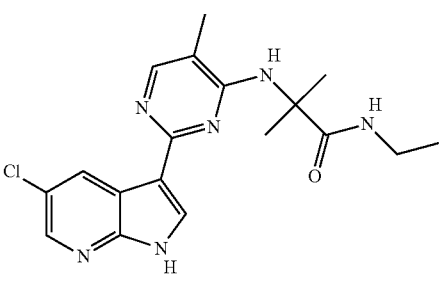
251
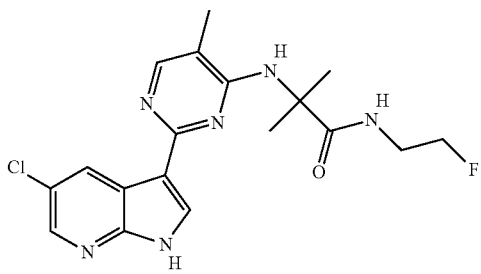

| | |
|---|---|
| 252 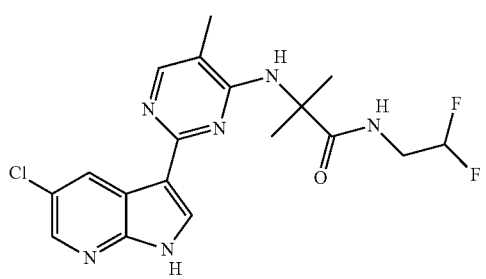 | 257 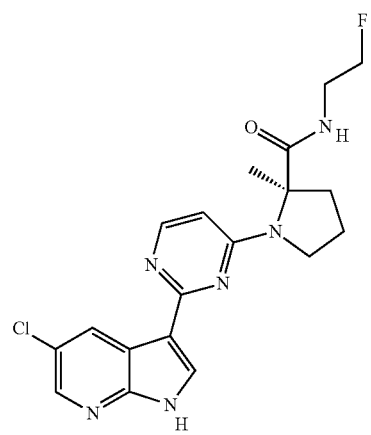 |
| 253 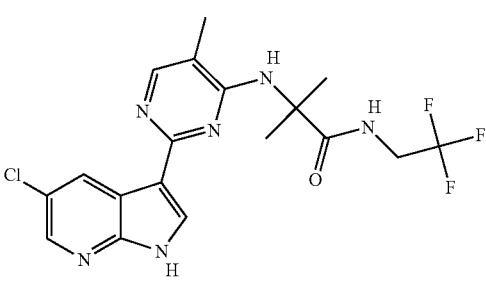 | |
| 254 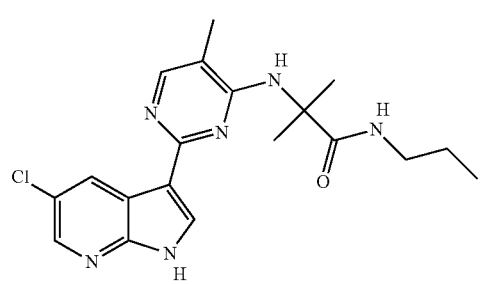 | 258 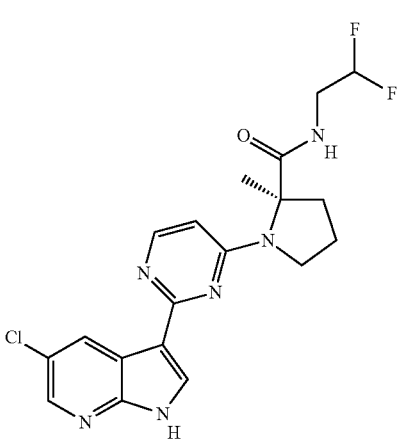 |
| 255 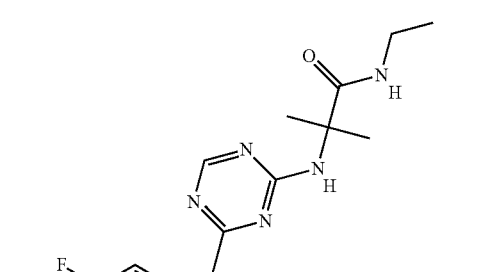 | |
| 256 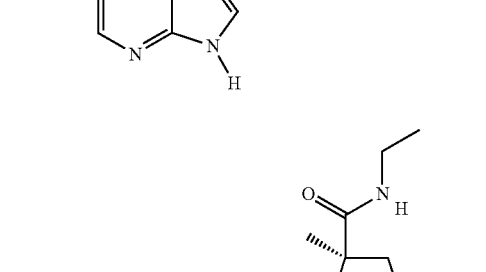 | 259 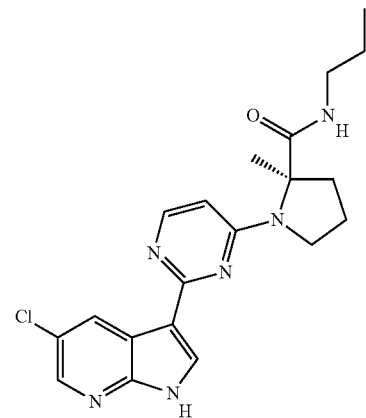 |

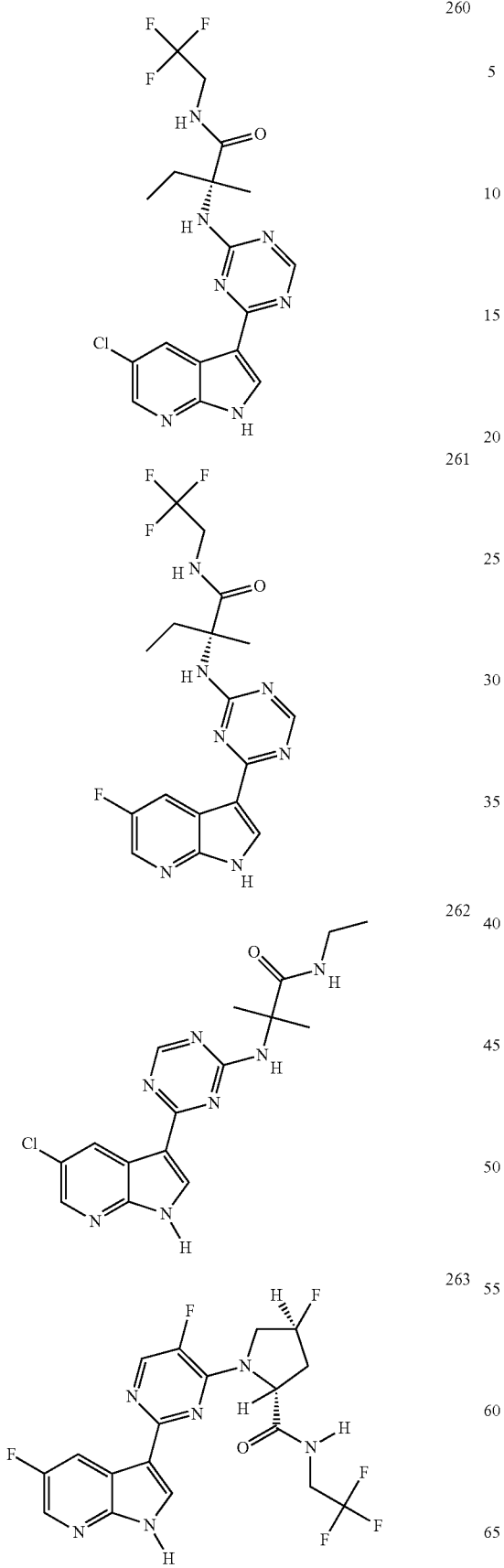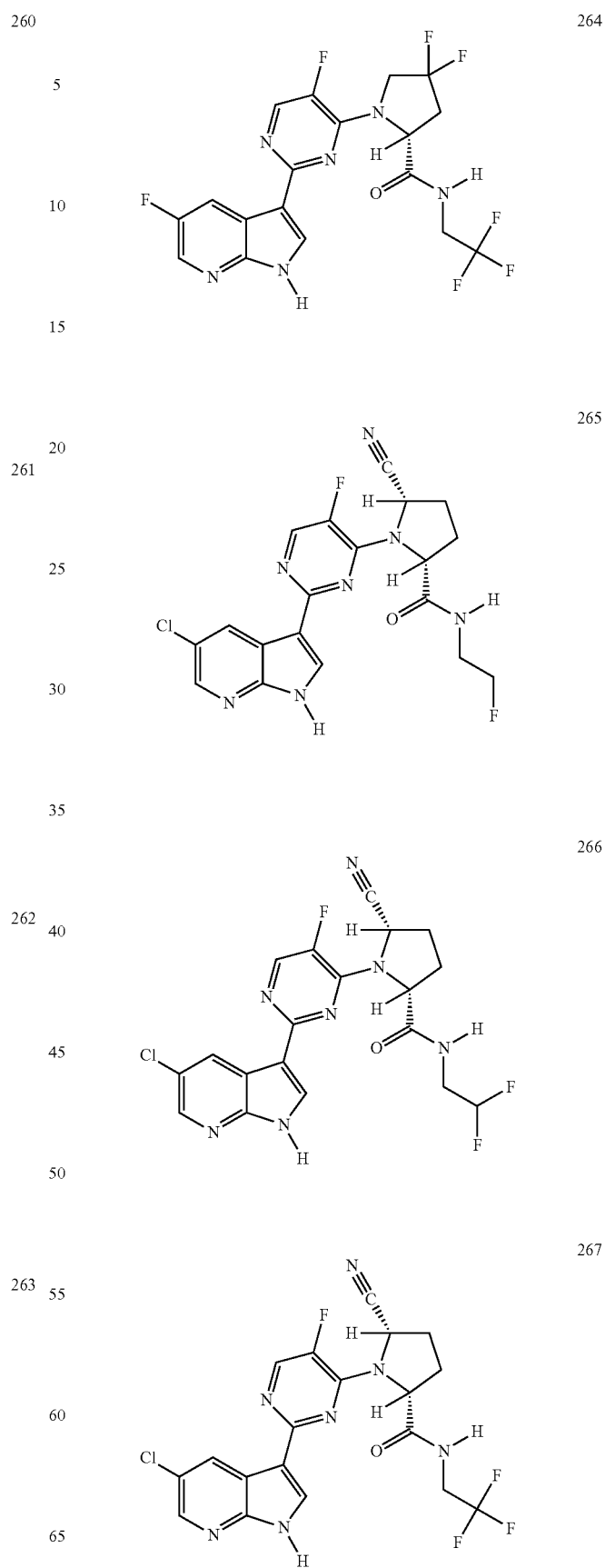

247
268 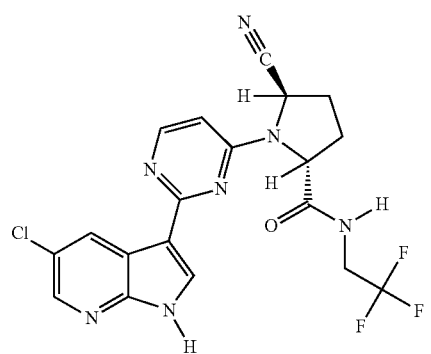
269 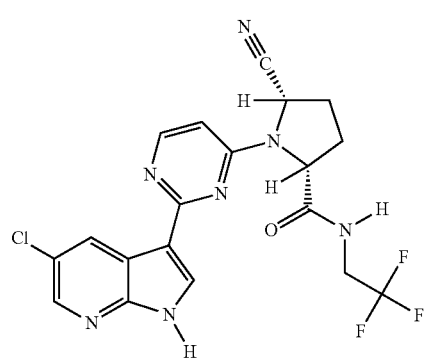
270 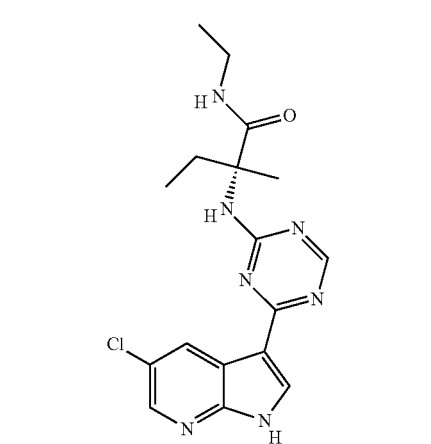
271 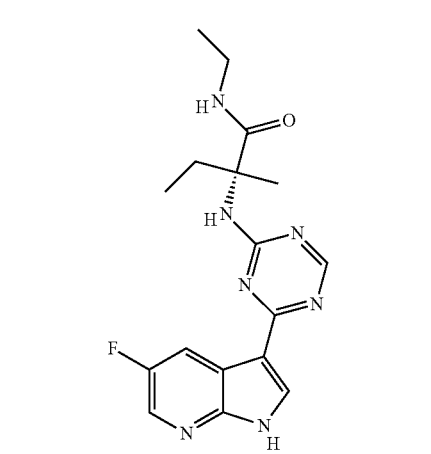
248
272 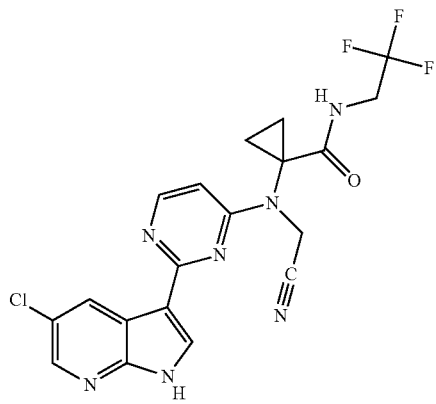
273 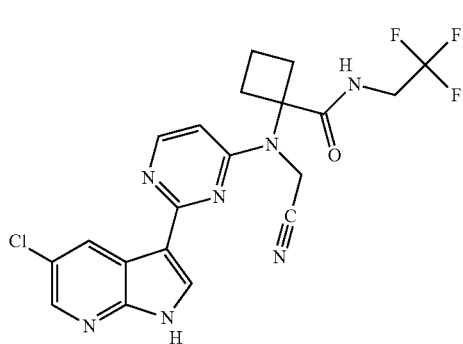
274 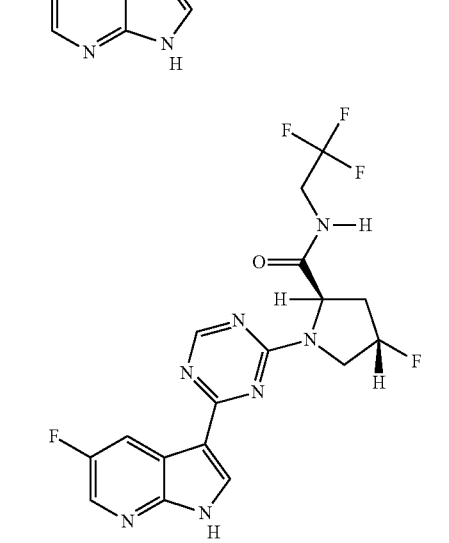
275 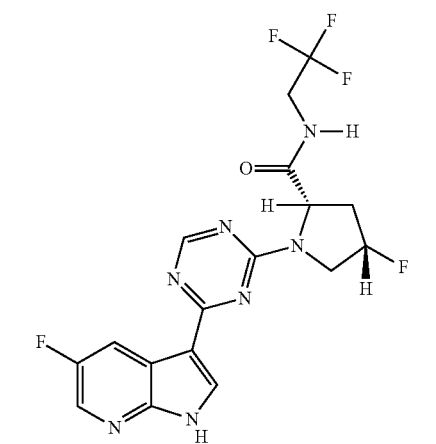

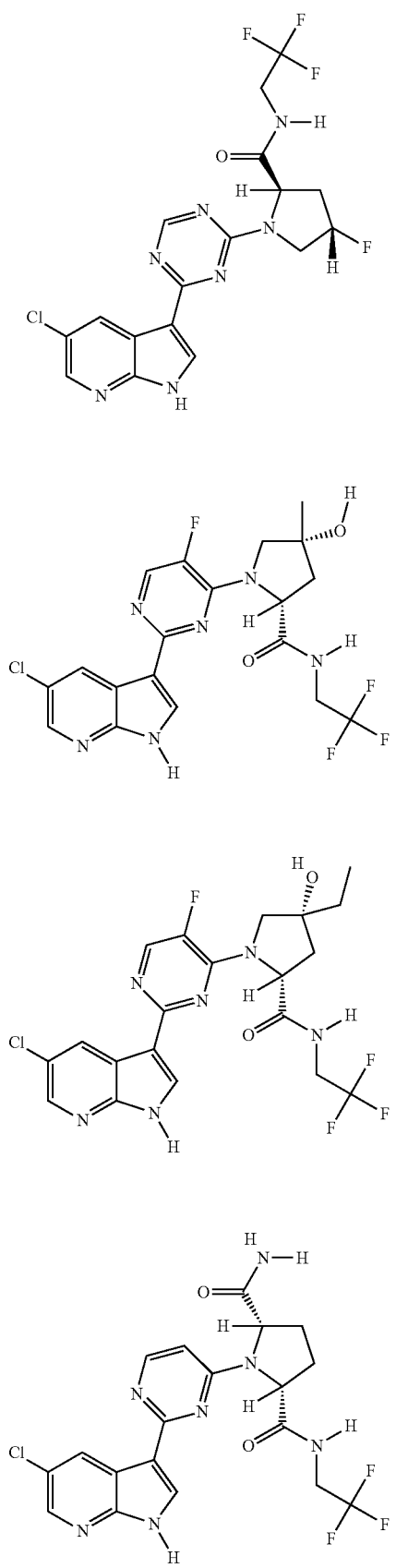
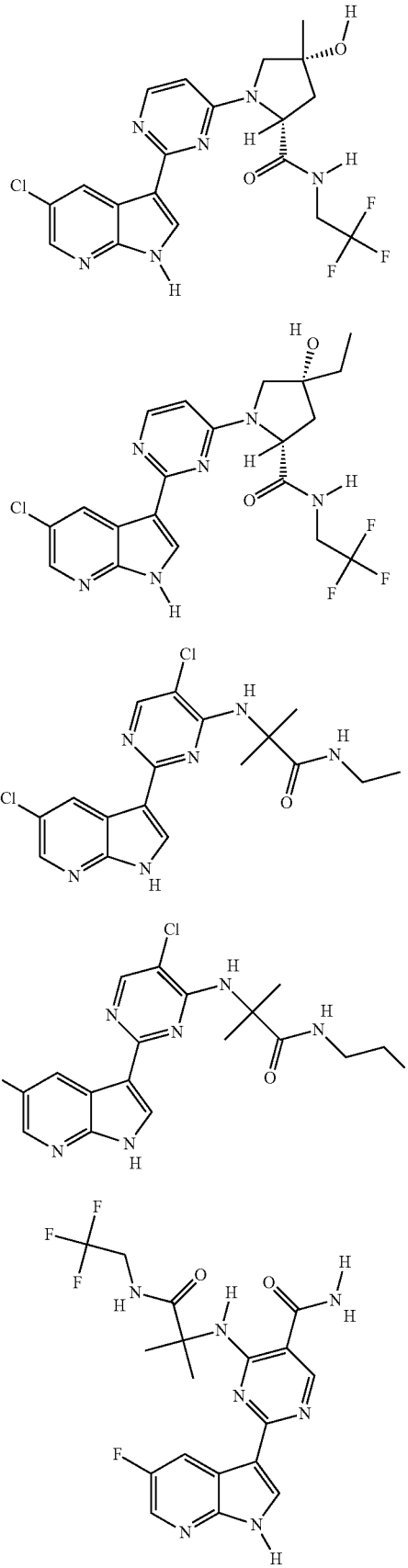

285
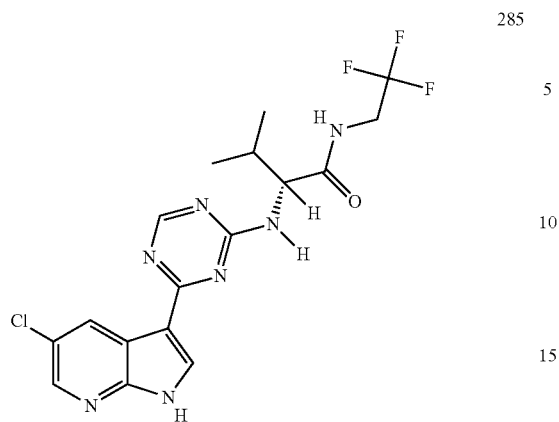
286
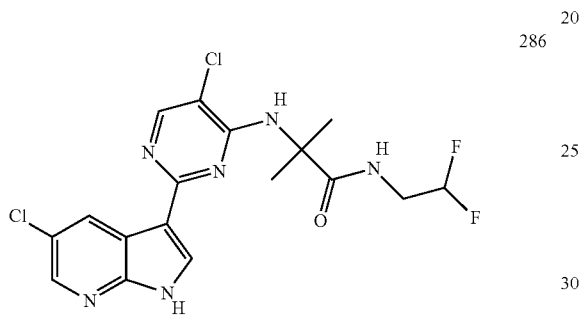
287
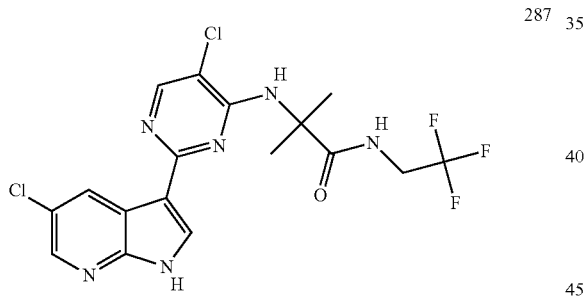
288
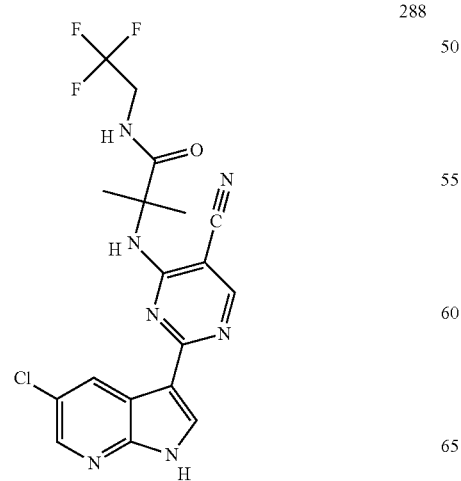
289
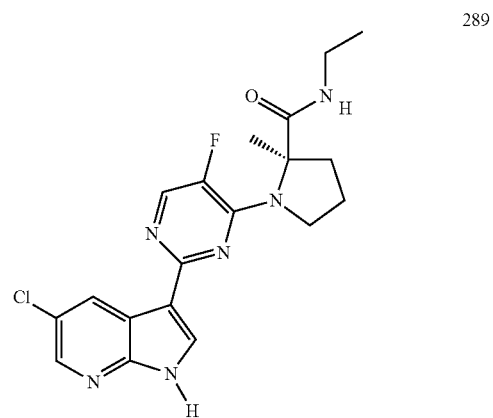
290
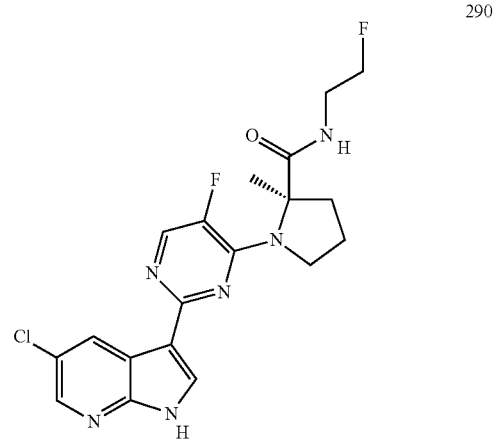
291

292
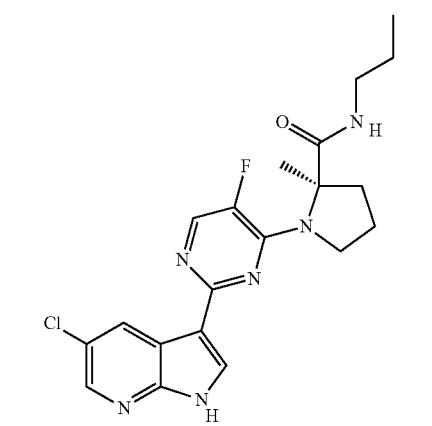
293
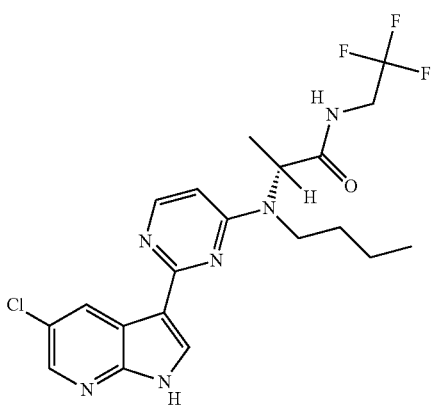
294
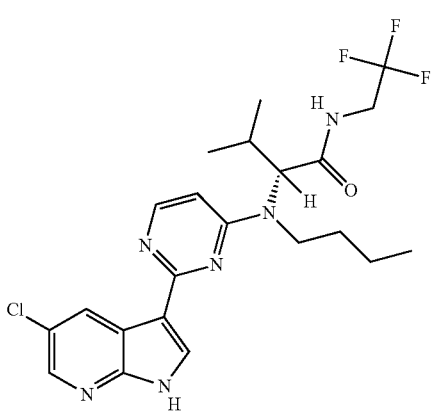
295
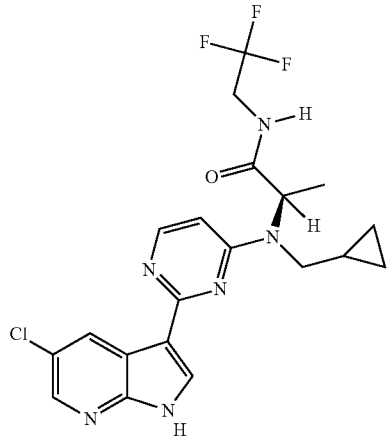
296
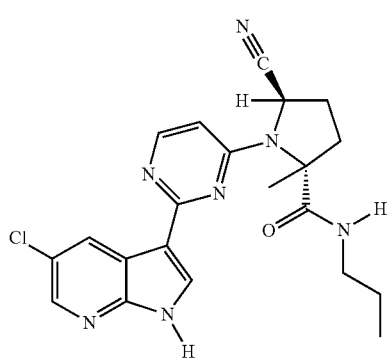
297
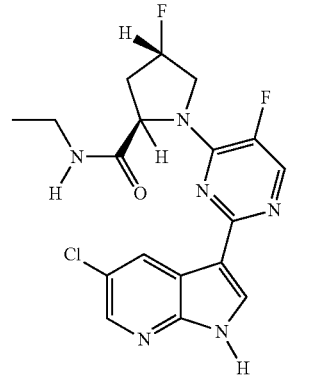
298
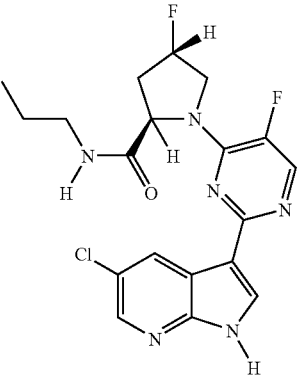

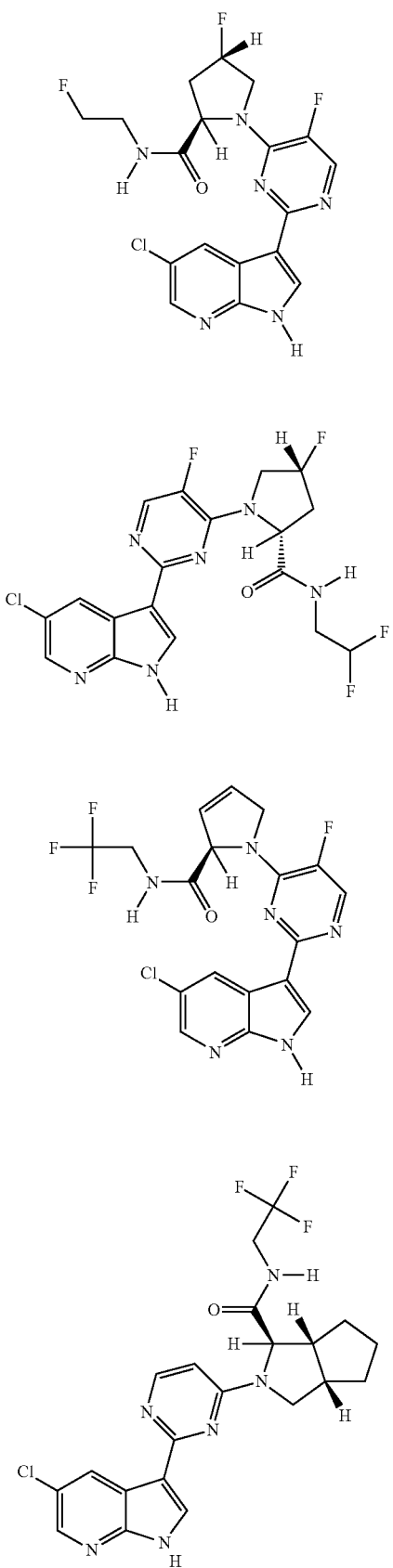
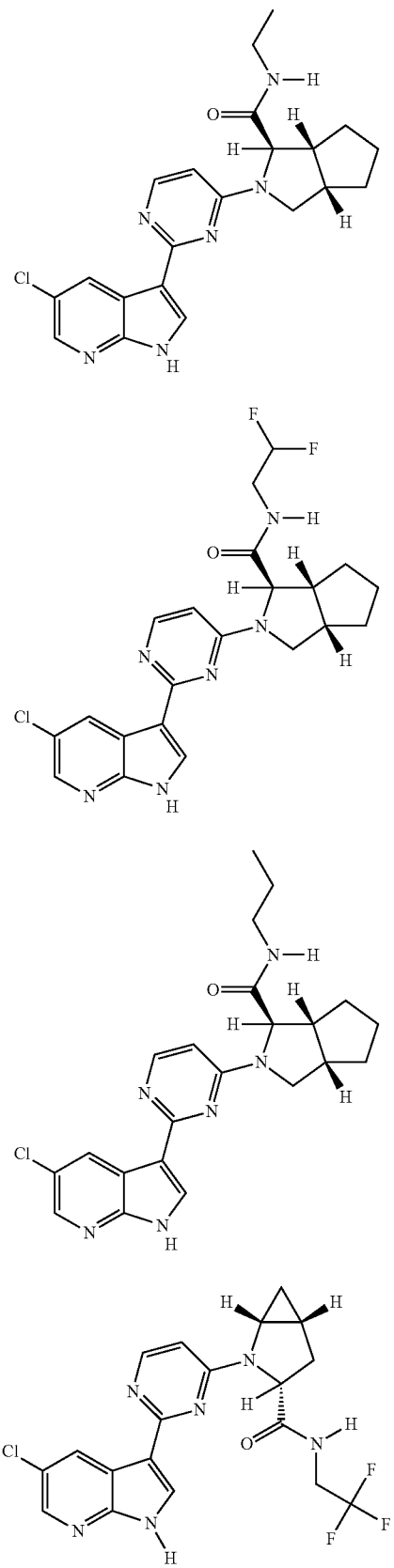

307 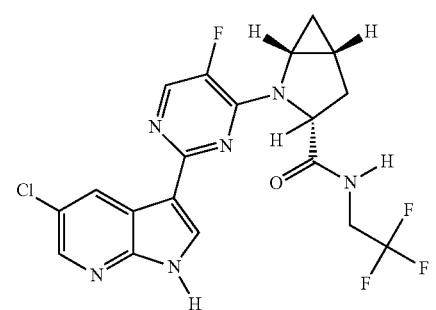
308 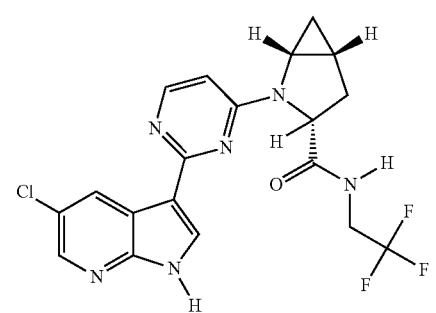
309 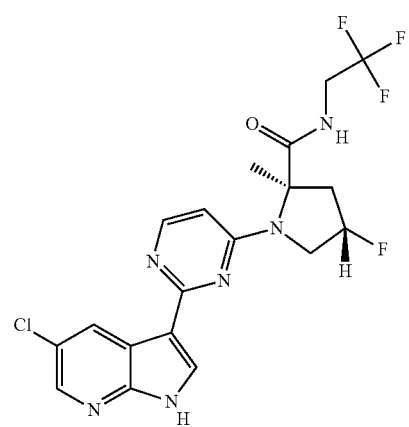
312 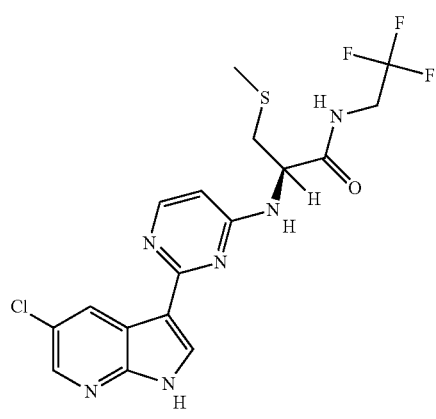
313 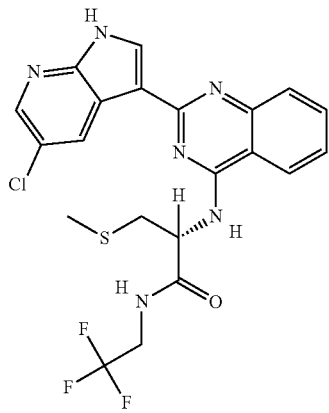
314 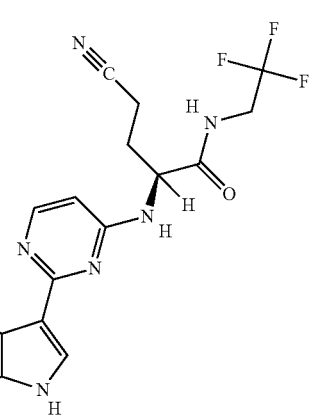
315 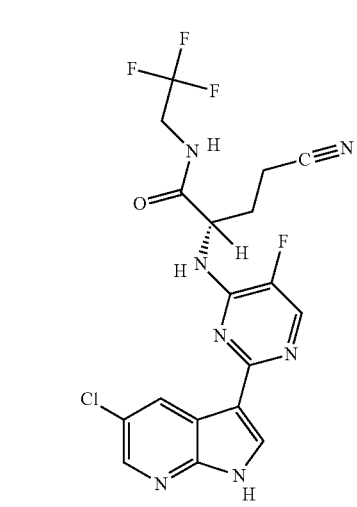

259
316
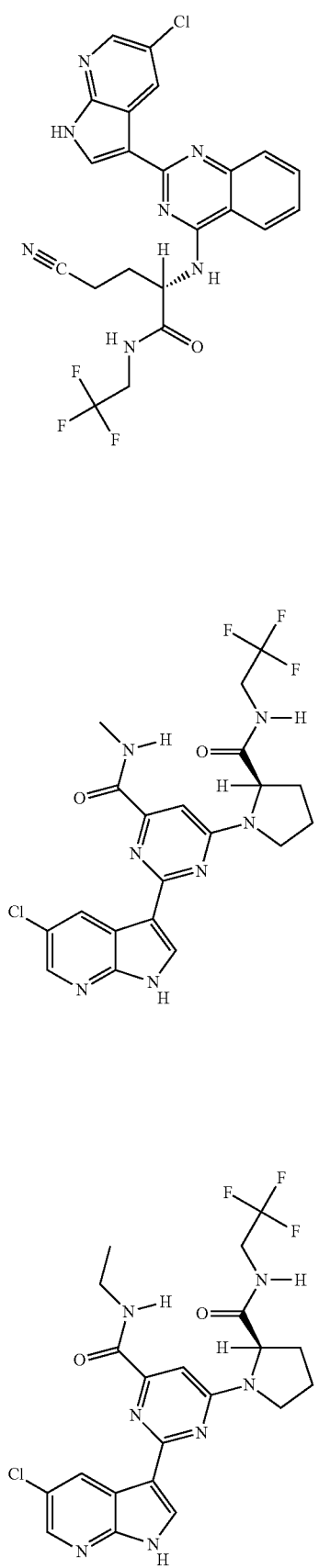
317
318
260
319
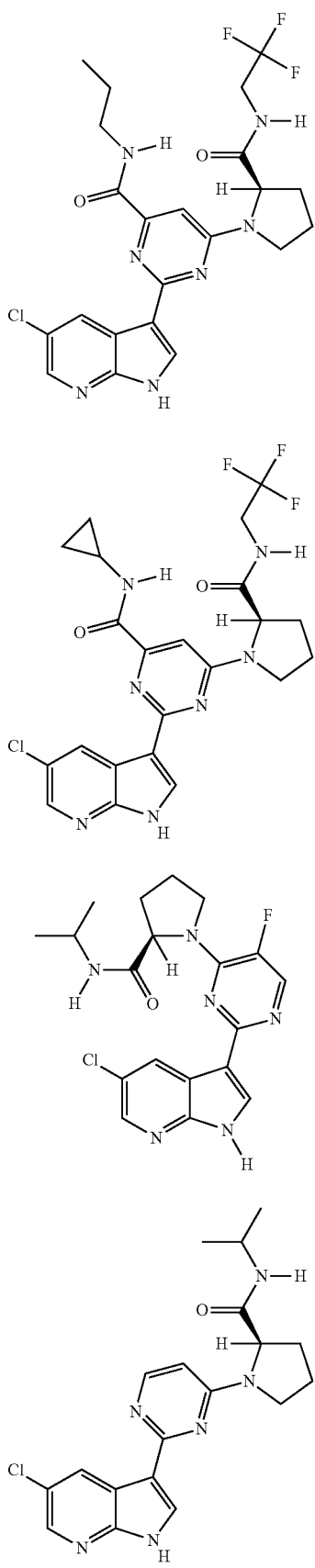
320
322
324

325 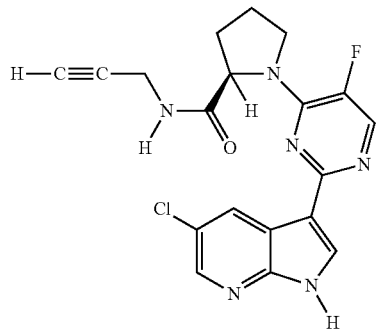
326 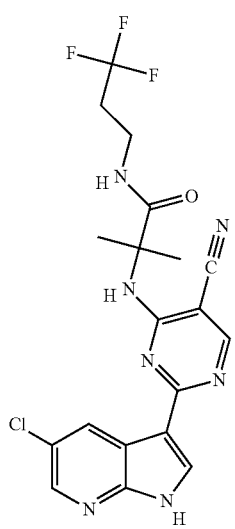
327 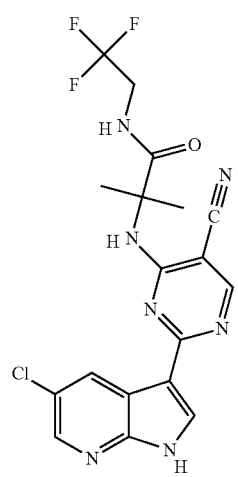
329 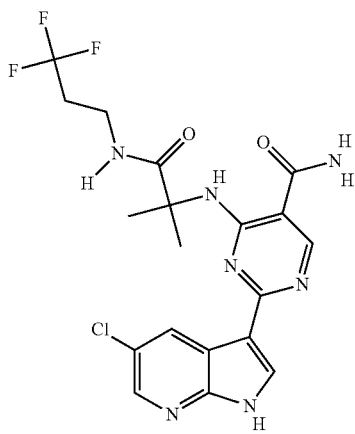
330 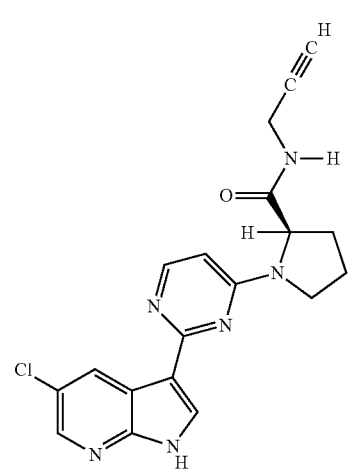
331 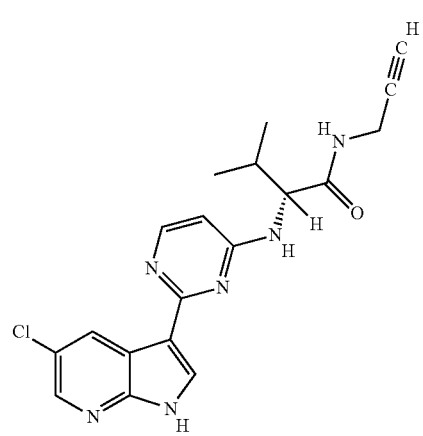

332 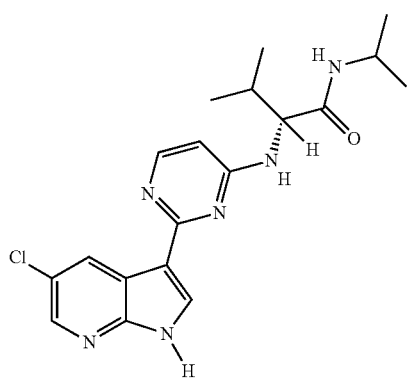
333 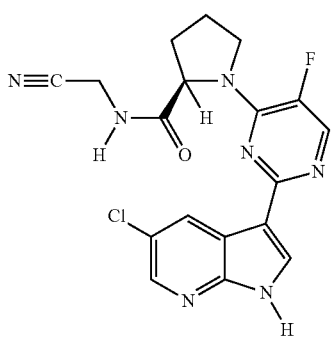
334 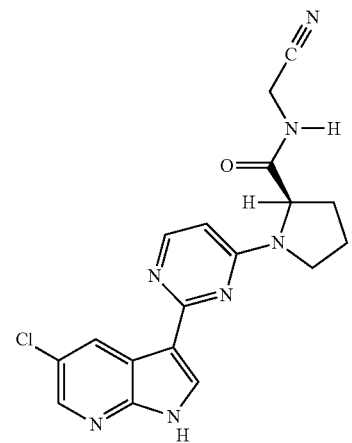
335 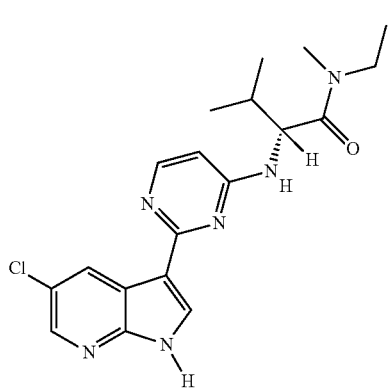
336 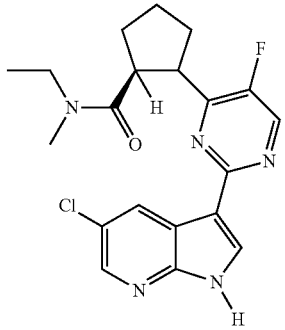
337 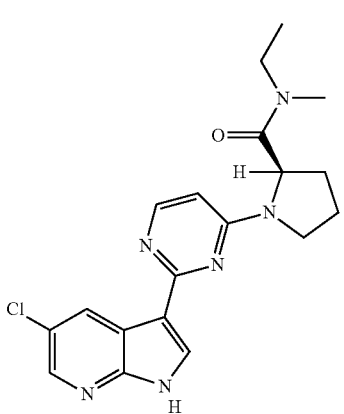
338 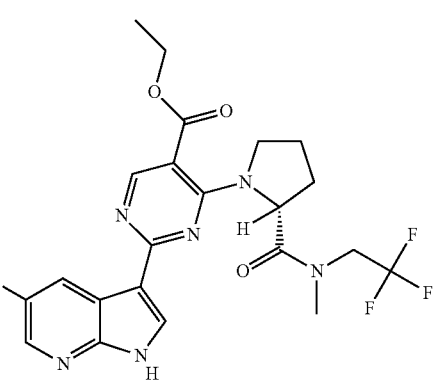
340 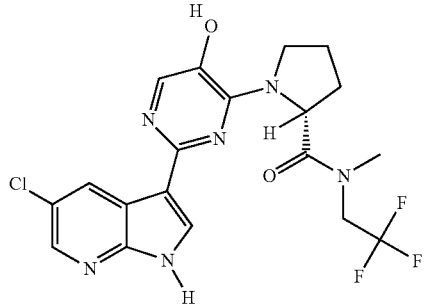

265
-continued
341
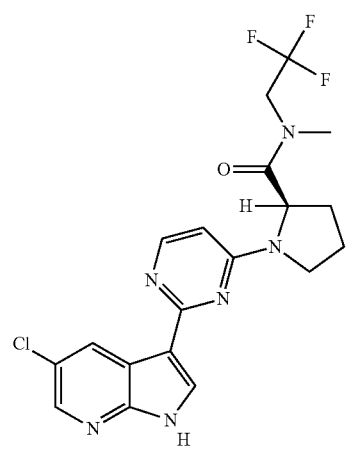
342
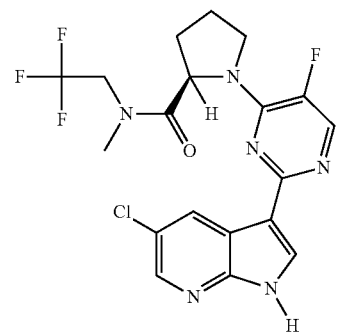
349
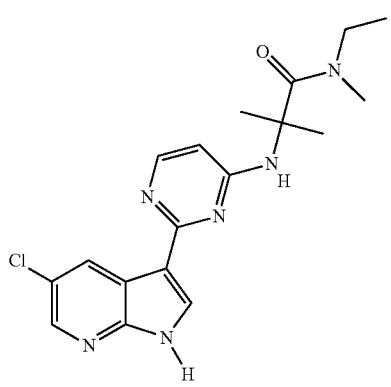
353
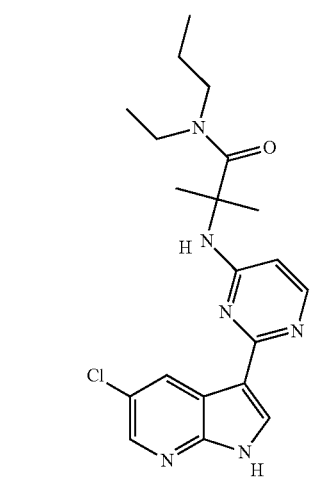
266
-continued
354
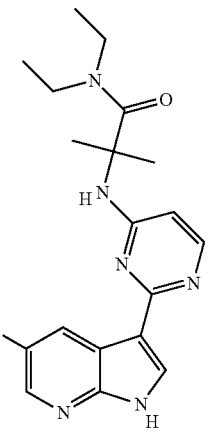
355
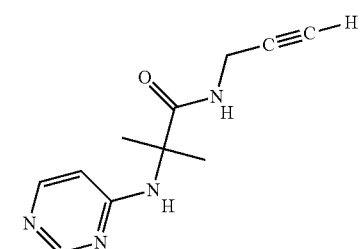
359
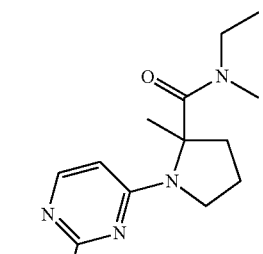
365
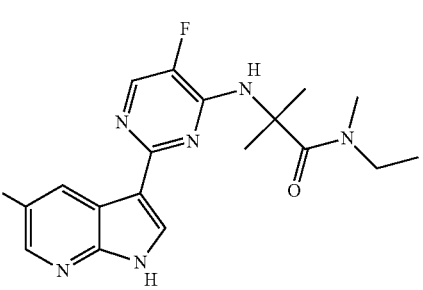
37. A pharmaceutical composition comprising a compound according to any one of claim 1, 17, or 36 and a pharmaceutically acceptable carrier, adjuvant, or vehicle.
38. The composition according to claim 37, additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

39. The compound according to claim 1, wherein $R^1$ is

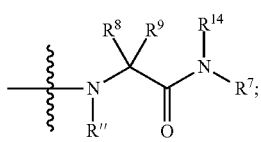

and $R^8$, $R^9$, and the carbon atom to which they are attached form

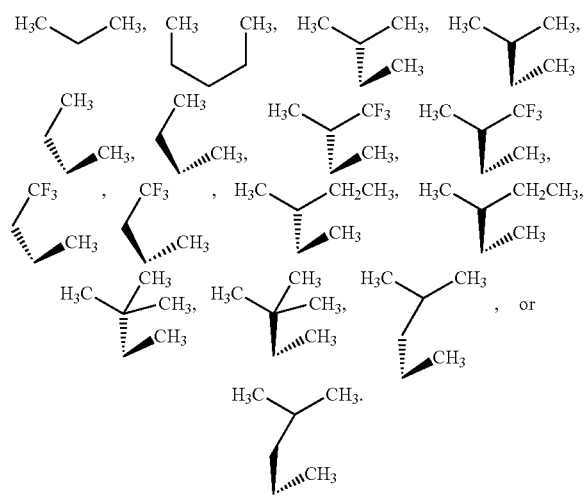

40. The compound of claim 39, wherein $R^3$ is Cl.
41. The compound of claim 39, wherein $R^3$ is F.
42. The compound according to claim 39, wherein $R^1$ is

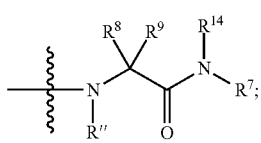

and $R^8$, $R^9$, and the carbon atom to which they are attached form

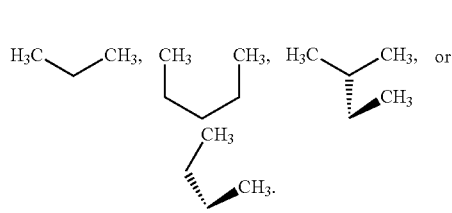

43. The compound according to claim 39, wherein $R^2$ is H or F, $R^4$ is H or F, and $R^7$ is $CH_2CH_3$, $CH_2CF_3$, $CH_2CHF_2$, $CH_2CH_2F$, $CH_2CH_2CH_3$, $CH_2CH_2CF_3$, $CH_2CH_2CH_2F$ or $CH_2CH_2CHF_2$.

44. The compound according to claim 43, wherein $R^2$ is H, $R^4$ is H or F, and $R^7$ is $CH_2CH_3$, $CH_2CF_3$, $CH_2CHF_2$ or $CH_2CH_2F$.

45. The compound according to claim 44, wherein $R^2$ is H, $R^4$ is H, and $R^7$ is $CH_2CF_3$.

46. The compound according to claim 39, wherein R'' is H or $CH_3$ and $R^{14}$ is H.

47. The compound according to claim 1, wherein $R^1$ is

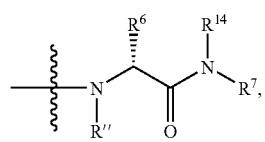

and $R^6$ and the carbon atom to which it is attached form

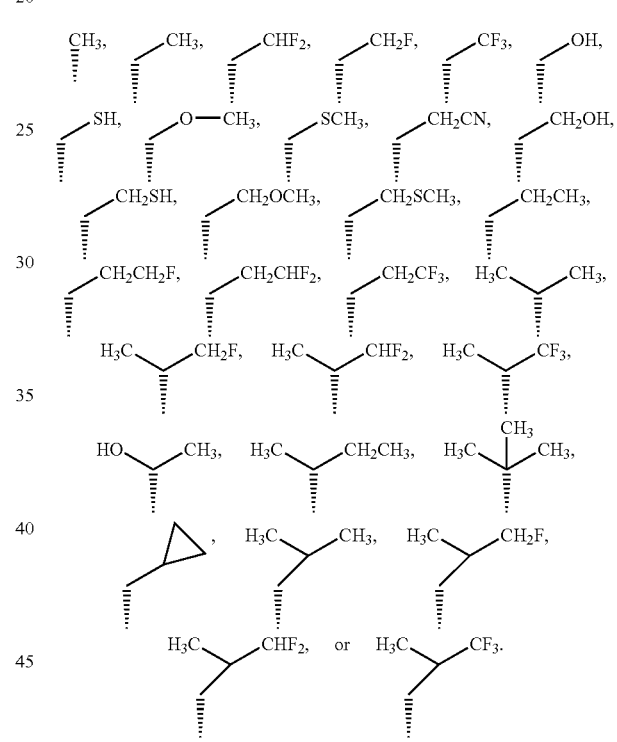

48. The compound according to claim 47, wherein $R^1$ is

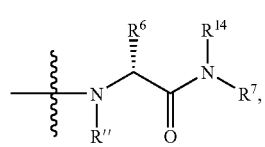

and $R^6$ and the carbon atom to which it is attached form

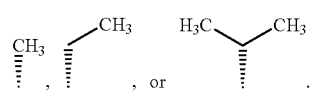

49. The compound according to claim 47, wherein $R^2$ is H or F, $R^4$ is H or F, and $R^7$ is $CH_2CH_3$, $CH_2CF_3$, $CH_2CHF_2$, $CH_2CH_2F$, $CH_2CH_2CH_3$, $CH_2CH_2CF_3$, $CH_2CH_2CH_2F$ or $CH_2CH_2CHF_2$.

50. The compound according to claim 49, wherein $R^2$ is H, $R^4$ is H or F, and $R^7$ is $CH_2CH_3$, $CH_2CF_3$, $CH_2CHF_2$ or $CH_2CH_2F$.

51. The compound according to claim 50, wherein $R^2$ is H, $R^4$ is H, and $R^7$ is $CH_2CF_3$.

52. The compound according to claim 47, wherein R" is H or $CH_3$ and $R^{14}$ is H.

53. The compound according to claim 1, wherein $R^1$ is

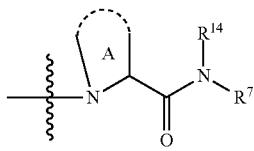

and Ring A is

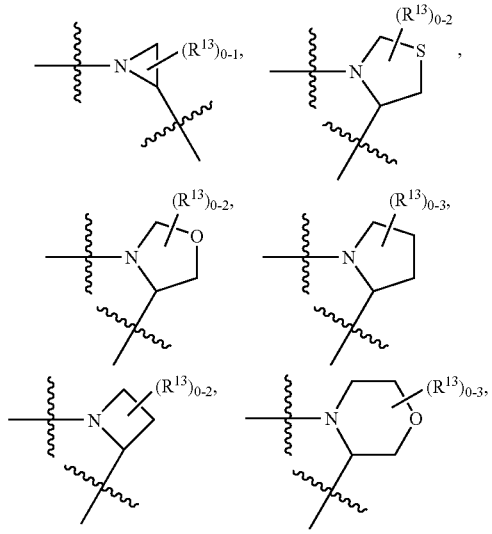

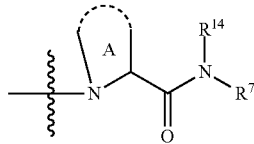

and $R^{13'}$ is H or $R^{13}$.

54. The compound according to claim 53, wherein $R^1$ is

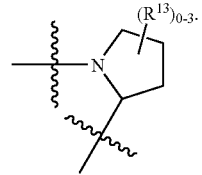

and Ring A is

55. The compound according to claim 53, wherein $R^2$ is H or F, $R^4$ is H or F, and $R^7$ is $CH_2CH_3$, $CH_2CF_3$, $CH_2CHF_2$, $CH_2CH_2F$, $CH_2CH_2CH_3$, $CH_2CH_2CF_3$, $CH_2CH_2CH_2F$ or $CH_2CH_2CHF_2$.

56. The compound according to claim 55, wherein $R^2$ is H, $R^4$ is H or F, and $R^7$ is $CH_2CH_3$, $CH_2CF_3$, $CH_2CHF_2$ or $CH_2CH_2F$.

57. The compound according to claim 56, wherein $R^2$ is H, $R^4$ is H, and $R^7$ is $CH_2CF_3$.

58. The compound according to claim 53, wherein $R^{14}$ is H or $CH_3$.

* * * * *